United States Patent
Heo et al.

(10) Patent No.: US 12,082,498 B2
(45) Date of Patent: Sep. 3, 2024

(54) ORGANIC LIGHT-EMITTING ELEMENT

(71) Applicant: LG Chem, Ltd., Seoul (KR)

(72) Inventors: Dong Uk Heo, Daejeon (KR); Dong Hoon Lee, Daejeon (KR); Jungoh Huh, Daejeon (KR); Boonjae Jang, Daejeon (KR); Min Woo Jung, Daejeon (KR); Ju Young Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 461 days.

(21) Appl. No.: 16/071,126

(22) PCT Filed: Apr. 24, 2017

(86) PCT No.: PCT/KR2017/004325
§ 371 (c)(1),
(2) Date: Jul. 19, 2018

(87) PCT Pub. No.: WO2017/188679
PCT Pub. Date: Nov. 2, 2017

(65) Prior Publication Data
US 2020/0136053 A1    Apr. 30, 2020

(30) Foreign Application Priority Data

Apr. 28, 2016 (KR) .................. 10-2016-0052237

(51) Int. Cl.
*H10K 85/60* (2023.01)
*H10K 50/155* (2023.01)
*H10K 50/165* (2023.01)

(52) U.S. Cl.
CPC ......... *H10K 85/654* (2023.02); *H10K 85/615* (2023.02); *H10K 85/655* (2023.02); *H10K 85/6572* (2023.02); *H10K 85/6574* (2023.02); *H10K 85/6576* (2023.02); *H10K 50/155* (2023.02); *H10K 50/165* (2023.02)

(58) Field of Classification Search
CPC ............. H01L 51/0067; H01L 51/0052; H01L 51/0068; H01L 51/0072; H01L 51/0073; H01L 51/0074; H01L 51/506; H01L 51/5076; H10K 85/654; H10K 85/655; H10K 85/6574; H10K 85/6576; H10K 85/615; H10K 85/6572; H10K 50/155; H10K 50/165; H10K 85/40; H10K 85/60; H10K 85/649; H10K 85/653; H10K 85/656; H10K 85/6565; H10K 85/657; H10K 85/658; H10K 85/791; H10K 85/322

See application file for complete search history.

(56) References Cited

U.S. PATENT DOCUMENTS

| 2003/0168970 A1* | 9/2003 | Tominaga ........... H01L 51/0036 313/504 |
| 2005/0249970 A1* | 11/2005 | Suzuri ................... C09K 11/06 313/506 |
| 2007/0051944 A1* | 3/2007 | Vestweber ........... C07D 239/26 257/E51.012 |
| 2007/0090753 A1 | 4/2007 | Arakane |
| 2009/0160323 A1 | 6/2009 | Nomura et al. |

(Continued)

FOREIGN PATENT DOCUMENTS

| CN | 107074784 A | 8/2017 |
| EP | 2128217 A1 | 12/2009 |

(Continued)

OTHER PUBLICATIONS

Kim et al., Machine Translation of KR-20150093440-A (2015) pp. 1-17. (Year: 2015).*

(Continued)

*Primary Examiner* — Dylan C Kershner
(74) *Attorney, Agent, or Firm* — Lerner David LLP

(57) ABSTRACT

The present specification relates to an organic light emitting device having high light emission efficiency. Such organic light emitting device comprises a light emitting layer provided between the cathode and the anode, and including an anthracene derivative represented by the following Chemical Formula 2, and an organic material layer provide between the cathode and the light emitting layer, and including a cyclic compound represented by the following Chemical Formula 1.

[Chemical Formula 1]

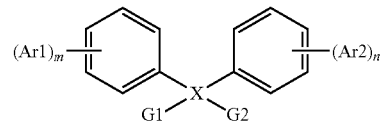

[Chemical Formula 2]

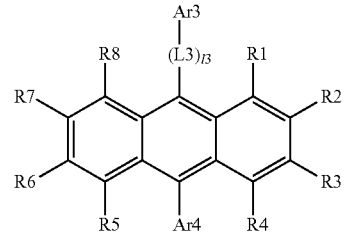

wherein Ar1, Ar2, X, G1, G2, m, n, R1-R8, Ar3, Ar4, L3, and l3 are described herein.

19 Claims, 4 Drawing Sheets

(56) References Cited

U.S. PATENT DOCUMENTS

| | | | |
|---|---|---|---|
| 2010/0102709 A1 | 4/2010 | Zeika et al. | |
| 2013/0015431 A1 | 1/2013 | Kamalasanan et al. | |
| 2013/0105787 A1 | 5/2013 | Tanaka et al. | |
| 2014/0291586 A1 | 10/2014 | Buesing et al. | |
| 2015/0243904 A1* | 8/2015 | Lin | H10K 85/6572 548/440 |
| 2015/0318510 A1 | 11/2015 | Ito et al. | |
| 2015/0325800 A1* | 11/2015 | Ito | H10K 85/6574 548/440 |
| 2015/0364693 A1 | 12/2015 | Ito et al. | |
| 2016/0276594 A1 | 9/2016 | Huh et al. | |
| 2016/0276596 A1 | 9/2016 | Jang et al. | |
| 2016/0293852 A1 | 10/2016 | Huh et al. | |
| 2017/0117469 A1 | 4/2017 | Ito et al. | |
| 2017/0301866 A1* | 10/2017 | Heo | C09K 11/06 |

FOREIGN PATENT DOCUMENTS

| | | | |
|---|---|---|---|
| EP | 2163550 A1 | 3/2010 | |
| EP | 2924029 A1 | 9/2015 | |
| EP | 3127988 A1 | 2/2017 | |
| EP | 3208864 A1 | 8/2017 | |
| EP | 3214084 A2 | 9/2017 | |
| JP | 09291274 A * | 11/1997 | |
| JP | 2002305084 A | 10/2002 | |
| JP | 3341090 B2 | 11/2002 | |
| JP | 2003206278 A | 7/2003 | |
| JP | 2004342391 A * | 12/2004 | |
| JP | 2005032488 A | 2/2005 | |
| JP | 2005340122 A | 12/2005 | |
| JP | 2007049055 A | 2/2007 | |
| JP | 2007131722 A | 5/2007 | |
| JP | 2009182088 A | 8/2009 | |
| JP | 2009182088 A * | 8/2009 | |
| JP | 2009188136 A | 8/2009 | |
| JP | 2009246097 A * | 10/2009 | |
| JP | 5326568 B2 | 10/2013 | |
| JP | 2014167946 A | 9/2014 | |
| KR | 20000051826 A | 8/2000 | |
| KR | 20090041999 A | 4/2009 | |
| KR | 20100131745 A | 12/2010 | |
| KR | 20140021969 A | 2/2014 | |
| KR | 20150006199 A | 1/2015 | |
| KR | 101537499 B1 | 7/2015 | |
| KR | 20150093440 A * | 8/2015 | |
| KR | 20150093440 A | 8/2015 | |
| KR | 20150106668 A | 9/2015 | |
| KR | 20150142822 A | 12/2015 | |
| TW | 200605723 A | 2/2006 | |
| TW | 201600512 A | 1/2016 | |
| WO | WO-2006104118 A1 * | 10/2006 | H01L 51/5052 |
| WO | 2012008281 A1 | 1/2012 | |
| WO | 2014141725 A1 | 9/2014 | |
| WO | 2015152634 A1 | 10/2015 | |
| WO | 2015152644 A1 | 10/2015 | |
| WO | 2016024728 A1 | 2/2016 | |
| WO | 2016039501 A1 | 3/2016 | |
| WO | 2016042781 A1 | 3/2016 | |
| WO | WO-2016068478 A2 * | 5/2016 | H01L 51/50 |

OTHER PUBLICATIONS

Suzuri et al., Machine Translation of WO-2006104118-A1 (2006) pp. 1-17. (Year: 2006).*
Oshiyama et al., Machine Translation of JP-2009182088-A (2009) pp. 1-110. (Year: 2009).*
Ueda, Noriko et al., Machine Translation of JP-2004342391-A (2004) pp. 1-75. (Year: 2004).*
Enokida, Toshio et al., Machine Translation of JP-09291274-A (1997) pp. 1-43. (Year: 1997).*
Kitazawa et al., Machine Translation of JP 2003-206278A (2003) pp. 1-9. (Year: 2003).*
Choi et al., "Improved Efficiency and Lifetime of Organic Light-Emitting Diode with Lithium-Quinolate-Doped Electron Transport Layer" Japanese Journal of Applied Physics, vol. 48 (2009) pp. 062101-1 through 062101-3. (Year: 2009).*
Suzuri et al., Machine Translation of JP 2009246097 (2009) pp. 1-49. (Year: 2009).*
Yi et al., "Silicon-based electron-transport materials with high thermal stability and triplet energy for efficient phosphorescent OLEDs" Organic Electronics, vol. 27 (2015) pp. 126-132. (Year: 2015).*
Extended European Search Report including Written Opinion for Application No. EP17789863.2 dated Dec. 19, 2018.
Search report from International Application No. PCT/KR2017/004325, mailed Aug. 11, 2017.
Search report from Tawain Application No. 20170113837 dated Mar. 20, 2017.
Chinese Search Report for Application No. CN 201780008427.8 dated Feb. 7, 2021, 9 pages.
Chinese Search Report for Application No. CN 201780008544.4 dated Jul. 16, 2019 from Office Action issued Jul. 42, 2019, 1 page.
Extended European Search Report including Written Opinion for Application No. EP17789864.0 dated Feb. 22, 2019, 7 pgs.
Riken Keiki; "Photoelectron Spectrophotometer in air. Surface Analyzer", Model AC-3, pp. 1-6, Jun. 2012.
Search report from International Application No. PCT/KR2017/004326, mailed Aug. 11, 2017, 3 pgs.
Search report from Office Action from Taiwan Applicaiton No. 106113834, mailed Feb. 6, 2018, 1 page.
Search report from Office Action from Taiwan Application No. 106113834, mailed Jun. 6, 2018, 1 page.
Cölle et al (J. Appl. Phys., 2004, 96, 11, p. 6133-6141 (Year: 2004).
Manninen et al J. Mater. Chem., 2012, 22, p. 22971 (Year: 2012).

* cited by examiner

[FIG. 1]
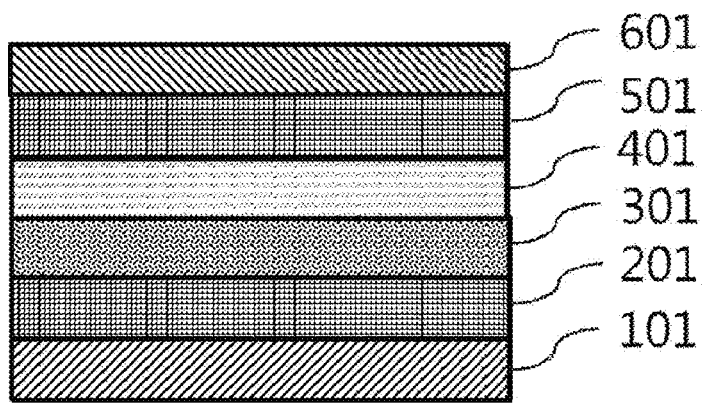
[FIG. 2]
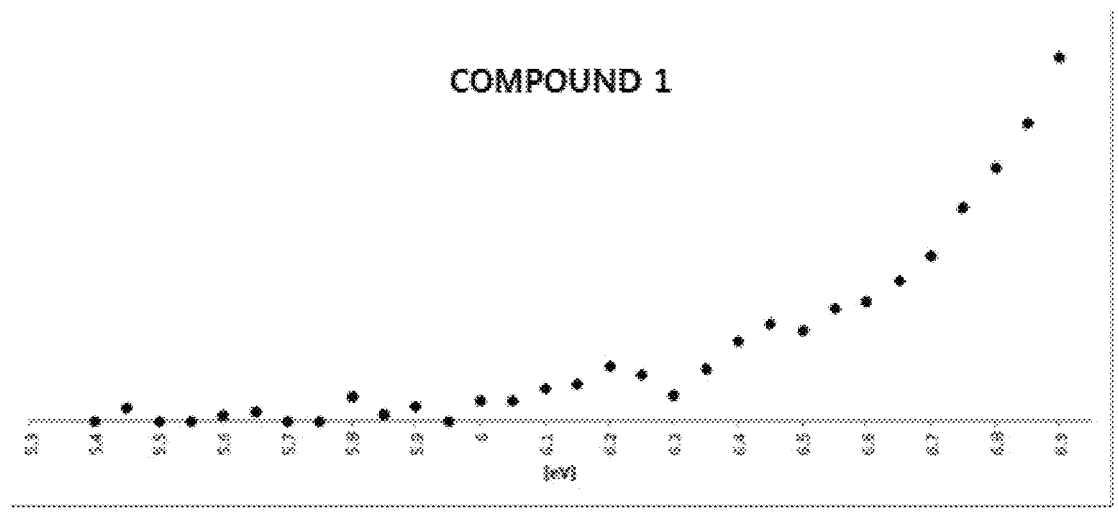

[FIG. 3]
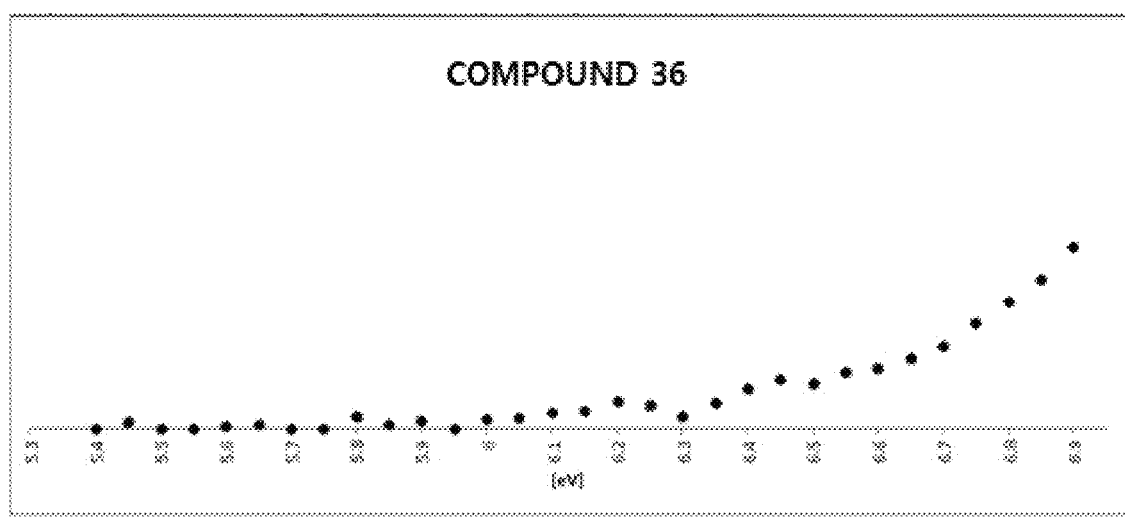
[FIG. 4]
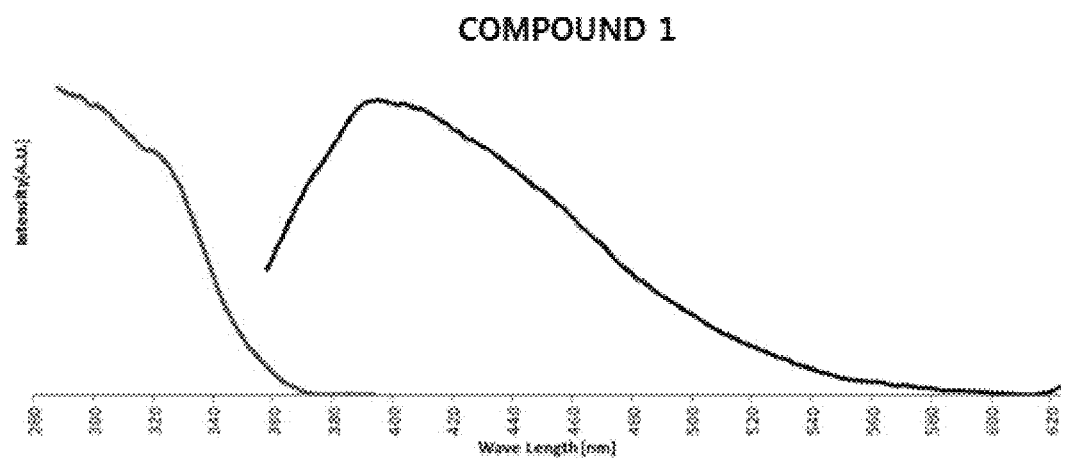

[FIG. 5]
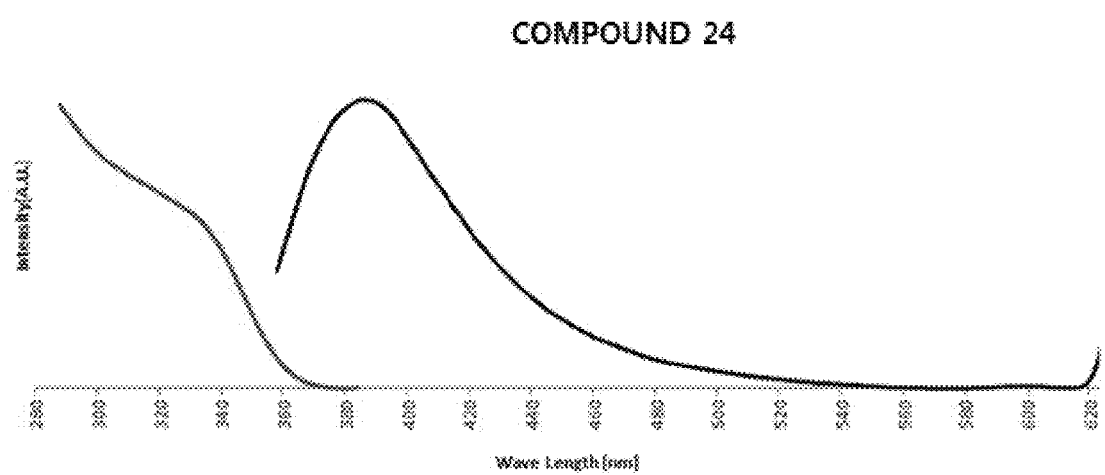
COMPOUND 24
[FIG. 6]
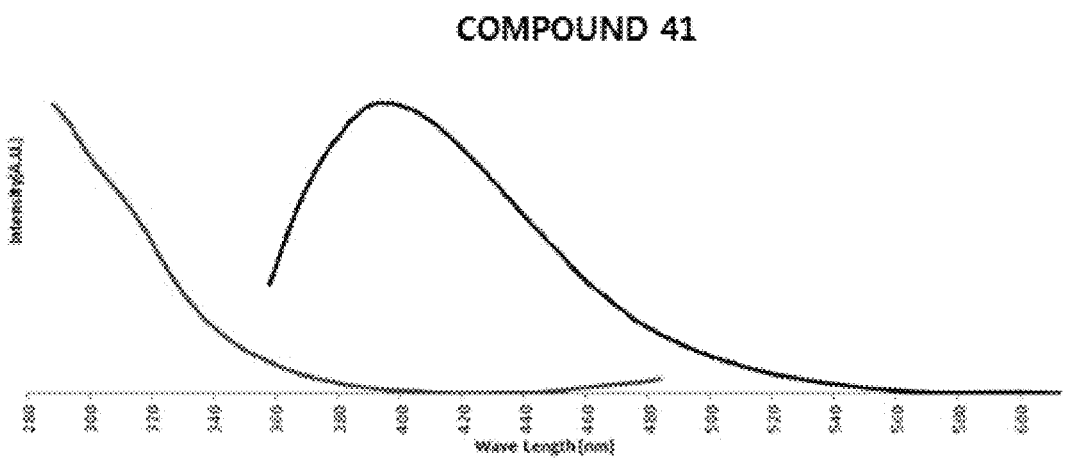
COMPOUND 41

[FIG. 7]
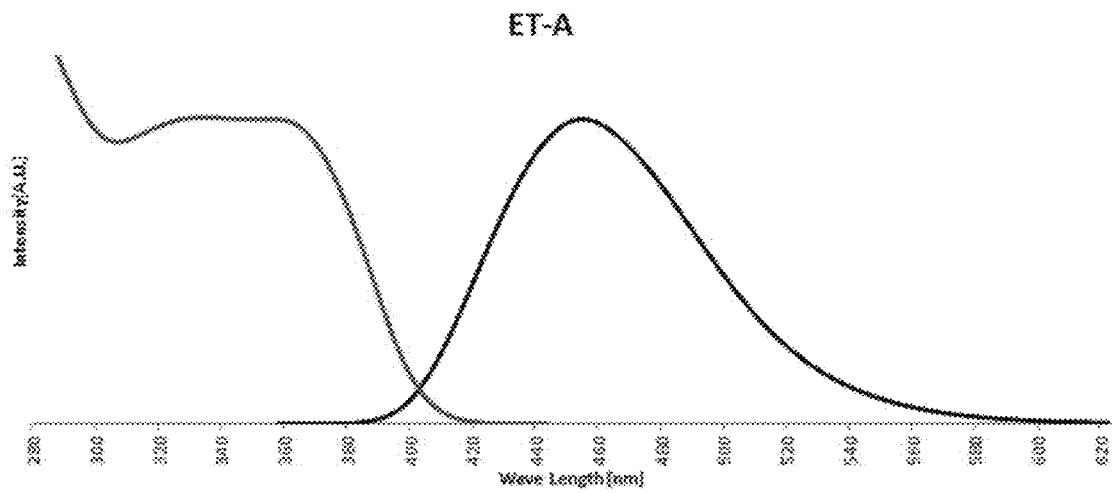
[FIG. 8]
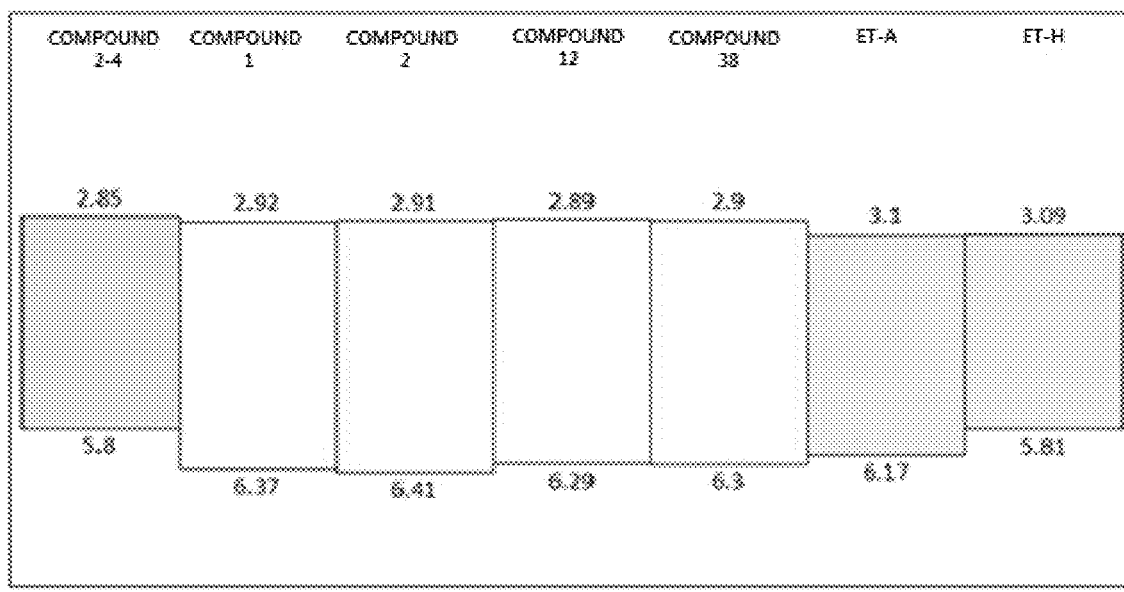

ORGANIC LIGHT-EMITTING ELEMENT

CROSS-REFERENCE TO RELATED APPLICATIONS

The present application is a national phase entry under 35 U.S.C. § 371 of International Application No. PCT/KR2017/004325 filed Apr. 24, 2017, which claims priority from Korean Patent Application No. 10-2016-0052237 filed Apr. 28, 2016, the disclosures of which are incorporated herein by reference.

TECHNICAL FIELD

The present specification relates to an organic light emitting device.

BACKGROUND ART

An organic light emission phenomenon is one of the examples converting a current to visible light by an internal process of a specific organic molecule. The principle of an organic light emission phenomenon is as follows.

When an organic material layer is placed between an anode and a cathode and a voltage is applied between the two electrodes, electrons and holes are injected to the organic material layer from the cathode and the anode, respectively. The electrons and the holes injected to the organic material layer are recombined to form excitons, and light emits when these excitons fall back to the ground state. An organic light emitting device using such a principle is generally formed with a cathode, an anode, and an organic material layer placed therebetween, which includes, for example, a hole injection layer, a hole transfer layer, a light emitting layer and an electron transfer layer.

Materials used in organic light emitting devices are mostly pure organic materials or complex compounds in which organic materials and metals form complexes, and may be divided into hole injection materials, hole transfer materials, light emitting materials, electron transfer materials, electron injection materials and the like. Herein, as the hole injection material or the hole transfer material, organic materials having a p-type property, that is, organic materials readily oxidized and electrochemically stable when oxidized, are generally used. Meanwhile, as the electron injection material or the electron transfer material, organic materials having an n-type property, that is, organic materials readily reduced and electrochemically stable when reduced, are generally used. As the light emitting layer material, materials having both a p-type property and an n-type property, that is, materials having a stable form in both oxidized and reduced states, are preferable, and materials having high light emission efficiency converting, when excitons are formed, the excitons to light are preferable.

Accordingly, the development of organic light emitting devices having high efficiency has been required in the art.

PRIOR ART DOCUMENTS

Patent Documents

Korean Patent Application Laid-Open Publication No. 2000-0051826

DISCLOSURE

Technical Problem

The present specification is directed to providing an organic light emitting device having high light emission efficiency and/or a low driving voltage.

Technical Solution

One embodiment of the present specification provides an organic light emitting device including a cathode; an anode provided opposite to the cathode; a light emitting layer provided between the cathode and the anode, and including an anthracene derivative represented by the following Chemical Formula 2; and an organic material layer provided between the cathode and the light emitting layer, and including a cyclic compound represented by the following Chemical Formula 1.

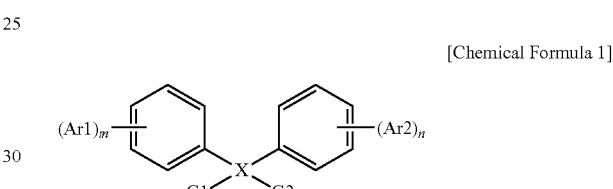

[Chemical Formula 1]

In Chemical Formula 1,

Ar1 and Ar2 are the same as or different from each other, and each independently selected from the group consisting of hydrogen; deuterium; a nitrile group; a substituted or unsubstituted monocyclic or multicyclic aryl group having 6 to 30 carbon atoms; and a substituted or unsubstituted monocyclic or multicyclic heteroaryl group having 2 to 30 carbon atoms, m and n are the same as or different from each other, and each independently an integer of 1 to 5, when m is 2 or greater, Ar1s are the same as or different from each other, when n is 2 or greater, Ar2s are the same as or different from each other, X is a non-conjugated group, and G1 and G2 are the same as or different from each other, and each independently selected from the group consisting of hydrogen; deuterium; a nitrile group; a substituted or unsubstituted linear or branched alkyl group having 1 to 30 carbon atoms; a substituted or unsubstituted monocyclic or multicyclic cycloalkyl group having 3 to 30 carbon atoms; a substituted or unsubstituted monocyclic or multicyclic aryl group having 6 to 30 carbon atoms; and a substituted or unsubstituted monocyclic or multicyclic heteroaryl group having 2 to 30 carbon atoms, or G1 and G2 bond to each other to form a substituted or unsubstituted monocyclic or multicyclic hydrocarbon ring; or a substituted or unsubstituted monocyclic or multicyclic heteroring,

[Chemical Formula 2]

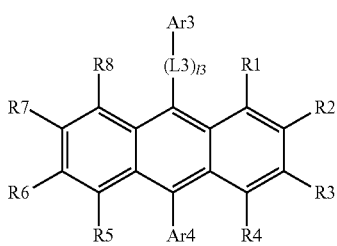

in Chemical Formula 2,

R1 to R8 are the same as or different from each other, and each independently hydrogen; halogen; a hydroxyl group; a nitrile group; a substituted or unsubstituted amine group; a substituted or unsubstituted linear or branched alkyl group having 1 to 20 carbon atoms; a substituted or unsubstituted linear or branched alkoxy group having 1 to 20 carbon atoms; a substituted or unsubstituted monocyclic or multicyclic aryloxy group having 6 to 30 carbon atoms; a substituted or unsubstituted monocyclic or multicyclic arylthioxy group having 6 to 30 carbon atoms; a substituted or unsubstituted monocyclic or multicyclic aryl group having 6 to 30 carbon atoms; or a substituted or unsubstituted monocyclic or multicyclic heteroaryl group having 5 to 30 carbon atoms, L3 is a direct bond; a substituted or unsubstituted monocyclic or multicyclic arylene group having 6 to 30 carbon atoms; or a substituted or unsubstituted monocyclic or multicyclic heteroarylene group having 5 to 30 carbon atoms, Ar3 is the following Chemical Formula a, Ar4 is a substituted or unsubstituted monocyclic or multicyclic aryl group having 6 to 30 carbon atoms; or a substituted or unsubstituted monocyclic or multicyclic heteroaryl group having 5 to 30 carbon atoms, l3 is an integer of 1 to 3, and when l3 is 2 or greater, the two or more L3s are the same as or different from each other,

[Chemical Formula a]

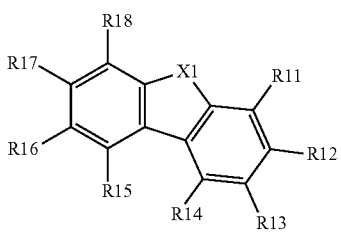

in Chemical Formula a,

X1 is the same as or different from each other, and each independently O or S, any one of R11 to R14 is a site bonding to L3 of Chemical Formula 2, and the rest and R15 to R18 are the same as or different from each other, and each independently hydrogen; halogen; a hydroxyl group; a nitrile group; a substituted or unsubstituted amine group; a substituted or unsubstituted linear or branched alkyl group having 1 to 20 carbon atoms; a substituted or unsubstituted linear or branched alkoxy group having 1 to 20 carbon atoms; a substituted or unsubstituted monocyclic or multicyclic aryloxy group having 6 to 30 carbon atoms; a substituted or unsubstituted monocyclic or multicyclic arylthioxy group having 6 to 30 carbon atoms; a substituted or unsubstituted monocyclic or multicyclic aryl group having 6 to 30 carbon atoms; or a substituted or unsubstituted monocyclic or multicyclic heteroaryl group having 5 to 30 carbon atoms, and adjacent groups among R1 to R8, R11 to R18, and L1 and Ar4 may bond to each other to form a substituted or unsubstituted ring.

Advantageous Effects

An organic light emitting device according to one embodiment of the present specification provides a low driving voltage and/or high light emission efficiency.

DESCRIPTION OF DRAWINGS

FIG. 1 is a diagram illustrating an organic light emitting device according to one embodiment of the present specification.

FIG. 2 is a diagram showing a result of data measuring a HOMO (AC3) level of Compound 1.

FIG. 3 is a diagram showing a result of data measuring a HOMO (AC3) level of Compound 36.

FIG. 4 is a diagram showing a result of data measuring photoluminescence (PL) of Compound 1.

FIG. 5 is a diagram showing a result of data measuring photoluminescence (PL) of Compound 24.

FIG. 6 is a diagram showing a result of data measuring photoluminescence (PL) of Compound 41.

FIG. 7 is a diagram showing a result of data measuring photoluminescence (PL) of Compound ET-A.

FIG. 8 is a diagram showing an energy chart of compounds in an organic light emitting device according to one embodiment of the present specification.

REFERENCE NUMERAL

101: Substrate
201: Anode
301: Hole Transfer Layer
401: Light Emitting Layer
501: Electron Transfer Layer
601: Cathode

MODE FOR DISCLOSURE

Hereinafter, the present specification will be described in more detail.

In the present specification, a description of one member being placed "on" another member includes not only a case of the one member adjoining the another member but a case of still another member being present between the two members.

In the present specification, a description of a certain part "including" certain constituents means capable of further including other constituents, and does not exclude other constituents unless particularly stated on the contrary.

One embodiment of the present specification provides an organic light emitting device including a cathode; an anode provided opposite to the cathode; a light emitting layer provided between the cathode and the anode, and including an anthracene derivative represented by Chemical Formula 2; and an organic material layer provided between the cathode and the light emitting layer, and including a cyclic compound represented by Chemical Formula 1.

In one embodiment of the present specification, the organic material layer including the cyclic compound represented by Chemical Formula 1 is an electron transfer layer, an electron injection layer or a layer carrying out electron transfer and electron injection at the same time.

According to one embodiment of the present specification, the organic material layer including the cyclic compound represented by Chemical Formula 1 is an electron transfer layer.

According to one embodiment of the present specification, the organic light emitting device emits blue fluorescent light.

According to one embodiment of the present specification, a HOMO energy level of the cyclic compound represented by Chemical Formula 1 is 6.1 eV or higher. According to one embodiment of the present specification, a HOMO energy level of the cyclic compound represented by Chemical Formula 1 is higher than or equal to 6.1 eV and lower than or equal to 7.0 eV. When having a deep HOMO energy level as the cyclic compound represented by Chemical Formula 1 according to one embodiment of the present specification, holes may be effectively blocked from the light emitting layer, and high light emission efficiency may be provided, and a device having a long lifespan may be provided by enhancing stability of the device.

According to one embodiment of the present specification, the light emitting layer includes a host and a dopant, and a difference between a HOMO energy level of the host and a HOMO energy level of the cyclic compound represented by Chemical Formula 1 is 0.2 eV or greater. When a difference in the HOMO energy level between the host material of the light emitting layer and the cyclic compound represented by Chemical Formula 1 is 0.2 eV or greater as described above, holes may be more effectively blocked from the light emitting layer, and an organic light emitting device with high light emission efficiency and a long lifespan may be provided.

According to one embodiment of the present specification, the organic material layer including the cyclic compound represented by Chemical Formula 1 is provided adjoining the light emitting layer. In this case, holes may be effectively blocked by the cyclic compound having a deeper HOMO energy level than the host compound of the light emitting layer.

As in one embodiment of the present specification, an organic light emitting device emitting blue fluorescence normally uses the anthracene derivative represented by Chemical Formula 2 as a host material, and in this case, has a HOMO energy level of lower than 6 eV. Accordingly, when providing the organic material layer including the cyclic compound represented by Chemical Formula 1 between the cathode and the light emitting layer, roles of electron transfer and hole blocking may be carried out at the same time.

In the present specification, an energy level means a size of energy. Accordingly, even when an energy level is expressed in a negative (−) direction from a vacuum level, the energy level is interpreted to mean an absolute value of the corresponding energy value. For example, a HOMO energy level means a distance from a vacuum level to a highest occupied molecular orbital, and a LUMO energy level means a distance from a vacuum level to a lowest unoccupied molecular orbital.

According to one embodiment of the present specification, the HOMO level may be measured using an atmospheric pressure photoelectron spectroscopy apparatus (manufactured by RIKEN KEIKI Co., Ltd.: AC3). Specifically, the HOMO level may be measured by irradiating light on a material, and measuring the amounts of electrons generated from charge separation at the time.

According to one embodiment of the present specification, triplet energy of the cyclic compound represented by Chemical Formula 1 is 2.6 eV or higher.

According to one embodiment of the present specification, when including the cyclic compound represented by Chemical Formula 1 having triplet energy in various ranges, triplet excitons of the light emitting layer are effectively blocked in an organic light emitting device, and a device with high efficiency and/or a long lifespan may be expected.

According to one embodiment of the present specification, the light emitting layer includes a host and a dopant, and triplet energy of the cyclic compound represented by Chemical Formula 1 is higher than triplet energy of the host.

When having higher triplet energy than the triplet energy of the host compound of the light emitting layer, triplet excitons of the light emitting layer may be effectively blocked. Specifically, anthracene host derivatives of a generally used light emitting layer have a triplet energy level of lower than 1.9 eV, and the organic material layer including the compound represented by Chemical Formula 1 provided between the cathode and the light emitting layer has a triplet energy level of 2.6 eV or higher, and therefore, device efficiency may be enhanced due to a high triplet exciton blocking effect. This may be identified from the fact that Compounds [ET-H] and [ET-J], anthracene derivatives, provided as a comparative example to be described later all have triplet energy of lower than 1.9 eV, and the compounds having such low triplet energy have low device efficiency. This is due to the fact that using the compounds having triplet energy of lower than 2.6 eV decreases an effect of triplet-triplet annihilation (TTA).

According to one embodiment of the present specification, when providing a plurality of layers between the cathode and the light emitting layer, the organic material layer including the cyclic compound represented by Chemical Formula 1 is provided relatively adjacent to the light emitting layer. In this case, triplet excitons may be more effectively blocked.

According to one embodiment of the present specification, the triplet energy ($E_T$) may be measured using a low temperature photoluminescence method. After measuring a $\lambda_{edge}$ value, the following conversion formula is used to obtain triplet energy.

$$E_T(eV)=1239.85/(\lambda_{edge})$$

In the conversion formula, "$\lambda_{edge}$" means, when showing a phosphorescence spectrum with phosphorescence intensity as the vertical axis and wavelength as the horizontal axis and drawing a tangent line with respect to the increase in the short wavelength side of the phosphorescence spectrum, a wavelength value at the intersection point of the tangent line and the horizontal axis, and the unit is nm.

According to another embodiment of the present specification, the triplet energy ($E_T$) may also be obtained by quantum chemistry calculations. Quantum chemistry calculations may be performed using Gaussian 03, a quantum chemistry calculation program made by Gaussian, Inc. of the US. In the calculation, a density functional theory (DFT) is used, and the triplet energy value may be calculated by a time-dependent density functional theory (TD-DFT) for an optimized structure using B3LYP as functional and 6-31G* as basis function.

According to another embodiment of the present specification, a phosphorescence spectrum is not observed for specific organic compounds in some cases, and with such organic compounds, triplet energy ($E_T$) obtained using quantum chemistry calculations may be calculated and used as described above.

According to one embodiment of the present specification, electron mobility of the cyclic compound represented by Chemical Formula 1 is $1 \times 10^{-6}$ cm$^2$/Vs or greater.

According to another embodiment, electron mobility of the cyclic compound represented by Chemical Formula 1 is $1 \times 10^{-6}$ cm$^2$/Vs or greater in an electric field of 0.1 MV/cm to 0.5 MV/cm. According to another embodiment, electron mobility of the cyclic compound represented by Chemical Formula 1 is $1 \times 10^{-6}$ cm$^2$/Vs or greater in an electric field of 0.1 MV/cm. In this case, high efficiency may be expected by increasing the number of excitons generated in the light emitting layer.

In the present specification, electron mobility may be measured using methods used in the art. Specifically, a time of flight (TOF) method, or a method of measuring a space charge limited current (SCLC) may be used, however, the method is not limited thereto.

Specifically, according to one embodiment of the present specification, bathophenanthroline and lithium (2%) are heated under vacuum and deposited on an ITO substrate to a thickness of 20 nm, and the cyclic compound represented by Chemical Formula 1 is deposited to a thickness of 200 nm. On the layer, bathophenanthroline and lithium (2%) are heated again under vacuum and deposited to a thickness of 20 nm again, and then aluminum is deposited to a thickness of 100 nm or greater to prepare a sample. Current density (mA/cm$^2$) of the sample with respect to voltage is measured to calculate electron mobility in a space charge limited current (SCLC) region.

According to one embodiment of the present specification, the cyclic compound represented by Chemical Formula 1 has a glass transition temperature of 100° C. or higher. The cyclic compound represented by Chemical Formula 1 more preferably has a glass transition temperature of 110° C. Bphen generally known as a hole blocking material has a low glass transition temperature of lower than 70° C., and has a problem in that it may not be used under an environment of 70° C. or higher. Accordingly, when using compounds having a glass transition temperature in the above-mentioned range, an organic light emitting device having excellent thermal stability may be used.

According to one embodiment of the present specification, the organic material layer including the cyclic compound represented by Chemical Formula 1 further includes an n-type dopant.

Specifically, according to one embodiment of the present specification, the organic material layer including the cyclic compound represented by Chemical Formula 1 further includes an n-type dopant represented by the following Chemical Formula 10.

[Chemical Formula 10]

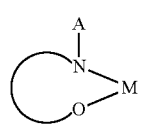

In Chemical Formula 10,

A is hydrogen; deuterium; a halogen group; a nitrile group; a nitro group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted heterocyclic group, a curve represents bonds and 2 or 3 atoms required for forming a 5-membered or 6-membered ring having M, and the atoms are unsubstituted or substituted with substituents having the same definition as one, two or greater As, and M is an alkali metal or an alkaline earth metal.

According to one embodiment of the present specification, the n-type dopant represented by Chemical Formula 10 is represented by the following Chemical Formula 10-1 or 10-2.

[Chemical Formula 10-1]

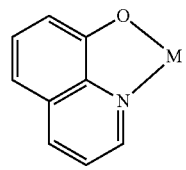

[Chemical Formula 10-2]

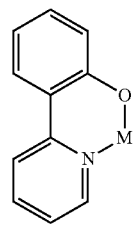

According to Chemical Formulae 10-1 and 10-2,

M has the same definition as in Chemical Formula 10, and structures of Chemical Formulae 10-1 and 10-2 are each independently unsubstituted or substituted with one, two or more substituents selected from the group consisting of deuterium; a halogen group; a nitrile group; a nitro group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; and a substituted or unsubstituted heterocyclic group, or adjacent substituents bond to each other to form a substituted or unsubstituted hydrocarbon ring; or a substituted or unsubstituted heteroring.

According to one embodiment of the present specification, the n-type dopant represented by Chemical Formula 10 may be any one of the following structures.

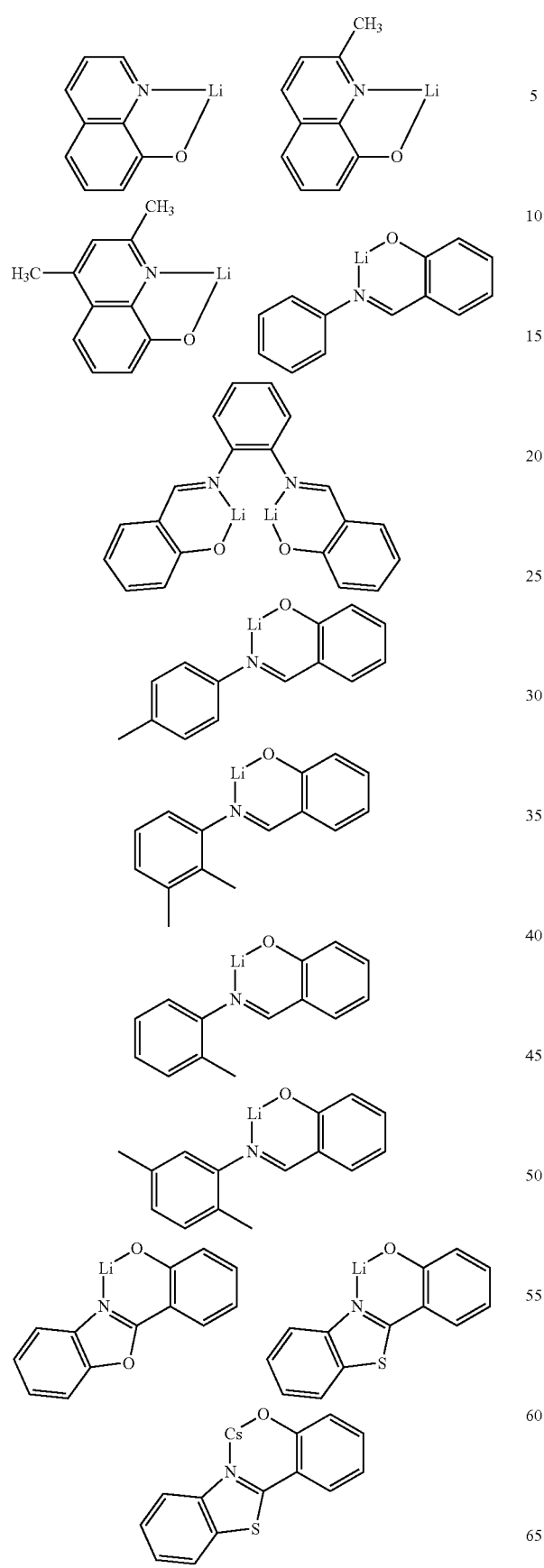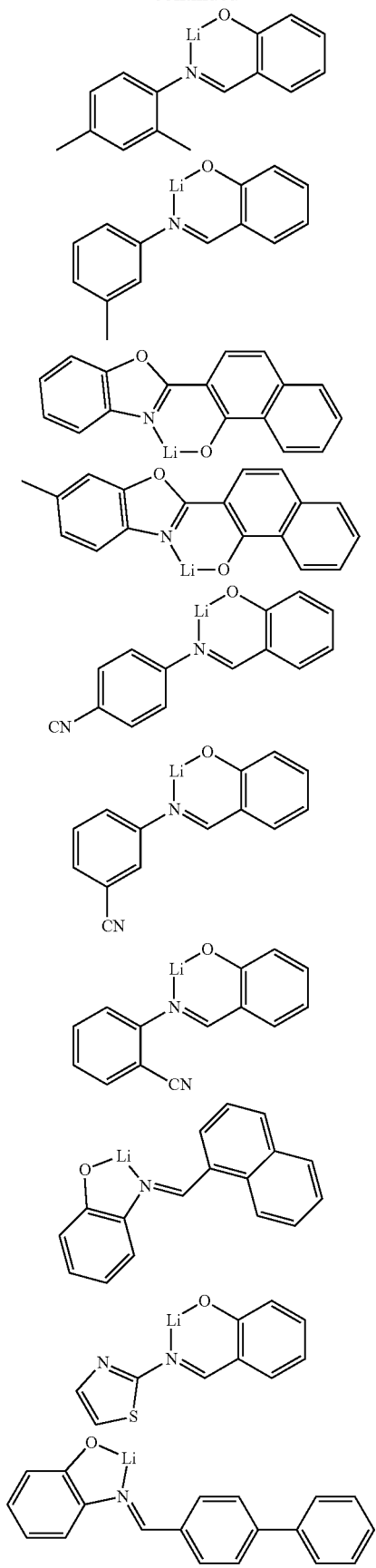

-continued
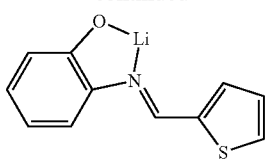
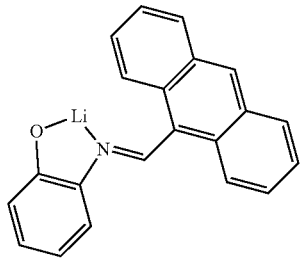
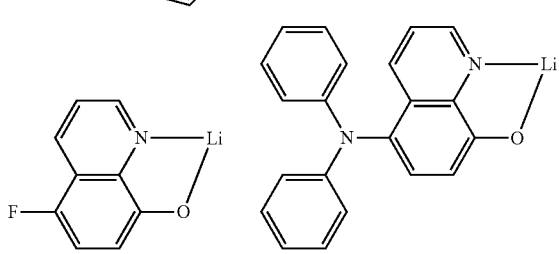
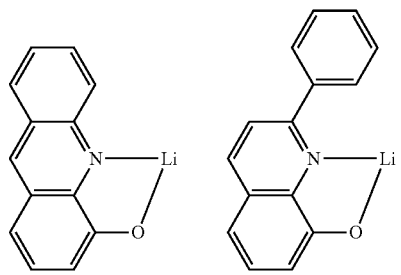
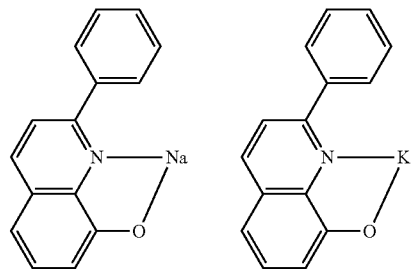
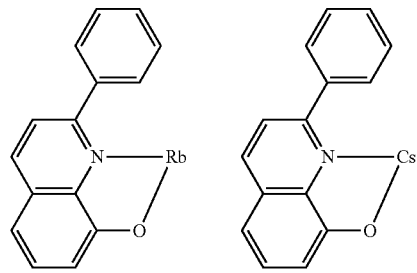
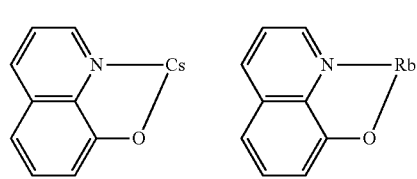
-continued
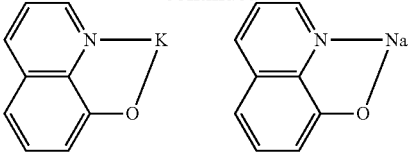
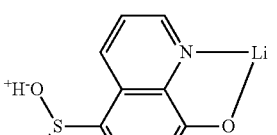
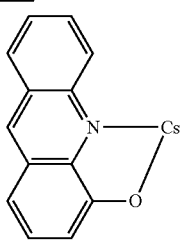
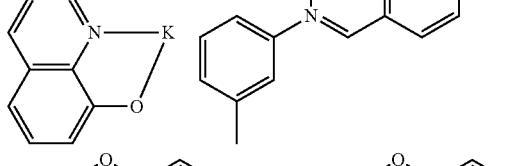
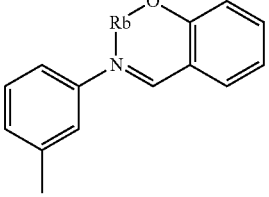
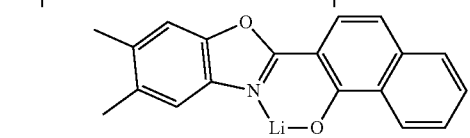
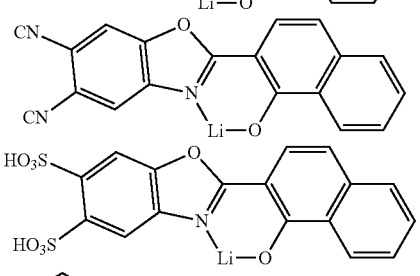
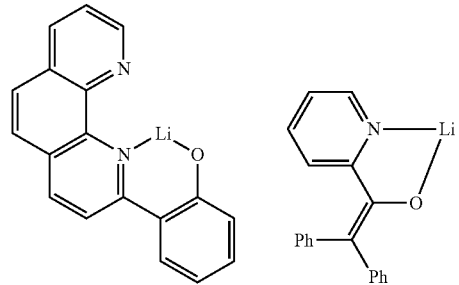
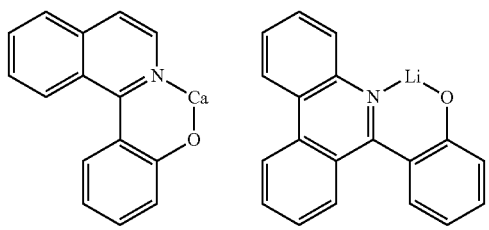

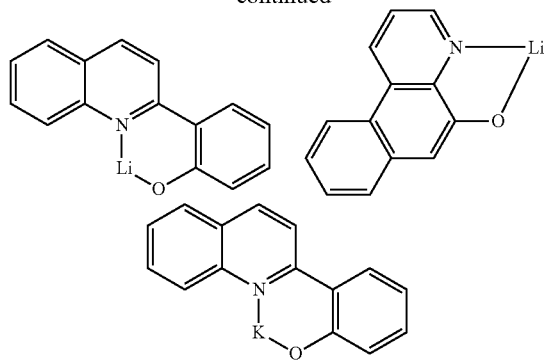

The structures may be unsubstituted or substituted with one, two or more substituents selected from the group consisting of deuterium; a halogen group; a nitrile group; a nitro group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; and a substituted or unsubstituted heterocyclic group.

In the present specification, the n-type dopant means a material making a host material to have an n-semiconductor property. An n-semiconductor property means a property receiving or transferring electrons to a lowest unoccupied molecular orbital (LUMO) energy level, that is, a property of a material having high electron conductivity.

According to the present specification, the n-type dopant is for facilitating electron extraction from a cathode by doping a donor represented by alkali metals into an electron transfer layer, and may include one or more selected from the group consisting of donor-type metal compounds and donor-type metal complexes.

According to one embodiment of the present specification, the n-type dopant of an organic alkali metal compound or an organic alkaline earth metal compound represented by Chemical Formula 10 is in 20 weight % to 80 weight %, and preferably in 50 weight %, based on the total weight of the organic material layer including the cyclic compound represented by Chemical Formula 1.

According to one embodiment of the present specification, the n-type dopant may be used either as one type alone, or as a combination of two or more types.

The organic light emitting device according to one embodiment of the present specification includes the cyclic compound represented by Chemical Formula 1 between the light emitting layer and the cathode as a host, and is provided with an electron transfer layer including the n-type dopant.

According to one embodiment of the present specification, the organic light emitting device may further include a hole blocking layer between the electron transfer layer and the light emitting layer described above.

Examples of the substituents in the present specification are described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one, two or more substituents selected from the group consisting of deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted alkenyl group; a substituted or unsubstituted amine group; a substituted or unsubstituted aryl group; and a substituted or unsubstituted heterocyclic group, or being substituted with a substituent linking two or more substituents among the substituents illustrated above, or having no substituents. For example, "a substituent linking two or more substituents" may include a biphenyl group. In other words, a biphenyl group may be an aryl group, or interpreted as a substituent linking two phenyl groups.

In the present specification, the halogen group may include fluorine, chlorine, bromine or iodine.

In the present specification, the alkyl group may be linear or branched, and although not particularly limited thereto, the number of carbon atoms is preferably from 1 to 40. According to one embodiment, the number of carbon atoms of the alkyl group is from 1 to 20. According to another embodiment, the number of carbon atoms of the alkyl group is from 1 to 10. According to another embodiment, the number of carbon atoms of the alkyl group is from 1 to 6. Specific examples of the alkyl group may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 60 carbon atoms, and according to one embodiment, the number of carbon atoms of the cycloalkyl group is from 3 to 30. According to another embodiment, the number of carbon atoms of the cycloalkyl group is from 3 to 20. According to another embodiment, the number of carbon atoms of the cycloalkyl group is from 3 to 6. Specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably from 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the alkenyl group may be linear or branched, and although not particularly limited thereto, the number of carbon atoms is preferably from 2 to 40. According to one embodiment, the number of carbon atoms of the alkenyl group is from 2 to 20. According to another embodiment, the number of carbon atoms of the alkenyl group is from 2 to 10. According to another embodiment, the number of carbon atoms of the alkenyl group is from 2 to 6. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, specific examples of the boron group may include a trimethylboron group, a triethylboron group, a t-butyldimethylboron group, a triphenylboron group, a phenylboron group and the like, but are not limited thereto.

In the present specification, the aryl group is not particularly limited, but preferably has 6 to 60 carbon atoms, and may be a monocyclic aryl group or a multicyclic aryl group. According to one embodiment, the number of carbon atoms of the aryl group is from 6 to 30. According to one embodiment, the number of carbon atoms of the aryl group is from 6 to 20. Examples of the monocyclic aryl group may include a phenyl group, a biphenyl group, a terphenyl group, a quaterphenyl group and the like, but are not limited thereto. Examples of the multicyclic aryl group may include a naphthyl group, an anthracenyl group, a phenanthryl group, a pyrenyl group, a perylenyl group, a chrysenyl group, a fluorenyl group and the like, but are not limited thereto.

In the present specification, the fluorenyl group may be substituted, and two substituents may bond to each other to form a spiro structure.

When the fluorenyl group is substituted,

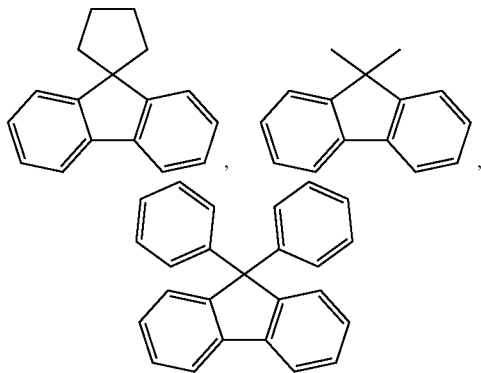

and the like may be included. However, the structure is not limited thereto.

In the present specification, the heterocyclic group is a heterocyclic group including one or more of O, N, S, Si and Se as a heteroatom, and although not particularly limited thereto, the number of carbon atoms is preferably from 2 to 60. Examples of the heterocyclic group may include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, an isoxazolyl group, an oxadiazolyl group, a thiadiazolyl group, a phenothiazinyl group, a dibenzofuranyl group and the like, but are not limited thereto.

The heteroaryl group may be monocyclic or multicyclic, and may be aromatic, aliphatic or a fused ring of aromatic and aliphatic.

In the present specification, descriptions on the aryl group provided above may be applied to the aryl group in the aryloxy group, the arylthioxy group and the arylsulfoxy group.

In the present specification, descriptions on the alkyl group provided above may be applied to the alkyl group in the alkylthioxy group and the alkylsulfoxy group.

In the present specification, the arylene group means an aryl group having two bonding sites, that is, a divalent group. Descriptions on the aryl group provided above may be applied thereto except for each being a divalent group.

In the present specification, the heteroarylene group means a heteroaryl group having two bonding sites, that is, a divalent group. Descriptions on the heteroaryl group provided above may be applied thereto except for each being a divalent group.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, two adjacent alkylene unsubstituted or substituted with a hydrocarbon or a heteroring, or alkenylene unsubstituted or substituted with a hydrocarbon or a heteroring may bond to each other to form a ring. In the present specification, the ring formed by adjacent groups bonding to each other may be monocyclic or multicyclic, and may be aromatic, aliphatic or a fused ring of aromatic and aliphatic, and may form a hydrocarbon ring; or a heteroring.

In the present specification, the meaning of forming a ring by adjacent groups bonding to each other means adjacent groups bonding to each other to form a substituted or unsubstituted aliphatic hydrocarbon ring; a substituted or unsubstituted aromatic hydrocarbon ring; a substituted or unsubstituted aliphatic heteroring; a substituted or unsubstituted aromatic heteroring; or a fused ring thereof.

The hydrocarbon ring may be selected from among the examples of the cycloalkyl group or the aryl group except for those that are not monovalent. The heteroring may be aliphatic, aromatic or a fused ring of aliphatic and aromatic, and may be selected from among the examples of the heterocyclic group except for those that are not monovalent.

In the present specification, the "spiro bond" may mean a structure obtained by substituents in the same carbon bonding to each other to link two cyclic compounds through one atom.

According to one embodiment of the present specification, in Chemical Formula 1, at least one of Ar1 is -L1-(Z1)p, L1 is selected from the group consisting of a direct bond; a substituted or unsubstituted monocyclic or multicyclic arylene group having 6 to 30 carbon atoms; and a substituted or unsubstituted monocyclic or multicyclic heteroarylene group having 2 to 30 carbon atoms, Z1 is selected from the group consisting of hydrogen; deuterium; a nitrile group; a substituted or unsubstituted monocyclic or multicyclic aryl group having 6 to 30 carbon atoms; and a substituted or unsubstituted monocyclic or multicyclic heteroaryl group having 2 to 30 carbon atoms, however, when L1 is a direct bond, Z1 is not hydrogen, and p is an integer of 1 to 3, and when p is 2 or greater, Z1s are the same as or different from each other.

According to another embodiment of the present specification, L1 is selected from the group consisting of a direct bond; a substituted or unsubstituted monocyclic or multicyclic arylene group having 6 to 20 carbon atoms; and a substituted or unsubstituted monocyclic or multicyclic heteroarylene group having 2 to 20 carbon atoms.

According to another embodiment of the present specification, L1 is selected from the group consisting of a direct bond; a substituted or unsubstituted monocyclic or multicyclic arylene group having 6 to 10 carbon atoms; and a substituted or unsubstituted monocyclic or multicyclic heteroarylene group having 2 to 10 carbon atoms.

According to another embodiment of the present specification, L1 is selected from the group consisting of a direct bond; a substituted or unsubstituted phenylene group; a substituted or unsubstituted biphenylylene group; a substituted or unsubstituted naphthylene group; a substituted or unsubstituted pyrimidylene group; a substituted or unsubstituted quinolylene group; a substituted or unsubstituted quinazolylene group; a substituted or unsubstituted pyridylene group; and a substituted or unsubstituted triazinylene group.

According to another embodiment of the present specification, L1 is selected from the group consisting of a direct bond; a phenylene group; a biphenylylene group; a naphthylene group; a pyrimidylene group; a quinolylene group; a quinazolylene group; a pyridylene group; and a triazinylene group.

According to another embodiment of the present specification, Z1 is selected from the group consisting of hydrogen; deuterium; a nitrile group; a substituted or unsubstituted monocyclic or multicyclic aryl group having 6 to 20 carbon atoms; and a substituted or unsubstituted monocyclic or multicyclic heteroaryl group having 2 to 20 carbon atoms.

According to another embodiment of the present specification, Z1 is selected from the group consisting of hydrogen; deuterium; a nitrile group; a substituted or unsubstituted monocyclic or multicyclic aryl group having 6 to 10 carbon atoms; and a substituted or unsubstituted monocyclic or multicyclic heteroaryl group having 2 to 10 carbon atoms.

According to another embodiment of the present specification, Z1 is selected from the group consisting of hydrogen; deuterium; a nitrile group; a substituted or unsubstituted phenyl group; a substituted or unsubstituted biphenyl group; a substituted or unsubstituted naphthyl group; a substituted or unsubstituted thiophene group; a substituted or unsubstituted quinolyl group; and a substituted or unsubstituted pyridyl group.

According to another embodiment of the present specification, Z1 is selected from the group consisting of hydrogen; deuterium; a nitrile group; a phenyl group; a biphenyl group; a naphthyl group; a thiophene group; a quinolyl group; a pyridyl group; a quinolyl group substituted with a phenyl group; a quinolyl group substituted with a pyridyl group; and a quinolyl group substituted with a pyridyl group and a phenyl group.

According to one embodiment of the present specification, in Chemical Formula 1, at least one of Ar2 is -L2-(Z2)q, L2 is selected from the group consisting of a direct bond; a substituted or unsubstituted monocyclic or multicyclic arylene group having 6 to 30 carbon atoms; and a substituted or unsubstituted monocyclic or multicyclic heteroarylene group having 2 to 30 carbon atoms, Z2 is selected from the group consisting of hydrogen; deuterium; a nitrile group; a substituted or unsubstituted monocyclic or multicyclic aryl group having 6 to 30 carbon atoms; and a substituted or unsubstituted monocyclic or multicyclic heteroaryl group having 2 to 30 carbon atoms, however, when L2 is a direct bond, Z2 is not hydrogen, and q is an integer of 1 to 3, and when q is 2 or greater, Z2s are the same as or different from each other.

According to another embodiment of the present specification, L2 is selected from the group consisting of a direct bond; a substituted or unsubstituted monocyclic or multicyclic arylene group having 6 to 20 carbon atoms; and a substituted or unsubstituted monocyclic or multicyclic heteroarylene group having 2 to 20 carbon atoms.

According to another embodiment of the present specification, L2 is selected from the group consisting of a direct bond; a substituted or unsubstituted monocyclic or multicyclic arylene group having 6 to 10 carbon atoms; and a substituted or unsubstituted monocyclic or multicyclic heteroarylene group having 2 to 10 carbon atoms.

According to another embodiment of the present specification, L2 is selected from the group consisting of a direct bond; a substituted or unsubstituted phenylene group; a substituted or unsubstituted biphenylylene group; a substituted or unsubstituted naphthylene group; a substituted or unsubstituted pyrimidylene group; a substituted or unsubstituted quinolylene group; a substituted or unsubstituted quinazolylene group; a substituted or unsubstituted pyridylene group; and a substituted or unsubstituted triazinylene group.

According to another embodiment of the present specification, L2 is selected from the group consisting of a direct bond; a phenylene group; a biphenylylene group; a naphthylene group; a pyrimidylene group; a quinolylene group; a quinazolylene group; a pyridylene group; and a triazinylene group.

According to another embodiment of the present specification, Z2 is selected from the group consisting of hydrogen; deuterium; a nitrile group; a substituted or unsubstituted monocyclic or multicyclic aryl group having 6 to 20 carbon atoms; and a substituted or unsubstituted monocyclic or multicyclic heteroaryl group having 2 to 20 carbon atoms.

According to another embodiment of the present specification, Z2 is selected from the group consisting of hydrogen; deuterium; a nitrile group; a substituted or unsubstituted monocyclic or multicyclic aryl group having 6 to 10 carbon atoms; and a substituted or unsubstituted monocyclic or multicyclic heteroaryl group having 2 to 10 carbon atoms.

According to another embodiment of the present specification, Z2 is selected from the group consisting of hydrogen; deuterium; a nitrile group; a substituted or unsubstituted phenyl group; a substituted or unsubstituted biphenyl group; a substituted or unsubstituted naphthyl group; a substituted or unsubstituted thiophene group; a substituted or unsubstituted quinolyl group; and a substituted or unsubstituted pyridyl group.

According to another embodiment of the present specification, Z2 is selected from the group consisting of hydrogen; deuterium; a nitrile group; a phenyl group; a biphenyl group; a naphthyl group; a thiophene group; a quinolyl group; a pyridyl group; a quinolyl group substituted with a phenyl group; a quinolyl group substituted with a pyridyl group; and a quinolyl group substituted with a pyridyl group and a phenyl group.

According to one embodiment of the present specification, in Chemical Formula 1, X is a non-conjugated group.

According to one embodiment of the present specification, X may be carbon.

By introducing a structure suppressing conjugation between Ar1 and Ar2, the cyclic compound represented by Chemical Formula 1 according to one embodiment of the present specification has a wider band gap than an organic material used in existing organic light emitting devices, and as a result, may have a deep HOMO level.

According to one embodiment of the present specification, a band gap of the cyclic compound represented by Chemical Formula 1 is 3.3 eV or greater, and the band gap means an absolute value of a difference between HOMO energy and LUMO energy of the cyclic compound represented by Chemical Formula 1.

According to one embodiment of the present specification, the LUMO energy level of the cyclic compound represented by Chemical Formula 1 is 3 eV or lower, preferably from 3 eV to 2 eV, and more preferably from 3 eV to 2.5 eV.

In the present specification, an energy level means a size of energy. Accordingly, even when an energy level is expressed in a negative (−) direction from a vacuum level, the energy level is interpreted to mean an absolute value of the corresponding energy value.

According to one embodiment of the present specification, in Chemical Formula 1, G1 and G2 are the same as or different from each other, and each independently selected from the group consisting of hydrogen; deuterium; a nitrile group; a substituted or unsubstituted linear or branched alkyl group having 1 to 20 carbon atoms; a substituted or unsubstituted monocyclic or multicyclic cycloalkyl group having 3 to 20 carbon atoms; a substituted or unsubstituted monocyclic or multicyclic aryl group having 6 to 20 carbon atoms; and a substituted or unsubstituted heteroaryl group having 2 to 20 carbon atoms.

According to another embodiment of the present specification, G1 and G2 are the same as or different from each other, and each independently selected from the group consisting of hydrogen; deuterium; a nitrile group; a substituted or unsubstituted linear or branched alkyl group having 1 to 10 carbon atoms; a substituted or unsubstituted monocyclic or multicyclic cycloalkyl group having 3 to 10 carbon atoms; a substituted or unsubstituted monocyclic or multicyclic aryl group having 6 to 10 carbon atoms; and a substituted or unsubstituted heteroaryl group having 2 to 10 carbon atoms.

According to another embodiment of the present specification, G1 and G2 are the same as or different from each other, and each independently selected from the group consisting of hydrogen; a substituted or unsubstituted phenyl group; and a substituted or unsubstituted naphthyl group.

According to another embodiment of the present specification, G1 and G2 are the same as or different from each other, and each independently selected from the group consisting of hydrogen; a phenyl group; and a naphthyl group.

According to another embodiment of the present specification, G1 and G2 are the same as or different from each other, and each independently selected from the group consisting of a substituted or unsubstituted methyl group; and a substituted or unsubstituted ethyl group.

According to another embodiment of the present specification, G1 and G2 may bond to each other to form a substituted or unsubstituted hydrocarbon ring.

According to another embodiment of the present specification, G1 and G2 may bond to each other to form a substituted or unsubstituted cyclohexyl ring.

According to another embodiment of the present specification, G1 and G2 may bond to each other to form a cyclohexyl ring.

According to another embodiment of the present specification, Ar1 and Ar2 are the same as or different from each other, and each independently a substituted or unsubstituted 6-membered heteroring-including monocyclic or multicyclic heteroaryl group.

According to another embodiment of the present specification, Ar1 and Ar2 are the same as or different from each other, and each independently a substituted or unsubstituted 6-membered heteroaryl group.

According to another embodiment of the present specification, Ar1 and Ar2 are the same as or different from each other, and each independently a substituted or unsubstituted 6-membered heteroring-including multicyclic heteroaryl group.

According to another embodiment of the present specification, Ar1 and Ar2 are the same as or different from each other, and each independently a substituted or unsubstituted pyridyl group; a substituted or unsubstituted pyrimidyl group; or a substituted or unsubstituted triazinyl group-including monocyclic or multicyclic heteroaryl group.

According to another embodiment of the present specification, Ar1 and Ar2 are the same as or different from each other, and each independently a substituted or unsubstituted pyridyl group; a substituted or unsubstituted pyrimidyl group; a substituted or unsubstituted triazinyl group; a substituted or unsubstituted quinolyl group; a substituted or unsubstituted quinazolinyl group; or a substituted or unsubstituted quinoxalinyl group.

According to another embodiment of the present specification, Ar1 and Ar2 are the same as or different from each other, and each independently a pyridyl group; a pyrimidyl group; a triazinyl group; a quinolyl group; or a quinazolinyl group.

Ar1 and Ar2 may be unsubstituted or substituted with one or more selected from the group consisting of a nitrile group; a phenyl group; a biphenyl group; a naphthyl group; a thiophene group; a quinolyl group substituted with a phenyl group; a quinolyl group substituted with a pyridyl group; and a pyridyl group.

According to another embodiment of the present specification, G1 and G2 are the same as or different from each other, and each independently selected from the group consisting of a substituted or unsubstituted methyl group;

and a substituted or unsubstituted ethyl group, and Ar1 and Ar2 are the same as or different from each other, and each independently a substituted or unsubstituted 6-membered heteroring-including monocyclic heteroaryl group. The cyclic compound represented by Chemical Formula 1 including G1, G2, Ar1 and Ar2 illustrated above as a substituent induces a wide band gap in the molecule due to sp3 bonding and a steric effect of Ar1 and Ar2, forms high triplet, and has a small π-π overlap in the intramolecular influence since only two directions excluding G1 and G2 are a conjugation group among the sp3-bonding substituents in the four directions, and therefore, efficiency of an organic light emitting device may be enhanced since excellent hole mobility and/or electron mobility are obtained in the organic light emitting device.

According to another embodiment of the present specification, G1 and G2 are the same as or different from each other and each independently selected from the group consisting of a substituted or unsubstituted methyl group; and a substituted or unsubstituted ethyl group, and Ar1 and Ar2 are the same as or different from each other and each independently a substituted or unsubstituted pyridyl group; a substituted or unsubstituted pyrimidyl group; or a substituted or unsubstituted triazinyl group.

According to another embodiment of the present specification, G1 and G2 are the same as or different from each other and each independently selected from the group consisting of a methyl group; and an ethyl group, and Ar1 and Ar2 are the same as or different from each other and each independently a pyridyl group, a pyrimidyl group, or a triazinyl group.

Ar1 and Ar2 may be unsubstituted or substituted with one or more selected from the group consisting of a nitrile group; a phenyl group; a biphenyl group; a naphthyl group; a thiophene group; a quinolyl group substituted with a phenyl group; a quinolyl group substituted with a pyridyl group; and a pyridyl group.

According to another embodiment of the present specification, G1 and G2 bond to each other to form a substituted or unsubstituted hydrocarbon ring, and Ar1 and Ar2 are the same as or different from each other and each independently a substituted or unsubstituted 6-membered heteroring-including monocyclic heteroaryl group.

According to another embodiment of the present specification, G1 and G2 bond to each other to form a substituted or unsubstituted cyclohexyl ring, and Ar1 and Ar2 are the same as or different from each other and each independently a substituted or unsubstituted 6-membered heteroring-including monocyclic heteroaryl group. The cyclic compound represented by Chemical Formula 1 including G1, G2, Ar1 and Ar2 illustrated above as a substituent induces a wide band gap in the molecule due to sp3 bonding and a steric effect of Ar1 and Ar2, forms high triplet, and has a small π-π overlap in the intramolecular influence since only two directions excluding G1 and G2 are a conjugation group among the sp3-bonding substituents in the four directions, and therefore, efficiency of an organic light emitting device may be enhanced since excellent hole mobility and/or electron mobility are obtained in the organic light emitting device.

According to another embodiment of the present specification, G1 and G2 bond to each other to form a substituted or unsubstituted cyclohexyl ring, and Ar1 and Ar2 are the same as or different from each other and each independently a substituted or unsubstituted pyridyl group; a substituted or unsubstituted pyrimidyl group; or a substituted or unsubstituted triazinyl group.

According to another embodiment of the present specification, G1 and G2 bond to each other to form a cyclohexyl ring, and Ar1 and Ar2 are the same as or different from each other and each independently a pyridyl group; a pyrimidyl group; or a triazinyl group.

Ar1 and Ar2 may be unsubstituted or substituted with one or more selected from the group consisting of a nitrile group; a phenyl group; a biphenyl group; a naphthyl group; a thiophene group; a quinolyl group substituted with a phenyl group; a quinolyl group substituted with a pyridyl group; and a pyridyl group.

According to another embodiment of the present specification, G1 and G2 bond to each other to form a substituted or unsubstituted hydrocarbon ring, and Ar1 and Ar2 are the same as or different from each other and each independently a substituted or unsubstituted 6-membered heteroring-including multicyclic heteroaryl group.

According to another embodiment of the present specification, G1 and G2 bond to each other to form a substituted or unsubstituted cyclohexyl ring, and Ar1 and Ar2 are the same as or different from each other and each independently a substituted or unsubstituted 6-membered heteroring-including multicyclic heteroaryl group. The cyclic compound represented by Chemical Formula 1 including G1, G2, Ar1 and Ar2 illustrated above as a substituent induces a wide band gap in the molecule due to sp3 bonding and a steric effect of Ar1 and Ar2, forms high triplet, and has a small π-π overlap in the intramolecular influence since only two directions excluding G1 and G2 are a conjugation group among the sp3-bonding substituents in the four directions, and therefore, efficiency of an organic light emitting device may be enhanced since excellent hole mobility and/or electron mobility are obtained in the organic light emitting device.

According to another embodiment of the present specification, G1 and G2 bond to each other to form a substituted or unsubstituted cyclohexyl ring, Ar1 and Ar2 are the same as or different from each other and each independently a substituted or unsubstituted pyridyl group; a substituted or unsubstituted pyrimidyl group; or a substituted or unsubstituted triazinyl group-including multicyclic heteroaryl group.

According to another embodiment of the present specification, G1 and G2 bond to each other to form a substituted or unsubstituted cyclohexyl ring, and Ar1 and Ar2 are the same as or different from each other and each independently a substituted or unsubstituted quinolyl group; or a substituted or unsubstituted quinazolinyl group.

According to another embodiment of the present specification, G1 and G2 bond to each other to form a cyclohexyl ring, and Ar1 and Ar2 are the same as or different from each other and each independently a quinolyl group; or a quinazolinyl group.

Ar1 and Ar2 may be unsubstituted or substituted with one or more selected from the group consisting of a nitrile group; a phenyl group; a biphenyl group; a naphthyl group; a thiophene group; a quinolyl group substituted with a phenyl group; a quinolyl group substituted with a pyridyl group; and a pyridyl group.

According to one embodiment of the present specification, the cyclic compound represented by Chemical Formula 1 may be any one selected from among the following Compounds 1 to 209.

Compound 1
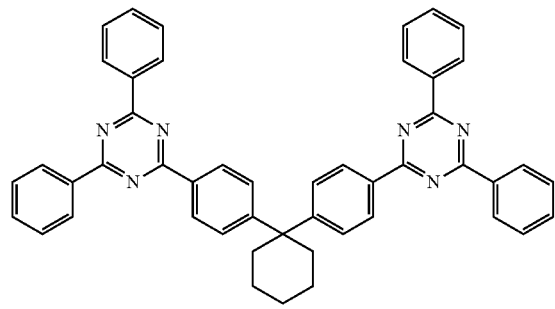
Compound 2
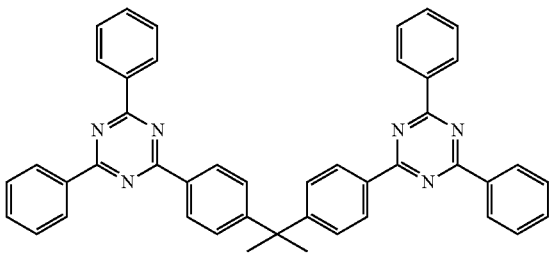
Compound 3
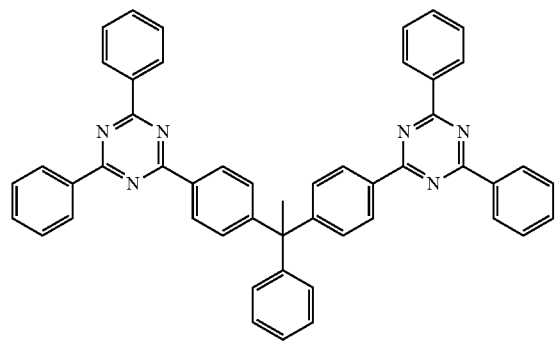
Compound 4
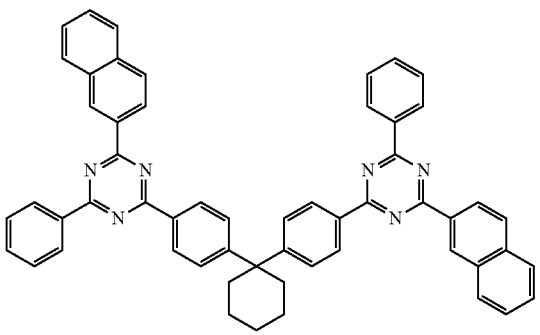
Compound 5
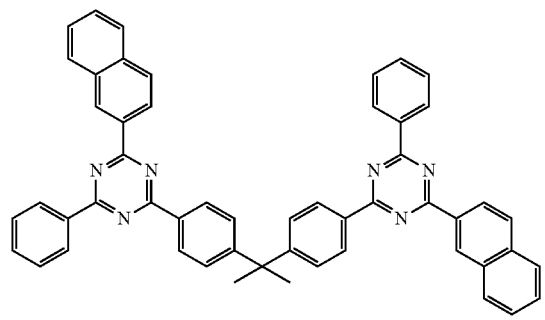
Compound 6
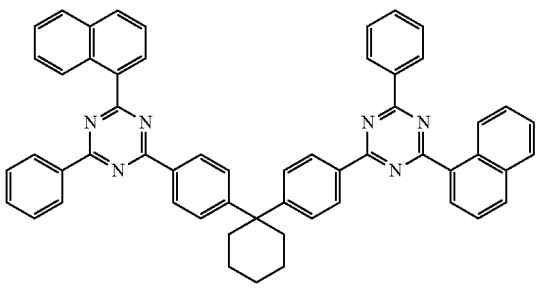
Compound 7
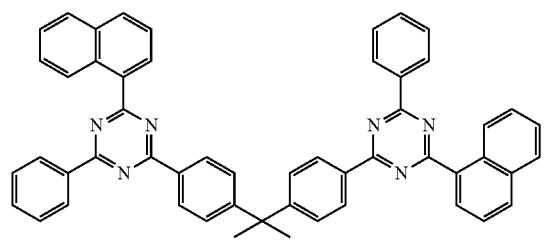
Compound 8
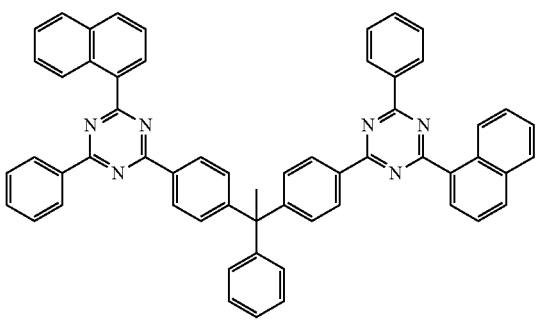

Compound 9
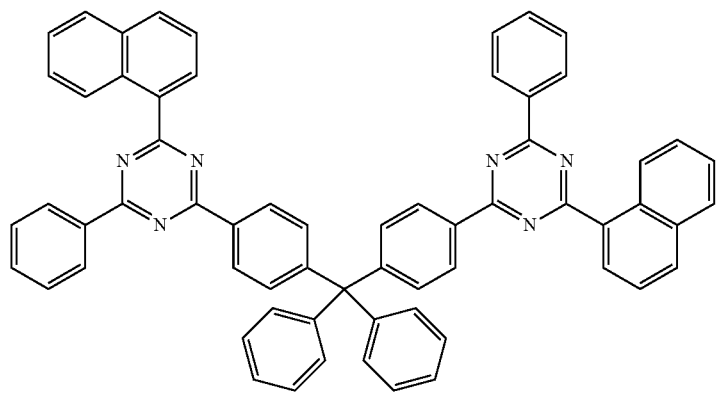
Compound 10
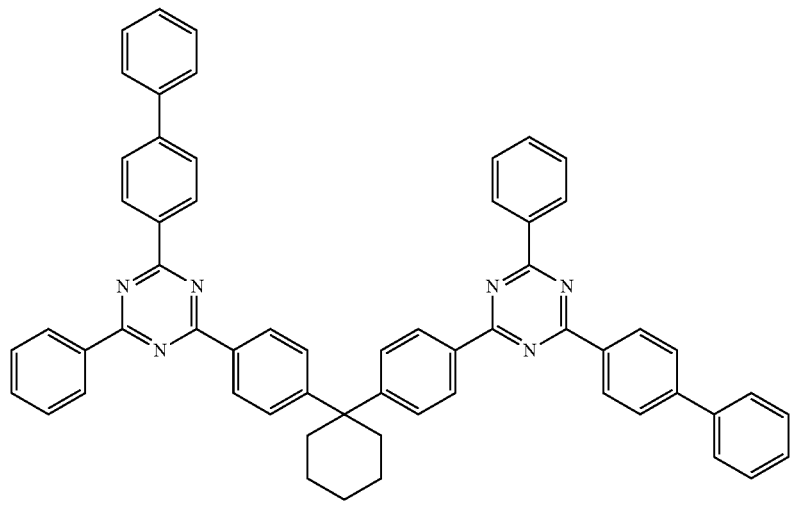
Compound 11
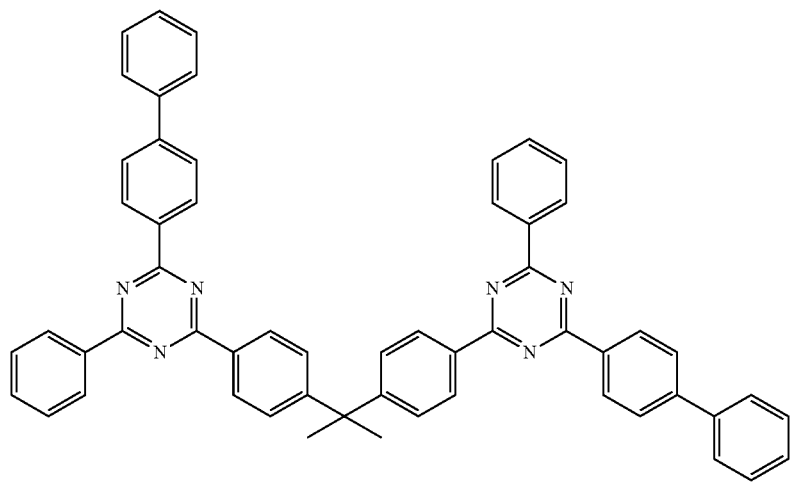

-continued
Compound 12
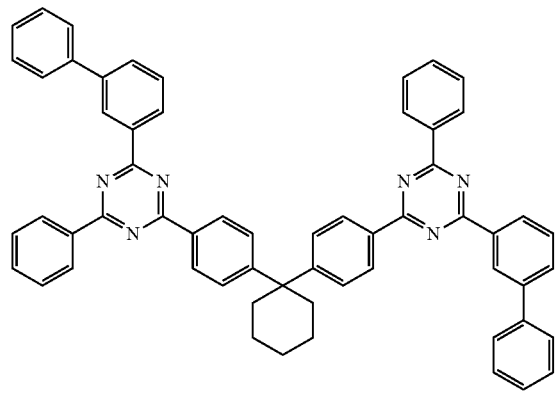
Compound 13
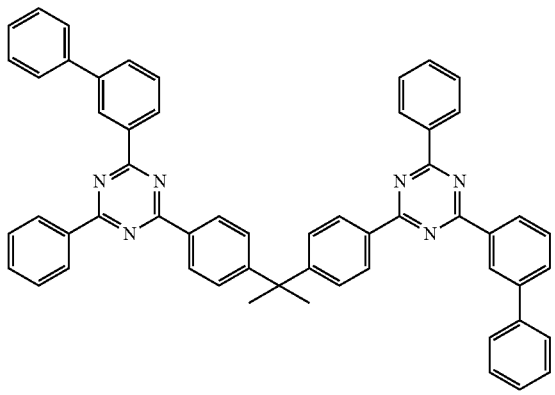
Compound 14
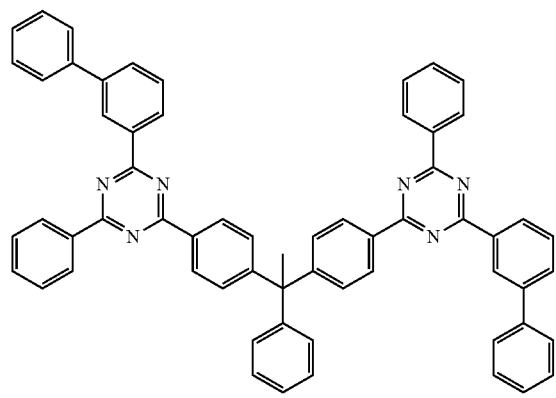
Compound 15
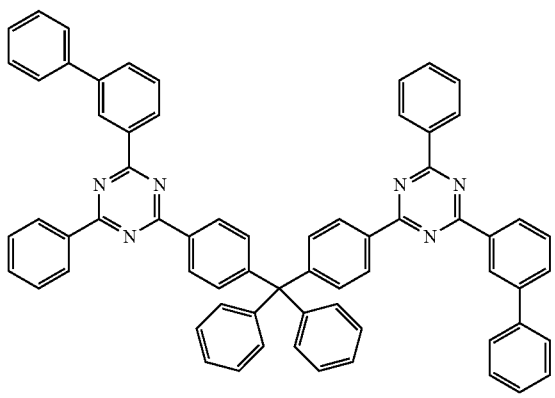
Compound 16
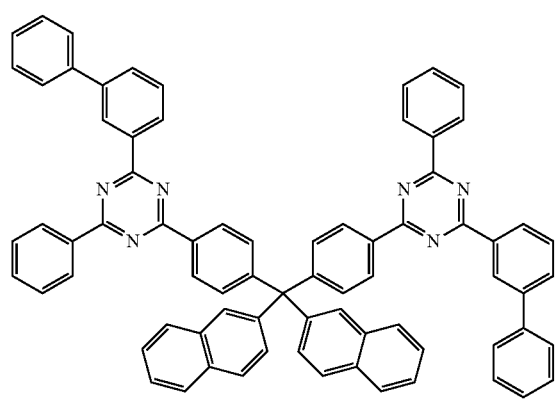
Compound 17
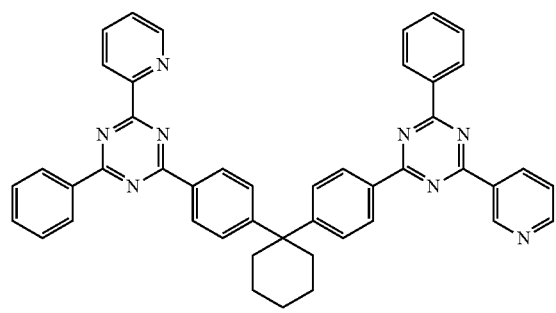
Compound 18
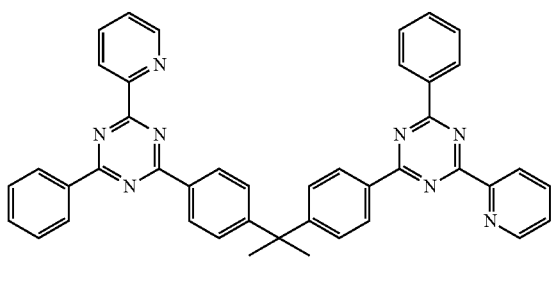

-continued
Compound 19
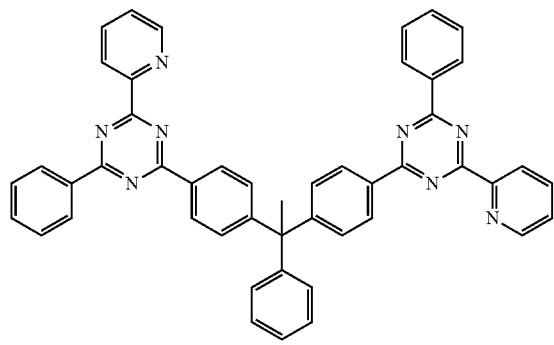
Compound 20
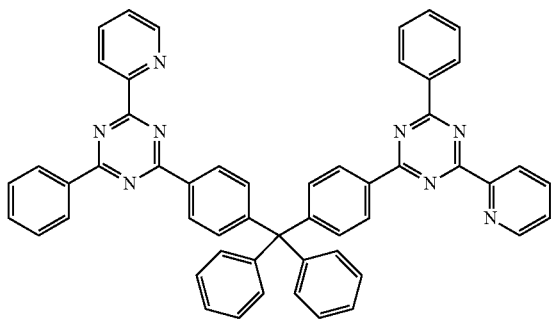
Compound 21
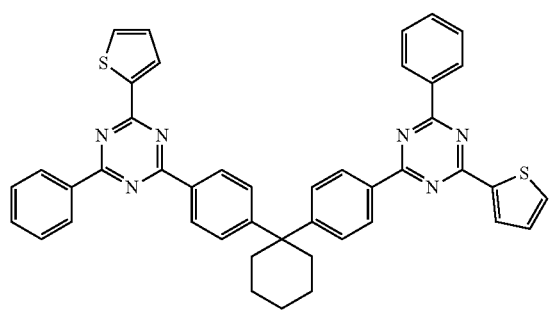
Compound 22
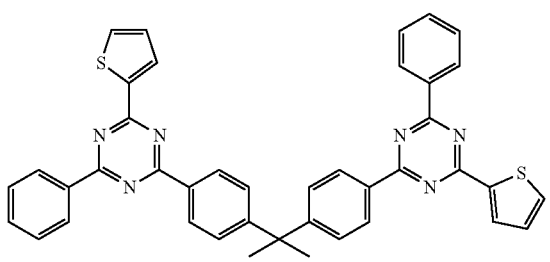
Compound 23
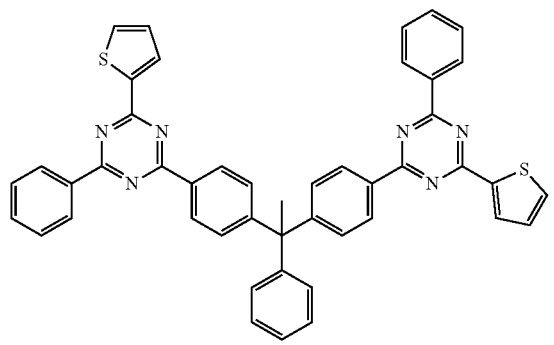
Compound 24
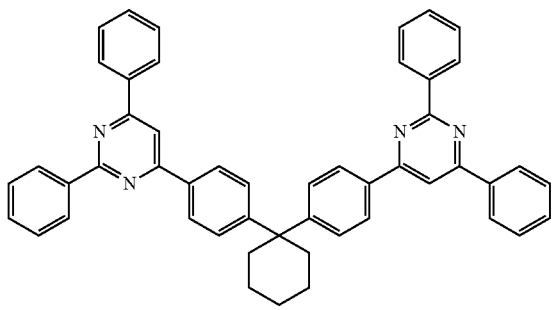
Compound 25
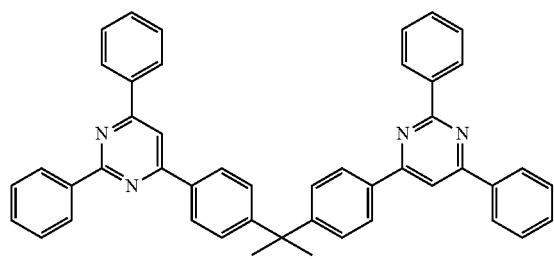
Compound 26
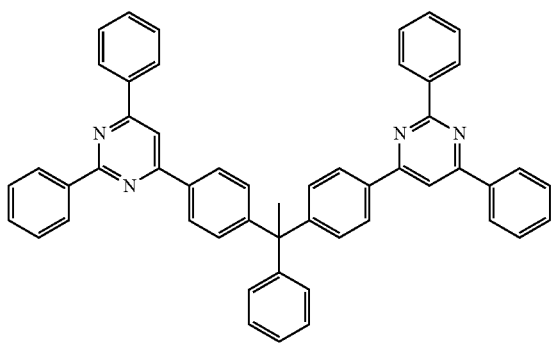

-continued
Compound 27
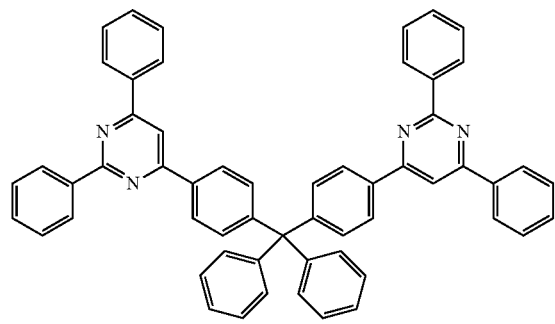
Compound 28
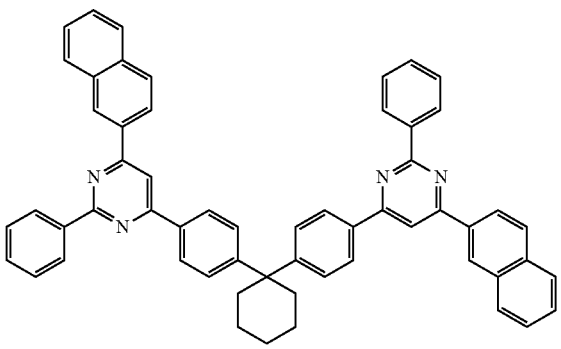
Compound 29
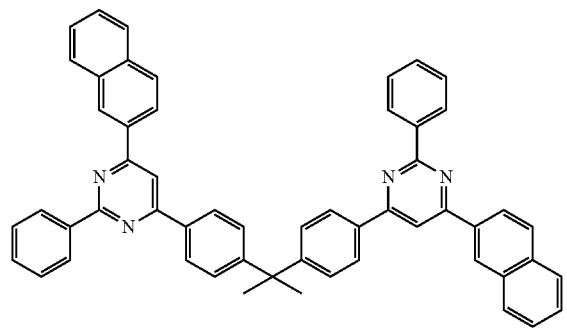
Compound 30
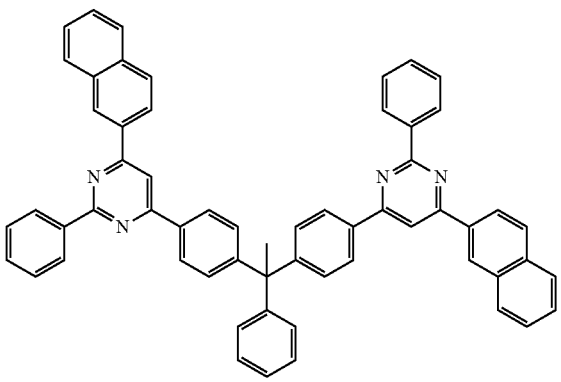
Compound 31
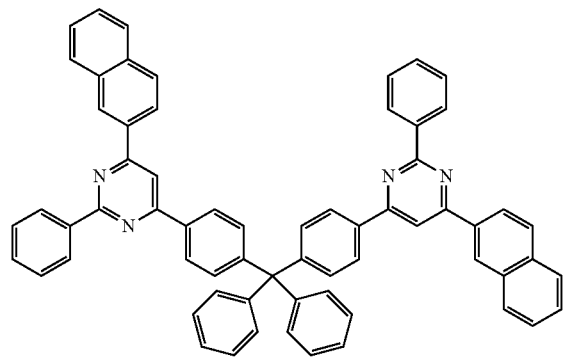
Compound 32
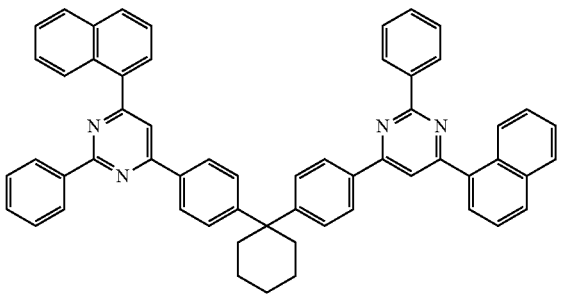
Compound 33
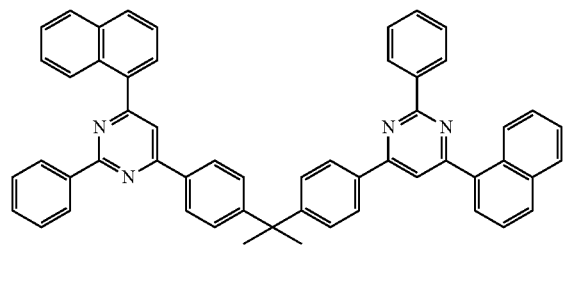
Compound 34
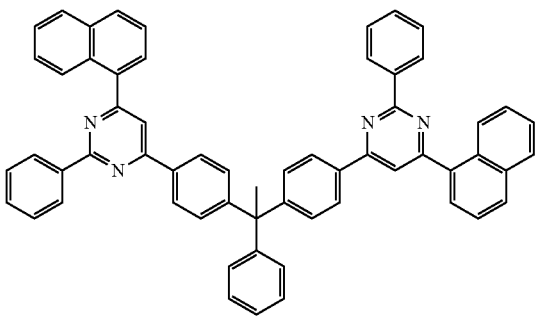

Compound 35
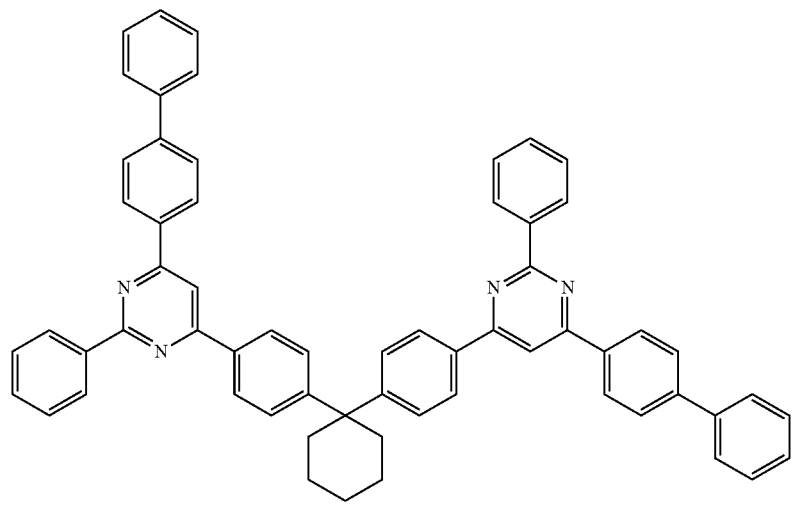
Compound 36
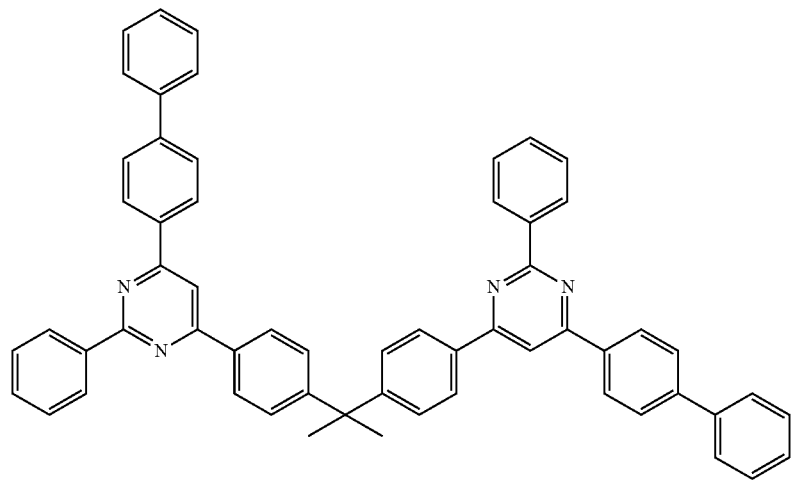
Compound 37
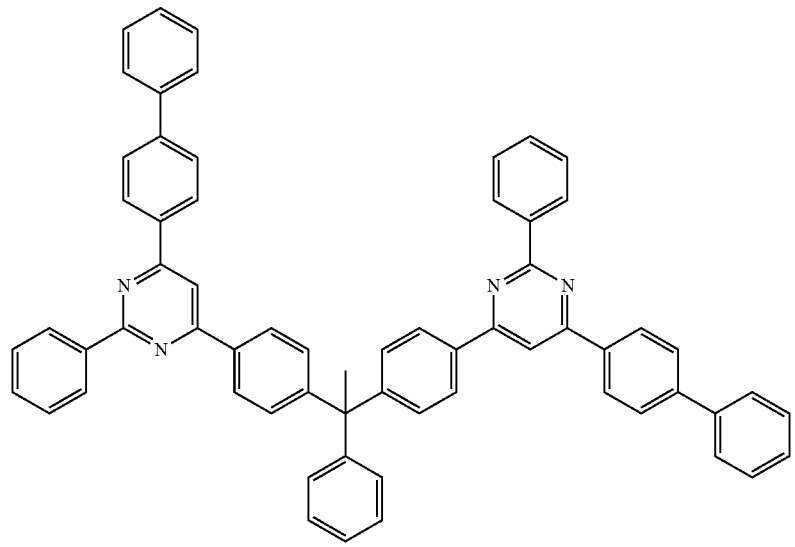

-continued
Compound 38
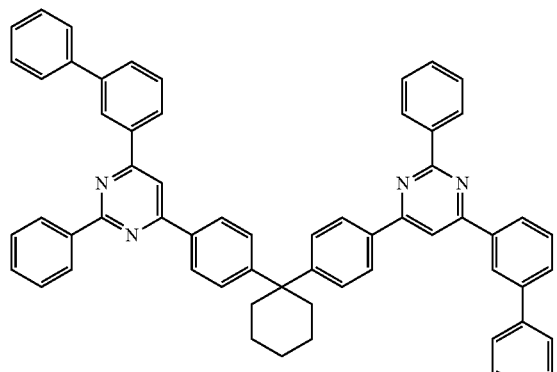
Compound 39
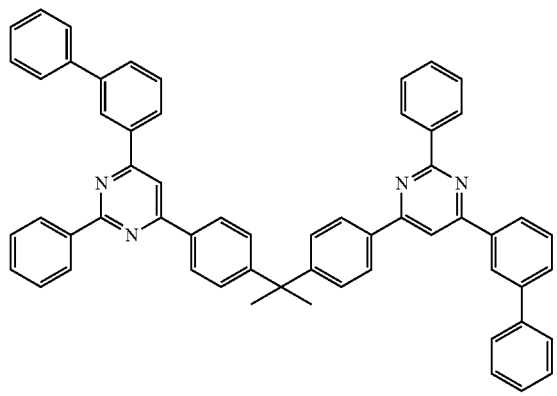
Compound 40
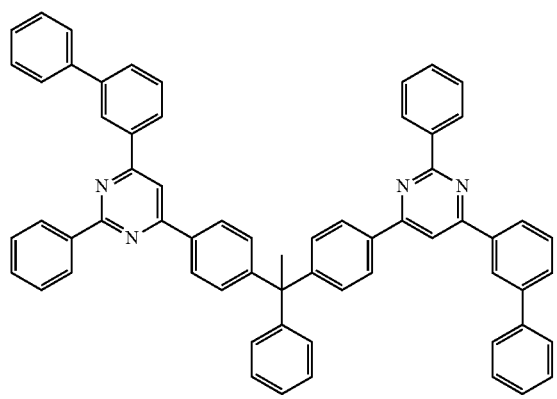
Compound 41
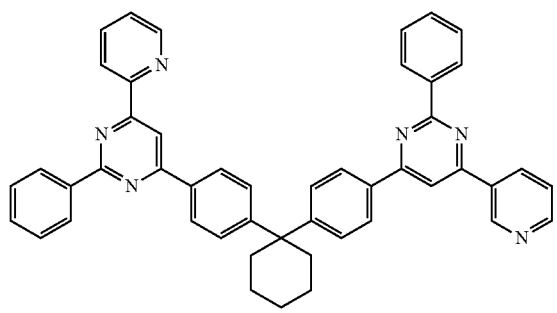
Compound 42
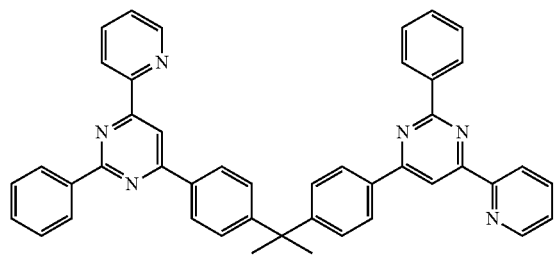
Compound 43
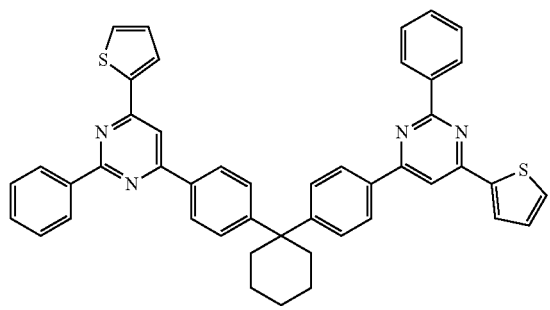
Compound 44
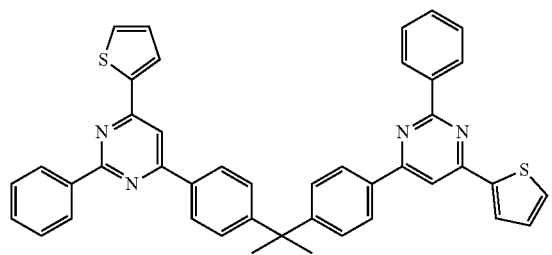
Compound 45
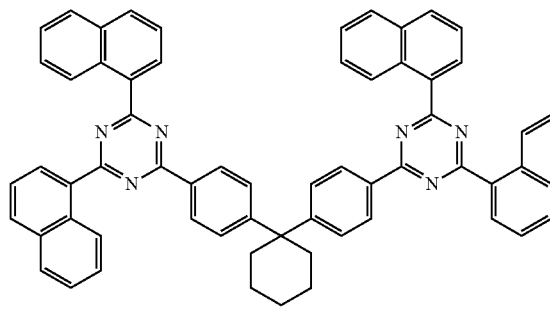

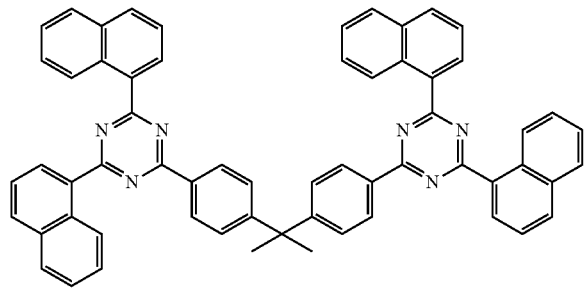
Compound 46
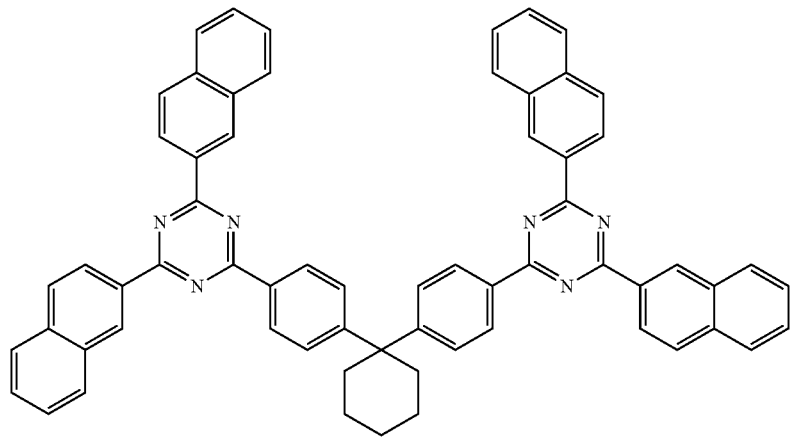
Compound 47
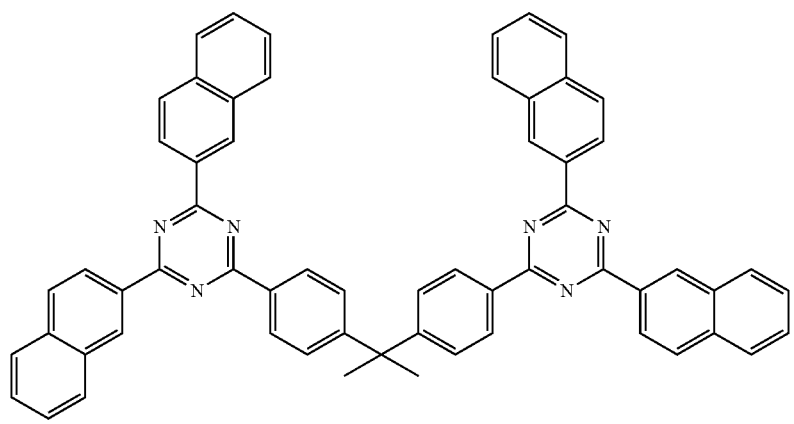
Compound 48
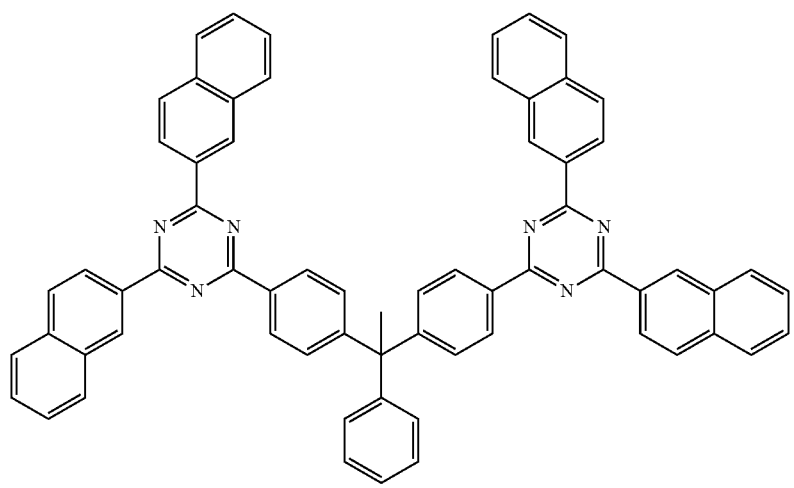
Compound 49

-continued
Compound 50
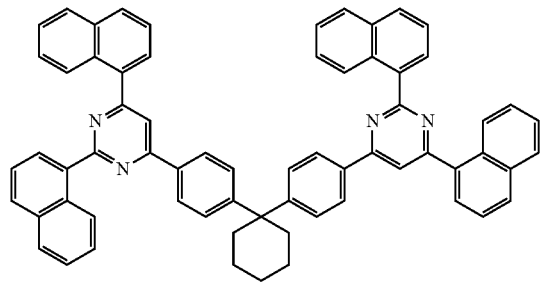
Compound 51
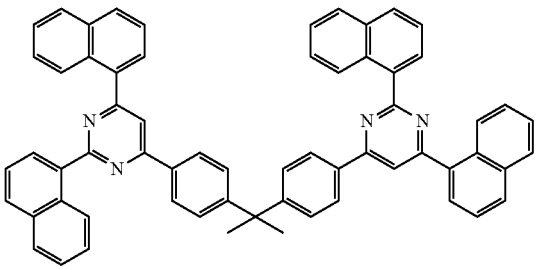
Compound 52
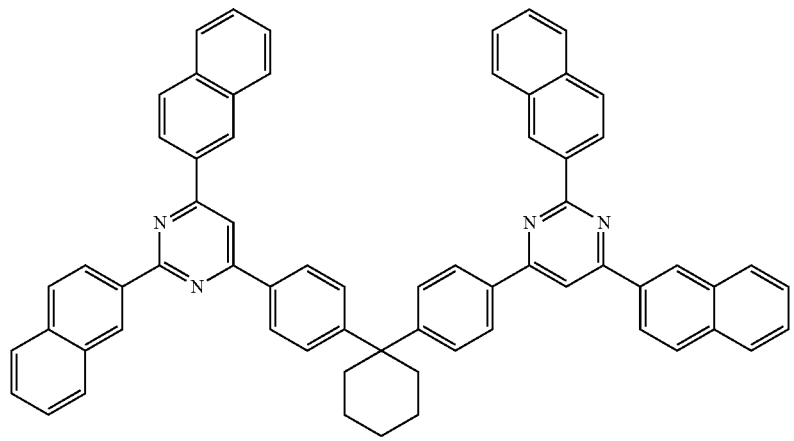
Compound 53
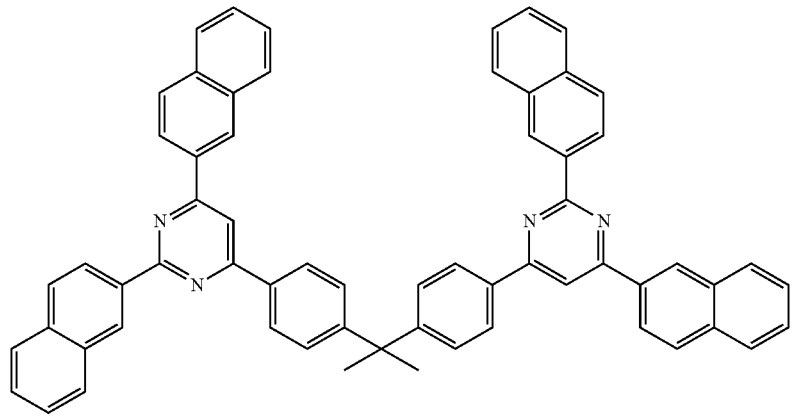
Compound 54
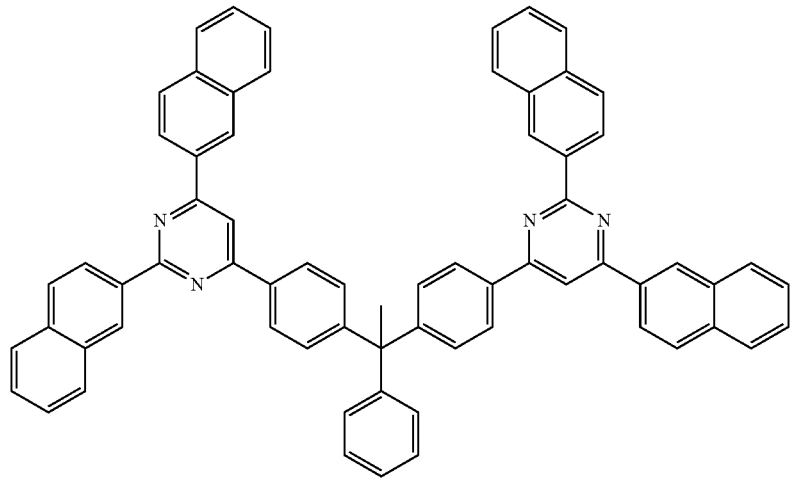

-continued
Compound 55
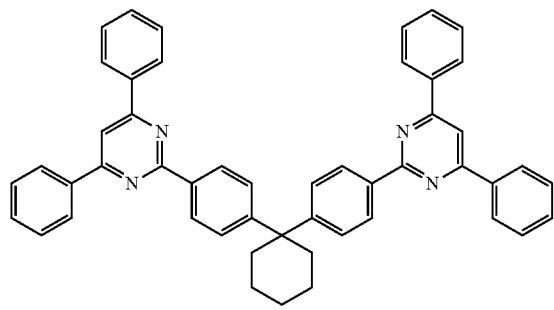
Compound 56
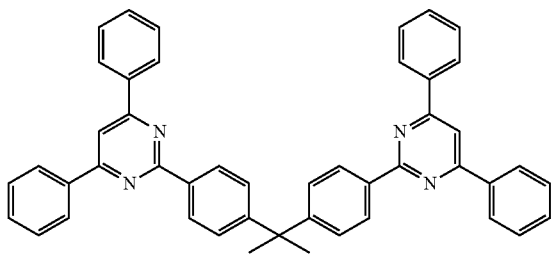
Compound 57
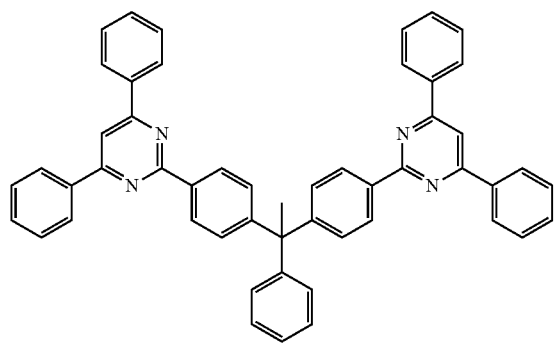
Compound 58
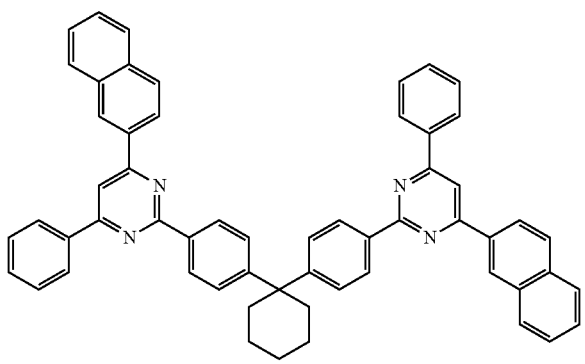
Compound 59
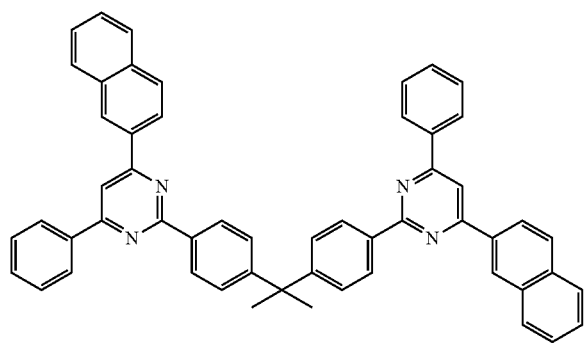
Compound 60
Compound 61
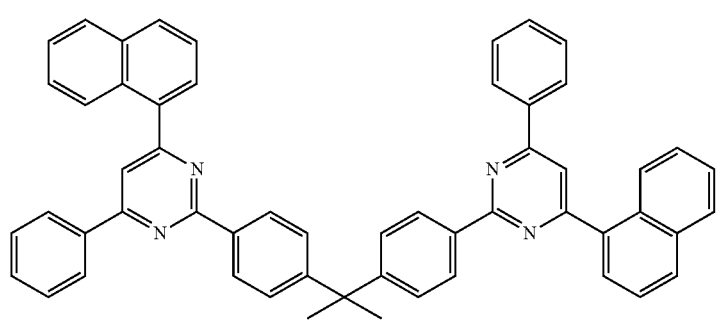

Compound 62
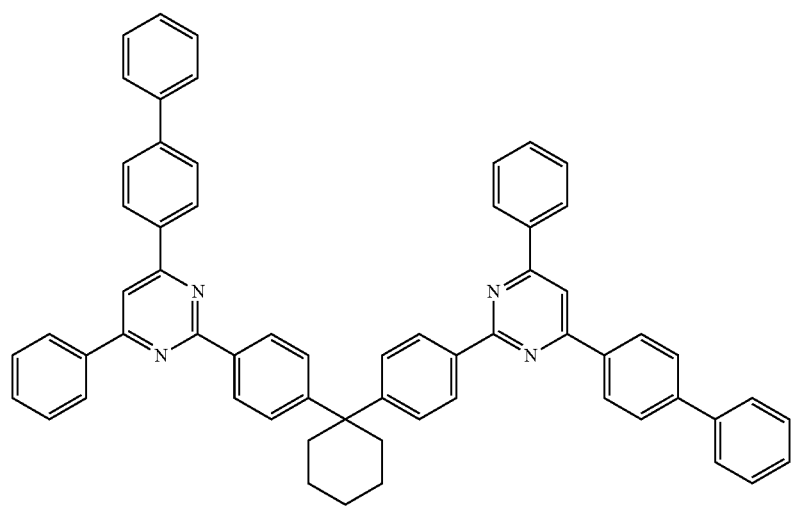
Compound 63
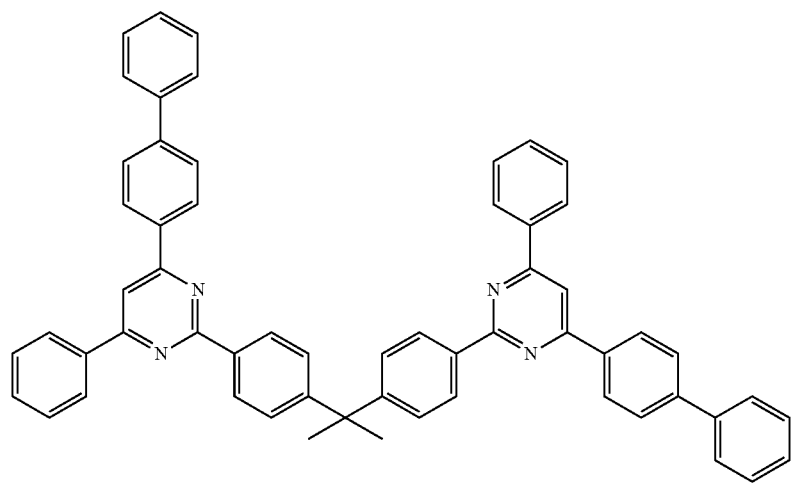
Compound 64
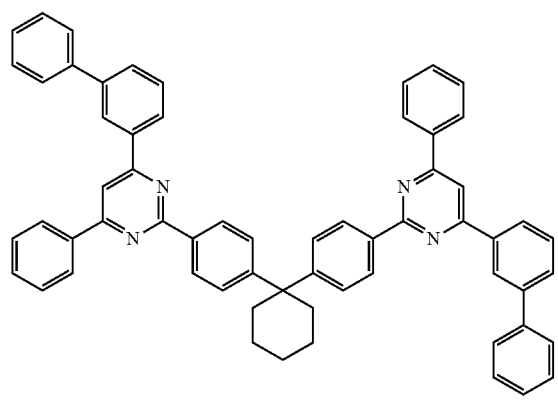
Compound 65
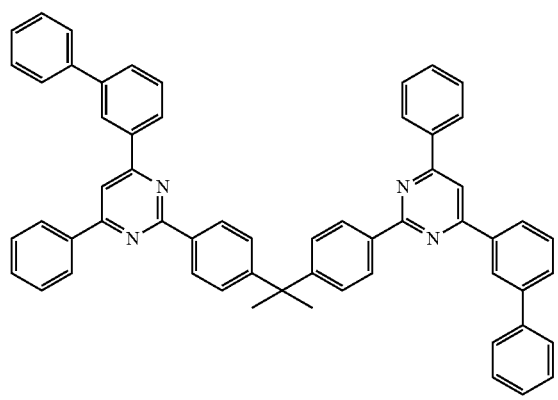

-continued
Compound 66
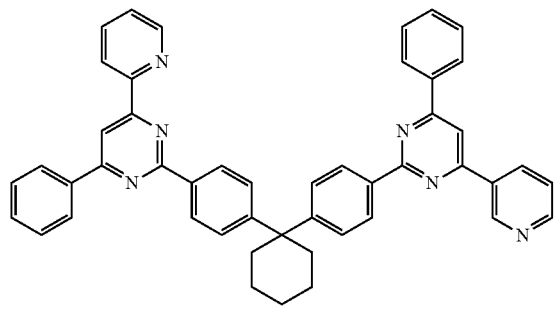
Compound 67
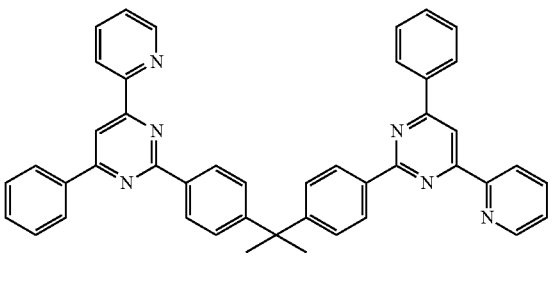
Compound 68
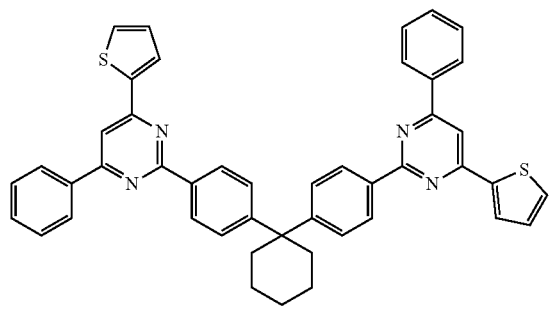
Compound 69
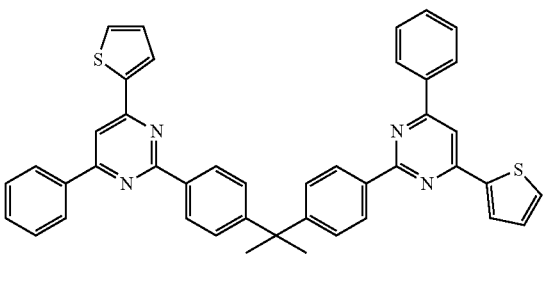
Compound 70
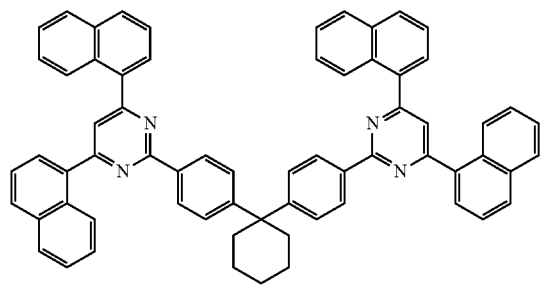
Compound 71
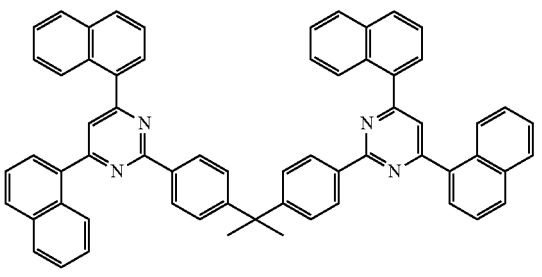
Compound 72
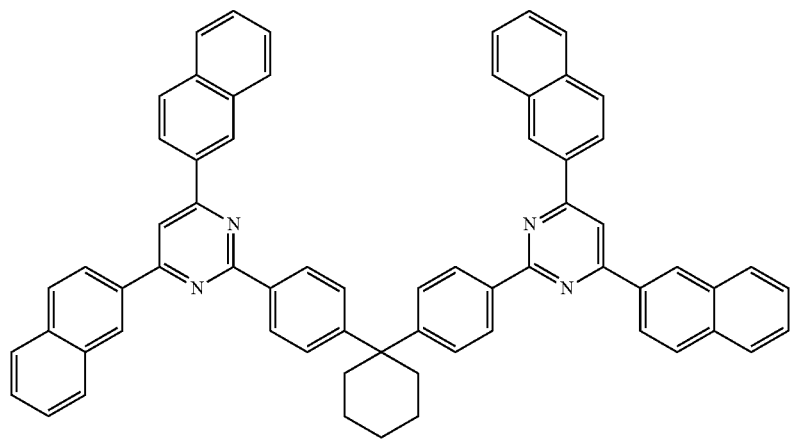

-continued
Compound 73
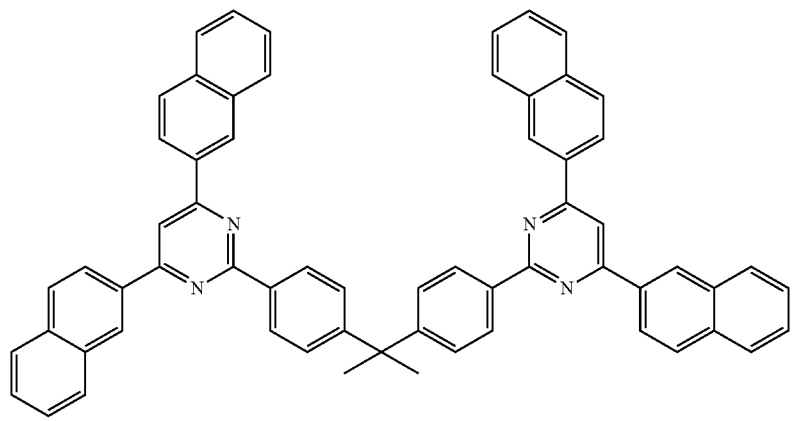
Compound 74
Compound 75
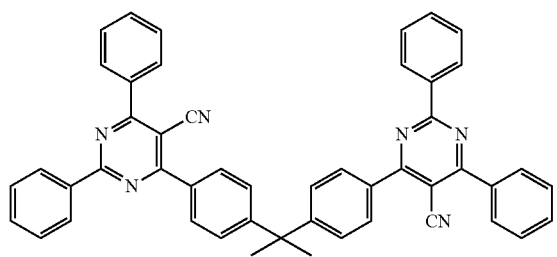
Compound 76
Compound 77
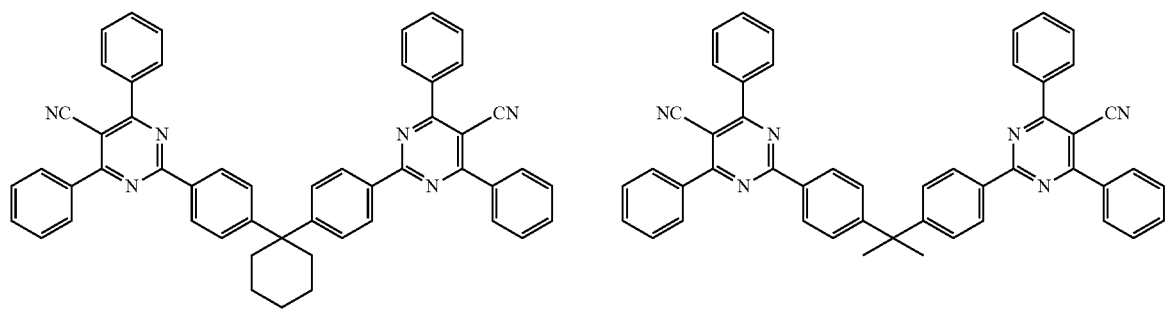
Compound 78
Compound 79
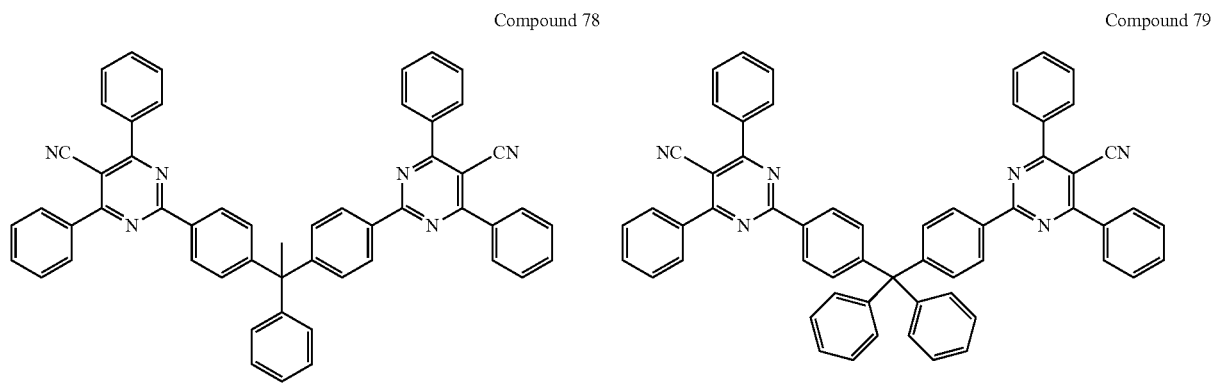

-continued
Compound 80
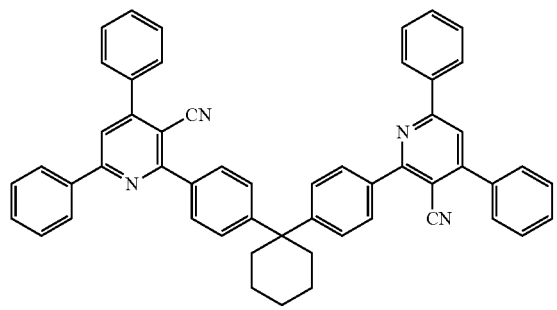
Compound 81
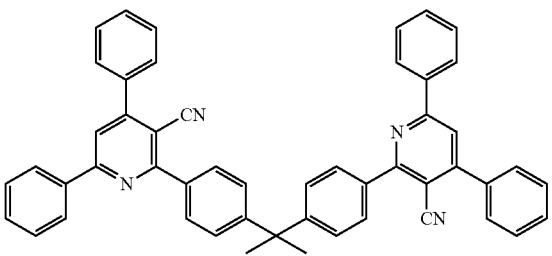
Compound 82
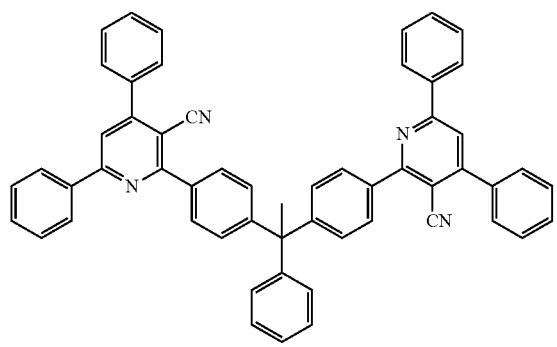
Compound 83
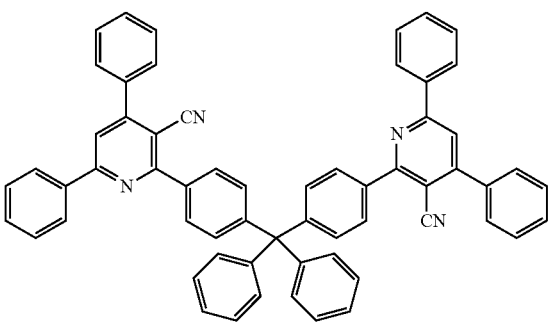
Compound 84
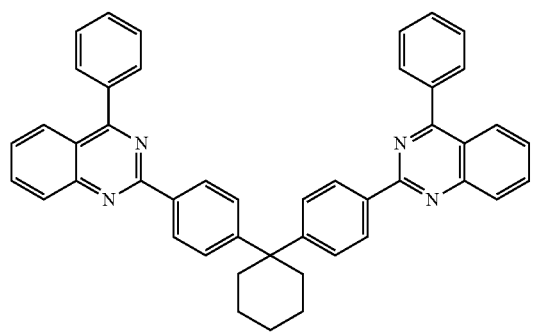
Compound 85
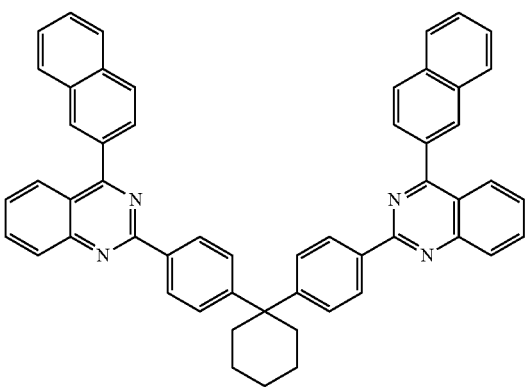
Compound 86
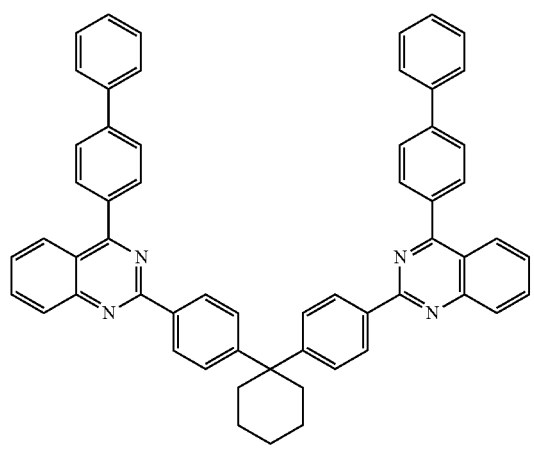
Compound 87
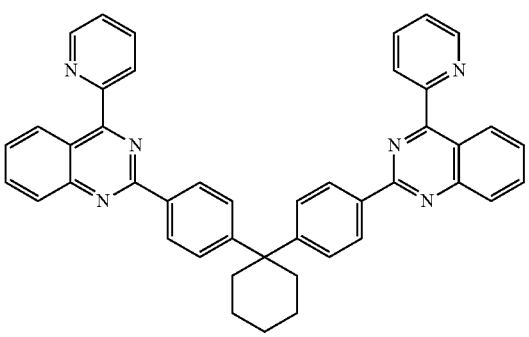

-continued
Compound 88
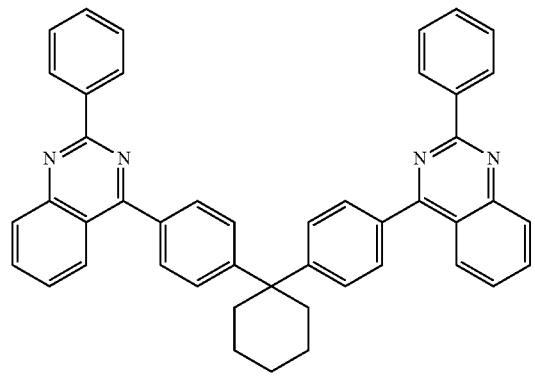
Compound 89
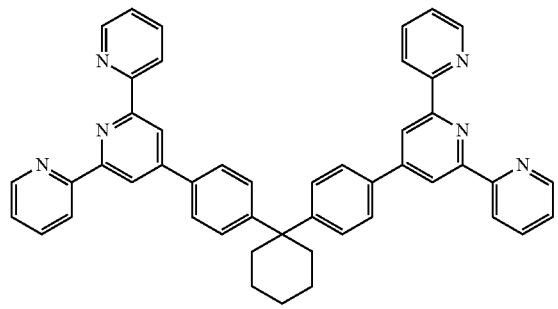
Compound 90
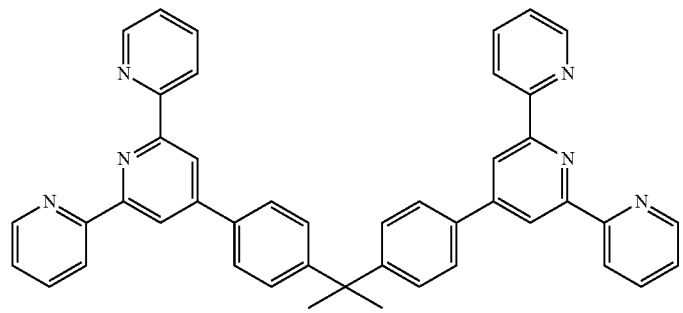
Compound 91
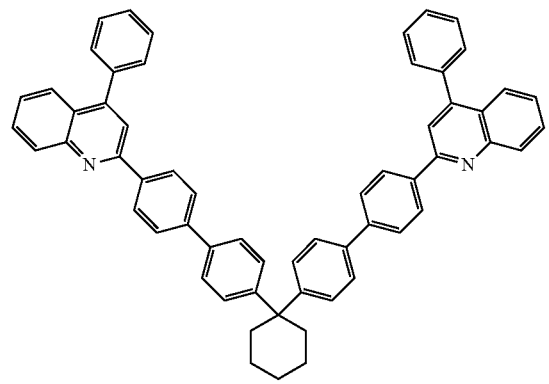
Compound 92
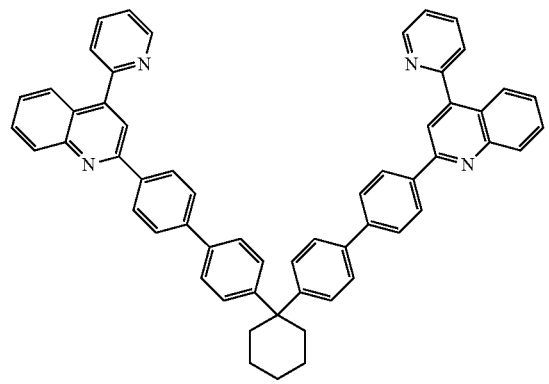
Compound 93
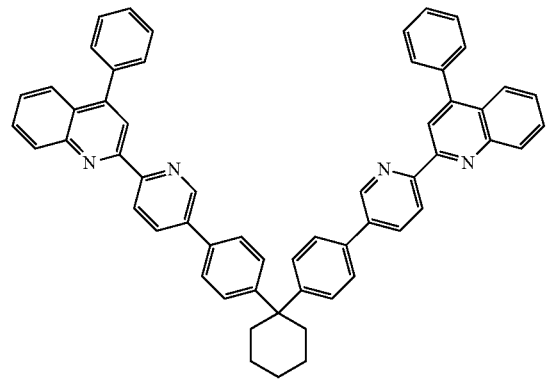
Compound 94
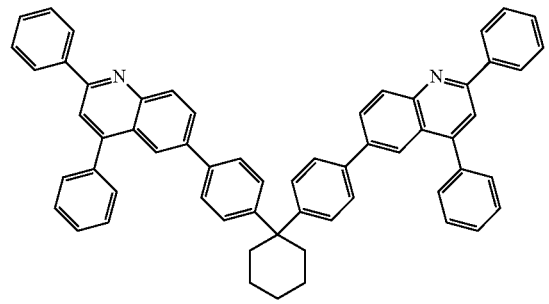

-continued
Compound 95
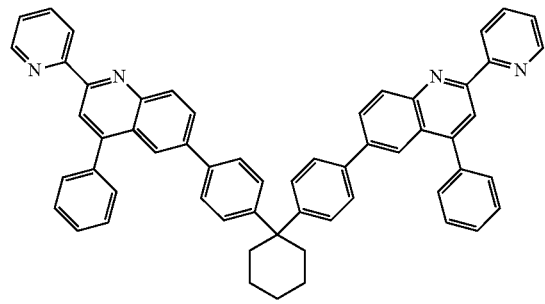
Compound 96
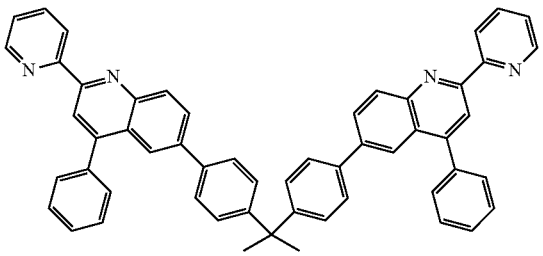
Compound 97
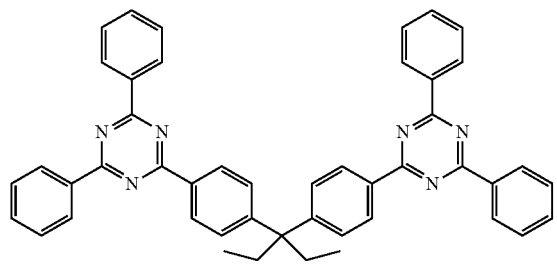
Compound 98
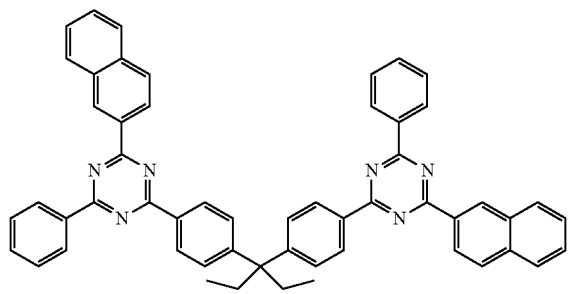
Compound 99
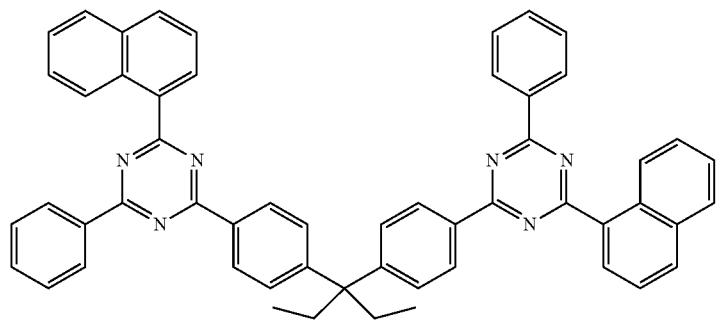
Compound 100
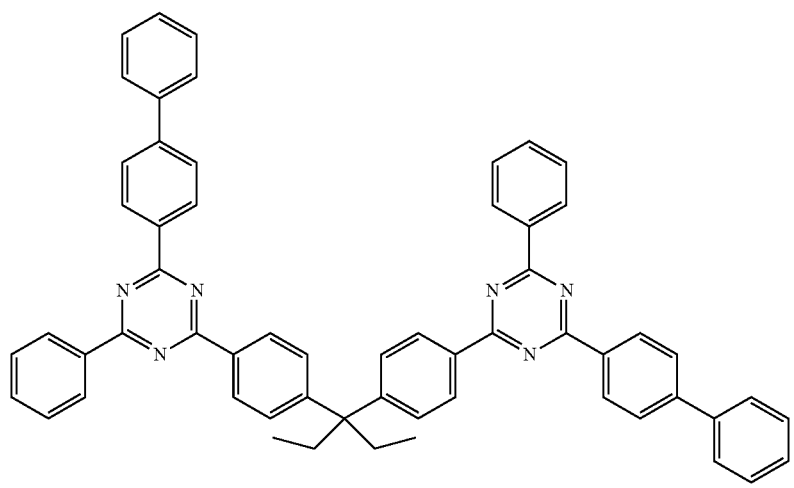

Compound 101
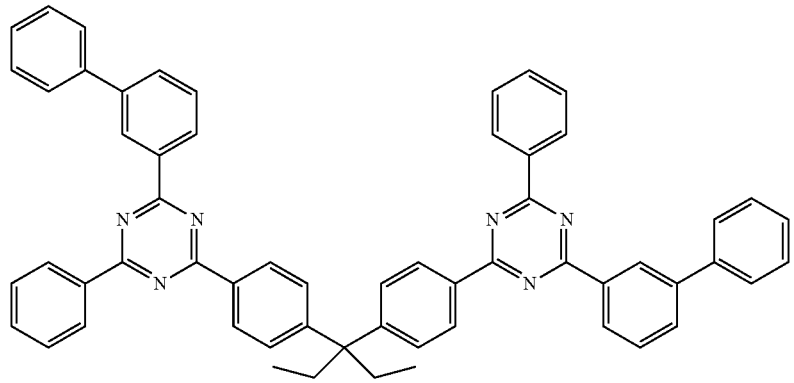
Compound 102
Compound 103
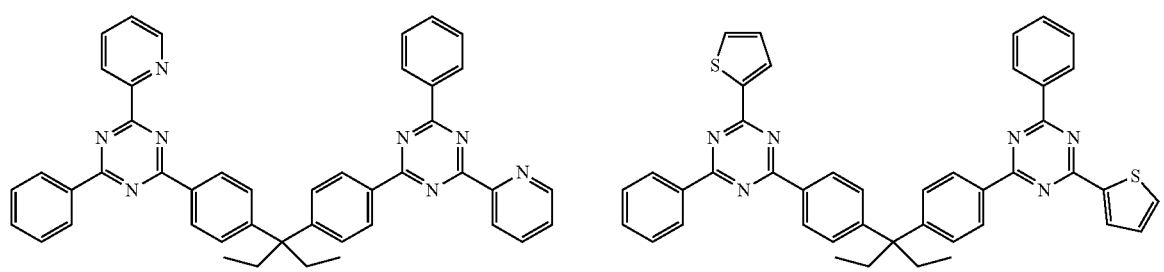
Compound 104
Compound 105
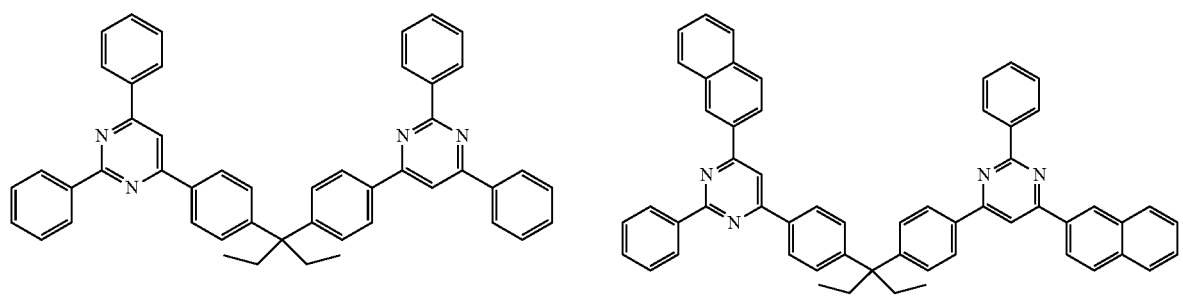
Compound 106
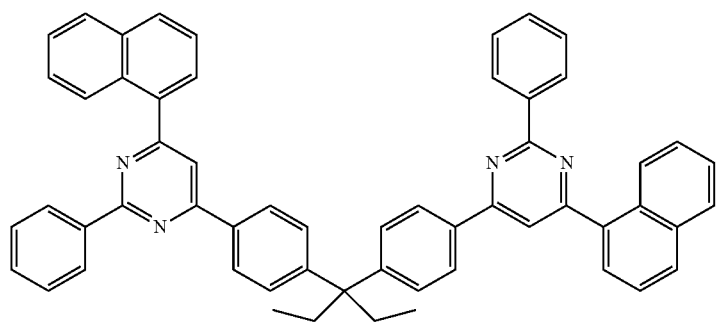

-continued
Compound 107
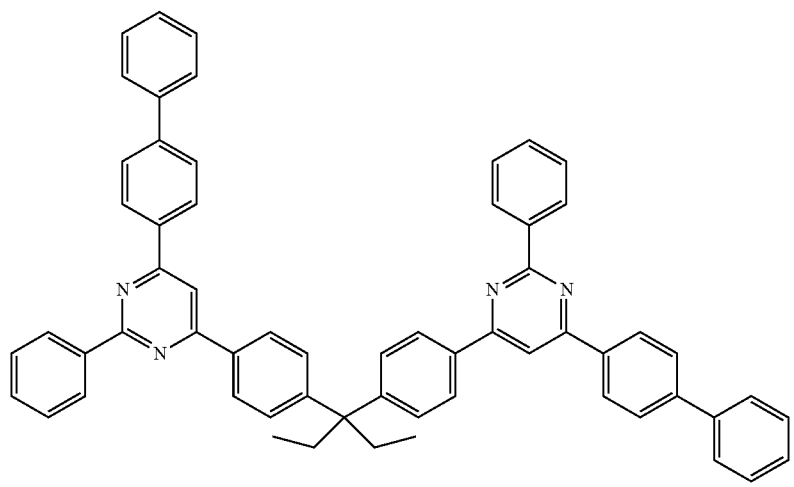
Compound 108
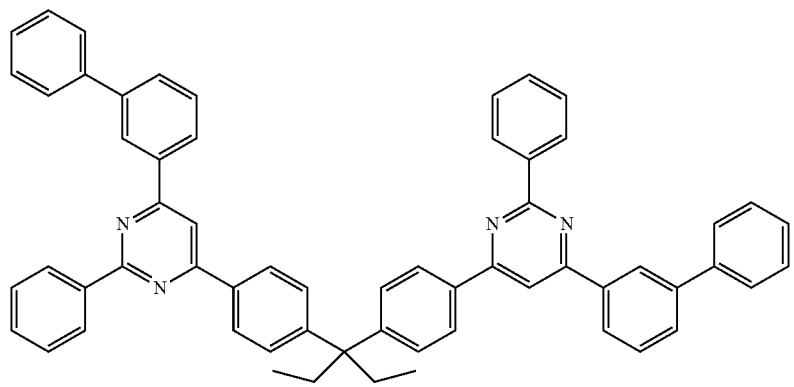
Compound 109 Compound 110
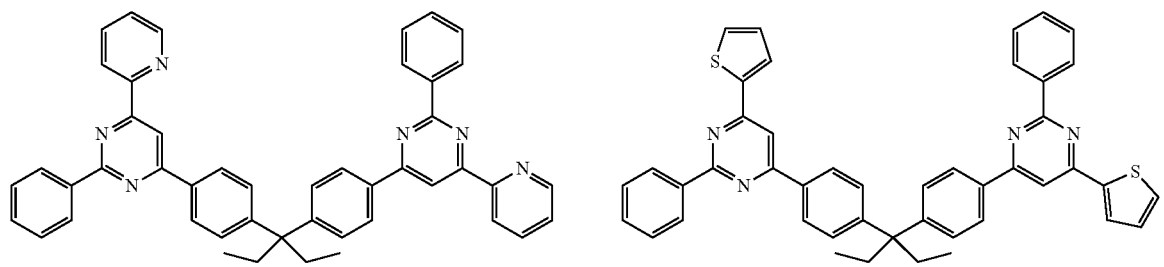
Compound 111
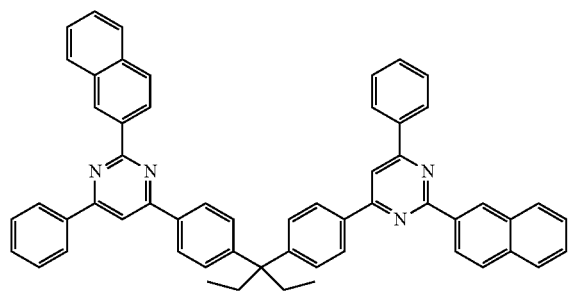
Compound 112
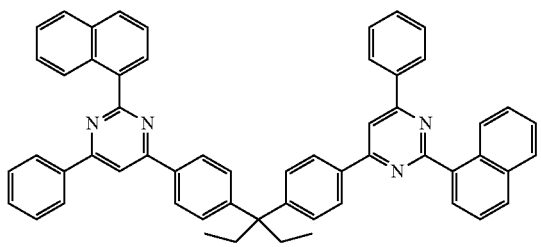

Compound 113
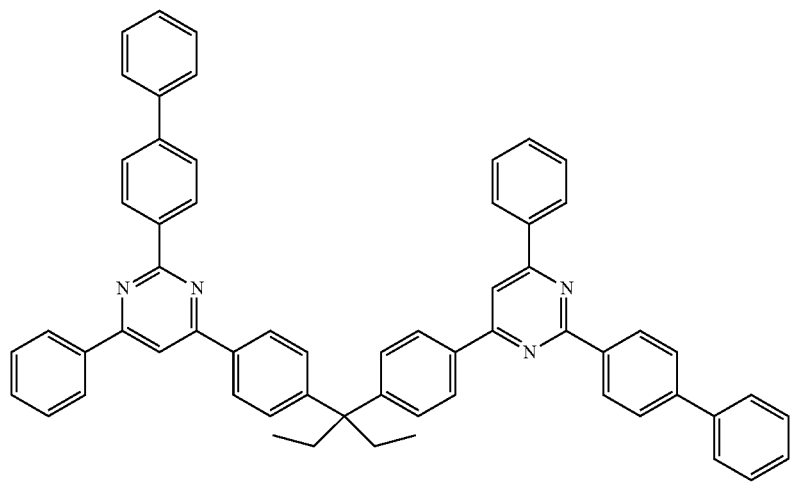
Compound 114                                              Compound 115
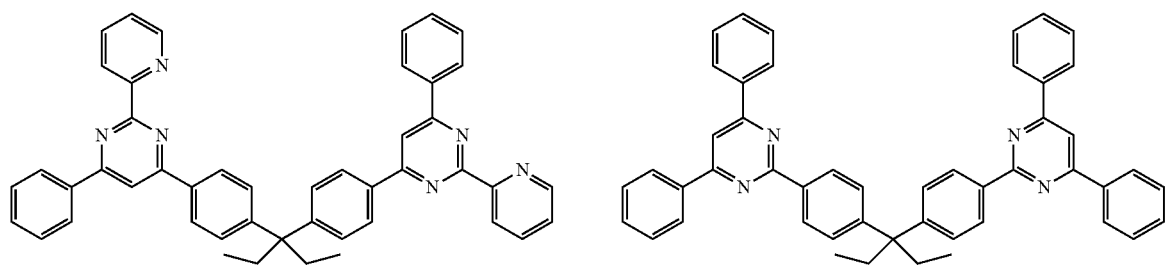
Compound 116                                              Compound 117
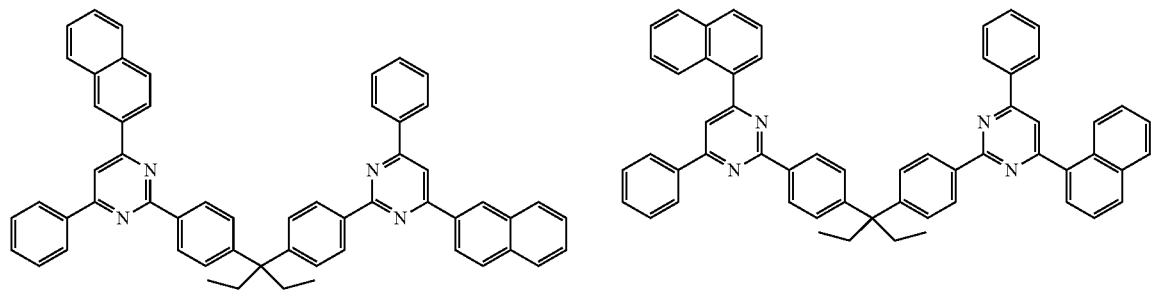
Compound 118
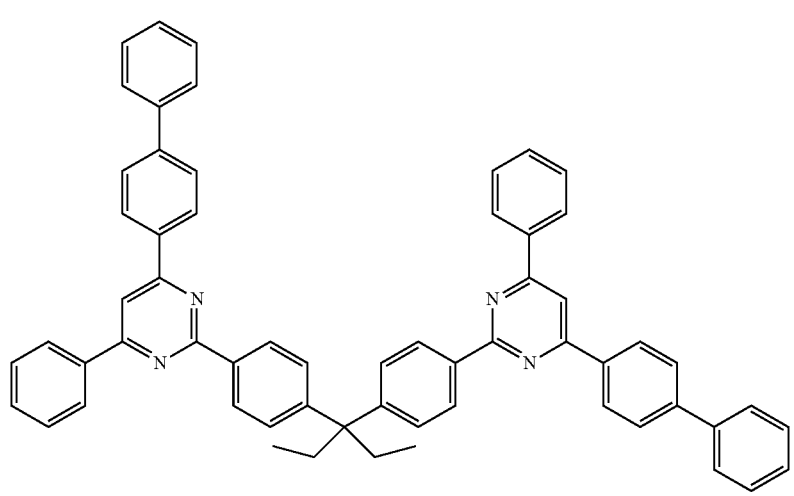

Compound 119
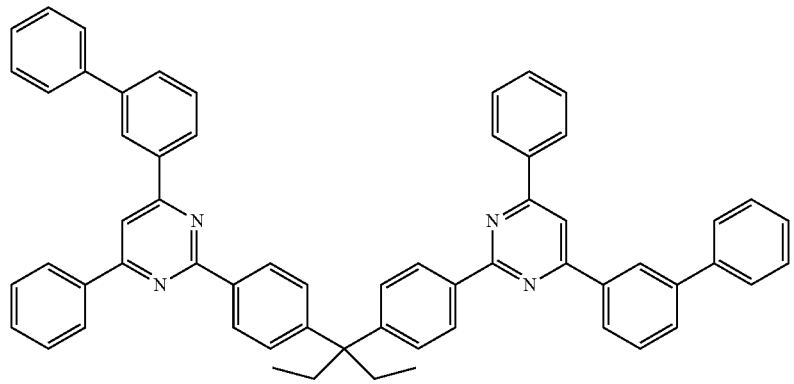
Compound 120
Compound 121
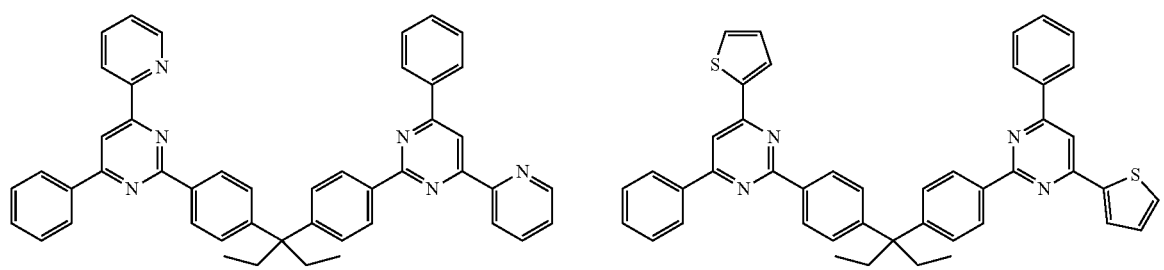
Comppound 122
Compound 123
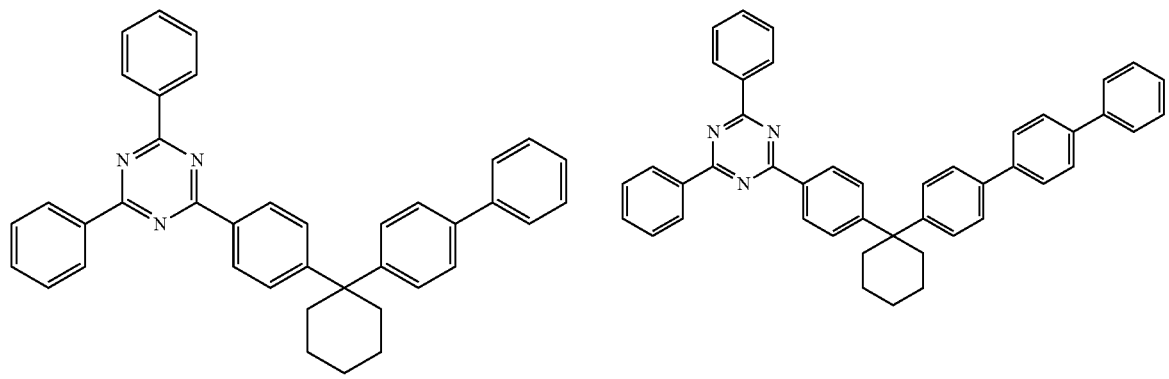
Compound 124
Compound 125
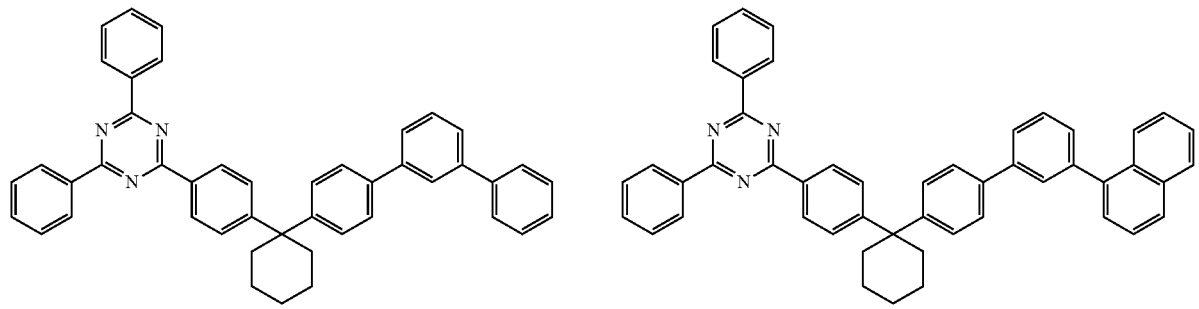

-continued
Compound 126
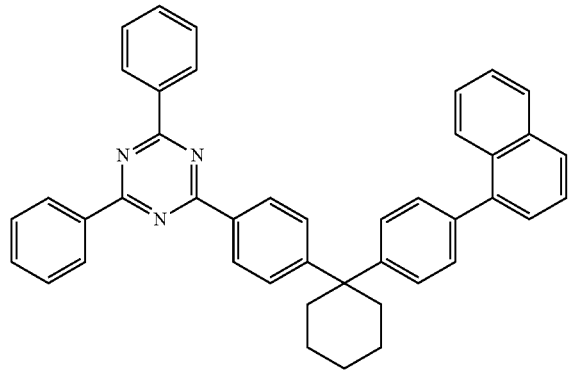
Compound 127
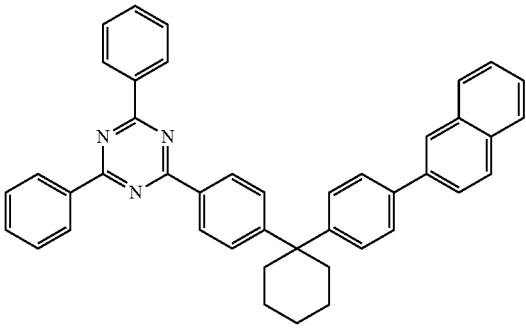
Compound 128
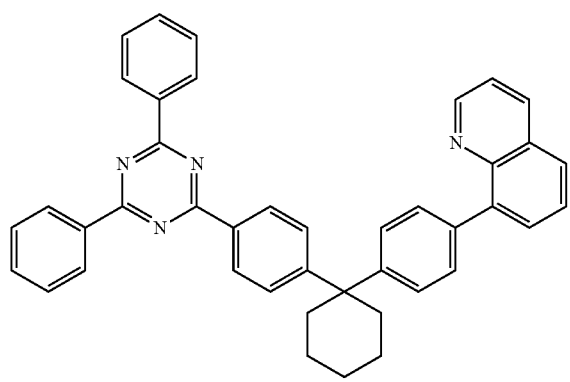
Compound 129
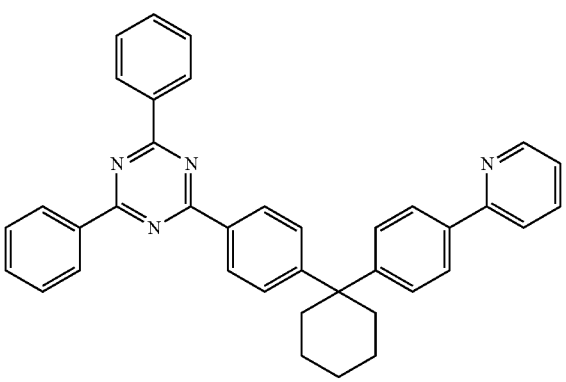
Compound 130
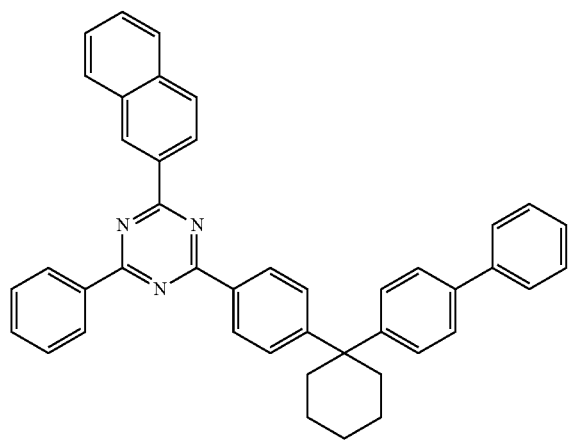
Compound 131
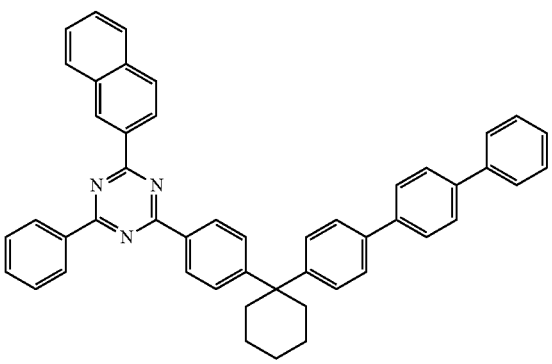
Compound 132
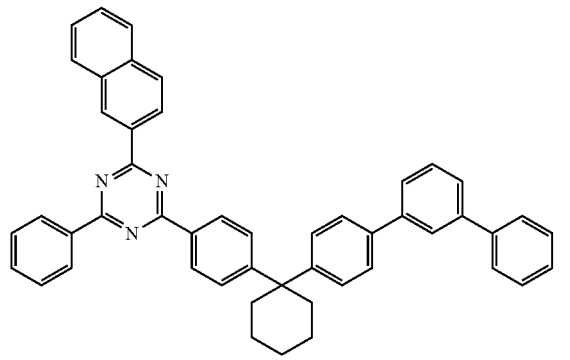
Compound 133
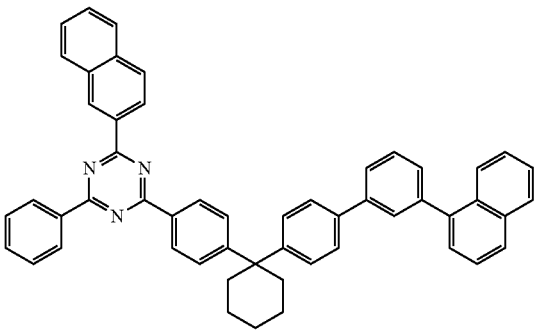

-continued
Compound 134
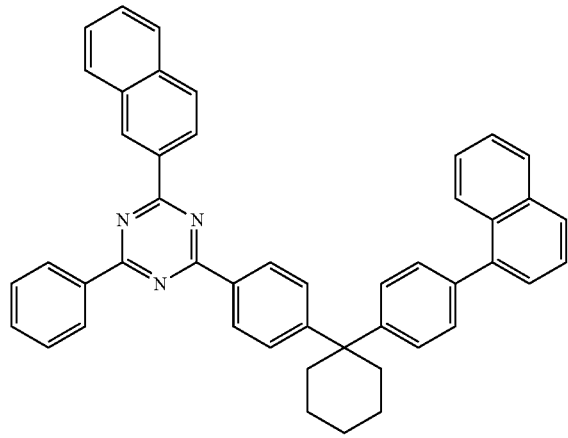
Compound 135
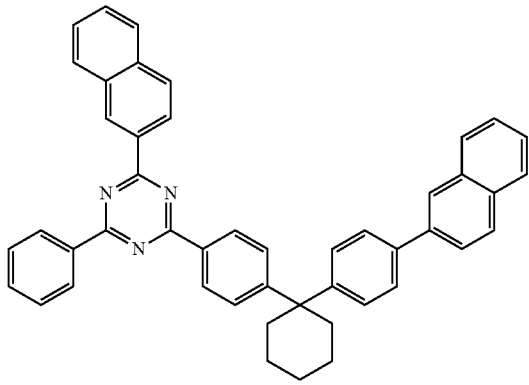
Compound 136
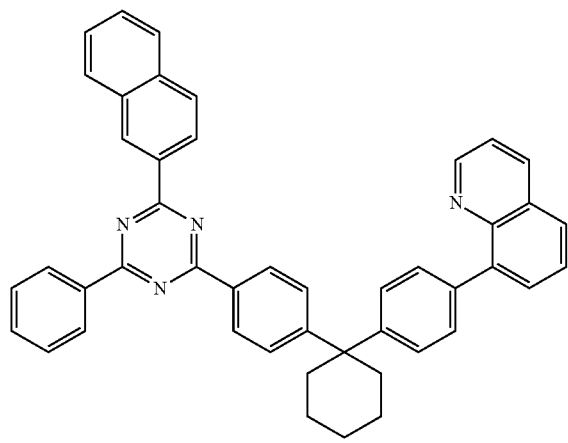
Compound 137
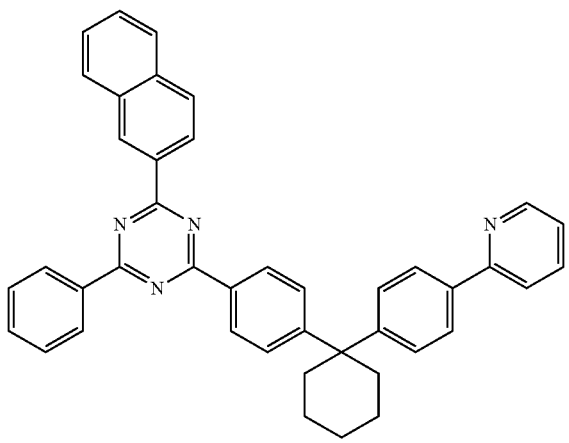
Compound 138
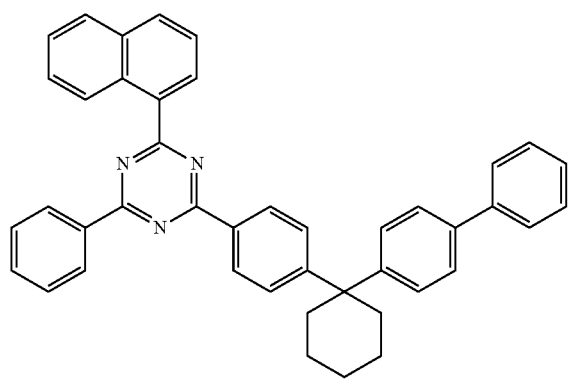
Compound 139
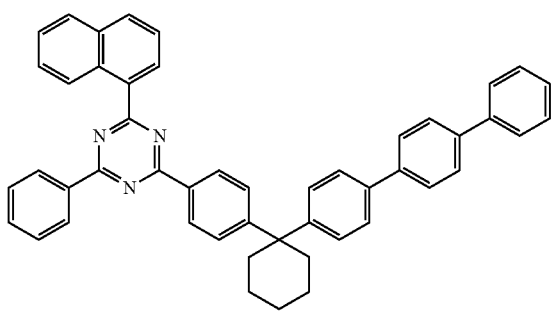
Compound 140
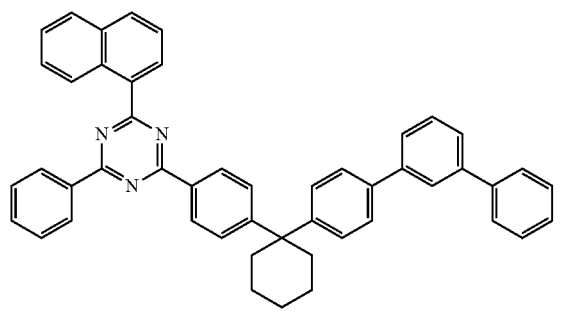
Compound 141
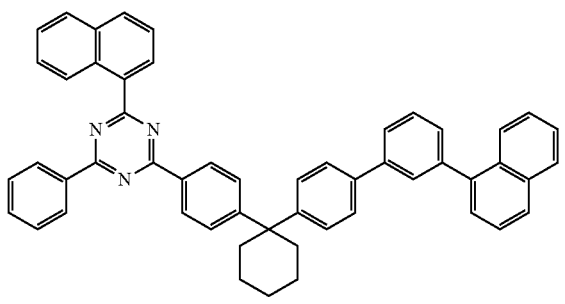

-continued
Compound 142
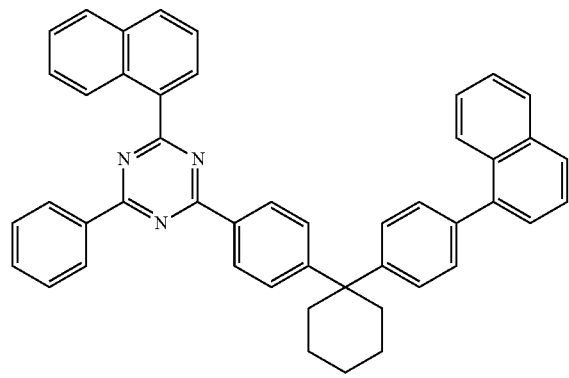
Compound 143
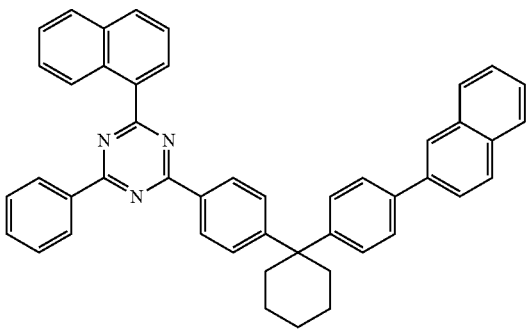
Compound 144
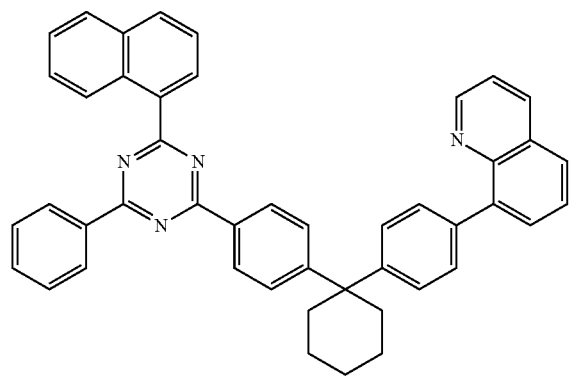
Compound 145
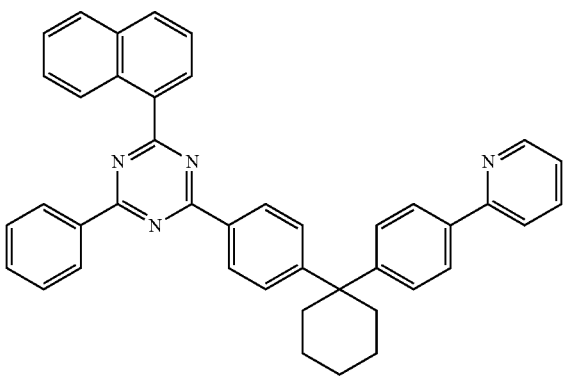
Compound 146
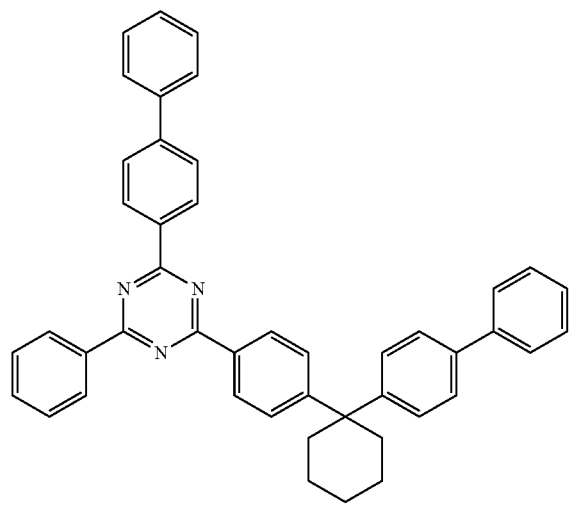
Compound 147
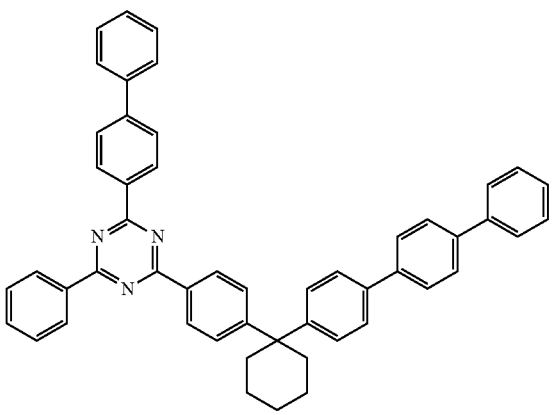

-continued
Compound 148
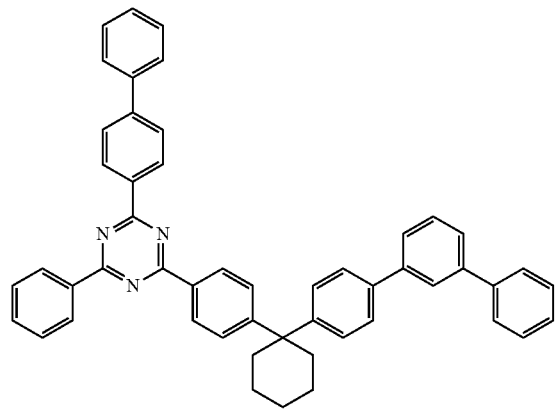
Compound 149
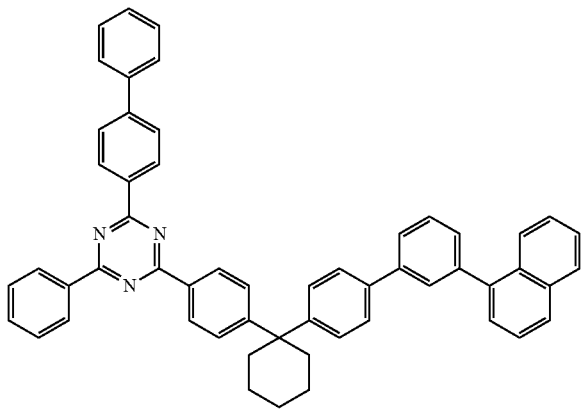
Compound 150
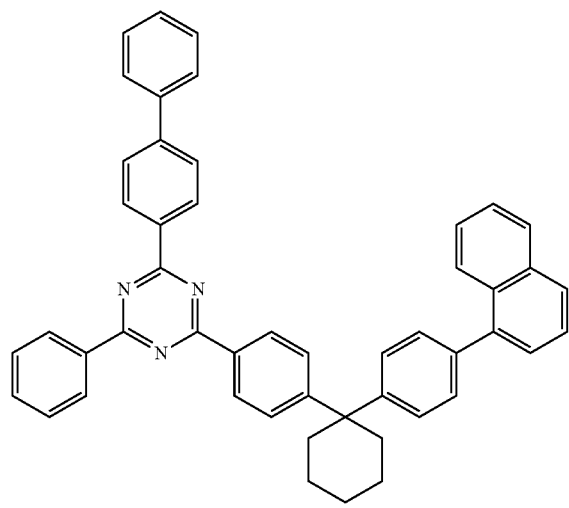
Compound 151
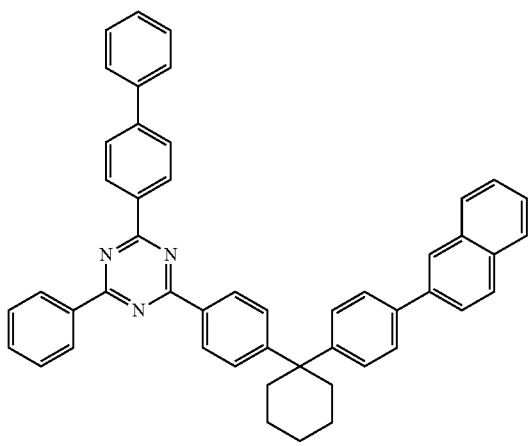
Compound 152
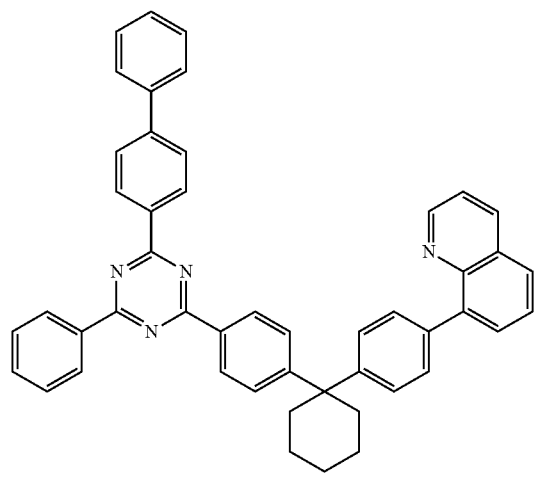
Compound 153
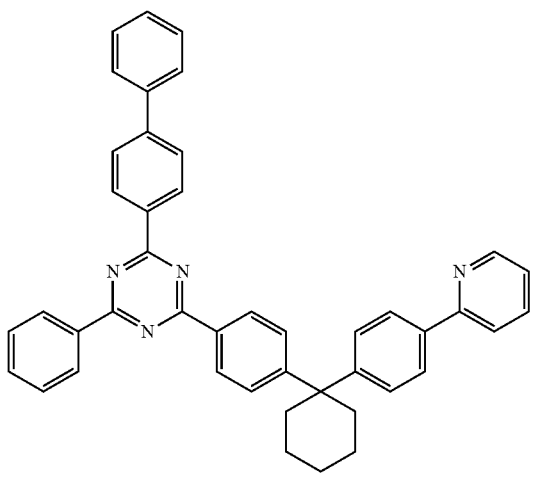

-continued
Compound 154
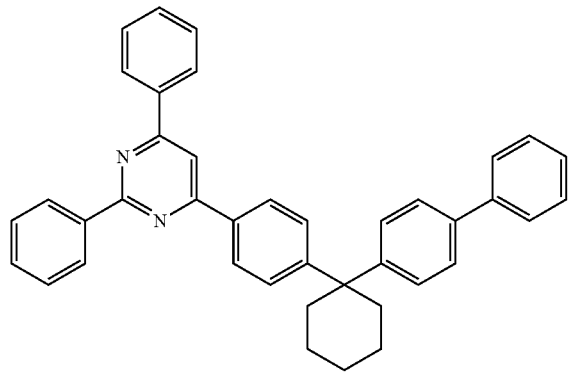
Compound 155
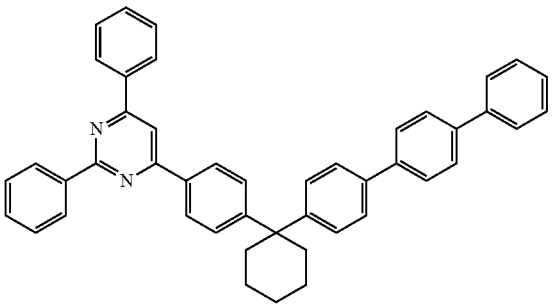
Compound 156
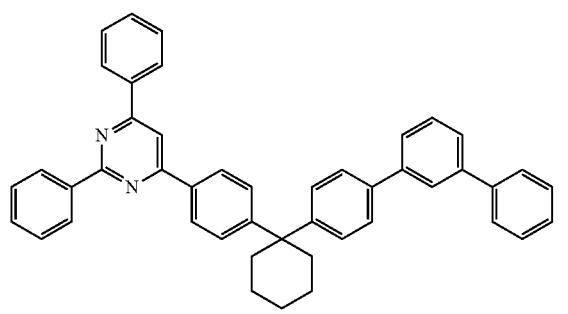
Compound 157
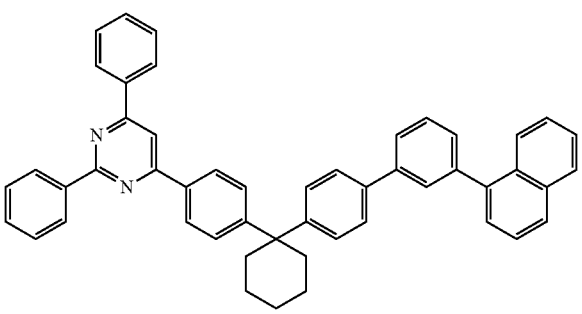
Compound 158
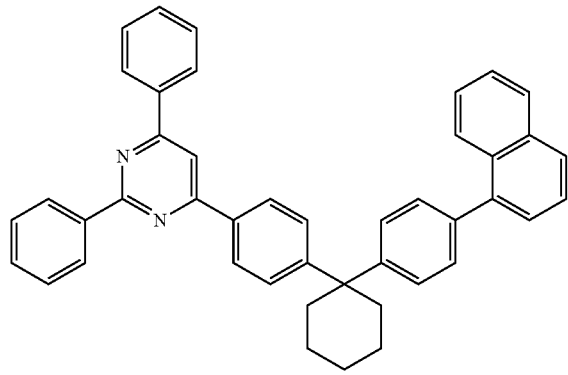
Compound 159
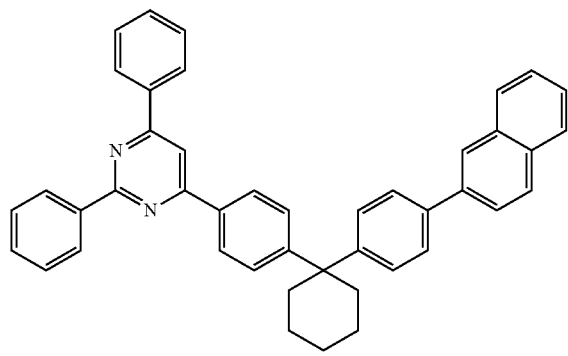
Compound 160
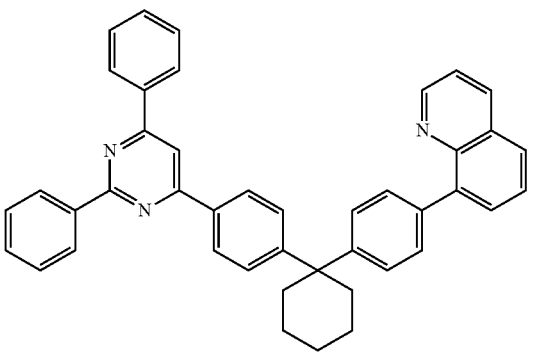

-continued
Compound 161
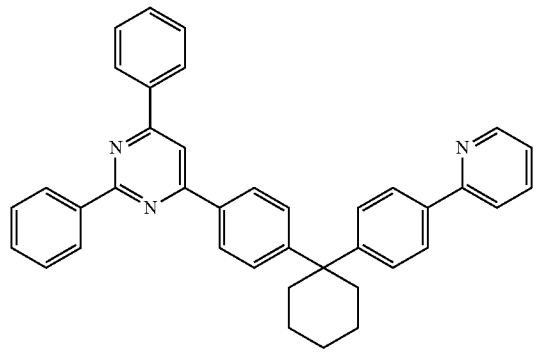
Compound 162
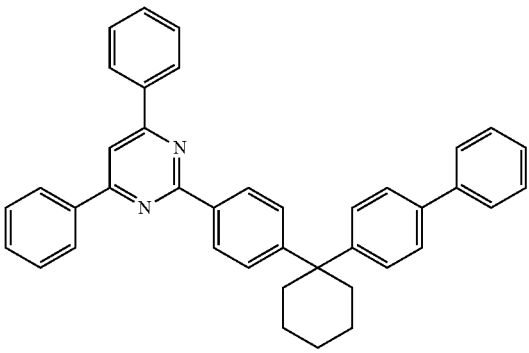
Compound 163
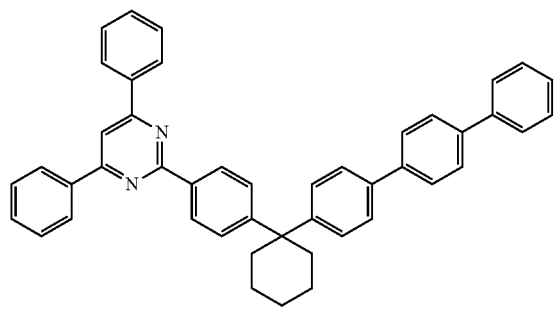
Compound 164
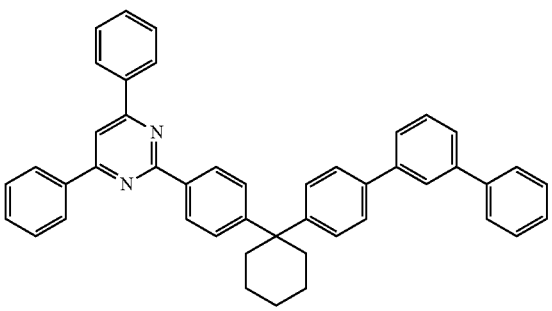
Compound 165
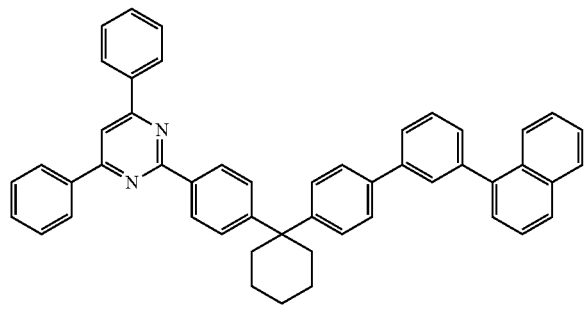
Compound 166
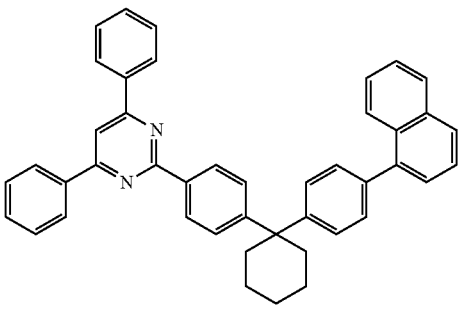
Compound 167
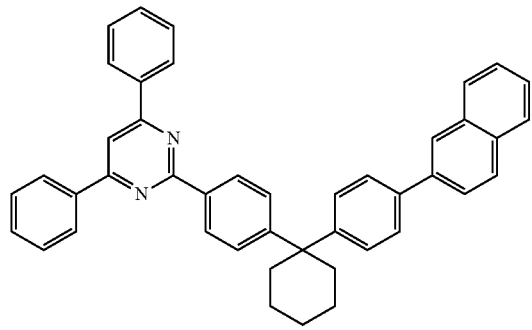
Compound 168
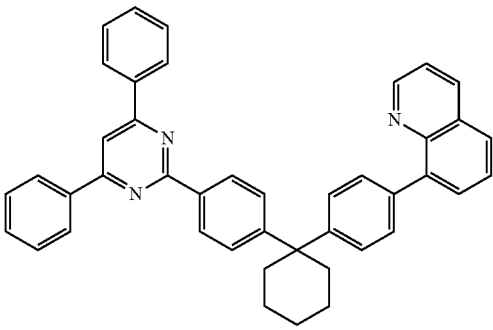

Compound 169
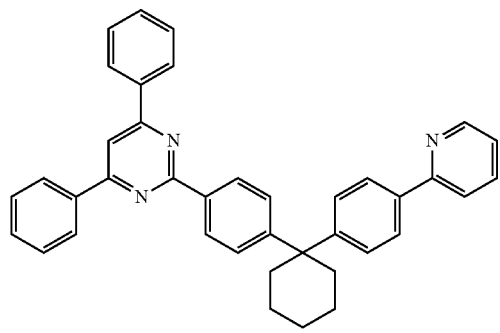
Compound 170
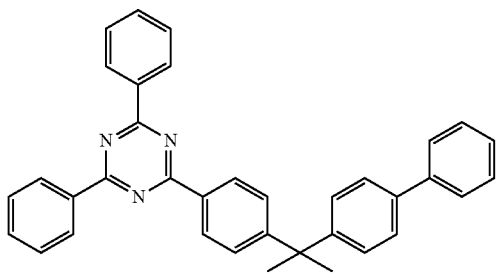
Compound 171
Compound 172
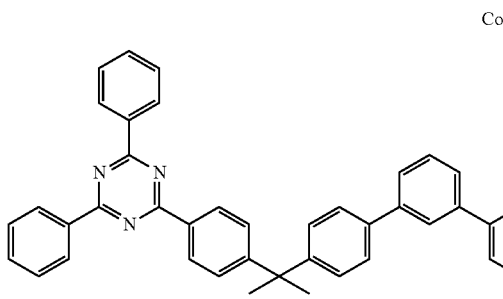
Compound 173
Compound 174
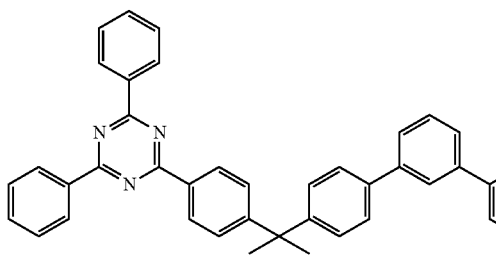
Compound 175
Compound 176
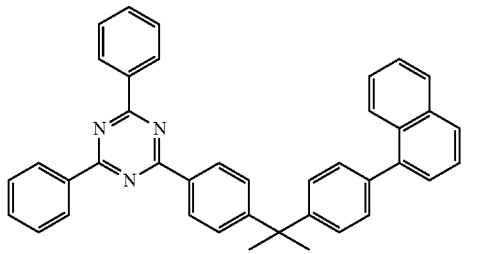
Compound 177
Compound 178
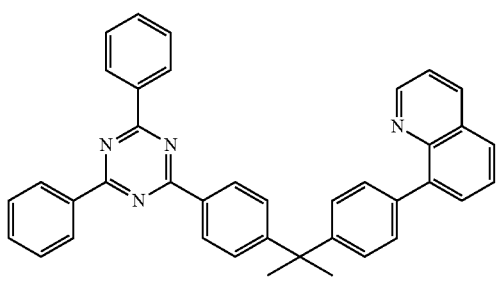
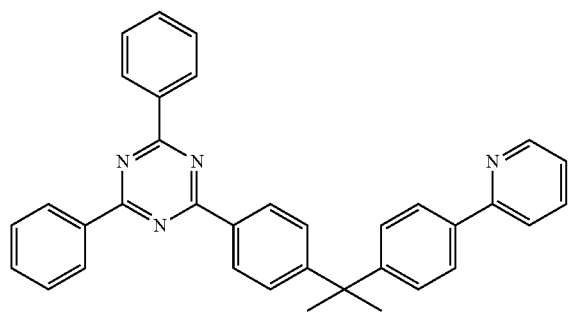
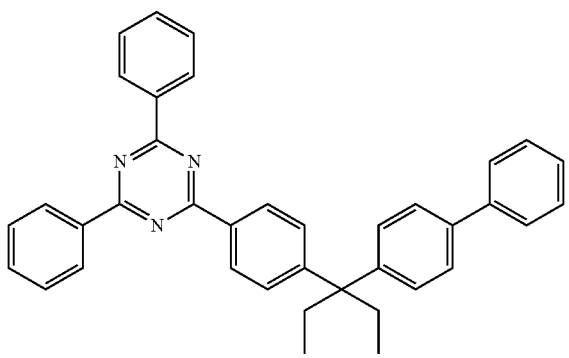

Compound 179
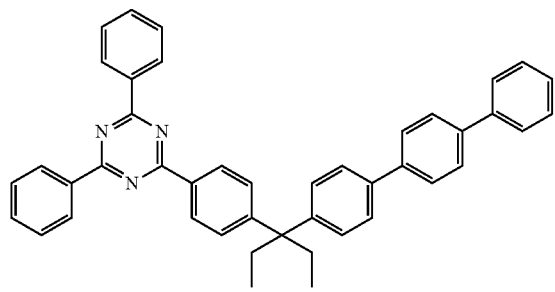
Compound 180
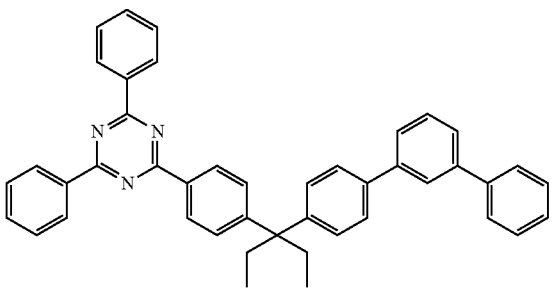
Compound 181
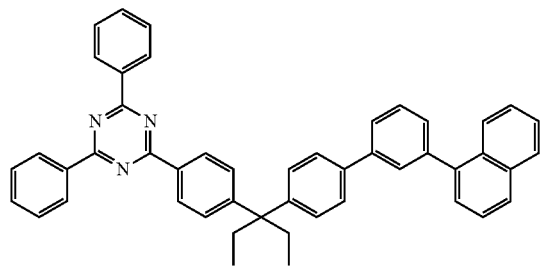
Compound 182
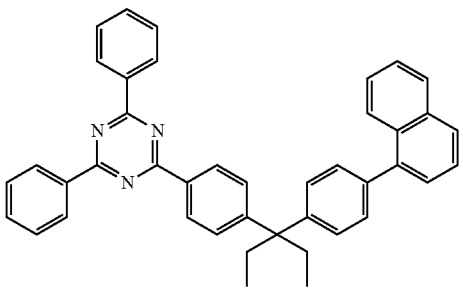
Compound 183
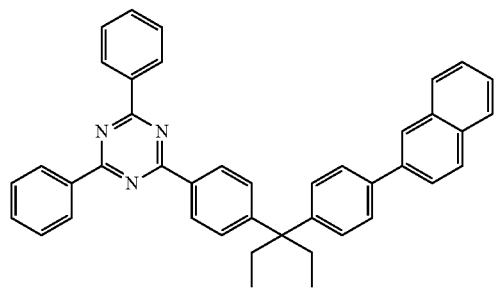
Compound 184
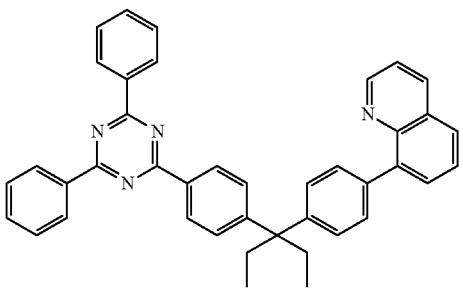
Compound 185
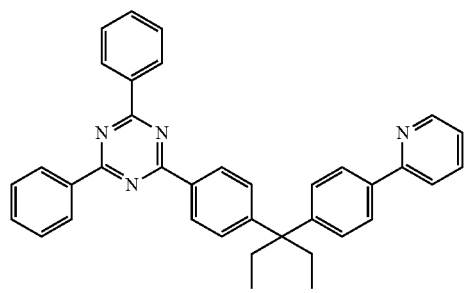
Compound 186
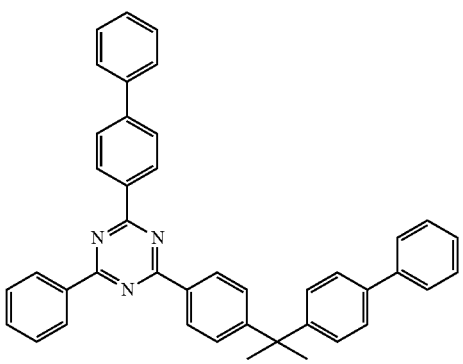

-continued
Compound 187
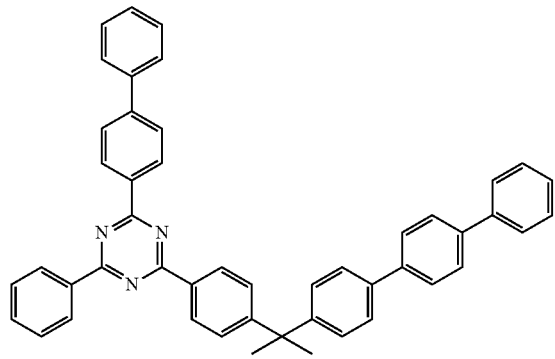
Compound 188
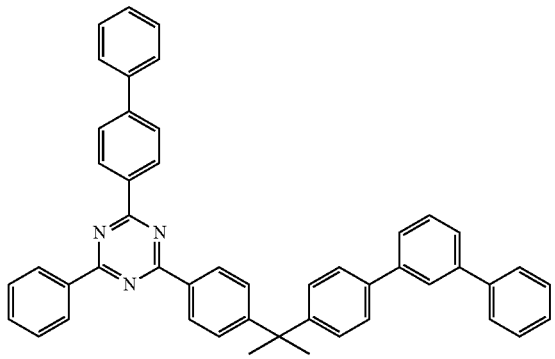
Compound 189
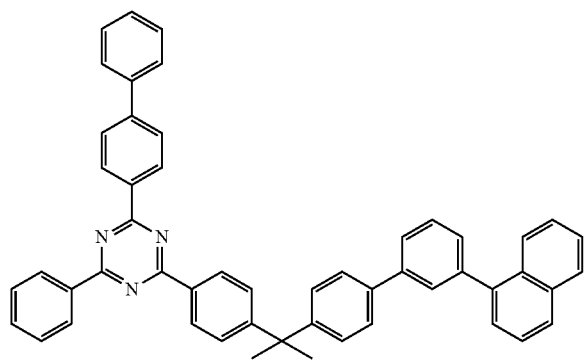
Compound 190
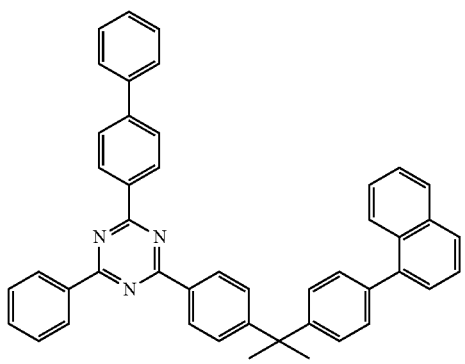
Compound 191
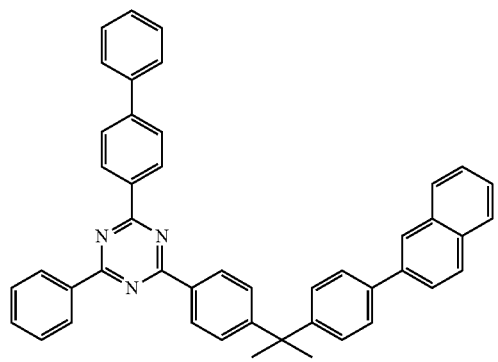
Compound 192
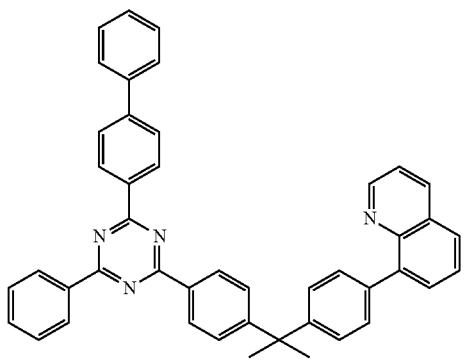
Compound 193
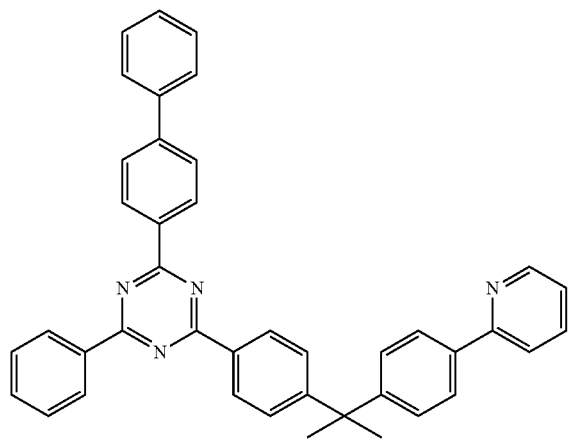
Compound 194
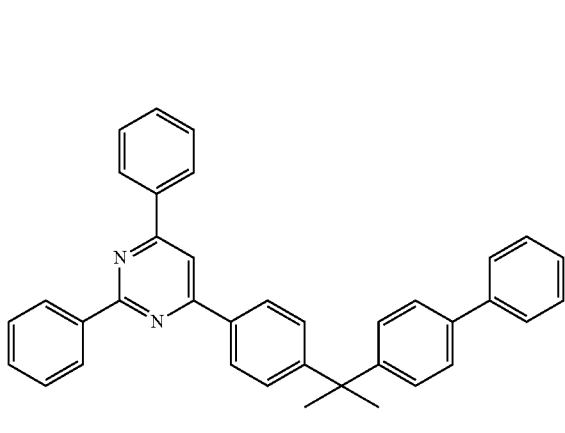

-continued
Compound 195
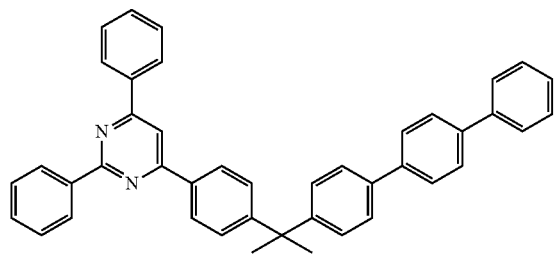
Compound 196
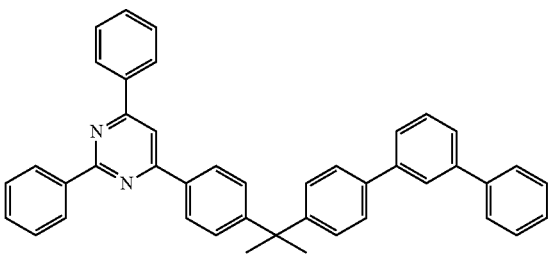
Compound 197
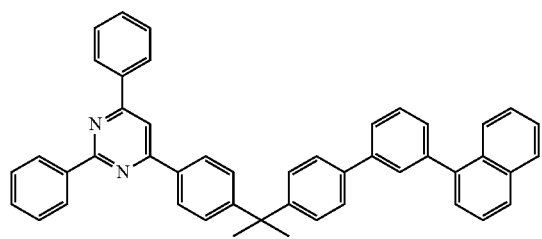
Compound 198
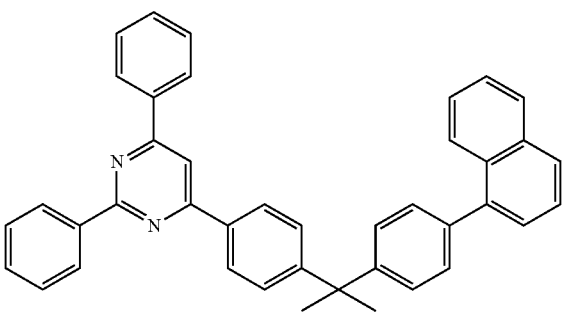
Compound 199
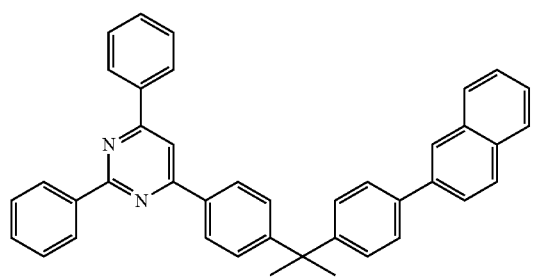
Compound 200
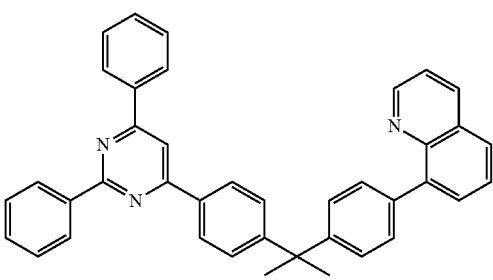
Compound 201
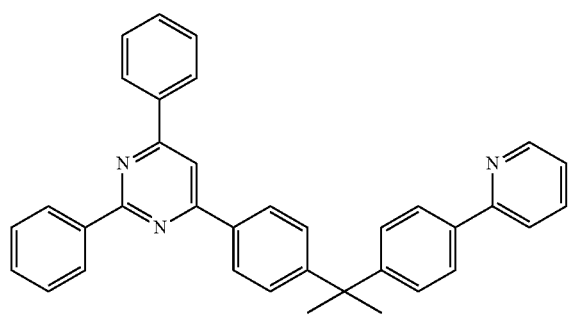
Compound 202
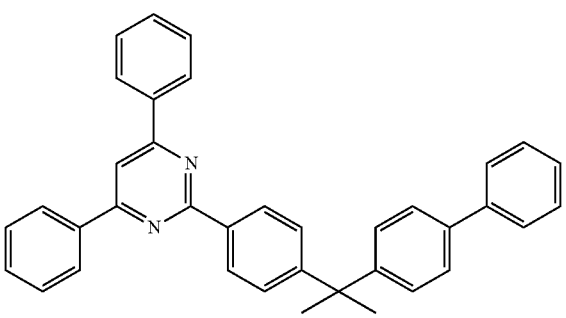
Compound 203
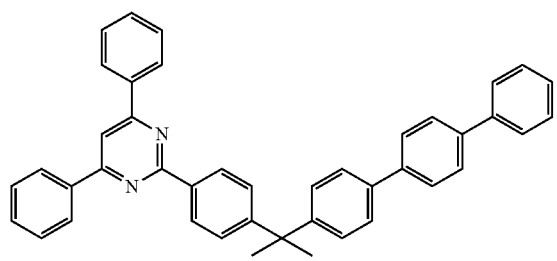
Compound 204
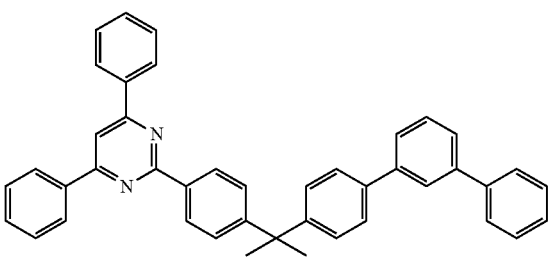

-continued

Compound 205

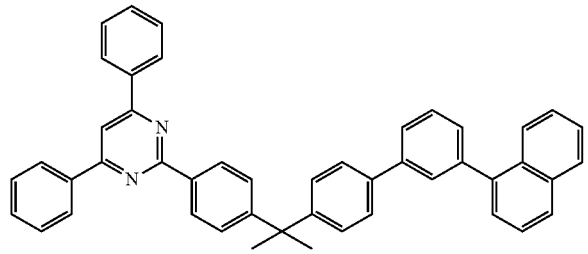

Compound 206

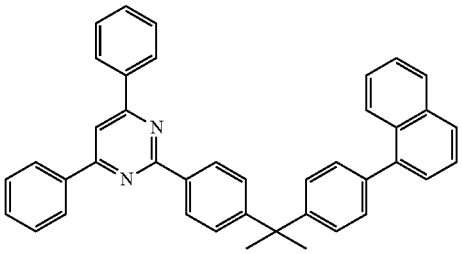

Compound 207

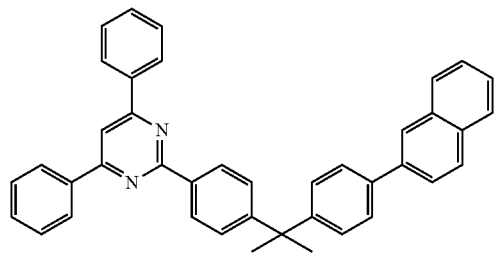

Compound 208

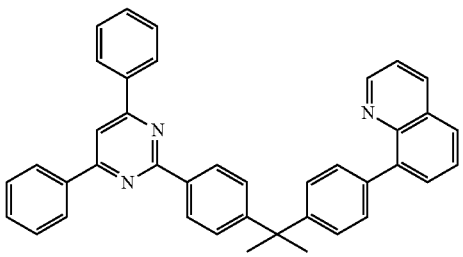

Compound 209

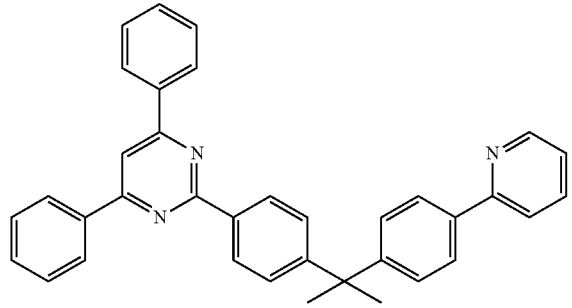

According to one embodiment of the present specification, Chemical Formula a is represented by any one of Chemical Formulae a-1 to a-3.

[Chemical Formula a-1]

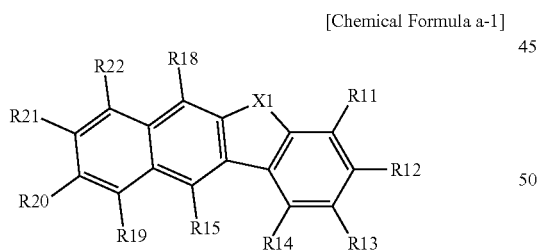

[Chemical Formula a-2]

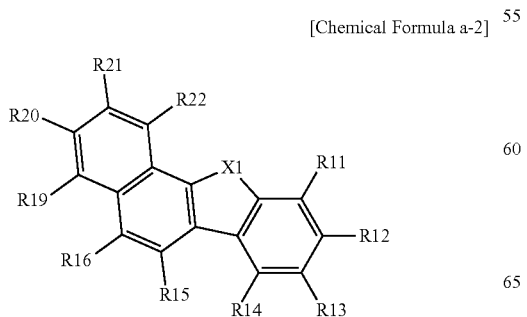

[Chemical Formula a-3]

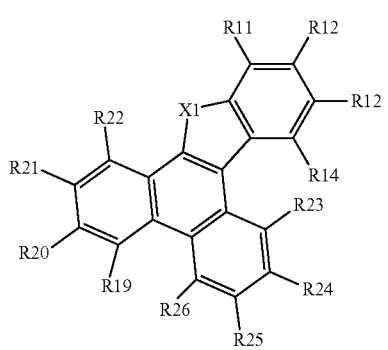

In Chemical Formulae a-1 to a-3,

X1 and R11 to R16 and R18 have the same definitions as in Chemical Formula a, and R19 to R26 are the same as or different from each other, and each independently hydrogen; halogen; a hydroxyl group; a nitrile group; a substituted or unsubstituted amine group; a substituted or unsubstituted linear or branched alkyl group having 1 to 20 carbon atoms; a substituted or unsubstituted linear or branched alkoxy group having 1 to 20 carbon atoms; a substituted or unsubstituted monocyclic or multicyclic aryloxy group having 6 to 30 carbon atoms; a substituted or unsubstituted monocyclic or multicyclic arylthioxy group having 6 to 30 carbon atoms; a substituted or unsubstituted monocyclic or multicyclic aryl group having 6 to 30 carbon atoms; or a substituted or unsubstituted monocyclic or multicyclic heteroaryl group having 5 to 30 carbon atoms, or adjacent groups may bond to each other to form a substituted or unsubstituted ring.

According to one embodiment of the present specification, the anthracene derivative represented by Chemical Formula 2 is represented by any one of the following Chemical Formulae 2-1 to 2-5.

[Chemical Formula 2-1]

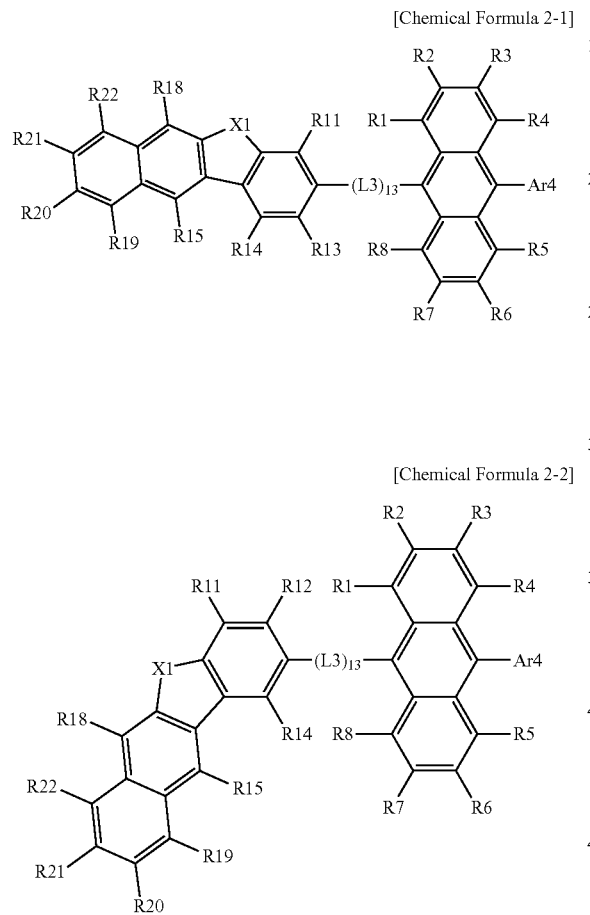

[Chemical Formula 2-2]

[Chemical Formula 2-3]

[Chemical Formula 2-4]

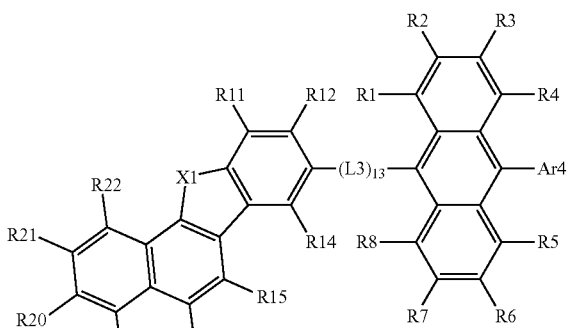

[Chemical Formula 2-5]

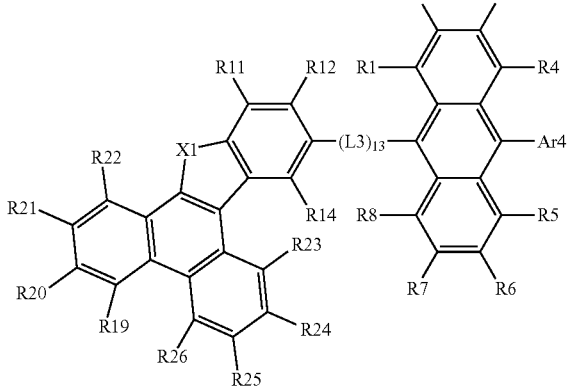

In Chemical Formulae 2-1 to 2-5,

R1 to R8, L3, l3 and Ar4 have the same definitions as in Chemical Formula 2,

X1 and R11 to R18 have the same definitions as in Chemical Formula a, and

R19 to R26 are the same as or different from each other, and each independently hydrogen; halogen; a hydroxyl group; a nitrile group; a substituted or unsubstituted amine group; a substituted or unsubstituted linear or branched alkyl group having 1 to 20 carbon atoms; a substituted or unsubstituted linear or branched alkoxy group having 1 to 20 carbon atoms; a substituted or unsubstituted monocyclic or multicyclic aryloxy group having 6 to 30 carbon atoms; a substituted or unsubstituted monocyclic or multicyclic arylthioxy group having 6 to 30 carbon atoms; a substituted or unsubstituted monocyclic or multicyclic aryl group having 6 to 30 carbon atoms; or a substituted or unsubstituted monocyclic or multicyclic heteroaryl group having 5 to 30 carbon atoms, or adjacent groups may bond to each other to form a substituted or unsubstituted ring.

According to one embodiment of the present specification, l3 is 1.

According to one embodiment of the present specification, l3 is 2.

According to one embodiment of the present specification, L3 is a direct bond; a substituted or unsubstituted monocyclic or multicyclic arylene group having 6 to 20 carbon atoms; or a substituted or unsubstituted monocyclic or multicyclic heteroarylene group having 5 to 20 carbon atoms.

According to one embodiment of the present specification, L3 is a direct bond; a substituted or unsubstituted phenylene group; or a substituted or unsubstituted divalent dibenzofuran group.

According to one embodiment of the present specification, L3 is a direct bond; a phenylene group; or a divalent dibenzofuran group.

According to one embodiment of the present specification, Ar4 is a substituted or unsubstituted monocyclic or multicyclic aryl group having 6 to 20 carbon atoms; or a substituted or unsubstituted monocyclic or multicyclic heteroaryl group having 5 to 20 carbon atoms.

According to one embodiment of the present specification, Ar4 is a substituted or unsubstituted phenyl group; a substituted or unsubstituted biphenyl group; a substituted or unsubstituted terphenyl group; a substituted or unsubstituted naphthyl group; a substituted or unsubstituted phenanthrenyl group; a substituted or unsubstituted pyrenyl group; a substituted or unsubstituted triphenylenyl group; a substituted or unsubstituted carbazolyl group; a substituted or unsubstituted dibenzofuranyl group; a substituted or unsubstituted dibenzothiophene group; or a substituted or unsubstituted benzonaphthofuranyl group.

According to one embodiment of the present specification, Ar4 is a phenyl group unsubstituted or substituted with an aryl group or a heteroaryl group; a biphenyl group unsubstituted or substituted with an aryl group; a terphenyl group; a naphthyl group; a phenanthrenyl group; a pyrenyl group; a triphenylenyl group; a carbazolyl group unsubstituted or substituted with an aryl group; a dibenzofuranyl group; a dibenzothiophene group; or a benzonaphthofuranyl group.

According to one embodiment of the present specification, Ar4 is a phenyl group unsubstituted or substituted with a phenyl group, a biphenyl group, a naphthyl group or a dibenzofuranyl group; a biphenyl group unsubstituted or substituted with a phenyl group; a terphenyl group; a naphthyl group; a phenanthrenyl group; a pyrenyl group; a triphenylenyl group; a carbazolyl group unsubstituted or substituted with a phenyl group; a dibenzofuranyl group; a dibenzothiophene group; or a benzonaphthofuranyl group.

According to one embodiment of the present specification, R1 to R8 are the same as or different from each other, and each independently hydrogen; or a substituted or unsubstituted monocyclic or multicyclic aryl group having 6 to 30 carbon atoms.

According to one embodiment of the present specification, R1 to R8 are the same as or different from each other, and each independently hydrogen; or a substituted or unsubstituted phenyl group.

According to one embodiment of the present specification, R1 to R8 are the same as or different from each other, and each independently hydrogen; or a phenyl group.

According to one embodiment of the present specification, in Chemical Formula a, X1 is O.

According to one embodiment of the present specification, in Chemical Formula a, X1 is S.

According to one embodiment of the present specification, in Chemical Formula a, R15 and R16 bond to each other to form a substituted or unsubstituted ring.

According to one embodiment of the present specification, in Chemical Formula a, R15 and R16 bond to each other to form a substituted or unsubstituted aromatic hydrocarbon ring.

According to one embodiment of the present specification, in Chemical Formula a, R15 and R16 bond to each other to form a substituted or unsubstituted benzene ring.

According to one embodiment of the present specification, in Chemical Formula a, R15 and R16 bond to each other to form a benzene ring.

According to one embodiment of the present specification, in Chemical Formula a, R16 and R17 bond to each other to form a substituted or unsubstituted ring.

According to one embodiment of the present specification, in Chemical Formula a, R16 and R17 bond to each other to form a substituted or unsubstituted aromatic hydrocarbon ring.

According to one embodiment of the present specification, in Chemical Formula a, R16 and R17 bond to each other to form a substituted or unsubstituted benzene ring.

According to one embodiment of the present specification, in Chemical Formula a, R16 and R17 bond to each other to form a benzene ring.

According to one embodiment of the present specification, in Chemical Formula a, R17 and R18 bond to each other to form a substituted or unsubstituted ring.

According to one embodiment of the present specification, in Chemical Formula a, R17 and R18 bond to each other to form a substituted or unsubstituted aromatic hydrocarbon ring.

According to one embodiment of the present specification, in Chemical Formula a, R17 and R18 bond to each other to form a substituted or unsubstituted benzene ring.

According to one embodiment of the present specification, in Chemical Formula a, R17 and R18 bond to each other to form a benzene ring.

According to one embodiment of the present specification, the anthracene derivative represented by Chemical Formula 2 is represented by any one of the following compounds.

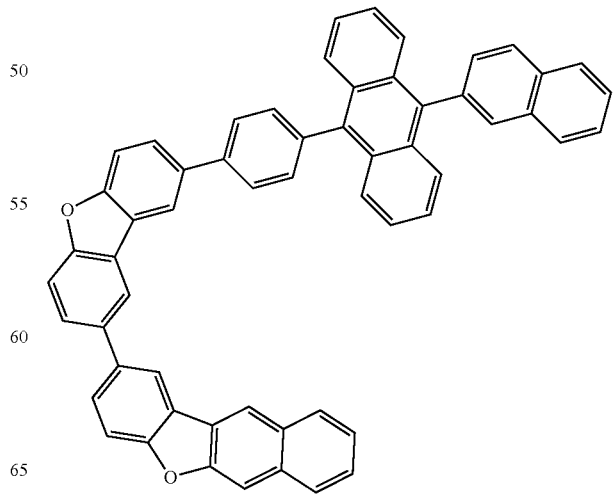

compound 2-1 compound 2-2
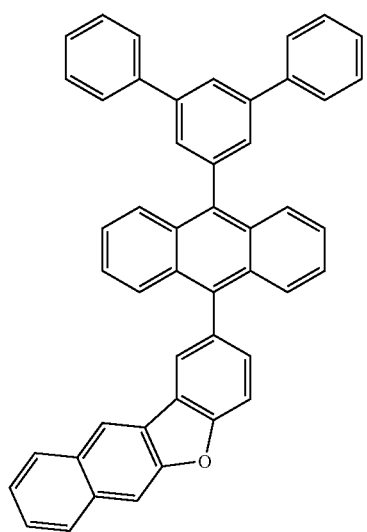
compound 2-3
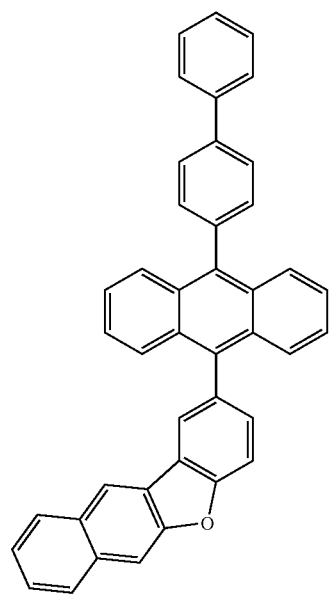
compound 2-4
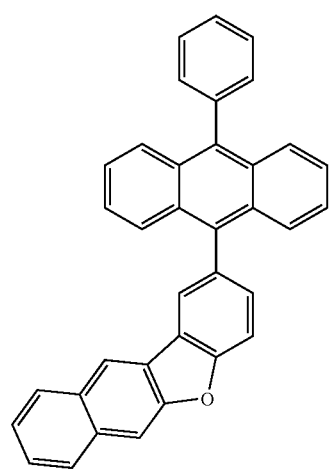
compound 2-5
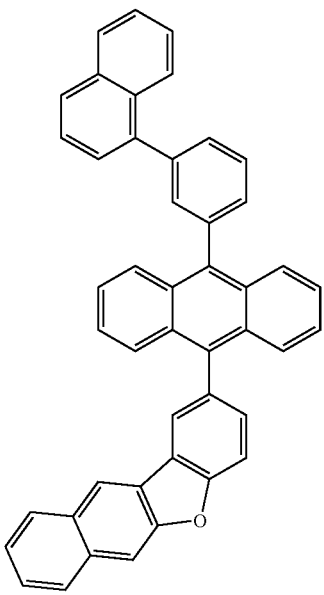
compound 2-6
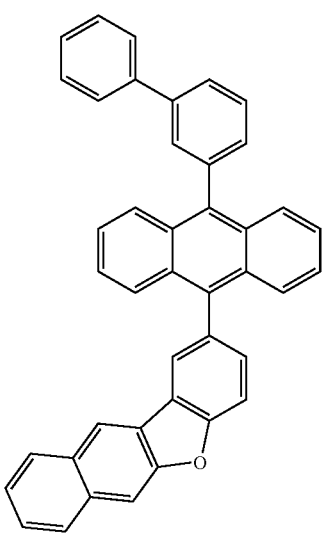
compound 2-7
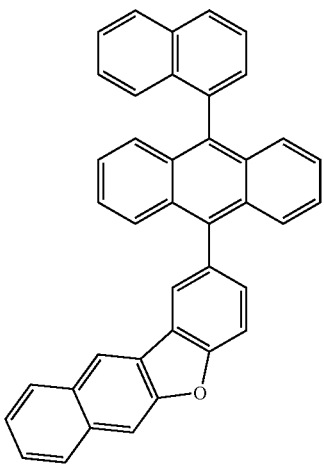

compound 2-8
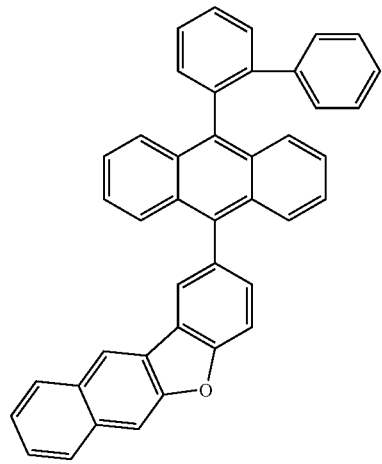
compound 2-9
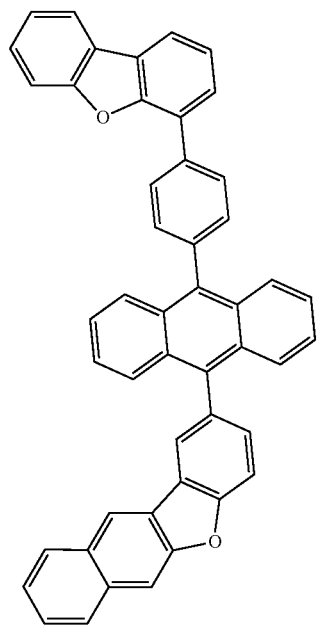
compound 2-10
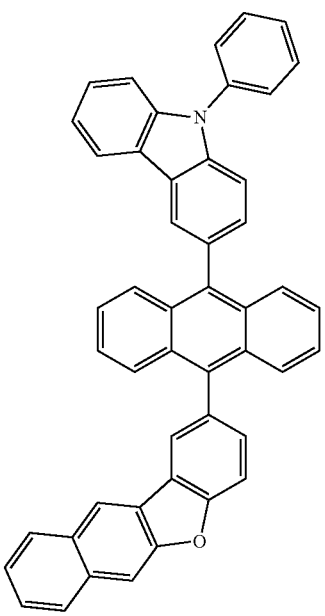
compound 2-11
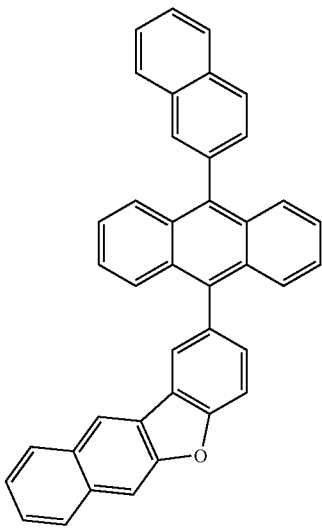

compound 2-12
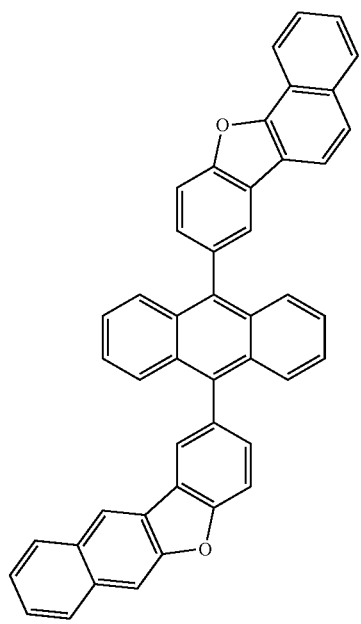
compound 2-14
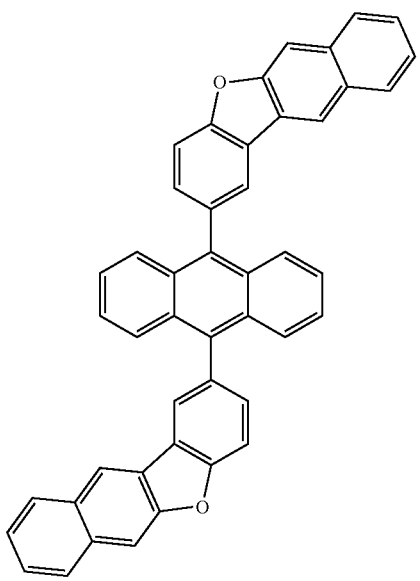
compound 2-13
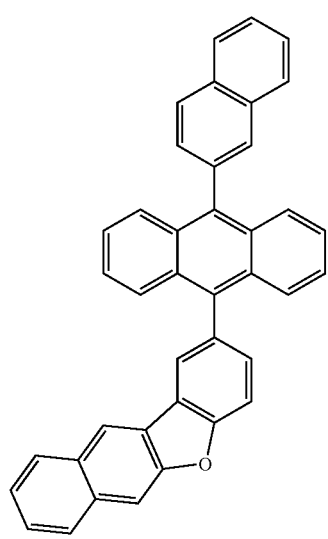
compound 2-15
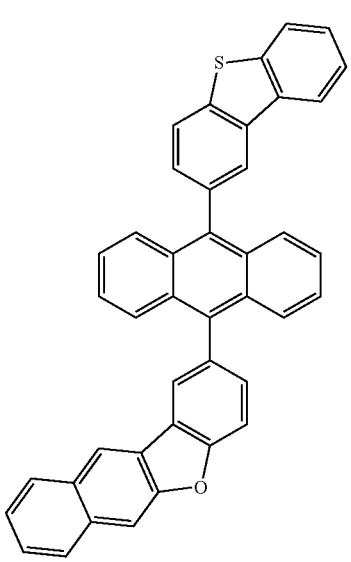

compound 2-16
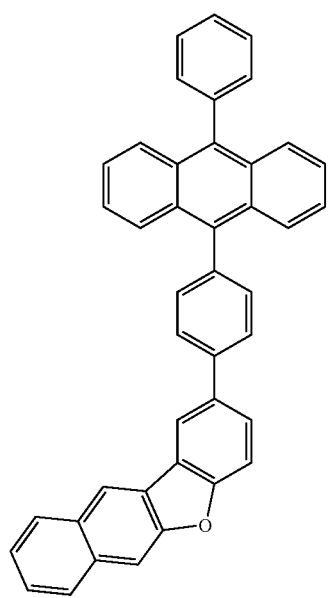
compound 2-17
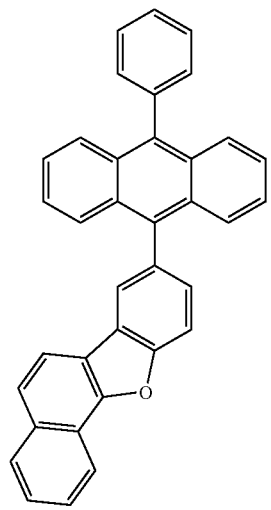
compound 2-18
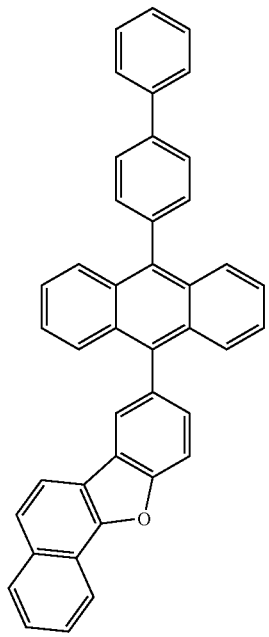
compound 2-19
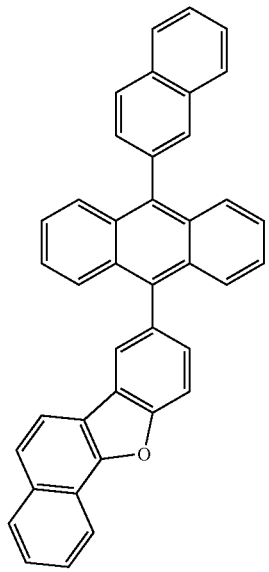

compound 2-20
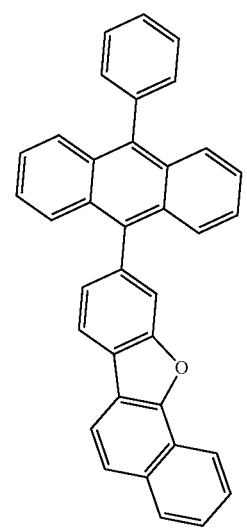
compound 2-21
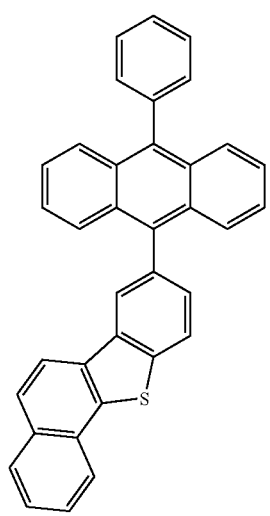
compound 2-22
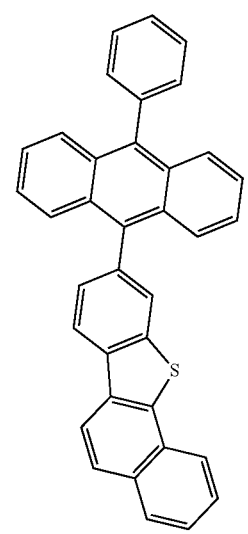
compound 2-23
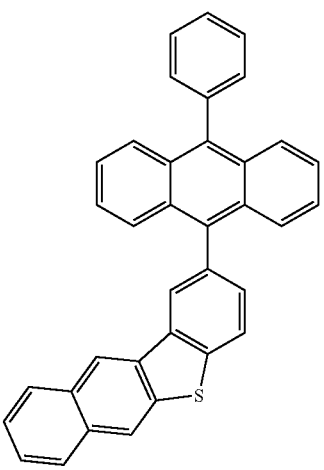
compound 2-24
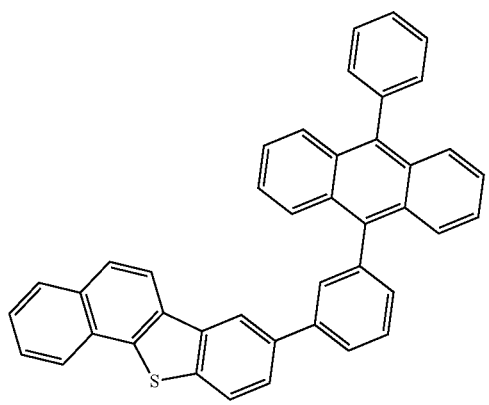
compound 2-25
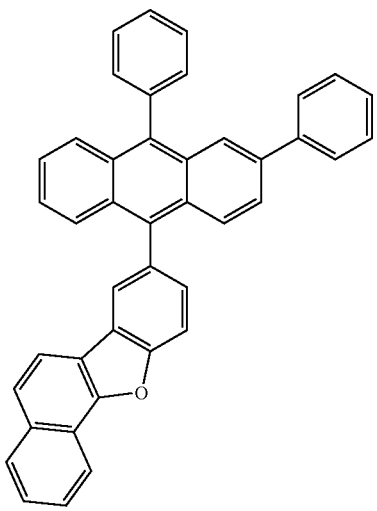

-continued
compound 2-26
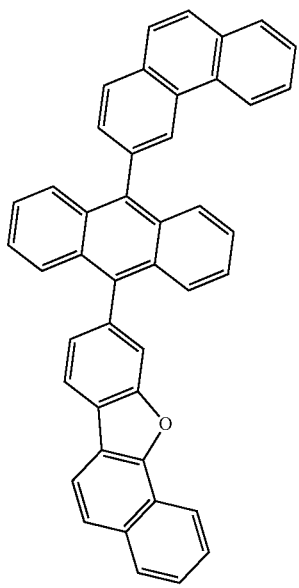
compound 2-28
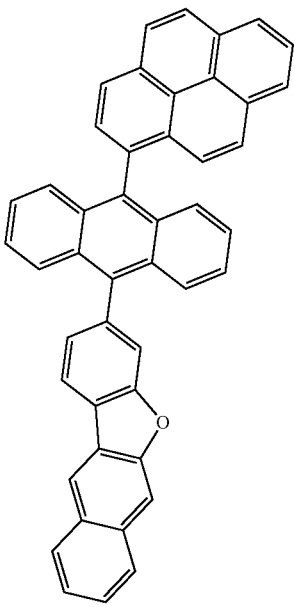
compound 2-29
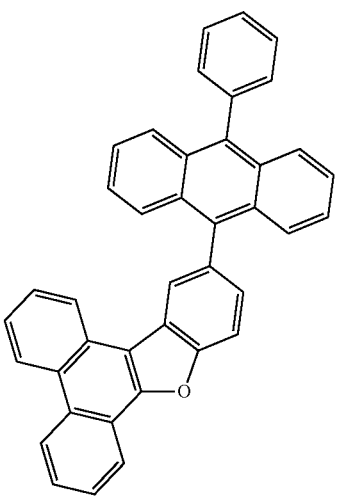
compound 2-27
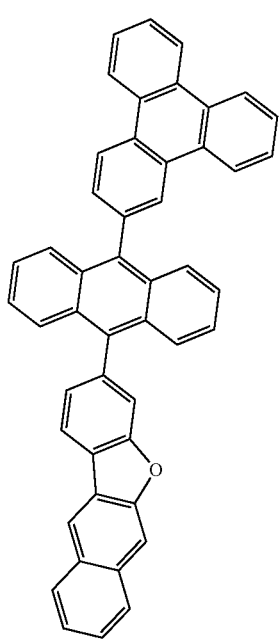
compound 2-30
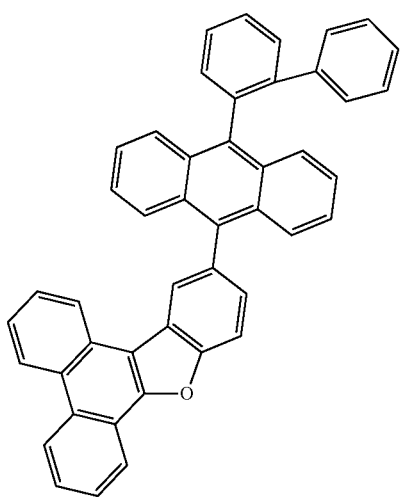

compound 2-31
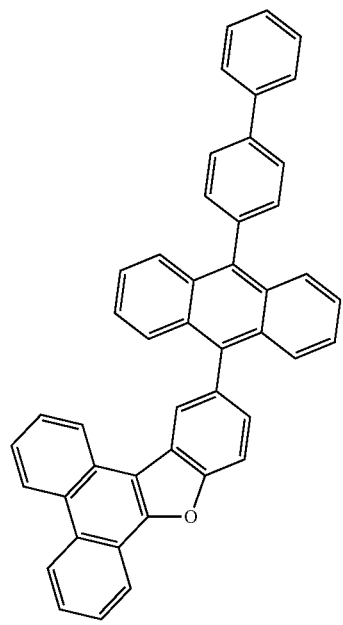
compound 2-34
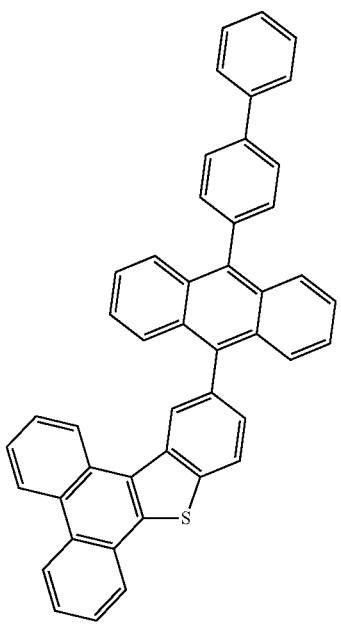
compound 2-32
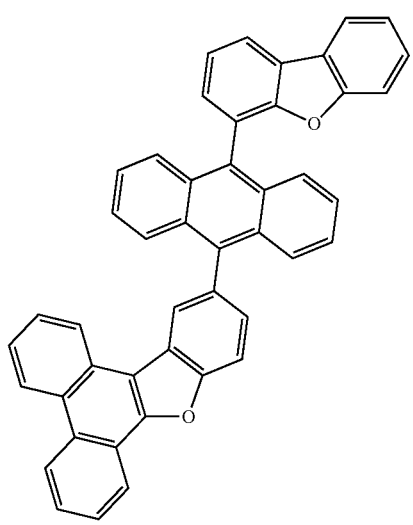
compound 2-33
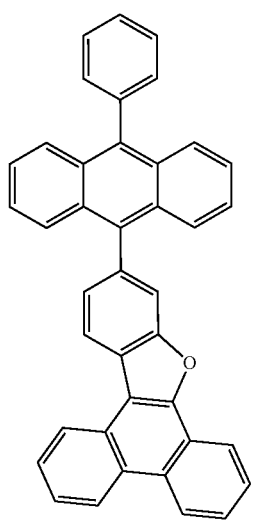
compound 2-35
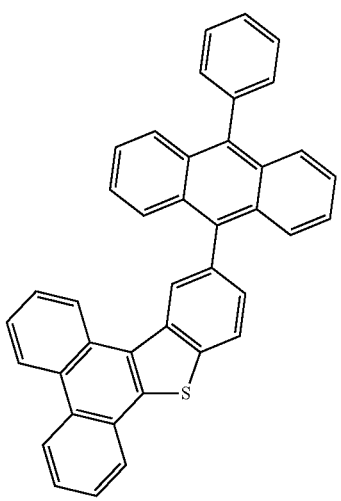

compound 2-36

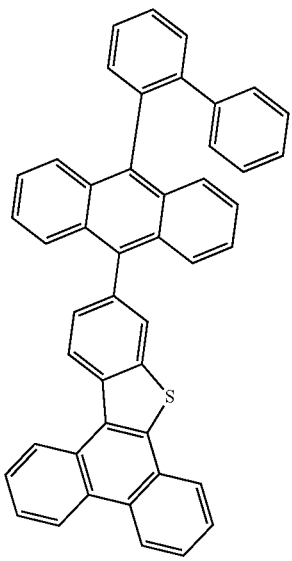

compound 2-37

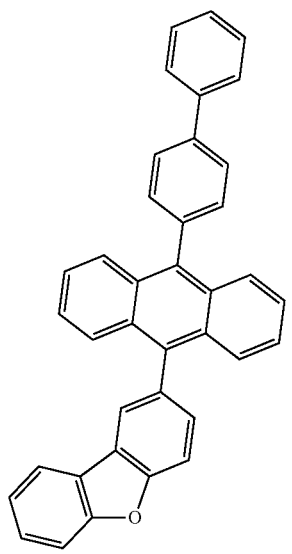

compound 2-38

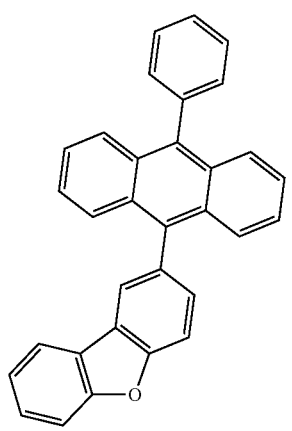

According to one embodiment of the present specification, the anthracene derivative represented by Chemical Formula 2 is in 30 mol % to 100 mol % based on the total weight of the light emitting layer.

Examples of materials capable of being used in the light emitting layer together with the anthracene derivative represented by Chemical Formula 2 may include fused multicyclic aromatic compounds such as naphthalene, phenanthrene, rubrene, anthracene, tetracene, pyrene, perylene, chrysene, decacyclene, coronene, tetraphenylcyclopentadiene, pentaphenylcyclopentadiene, fluorenene or spirofluorene and derivatives thereof, organic metal complexes such as tris(8-quinolinolate)aluminum, triarylamine derivatives, styrylamine derivatives, stilbene derivatives, coumarin derivatives, pyran derivatives, oxazone derivatives, benzothiazole derivatives, benzoxazole derivatives, benzimidazole derivatives, pyrazine derivatives, cinnamate derivatives, diketopyrrolopyrrole derivatives, acridone derivatives, quinacridone derivatives and the like, but are not limited thereto.

In the organic light emitting device, the light emitting layer may contain light emitting dopants (phosphorescent dopants and/or fluorescent dopants) in addition to the above-mentioned light emitting materials. In addition, a light emitting layer including these dopants may be laminated on the light emitting layer including the anthracene derivative represented by Chemical Formula 2.

The fluorescent dopant is a compound capable of emitting light from singlet excitons. The fluorescent dopant is preferably a compound selected from among, depending on the required light emitting colors, amine-based compounds, aromatic compounds, chelate complexes such as tris(8-quinolinolate)aluminum complexes, coumarin derivatives, tetraphenyl butadiene derivatives, bisstyrylarylene derivatives, oxadiazole derivatives and the like, and styrylamine compounds, styryldiamine compounds, arylamine compounds, aryldiamine compounds are more preferred, and arylamine derivatives are even more preferred. This fluorescent dopant may be used either alone or as a combination of a plurality of these.

According to one embodiment of the present specification, the anthracene derivative represented by Chemical Formula 2 is a host material of the light emitting layer.

According to one embodiment of the present specification, the light emitting layer may further contain a dopant material.

According to one embodiment of the present specification, the dopant material may be an arylamine compound or a styrylamine compound.

According to one embodiment of the present specification, the dopant material is an amine derivative represented by the following Chemical Formula 3.

[Chemical Formula 3]

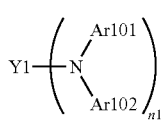

In Chemical Formula 3,

Y1 is a substituted or unsubstituted multicyclic mono to tetravalent aromatic hydrocarbon group having 10 to 50 carbon atoms, Ar101 and Ar102 are the same as or different from each other, and each independently a substituted or unsubstituted monocyclic or multicyclic aryl group having 6 to 50 carbon atoms; or a monocyclic or multicyclic heteroaryl group having 2 to 50 carbon atoms, n1 is an integer of 1 to 4, and when n1 is 2 or greater, structures in the two or more parentheses are the same as or different from each other.

In the present specification, the mono to tetravalent aromatic hydrocarbon group may be monocyclic or multicyclic, and means having 1 to 4 bonding sites in the aryl group, that is, a mono to tetravalent group. Descriptions on the aryl group provided above may be applied thereto except that these are each a mono to tetravalent group.

According to one embodiment of the present specification, n1 is 2.

According to one embodiment of the present specification, Y1 is a substituted or unsubstituted divalent chrysene group; a substituted or unsubstituted divalent pyrene group; and a substituted or unsubstituted divalent anthracene group.

According to one embodiment of the present specification, Chemical Formula 3 is an amine derivative represented by any one of the following Chemical Formulae 3-1 to 3-4.

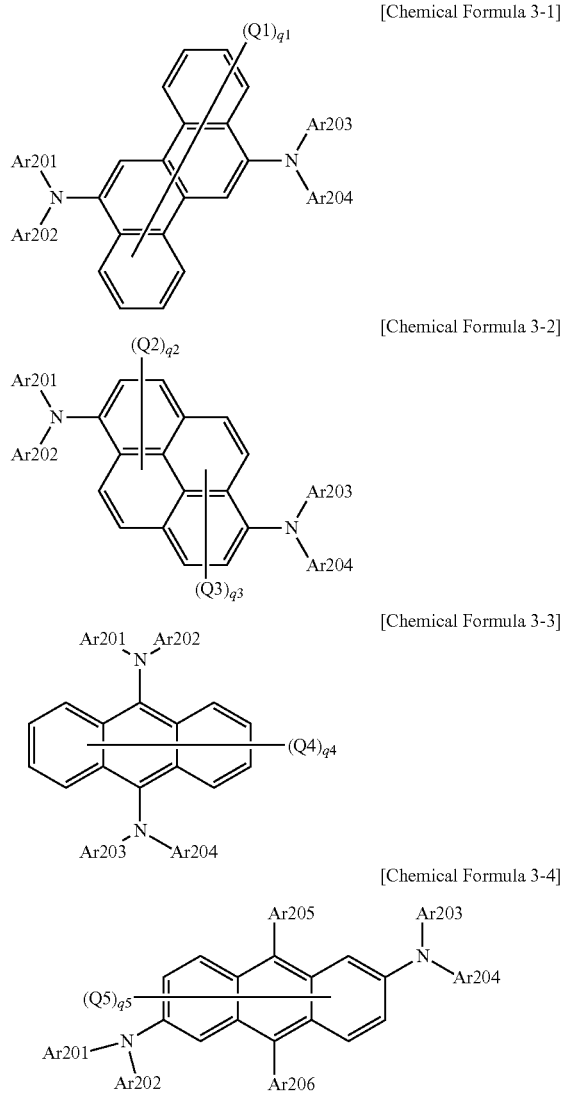

In Chemical Formulae 3-1 to 3-4,

Ar201 to Ar206 are the same as or different from each other, and each independently a substituted or unsubstituted monocyclic or multicyclic aryl group having 6 to 50 carbon atoms; or a monocyclic or multicyclic heteroaryl group having 2 to 50 carbon atoms, Q1 to Q5 are the same as or different from each other, and each independently hydrogen; halogen; a hydroxyl group; a nitrile group; a substituted or unsubstituted amine group; a substituted or unsubstituted linear or branched alkyl group having 1 to 20 carbon atoms; a substituted or unsubstituted linear or branched alkoxy group having 1 to 20 carbon atoms; a substituted or unsubstituted monocyclic or multicyclic aryloxy group having 6 to 30 carbon atoms; a substituted or unsubstituted monocyclic or multicyclic arylthioxy group having 6 to 30 carbon atoms; a substituted or unsubstituted monocyclic or multicyclic aryl group having 6 to 30 carbon atoms; or a substituted or unsubstituted monocyclic or multicyclic heteroaryl group having 5 to 30 carbon atoms, q1 is an integer of 1 to 10, q2 and q3 are each an integer of 1 to 4, q4 is an integer of 1 to 8, q5 is an integer of 1 to 6, and when q1 to q5 are each 2 or greater, structures in the two or more parentheses are the same as or different from each other.

According to one embodiment of the present specification, Ar101 and Ar102 are the same as or different from each other, and each independently a substituted or unsubstituted monocyclic or multicyclic aryl group having 6 to 20 carbon atoms; or a substituted or unsubstituted monocyclic or multicyclic heteroaryl group having 2 to 20 carbon atoms.

According to one embodiment of the present specification, Ar101 and Ar102 are the same as or different from each other, and each independently a monocyclic or multicyclic aryl group having 6 to 20 carbon atoms unsubstituted or substituted with an alkyl group; or a monocyclic or multicyclic heteroaryl group having 2 to 20 carbon atoms unsubstituted or substituted with an alkyl group.

According to one embodiment of the present specification, Ar101 and Ar102 are the same as or different from each other, and each independently a phenyl group unsubstituted or substituted with an alkyl group; or a dibenzofuranyl group unsubstituted or substituted with an alkyl group.

According to one embodiment of the present specification, Ar101 and Ar102 are the same as or different from each other, and each independently a phenyl group unsubstituted or substituted with a methyl group; or a dibenzofuranyl group unsubstituted or substituted with a t-butyl group.

According to one embodiment of the present specification, Ar201 to Ar206 are the same as or different from each other, and each independently a substituted or unsubstituted monocyclic or multicyclic aryl group having 6 to 20 carbon atoms; or a substituted or unsubstituted monocyclic or multicyclic heteroaryl group having 2 to 20 carbon atoms.

According to one embodiment of the present specification, Ar201 to Ar206 are the same as or different from each other, and each independently a monocyclic or multicyclic aryl group having 6 to 20 carbon atoms unsubstituted or substituted with an alkyl group; or a monocyclic or multicyclic heteroaryl group having 2 to 20 carbon atoms unsubstituted or substituted with an alkyl group.

According to one embodiment of the present specification, Ar201 to Ar206 are the same as or different from each other, and each independently a phenyl group unsubstituted or substituted with an alkyl group; or a dibenzofuranyl group unsubstituted or substituted with an alkyl group.

According to one embodiment of the present specification, Ar201 to Ar206 are the same as or different from each other, and each independently a phenyl group unsubstituted or substituted with a methyl group; or a dibenzofuranyl group unsubstituted or substituted with a t-butyl group.

According to one embodiment of the present specification, Chemical Formula 3 is an amine derivative represented by any one of the following Compounds 3-1 to 3-6.

[compound 3-1]

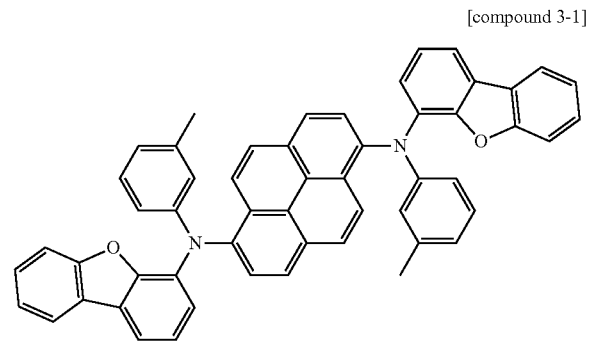

[compound 3-2]

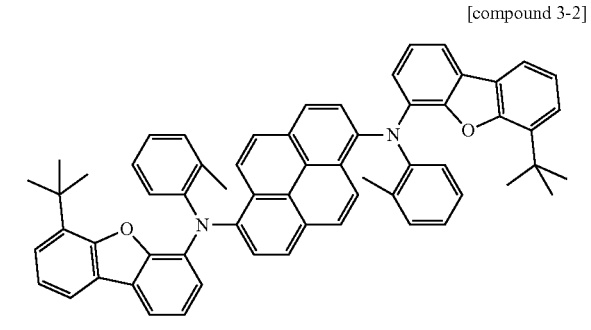

[compound 3-3]

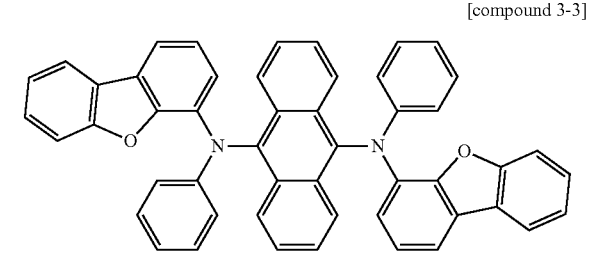

[compound 3-4]

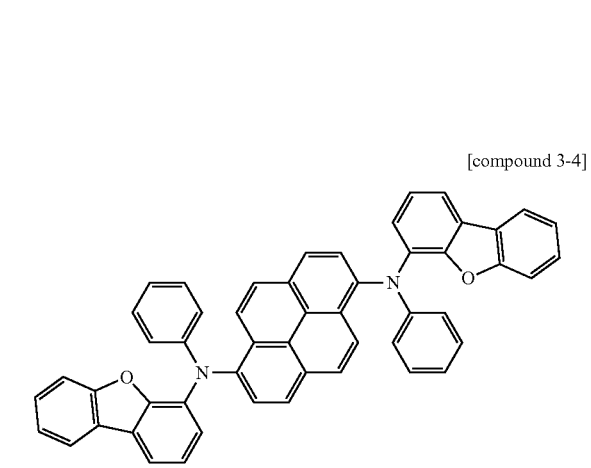

[compound 3-5]

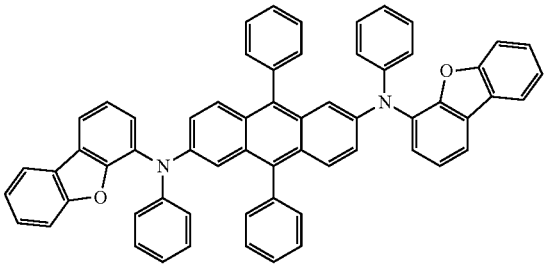

[compound 3-6]

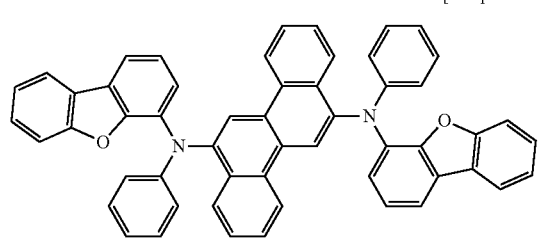

The organic light emitting device according to one embodiment of the present specification may be manufactured using materials and methods known in the art, except that the anthracene derivative represented by Chemical Formula 2 described above is included in the light emitting layer, and the cyclic compound represented by Chemical Formula 1 described above is included between the cathode and the light emitting layer.

For example, the organic light emitting device of the present specification may be manufactured by consecutively laminating an anode, an organic material layer and a cathode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, an electron blocking layer, a light emitting layer, an electron transfer layer and an electron injection layer thereon, and then depositing a material capable of being used as a cathode thereon. In addition to such a method, the organic light emitting device may be manufactured by consecutively depositing a cathode material, an organic material layer and an anode material on a substrate. In addition to such a method, the organic light emitting device may also be manufactured by consecutively depositing an anode material, an organic material layer and a cathode material on a substrate.

The organic material layer of the organic light emitting device of the present specification may be formed in a multilayer in which one or more organic material layers are laminated.

In one embodiment of the present specification, the organic light emitting device may further include one, two or more layers selected from the group consisting of a hole injection layer, a hole transfer layer, an electron transfer layer, an electron injection layer, an electron blocking layer and a hole blocking layer.

For example, structures of the organic light emitting device of the present specification may be as illustrated in FIG. 1 and FIG. 2, but are not limited thereto.

FIG. 1 illustrates a structure of an organic light emitting device in which an anode (201), a hole transfer layer (301), a light emitting layer (401), an electron transfer layer (501) and a cathode (601) are consecutively laminated on a substrate (101). In FIG. 1, the electron transfer layer (501) includes the cyclic compound represented by Chemical Formula 1, and the light emitting layer (401) includes the anthracene derivative represented by Chemical Formula 2.

FIG. 1 is an illustrative structure according to an embodiment of the present specification, and other organic material layers may be further included.

When the organic light emitting device includes a plurality of organic material layers, the organic material layers may be formed with materials the same as or different from each other.

As the anode material, materials having large work function are normally preferable so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferable so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition thereto, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suitable. Specific examples thereof include arylamine-based organic materials, conductive polymers, block copolymers having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$); carbazole series compounds; dimerized styryl compounds; BAlq; 10-hydroxybenzo quinoline-metal compounds; benzoxazole, benzothiazole and benzimidazole series compounds; poly(p-phenylenevinylene) (PPV) series polymers; spiro compounds; polyfluorene, rubrene, and the like, but are not limited thereto.

The light emitting layer may include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, but the material is not limited thereto.

As the host material of the fluorescent light emitting layer, one, two or more are selected from the group consisting of distyrylarylene (DSA), distyrylarylene derivatives, distyrylbenzene (DSB), distyrylbenzene derivatives, 4,4'-bis(2,2'-diphenyl vinyl)-1,1'-biphenyl (DPVBi), DPVBi derivatives, spiro-DPVBi and spiro-6P.

As a dopant material of the fluorescent light emitting layer, one, two or more are selected from the group consisting of styrylamine-based, perylene-based and distyrylbiphenyl (DSBP)-based.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition thereto, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)berylium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium and the like, but is not limited thereto.

The hole blocking layer is a layer blocking holes from reaching a cathode and generally, may be formed under the same condition as the hole injection layer. Specifically, oxadiazole derivatives, triazole derivatives, phenanthroline derivatives, BCP, aluminum complexes and the like are included, however, the hole blocking layer is not limited thereto.

The organic light emitting device according to the present specification may be a top-emission type, a bottom-emission type or a dual-emission type depending on the materials used.

In addition, the organic light emitting device according to the present specification may be a normal type in which a lower electrode is an anode and an upper electrode is a cathode, and may also be an inverted type in which a lower electrode is a cathode and an upper electrode is an anode.

The structure according to one embodiment of the present specification may also be used in organic electronic devices including organic solar cells, organic photo conductors, organic transistors and the like under a similar principle as in organic light emitting devices.

Hereinafter, the present specification will be described in detail with reference to examples. However, the examples according to the present specification may be modified to various other forms, and the scope of the present specification is not to be construed as being limited to the examples described below. Examples of the present specification are provided in order to more completely describe the present specification to those having average knowledge in the art.

Example 1

HOMO energy level and triplet energy ($E_T$) values of the cyclic compound represented by Chemical Formula 1 according to one embodiment of the present specification, and compounds represented by the following Compound 2-4 and the following Compounds ET-A, ET-H, ET-I and ET-J are shown in the following Table 1.

[ET-A]

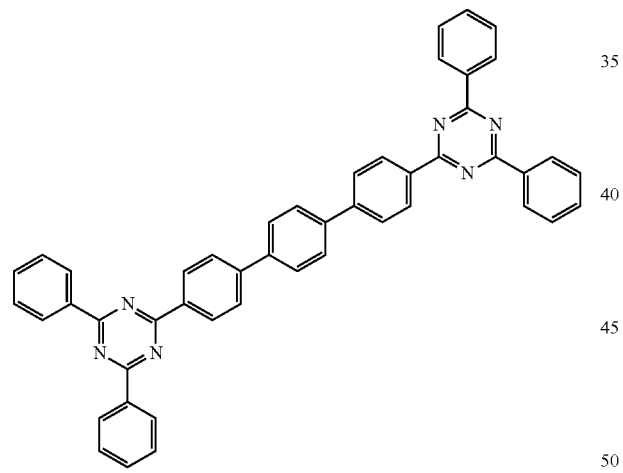

[ET-H]

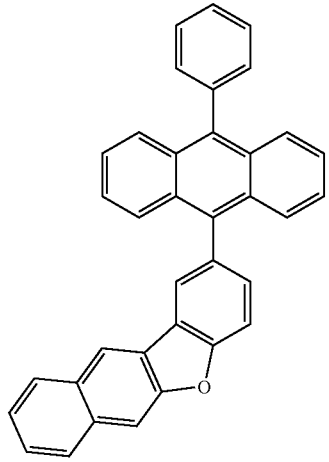

[ET-I]

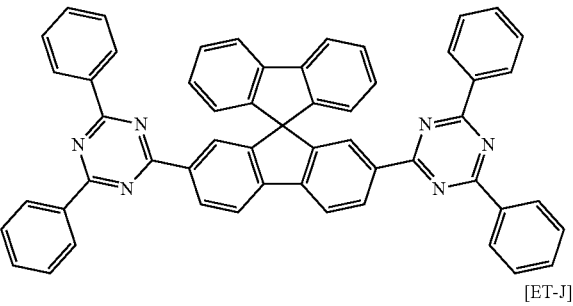

[ET-J]

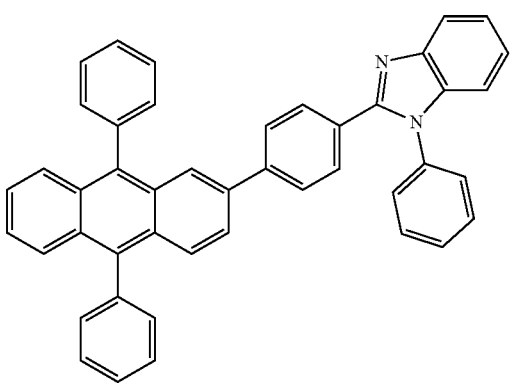

[화합물 2-4]

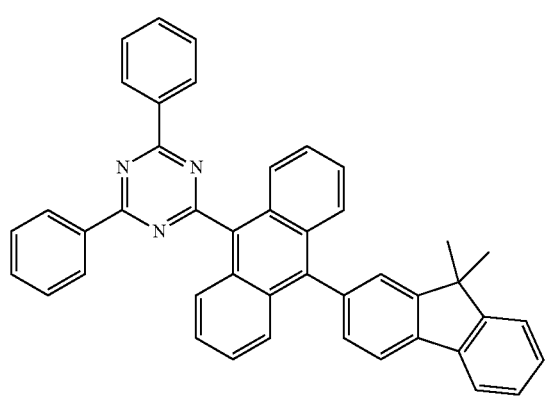

FIGS. 2 and 3 are each a diagram showing a result of data measuring a HOMO (AC3) level of Compounds 1 and 36.

FIGS. 4 to 7 are each a diagram showing a result of data measuring photoluminescence (PL) of Compounds 1, 24, 41 and following compound ET-A.

In examples of the present specification, the HOMO level was measured using an atmospheric pressure photoelectron spectroscopy apparatus (manufactured by RIKEN KEIKI Co., Ltd.: AC3).

In examples of the present specification, the LUMO level was calculated by a wavelength value measured through photoluminescence (PL).

In addition, the triplet energy ($E_T$) was obtained using Gaussian 03, a quantum chemistry calculation program made by Gaussian, Inc. of the US, and using a density functional theory (DFT), the calculated triplet energy value was obtained by a time-dependent density functional theory for an optimized structure using B3LYP as functional and 6-31G* as basis function.

TABLE 1

| Chemical Formula | HOMO (eV) | LUMO (eV) | $E_T$ (eV) |
| --- | --- | --- | --- |
| Compound 1 | 6.37 | 2.92 | 2.9 |
| Compound 2 | 6.41 | 2.91 | 2.91 |
| Compound 12 | 6.29 | 2.89 | 2.77 |
| Compound 13 | 6.24 | 2.80 | 2.76 |
| Compound 36 | 6.24 | 2.95 | 2.85 |
| Compound 38 | 6.30 | 2.90 | 2.84 |
| Compound 56 | 6.20 | 2.90 | 2.87 |
| Compound 75 | 6.44 | 2.97 | 2.70 |
| Compound 2-4 | 5.80 | 2.85 | 1.60 |
| ET-A | 6.17 | 3.10 | 2.57 |
| ET-H | 5.81 | 3.09 | 1.67 |
| ET-I | 6.02 | 3.02 | 2.39 |
| ET-J | 5.7 | 2.87 | 1.56 |

Example 1-1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing the following Compound [HI-A] to a thickness of 600 Å. A hole transfer layer was formed on the hole injection layer by vacuum depositing hexaazatriphenylene (HAT) of the following chemical formula to a thickness of 50 Å and the following Compound [HT-A] (600 Å) in consecutive order.

Subsequently, a light emitting layer was formed on the hole transfer layer to a film thickness of 200 Å by vacuum depositing Compound 2-4 and Compound 3-1 in a weight ratio of 25:1.

On the light emitting layer, an electron injection and transfer layer was formed to a thickness of 350 Å by vacuum depositing Compound 1 and the following lithiumquinolate [LiQ] Compound in a weight ratio of 1:1. A cathode was formed on the electron injection and transfer layer by depositing lithium fluoride (LiF) to a thickness of 10 Å and aluminum to a thickness of 1,000 Å in consecutive order.

An organic light emitting device was manufactured by maintaining, in the above-mentioned processes, the deposition rates of the organic materials at 0.4 Å/sec to 0.9 Å/sec, the deposition rates of the lithium fluoride and the aluminum of the cathode at 0.3 Å/sec and 2 Å/sec, respectively, and the degree of vacuum during the deposition at $2\times10^{-7}$ torr to $5\times10^{-8}$ torr.

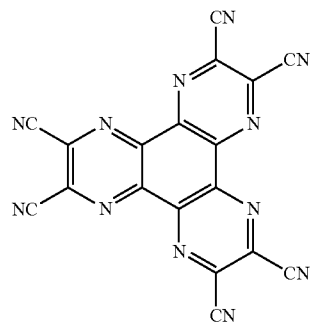
[HAT]

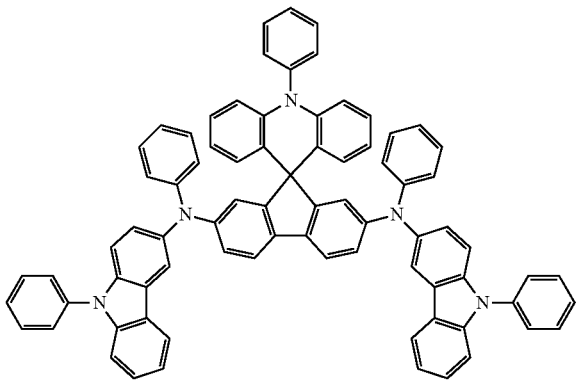
[HI-A]

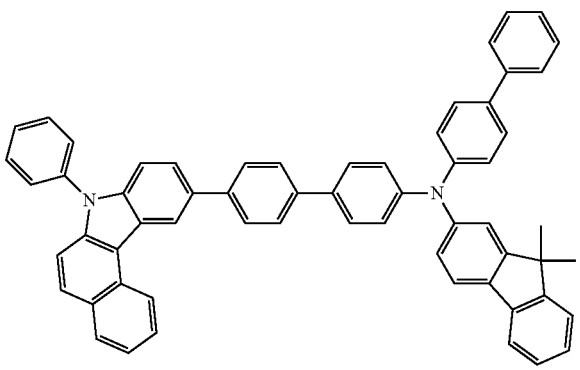
[HT-A]

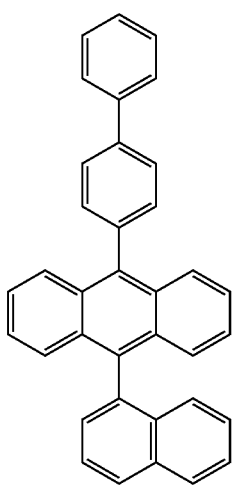
[BH-1]

[BH-2]
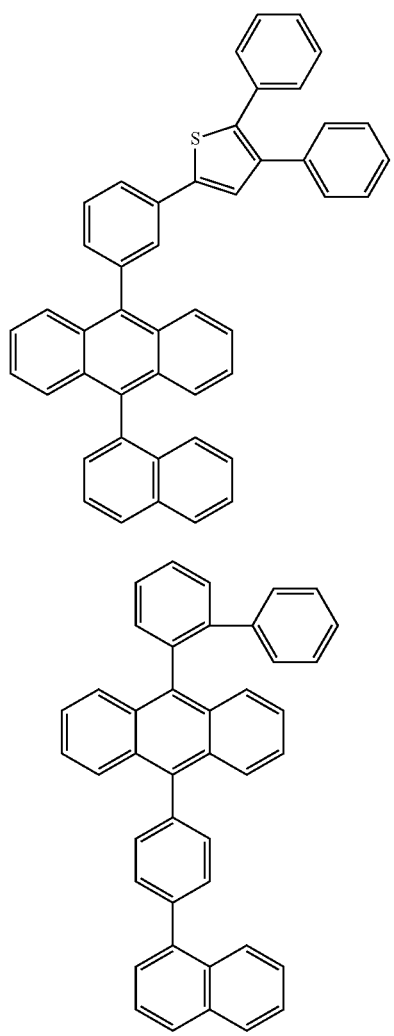
[BH-3]
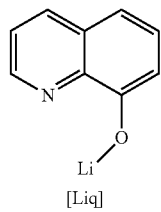
[Liq]
[ET-B]
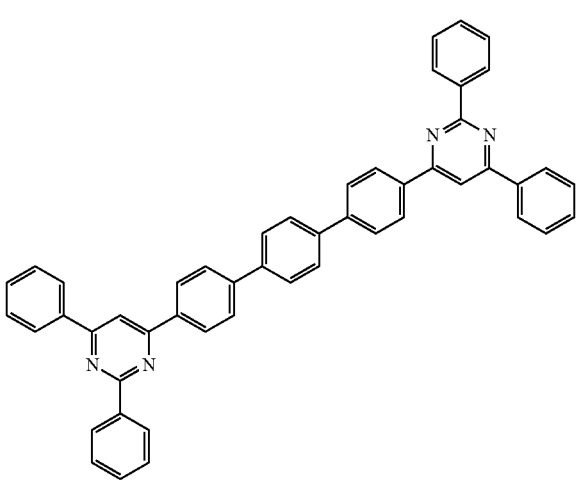
[ET-C]
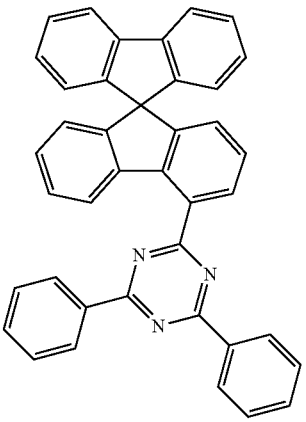
[ET-A]
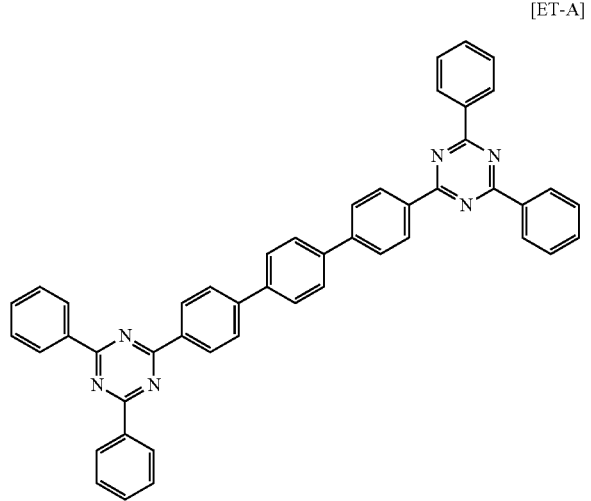
[ET-D]
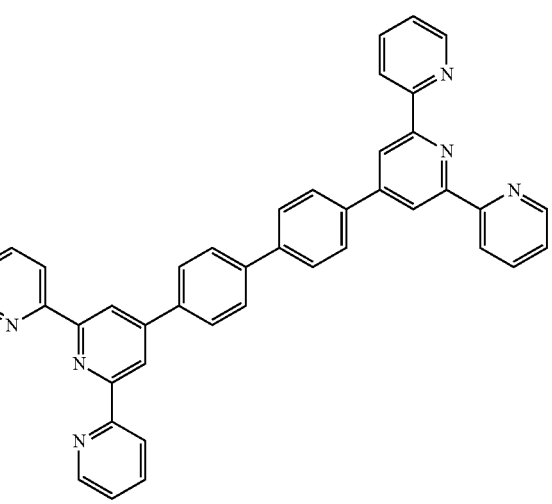

[ET-E]
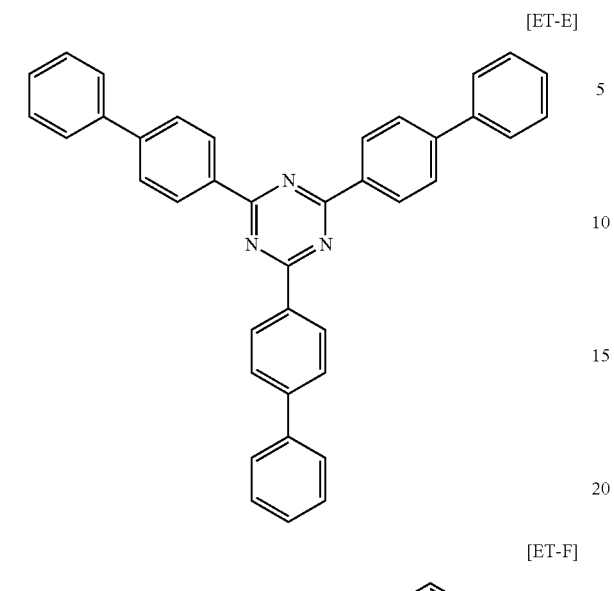
[ET-F]
[ET-G]
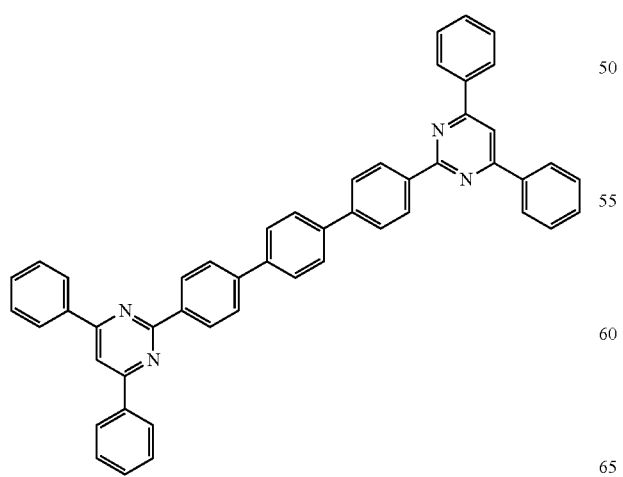
[ET-H]
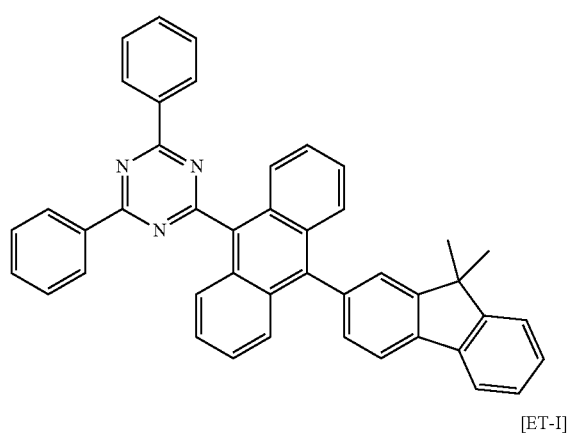
[ET-I]
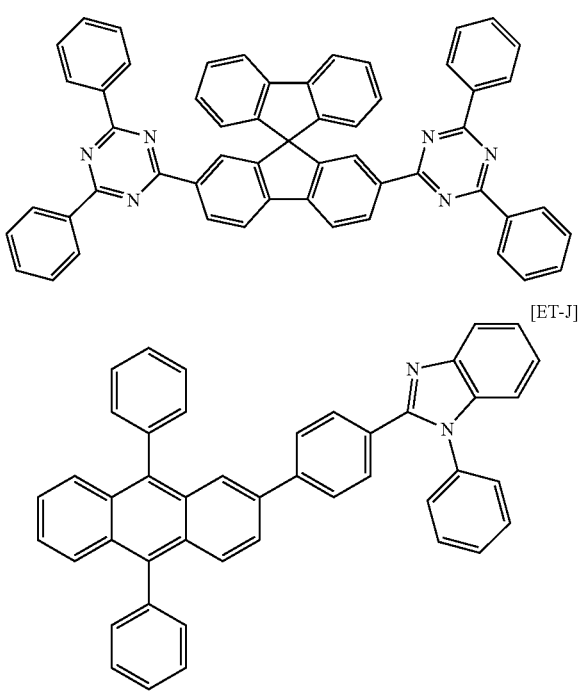
[ET-J]
[Alq3]
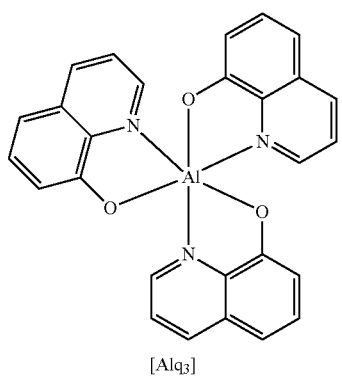

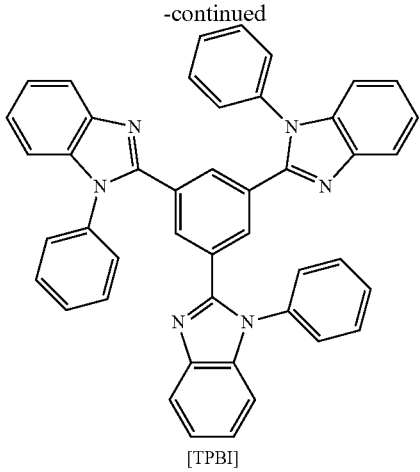

[TPBI]

Example 1-2

An organic light emitting device was manufactured in the same manner as in [Example 1-1] except that [Compound 2] was used instead of [Compound] of [Example 1-1].

Example 1-3

An organic light emitting device was manufactured in the same manner as in [Example 1-1] except that [Compound 6] was used instead of [Compound 1] of [Example 1-1].

Example 1-4

An organic light emitting device was manufactured in the same manner as in [Example 1-1] except that [Compound 12] was used instead of [Compound 1] of [Example 1-1].

Example 1-5

An organic light emitting device was manufactured in the same manner as in [Example 1-1] except that [Compound 13] was used instead of [Compound 1] of [Example 1-1].

Example 1-6

An organic light emitting device was manufactured in the same manner as in [Example 1-1] except that [Compound 15] was used instead of [Compound 1] of [Example 1-1].

Example 1-7

An organic light emitting device was manufactured in the same manner as in [Example 1-1] except that [Compound 17] was used instead of [Compound 1] of [Example 1-1].

Example 1-8

An organic light emitting device was manufactured in the same manner as in [Example 1-1] except that [Compound 21] was used instead of [Compound 1] of [Example 1-1].

Example 1-9

An organic light emitting device was manufactured in the same manner as in [Example 1-1] except that [Compound 36] was used instead of [Compound 1] of [Example 1-1].

Example 1-10

An organic light emitting device was manufactured in the same manner as in [Example 1-1] except that [Compound 38] was used instead of [Compound 1] of [Example 1-1].

Example 1-11

An organic light emitting device was manufactured in the same manner as in [Example 1-1] except that [Compound 41] was used instead of [Compound 1] of [Example 1-1].

Example 1-12

An organic light emitting device was manufactured in the same manner as in [Example 1-1] except that [Compound 56] was used instead of [Compound 1] of [Example 1-1].

Example 1-13

An organic light emitting device was manufactured in the same manner as in [Example 1-1] except that [Compound 57] was used instead of [Compound 1] of [Example 1-1].

Example 1-14

An organic light emitting device was manufactured in the same manner as in [Example 1-1] except that [Compound 66] was used instead of [Compound 1] of [Example 1-1].

Example 1-15

An organic light emitting device was manufactured in the same manner as in [Example 1-1] except that [Compound 74] was used instead of [Compound 1] of [Example 1-1].

Example 1-16

An organic light emitting device was manufactured in the same manner as in [Example 1-1] except that [Compound 75] was used instead of [Compound 1] of [Example 1-1].

Example 1-17

An organic light emitting device was manufactured in the same manner as in [Example 1-1] except that [Compound 86] was used instead of [Compound 1] of [Example 1-1] and [Compound 2-19] was used instead of [Compound 2-4].

Example 1-18

An organic light emitting device was manufactured in the same manner as in [Example 1-17] except that [Compound 89] was used instead of [Compound 86] of [Example 1-17].

Example 1-19

An organic light emitting device was manufactured in the same manner as in [Example 1-17] except that [Compound 93] was used instead of [Compound 86] of [Example 1-17].

Example 1-20

An organic light emitting device was manufactured in the same manner as in [Example 1-17] except that [Compound 100] was used instead of [Compound 86] of [Example 1-17].

Example 1-21

An organic light emitting device was manufactured in the same manner as in [Example 1-17] except that [Compound 104] was used instead of [Compound 86] of [Example 1-17].

Example 1-22

An organic light emitting device was manufactured in the same manner as in [Example 1-1] except that [Compound 123] was used instead of [Compound 1] of [Example 1-1] and [Chemical Formula 2-30] was used instead of [Chemical Formula 2-4].

Example 1-23

An organic light emitting device was manufactured in the same manner as in [Example 1-22] except that [Compound 129] was used instead of [Compound 123] of [Example 1-22].

Example 1-24

An organic light emitting device was manufactured in the same manner as in [Example 1-22] except that [Compound 161] was used instead of [Compound 123] of [Example 1-22].

Example 1-25

An organic light emitting device was manufactured in the same manner as in [Example 1-22] except that [Compound 176] was used instead of [Compound 123] of [Example 1-22].

Example 1-26

An organic light emitting device was manufactured in the same manner as in [Example 1-22] except that [Compound 179] was used instead of [Compound 123] of [Example 1-22].

Comparative Example 1-1

An organic light emitting device was manufactured in the same manner as in [Example 1-1] except that Chemical Formula [BH-1] was used instead of [Chemical Formula 2-4] of [Example 1-1].

Comparative Example 1-2

An organic light emitting device was manufactured in the same manner as in [Example 1-2] except that Chemical Formula [BH-1] was used instead of [Chemical Formula 2-4] of [Example 1-2].

Comparative Example 1-3

An organic light emitting device was manufactured in the same manner as in [Example 1-5] except that Chemical Formula [BH-1] was used instead of [Chemical Formula 2-4] of [Example 1-5].

Comparative Example 1-4

An organic light emitting device was manufactured in the same manner as in [Example 1-11] except that Chemical Formula [BH-1] was used instead of [Chemical Formula 2-4] of [Example 1-11].

Comparative Example 1-5

An organic light emitting device was manufactured in the same manner as in [Example 1-14] except that Chemical Formula [BH-2] was used instead of [Chemical Formula 2-4] of [Example 1-14].

Comparative Example 1-6

An organic light emitting device was manufactured in the same manner as in [Example 1-17] except that Chemical Formula [BH-2] was used instead of [Chemical Formula 2-19] of [Example 1-17].

Comparative Example 1-7

An organic light emitting device was manufactured in the same manner as in [Example 1-22] except that Chemical Formula [BH-2] was used instead of [Chemical Formula 2-30] of [Example 1-22].

Comparative Example 1-8

An organic light emitting device was manufactured in the same manner as in [Example 1-10] except that Chemical Formula [BH-2] was used instead of [Chemical Formula 2-4] of [Example 1-10].

Comparative Example 1-9

An organic light emitting device was manufactured in the same manner as in [Example 1-9] except that Chemical Formula [BH-3] was used instead of [Chemical Formula 2-4] of [Example 1-9].

Comparative Example 1-10

An organic light emitting device was manufactured in the same manner as in [Example 1-15] except that Chemical Formula [BH-3] was used instead of [Chemical Formula 2-4] of [Example 1-15].

Comparative Example 1-11

An organic light emitting device was manufactured in the same manner as in [Example 1-24] except that Chemical Formula [BH-3] was used instead of [Chemical Formula 2-30] of [Example 1-24].

Comparative Example 1-12

An organic light emitting device was manufactured in the same manner as in [Example 1-1] except that Chemical Formula [ET-A] was used instead of [Compound 1] of [Example 1-1].

Comparative Example 1-13

An organic light emitting device was manufactured in the same manner as in [Example 1-1] except that Chemical Formula [ET-B] was used instead of [Compound 1] of [Example 1-1].

Comparative Example 1-14

An organic light emitting device was manufactured in the same manner as in [Example 1-1] except that Chemical Formula [ET-C] was used instead of [Compound 1] of [Example 1-1].

Comparative Example 1-15

An organic light emitting device was manufactured in the same manner as in [Example 1-1] except that Chemical Formula [ET-D] was used instead of [Compound 1] of [Example 1-1].

Comparative Example 1-16

An organic light emitting device was manufactured in the same manner as in [Example 1-1] except that Chemical Formula [ET-E] was used instead of [Compound 1] of [Example 1-1].

Comparative Example 1-17

An organic light emitting device was manufactured in the same manner as in [Example 1-1] except that Chemical Formula [ET-F] was used instead of [Compound 1] of [Example 1-1].

Comparative Example 1-18

An organic light emitting device was manufactured in the same manner as in [Example 1-20] except that Chemical Formula [ET-G] was used instead of [Compound 100] of [Example 1-20].

Comparative Example 1-19

An organic light emitting device was manufactured in the same manner as in [Example 1-20] except that Chemical Formula [ET-H] was used instead of [Compound 100] of [Example 1-20].

Comparative Example 1-20

An organic light emitting device was manufactured in the same manner as in [Example 1-20] except that Chemical Formula [ET-I] was used instead of [Compound 100] of [Example 1-20].

Comparative Example 1-21

An organic light emitting device was manufactured in the same manner as in [Example 1-25] except that Chemical Formula [ET-J] was used instead of [Compound 176] of [Example 1-25].

Comparative Example 1-22

An organic light emitting device was manufactured in the same manner as in [Example 1-1] except that Chemical Formula [Alq$_3$] was used instead of [Compound 1] of [Example 1-1].

Comparative Example 1-23

An organic light emitting device was manufactured in the same manner as in [Example 1-1] except that Chemical Formula [TPBI] was used instead of [Compound 1] of [Example 1-1].

For the organic light emitting devices manufactured using the methods described above, a driving voltage and light emission efficiency were measured at current density of 10 mA/cm$^2$, and time taken for the luminance decreasing to 90% compared to its initial luminance (T$_{90}$) was measured at current density of 20 mA/cm$^2$. The results are shown in the following Table 2.

FIG. 8 is a diagram showing an energy chart of compounds in an organic light emitting device according to one embodiment of the present specification.

TABLE 2

| | Voltage (V) | Efficiency (Cd/A) | Color Coordinate (x, y) | Lifespan (h) T$_{90}$ at 20 mA/cm$^2$ |
|---|---|---|---|---|
| Example 1-1 | 3.25 | 7.96 | (0.139, 0.110) | 204 |
| Example 1-2 | 3.21 | 8.11 | (0.138, 0.111) | 199 |
| Example 1-3 | 3.46 | 7.7 | (0.138, 0.110) | 227 |
| Example 1-4 | 3.22 | 7.64 | (0.139, 0.111) | 220 |
| Example 1-5 | 3.22 | 7.87 | (0.138, 0.113) | 219 |
| Example 1-6 | 3.50 | 7.18 | (0.138, 0.109) | 190 |
| Example 1-7 | 3.58 | 7.92 | (0.138, 0.112) | 200 |
| Example 1-8 | 3.55 | 7.67 | (0.138, 0.100) | 210 |
| Example 1-9 | 3.20 | 7.94 | (0.138, 0.111) | 180 |
| Example 1-10 | 3.17 | 8.12 | (0.138, 0.109) | 182 |
| Example 1-11 | 3.25 | 8.02 | (0.138, 0.113) | 215 |
| Example 1-12 | 3.70 | 7.54 | (0.138, 0.110) | 170 |
| Example 1-13 | 3.76 | 7.49 | (0.138, 0.112) | 181 |
| Example 1-14 | 3.40 | 7.70 | (0.138, 0.111) | 209 |
| Example 1-15 | 3.75 | 7.16 | (0.138, 0.108) | 290 |
| Example 1-16 | 3.81 | 7.24 | (0.138, 0.111) | 277 |
| Example 1-17 | 3.40 | 7.78 | (0.138, 0.111) | 200 |
| Example 1-18 | 3.60 | 7.15 | (0.138, 0.111) | 190 |
| Example 1-19 | 3.65 | 7.46 | (0.138, 0.110) | 187 |
| Example 1-20 | 3.30 | 7.91 | (0.138, 0.111) | 206 |
| Example 1-21 | 3.30 | 7.88 | (0.138, 0.111) | 179 |
| Example 1-22 | 3.10 | 8.10 | (0.138, 0.111) | 187 |
| Example 1-23 | 3.30 | 7.89 | (0.138, 0.113) | 170 |

TABLE 2-continued

| | Voltage (V) | Efficiency (Cd/A) | Color Coordinate (x, y) | Lifespan (h) $T_{90}$ at 20 mA/cm$^2$ |
|---|---|---|---|---|
| Example 1-24 | 3.22 | 7.80 | (0.138, 0.111) | 194 |
| Example 1-25 | 3.23 | 7.98 | (0.139, 0.111) | 169 |
| Example 1-26 | 3.24 | 7.92 | (0.138, 0.110) | 161 |
| Comparative Example 1-1 | 4.09 | 5.40 | (0.138, 0.115) | 113 |
| Comparative Example 1-2 | 3.94 | 5.67 | (0.138, 0.115) | 120 |
| Comparative Example 1-3 | 5.17 | 4.97 | (0.138, 0.111) | 131 |
| Comparative Example 1-4 | 5.08 | 5.16 | (0.138, 0.110) | 122 |
| Comparative Example 1-5 | 5.61 | 4.74 | (0.138, 0.112) | 111 |
| Comparative Example 1-6 | 5.57 | 5.41 | (0.138, 0.110) | 117 |
| Comparative Example 1-7 | 5.51 | 4.91 | (0.138, 0.114) | 86 |
| Comparative Example 1-8 | 5.75 | 5.00 | (0.138, 0.109) | 97 |
| Comparative Example 1-9 | 4.76 | 5.74 | (0.138, 0.112) | 110 |
| Comparative Example 1-10 | 4.72 | 5.91 | (0.138, 0.114) | 106 |
| Comparative Example 1-11 | 5.00 | 5.72 | (0.138, 0.112) | 111 |
| Comparative Example 1-12 | 4.17 | 4.89 | (0.138, 0.110) | 140 |
| Comparative Example 1-13 | 4.12 | 5.21 | (0.138, 0.111) | 97 |
| Comparative Example 1-14 | 4.23 | 6.01 | (0.138, 0.110) | 103 |
| Comparative Example 1-15 | 5.13 | 4.57 | (0.138, 0.112) | 87 |
| Comparative Example 1-16 | 4.50 | 5.90 | (0.138, 0.110) | 37 |
| Comparative Example 1-17 | 5.08 | 5.62 | (0.138, 0.113) | 108 |
| Comparative Example 1-18 | 5.99 | 5.34 | (0.138, 0.110) | 98 |
| Comparative Example 1-19 | 4.88 | 5.86 | (0.138, 0.111) | 117 |
| Comparative Example 1-20 | 4.42 | 3.03 | (0.138, 0.110) | 140 |
| Comparative Example 1-21 | 4.30 | 5.99 | (0.138, 0.110) | 110 |
| Comparative Example 1-22 | 5.91 | 5.22 | (0.138, 0.112) | 106 |
| Comparative Example 1-23 | 5.46 | 5.67 | (0.138, 0.110) | 100 |

From the results of Table 2, it was identified that the cyclic compound represented by Chemical Formula 1 according to one embodiment of the present specification was able to be used in an organic layer capable of carrying out electron injection and electron transfer at the same time of an organic light emitting device.

In the organic light emitting device using the same, it was identified that high efficiency, low driving voltage and long lifespan were obtained compared to when using X substituted with a conjugation group in an organic layer capable of carrying out electron injection and electron transfer at the same time.

Particularly, the cyclic compound represented by Chemical Formula 1 according to the present disclosure exhibited excellent properties with excellent thermal stability, a deep HOMO level of 6.1 eV or higher, high triplet energy ($E_T$) and hole stability. When used in an organic layer capable of carrying out electron injection and electron transfer at the same time, an n-type dopant may be mixed thereto to be used. The resulting cyclic compound represented by Chemical Formula 1 has low driving voltage and high efficiency, and is capable of enhancing device stability due to hole stability of the compound.

From the results of Table 1, it was identified that the compounds represented by Chemical Formulae [ET-A], [ET-H], [ET-I] and [ET-J] all had triplet energy of lower than 2.6 eV, and based on the results of the examples and the comparative examples of Table 2, it was identified that the compounds having low triplet energy of lower than 2.6 eV had low device efficiency. This is due to the fact that a triplet-triplet annihilation (TTA) effect is reduced when using compounds having triplet energy of lower than 2.6 eV.

In addition, the compounds represented by Chemical Formulae [ET-H] and [ET-I] having a HOMO level of lower than 6.1 eV was identified through Table 1, and from the device evaluation results of Table 2, it was identified that a short lifespan was resulted when including the compounds. Such results are obtained since a hole blocking effect transferred from a light emitting layer is reduced in an organic light emitting device including compounds having a HOMO energy level of lower than 6.1 eV.

In addition, through Table 2, the compounds represented by Chemical Formulae [ET-A], [ET-H], [ET-I] and [ET-J] all had energy having a band gap of less than 3.3 eV, and therefore, having LUMO energy of higher than 3.0 eV was identified, and among these, [ET-A] was identified to generate a barrier in the electron transfer ability to a light emitting layer resulting in low device efficiency since [ET-A] had LUMO energy of 3.1 eV even with low HOMO energy of 6.17 eV.

Particularly, the ranges of the triplet energy and the HOMO energy level values were identified from the compounds including anthracene, and effects thereof were identified in the comparative examples using [ET-I] and [ET-J].

Accordingly, having the cyclic compound represented by Chemical Formula 1 according to one embodiment of the present disclosure, a HOMO energy level of 6.1 eV or higher, a band gap of 3.3 eV or greater, a LUMO energy level of 3.0 eV or lower and triplet energy of 2.6 eV or higher are more preferred in terms of driving voltage, efficiency and/or lifespan of a device.

In addition, when comparing the results of Comparative Examples 1-1 to 1-23 and Examples 1-1 to 1-26, it can be identified that the organic light emitting device provided with the organic material layer including the cyclic compound represented by Chemical Formula 1 between the cathode and the light emitting layer and provided with the anthracene derivative represented by Chemical Formula 2 as the light emitting layer is capable of providing an organic light emitting device having a low driving voltage, high light emission efficiency and/or a long lifespan.

The invention claimed is:
1. An organic light emitting device comprising:
a cathode;
an anode provided opposite to the cathode;
a light emitting layer provided between the cathode and the anode, and including an anthracene derivative represented by the following Chemical Formula 2; and
an organic material layer provided between the cathode and the light emitting layer, and including a cyclic compound represented by the following Chemical Formula 1:

[Chemical Formula 1]

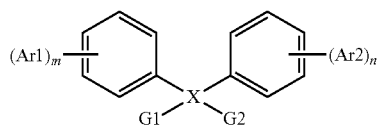

wherein, in Chemical Formula 1,

Ar1 and Ar2 are the same as or different from each other, and each independently selected from the group consisting of hydrogen; deuterium; a nitrile group; a substituted or unsubstituted monocyclic or multicyclic aryl group having 6 to 30 carbon atoms; and a substituted or unsubstituted monocyclic or multicyclic heteroaryl group selected from a thiophene group, a furan group, a pyrrole group, an imidazole group, a thiazole group, an oxazole group, an oxadiazole group, a pyridyl group, a bipyridyl group, a pyrimidyl group, a triazine group, an acridyl group, a pyridazine group, a pyrazinyl group, a quinolinyl group, a quinoxalinyl group, an isoquinoline group, an indole group, a benzoxazole group, a benzimidazole group, a benzothiazole group, a benzocarbazole group, a benzothiophene group, a dibenzothiophene group, a benzofuranyl group, a phenanthroline group, an isoxazolyl group, an oxadiazolyl group, a thiadiazolyl group, a phenothiazinyl group, or a dibenzofuranyl group; provided when Ar1 and Ar2 are each independently a phenyl group substituted with a substitution group, then the substitution group is independently deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted alkenyl group; a substituted or unsubstituted amine group; a substituted or unsubstituted aryl group; or a substituted or unsubstituted heterocyclic group selected from a thiophene group, a furan group, a pyrrole group, an imidazole group, a thiazole group, an oxazole group, an oxadiazole group, a triazole group, a pyridyl group, a bipyridyl group, an acridly group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, an isoxazolyl group, an oxadiazolyl group, a thiadiazolyl group, a phenothiazinyl group, or a dibenzofuranyl group;

m and n are an integer of 1;

X is carbon; and

G1 and G2 are the same as or different from each other, and each independently selected from the group consisting of hydrogen; deuterium; a nitrile group; a substituted or unsubstituted linear or branched alkyl group having 1 to 30 carbon atoms; a substituted or unsubstituted monocyclic or multicyclic cycloalkyl group having 3 to 30 carbon atoms; a substituted or unsubstituted monocyclic or multicyclic aryl group having 6 to 30 carbon atoms; and a substituted or unsubstituted monocyclic or multicyclic heteroaryl group having 2 to 30 carbon atoms, or G1 and G2 bond to each other to form a substituted or unsubstituted monocyclic or multicyclic aliphatic hydrocarbon ring system; or a substituted or unsubstituted monocyclic or multicyclic aliphatic heteroring system, provided that when Ar1 or Ar2 is a phenyl group, a naphthalene group, an anthracene group, a phenanthrene group, a pyrene or the monocyclic or multicyclic heteroaryl group, each of which is unsubstituted or substituted, and when both Ar1 and Ar2 are hydrogen, then at least one G1 or G2 is not a substituted or unsubstituted phenyl group or a substituted or unsubstituted naphthyl group, wherein a HOMO energy level of the cyclic compound represented by Chemical Formula 1, when measured using an atmospheric pressure photoelectron spectroscopy apparatus, is 6.1 eV or higher,

[Chemical Formula 2]

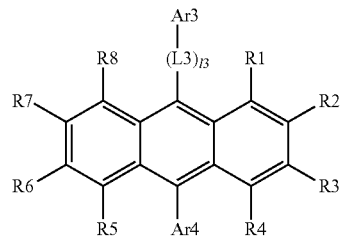

in Chemical Formula 2,

R1 to R8 are the same as or different from each other, and each independently hydrogen; halogen; a hydroxyl group; a nitrile group; a substituted or unsubstituted amine group; a substituted or unsubstituted linear or branched alkyl group having 1 to 20 carbon atoms; a substituted or unsubstituted linear or branched alkoxy group having 1 to 20 carbon atoms; a substituted or unsubstituted monocyclic or multicyclic aryloxy group having 6 to 30 carbon atoms; a substituted or unsubstituted monocyclic or multicyclic arylthioxy group having 6 to 30 carbon atoms; a substituted or unsubstituted monocyclic or multicyclic aryl group having 6 to 30 carbon atoms; or a substituted or unsubstituted monocyclic or multicyclic heteroaryl group having 5 to 30 carbon atoms;

L3 is a direct bond; a substituted or unsubstituted monocyclic or multicyclic arylene group having 6 to 30 carbon atoms; or a substituted or unsubstituted monocyclic or multicyclic heteroarylene group having 5 to 30 carbon atoms;

Ar3 is the following Chemical Formula a;

Ar4 is a substituted or unsubstituted monocyclic or multicyclic aryl group having 6 to 30 carbon atoms; or a substituted or unsubstituted monocyclic or multicyclic heteroaryl group having 5 to 30 carbon atoms;

l3 is an integer of 1 to 3; and when l3 is 2 or greater, the two or more L3s are the same as or different from each other,

[Chemical Formula a]

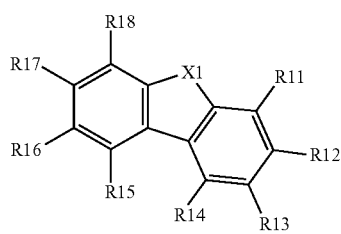

in Chemical Formula a,

X1 is O or S;

any one of R11 to R14 is a site bonding to L3 of Chemical Formula 2, and the rest and R15 to R18 are the same as or different from each other, and each independently hydrogen; halogen; a hydroxyl group; a nitrile group; a substituted or unsubstituted amine group; a substituted or unsubstituted linear or branched alkyl group having 1 to 20 carbon atoms; a substituted or unsubstituted linear or branched alkoxy group having 1 to 20 carbon atoms; a substituted or unsubstituted monocyclic or multicyclic aryloxy group having 6 to 30 carbon atoms; a substituted or unsubstituted monocyclic or multicyclic arylthioxy group having 6 to 30 carbon atoms; a substituted or unsubstituted monocyclic or multicyclic aryl group having 6 to 30 carbon atoms; or a substituted or unsubstituted monocyclic or multicyclic heteroaryl group having 5 to 30 carbon atoms; and adjacent groups among R1 to R8, R11 to R18, L3 and Ar4 optionally bond to each other to form a substituted or unsubstituted ring.

2. The organic light emitting device of claim 1, wherein the organic material layer including the cyclic compound represented by Chemical Formula 1 is an electron transfer layer, an electron injection layer, or a layer carrying out electron transfer and electron injection at the same time.

3. The organic light emitting device of claim 1, wherein a triplet energy of the cyclic compound represented by Chemical Formula 1, when measured using a low temperature photoluminescence method or obtained by quantum chemistry calculations using Gaussian 03, is 2.6 eV or higher.

4. The organic light emitting device of claim 1, wherein a band gap of the cyclic compound represented by Chemical Formula 1, an absolute value of a difference between a HOMO energy and a LUMO energy of the cyclic compound represented by Chemical Formula 1, wherein the HOMO energy level is measured using an atmospheric pressure photoelectron spectroscopy apparatus, and the LUMO energy level is calculated by a wavelength value measured through photoluminescence (PL), is 3.3 eV or greater.

5. The organic light emitting device of claim 1, wherein a LUMO energy level of the cyclic compound represented by Chemical Formula 1, when calculated by a wavelength value measured through photoluminescence (PL), is 3 eV or lower.

6. The organic light emitting device of claim 1, wherein an electron mobility of the cyclic compound represented by Chemical Formula 1, when measured by a time of flight (TOF) method, or a method of measuring a space charge limited current (SCLC), is $1 \times 10^{-6}$ cm$^2$/Vs or greater.

7. The organic light emitting device of claim 1, wherein the organic material layer including the cyclic compound represented by Chemical Formula 1 further includes an n-type dopant represented by the following Chemical Formula 10:

[Chemical Formula 10]

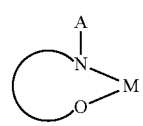

A is hydrogen; deuterium; a halogen group; a nitrile group; a nitro group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted heterocyclic group;

a curve represents bonds and 2 or 3 atoms required for forming a 5-membered or 6-membered ring having M, and the atoms are unsubstituted or substituted with substituents having the same definition as one, two or greater As; and M is an alkali metal or an alkaline earth metal.

8. The organic light emitting device of claim 7, wherein the n-type dopant represented by Chemical Formula 10 is represented by the following Chemical Formula 10-1 or 10-2:

[Chemical Formula 10-1]

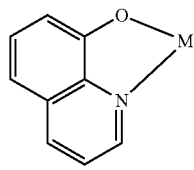

[Chemical Formula 10-2]

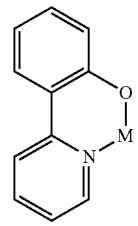

wherein, in Chemical Formulae 10-1 and 10-2,

M has the same definition as in Chemical Formula 10; and

Chemical Formulae 10-1 and 10-2 are each independently unsubstituted or substituted with one, two or more substituents selected from the group consisting of deuterium; a halogen group; a nitrile group; a nitro group; a hydroxyl group; a substituted or unsubstituted alkyl group; a substituted or unsubstituted cycloalkyl group;

a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; and a substituted or unsubstituted heterocyclic group, or adjacent substituents bond to each other to form a substituted or unsubstituted hydrocarbon ring; or a substituted or unsubstituted heteroring.

9. An organic light emitting device comprising:

a cathode;

an anode provided opposite to the cathode;

a light emitting layer provided between the cathode and the anode, and including an anthracene derivative represented by the following Chemical Formula 2,

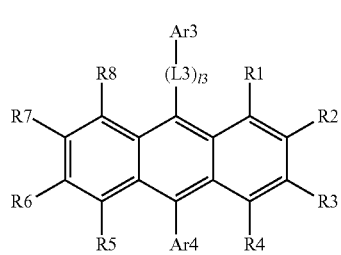

[Chemical Formula 2]

in Chemical Formula 2,

R1 to R8 are the same as or different from each other, and each independently hydrogen; halogen; a hydroxyl group; a nitrile group; a substituted or unsubstituted amine group; a substituted or unsubstituted linear or branched alkyl group having 1 to 20 carbon atoms; a substituted or unsubstituted linear or branched alkoxy group having 1 to 20 carbon atoms; a substituted or unsubstituted monocyclic or multicyclic aryloxy group having 6 to 30 carbon atoms; a substituted or unsubstituted monocyclic or multicyclic arylthioxy group having 6 to 30 carbon atoms; a substituted or unsubstituted monocyclic or multicyclic aryl group having 6 to 30 carbon atoms; or a substituted or unsubstituted monocyclic or multicyclic heteroaryl group having 5 to 30 carbon atoms;

L3 is a direct bond; a substituted or unsubstituted monocyclic or multicyclic arylene group having 6 to 30 carbon atoms; or a substituted or unsubstituted monocyclic or multicyclic heteroarylene group having 5 to 30 carbon atoms;

Ar3 is the following Chemical Formula a;

Ar4 is a substituted or unsubstituted monocyclic or multicyclic aryl group having 6 to 30 carbon atoms; or a substituted or unsubstituted monocyclic or multicyclic heteroaryl group having 5 to 30 carbon atoms;

l3 is an integer of 1 to 3; and when l3 is 2 or greater, the two or more L3s are the same as or different from each other,

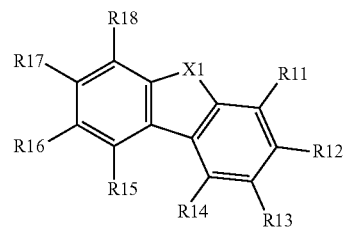

[Chemical Formula a]

in Chemical Formula a,

X1 is O or S;

any one of R11 to R14 is a site bonding to L3 of Chemical Formula 2, and the rest and R15 to R18 are the same as or different from each other, and each independently hydrogen; halogen; a hydroxyl group; a nitrile group; a substituted or unsubstituted amine group; a substituted or unsubstituted linear or branched alkyl group having 1 to 20 carbon atoms; a substituted or unsubstituted linear or branched alkoxy group having 1 to 20 carbon atoms; a substituted or unsubstituted monocyclic or multicyclic aryloxy group having 6 to 30 carbon atoms; a substituted or unsubstituted monocyclic or multicyclic arylthioxy group having 6 to 30 carbon atoms; a substituted or unsubstituted monocyclic or multicyclic aryl group having 6 to 30 carbon atoms; or a substituted or unsubstituted monocyclic or multicyclic heteroaryl group having 5 to 30 carbon atoms; and adjacent groups among R1 to R8, R11 to R18, L3 and Ar4 optionally bond to each other to form a substituted or unsubstituted ring; and an organic material layer provided between the cathode and the light emitting layer, and including a cyclic compound represented by any one of the following Compounds 1 to 209:

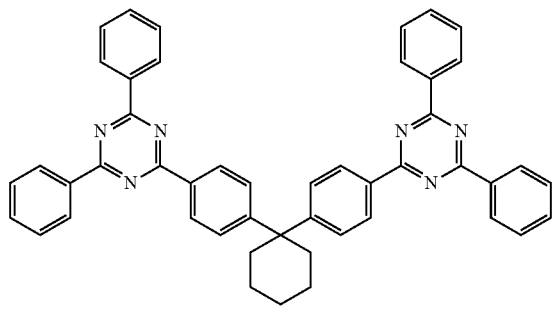

Compound 1

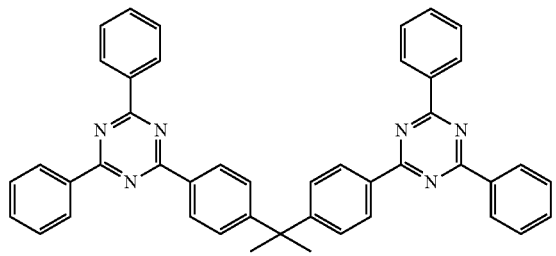

Compound 2

Compound 3
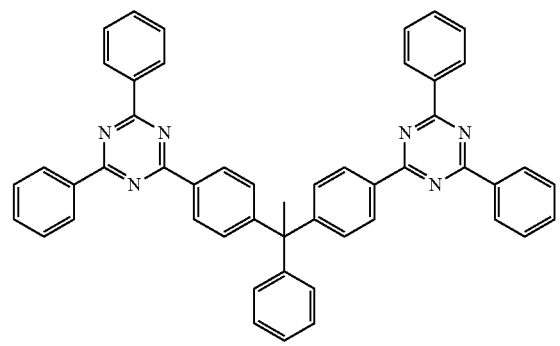
Compound 4
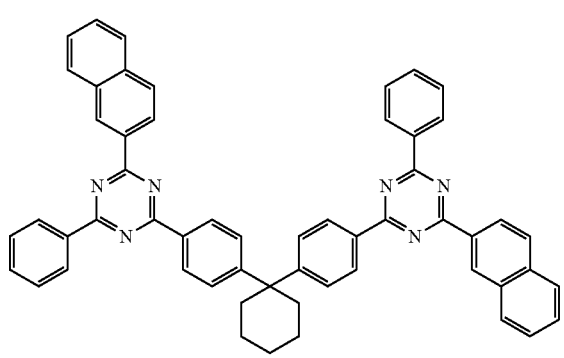
Compound 7
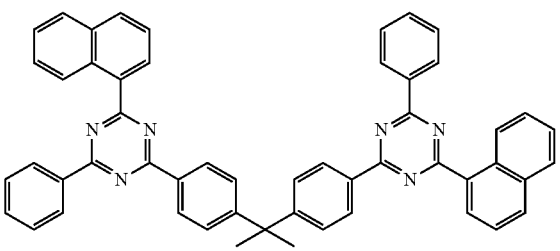
Compound 8
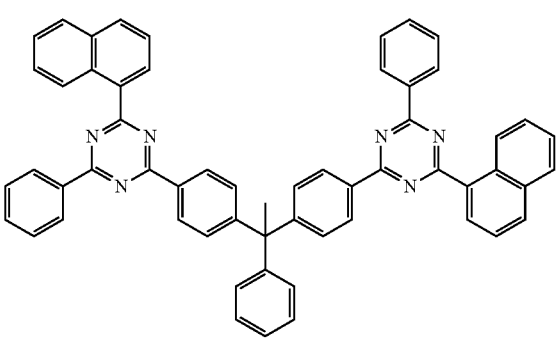
Compound 5
Compound 9
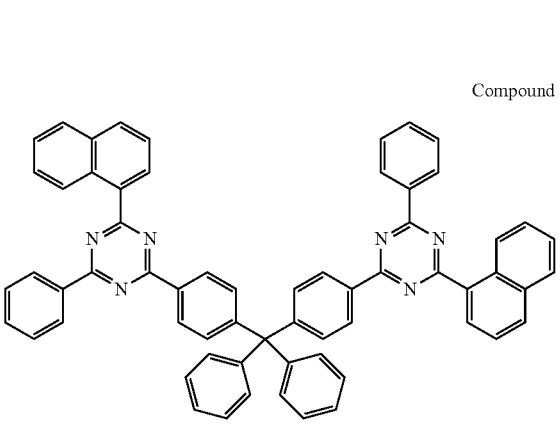
Compound 6
Compound 10
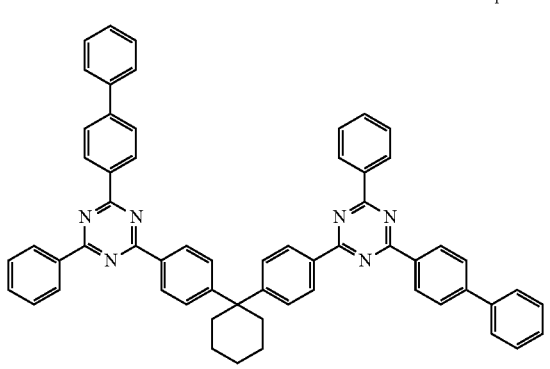

Compound 11
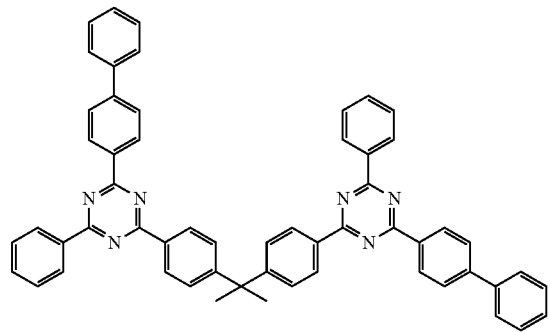
Compound 12
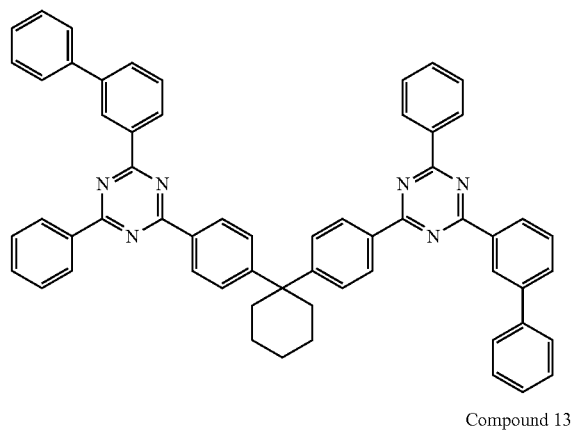
Compound 13
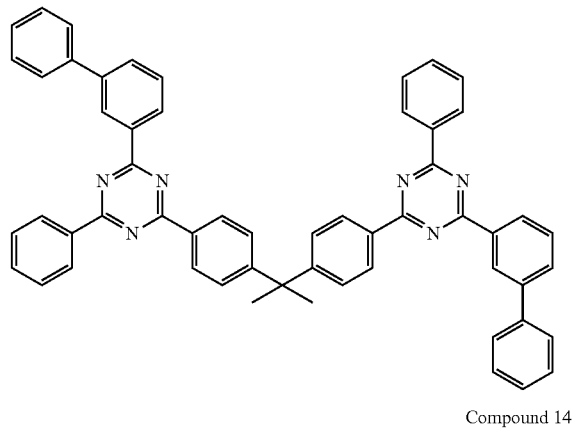
Compound 14
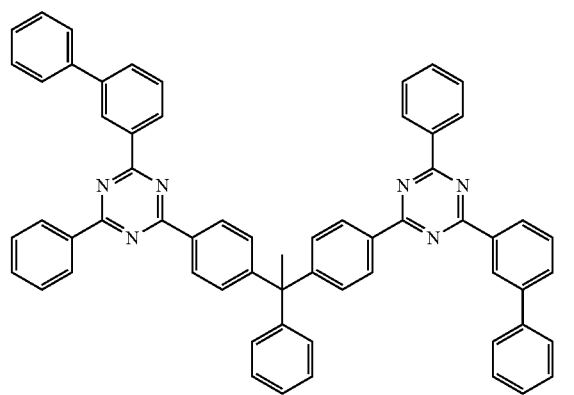
Compound 15
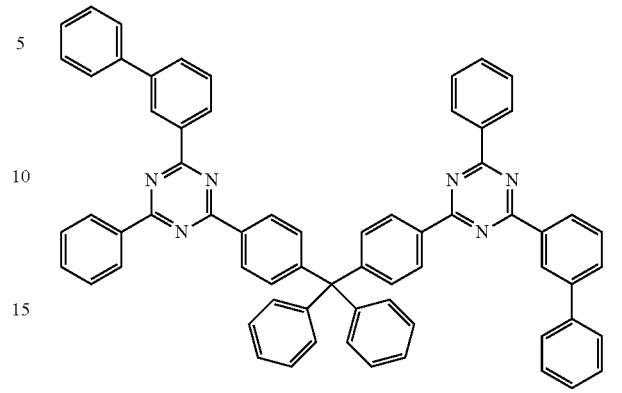
Compound 16
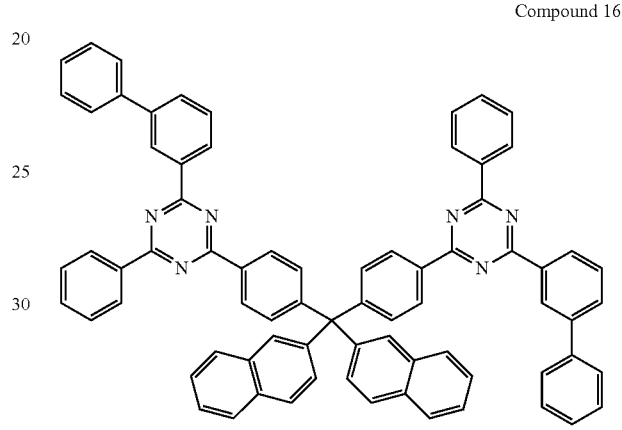
Compound 17
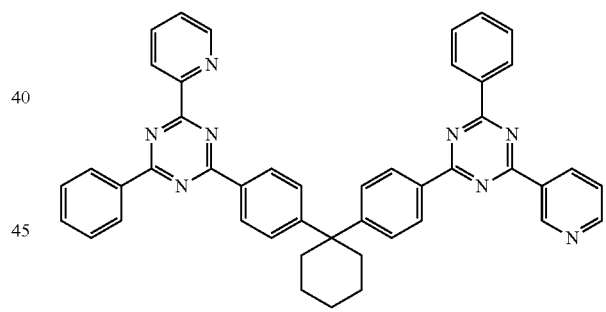
Compound 18
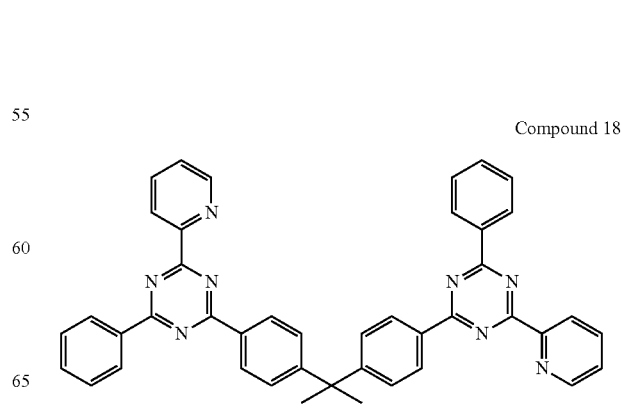

Compound 19
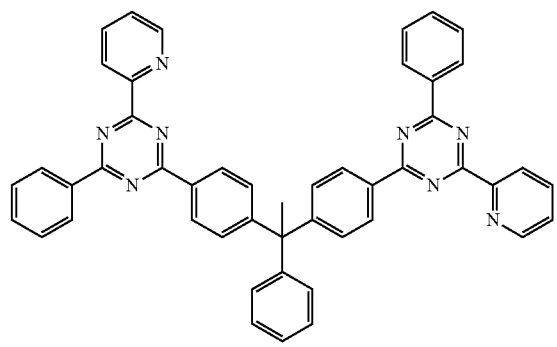
Compound 20
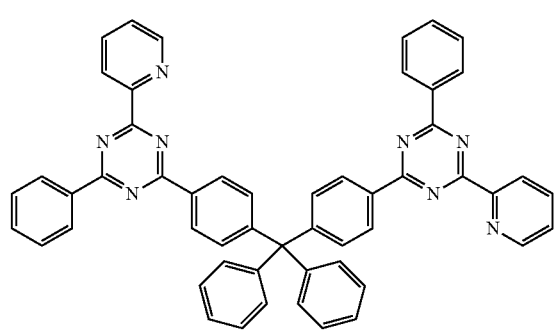
Compound 21
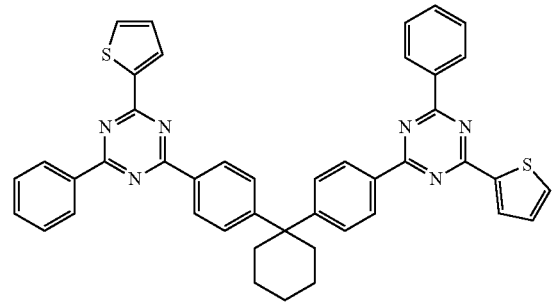
Compound 22
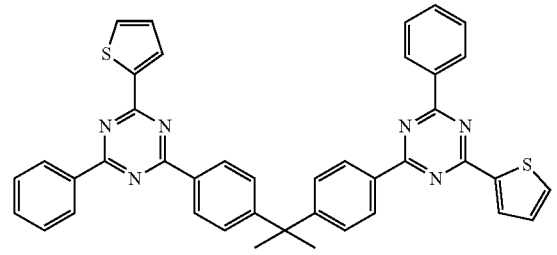
Compound 23
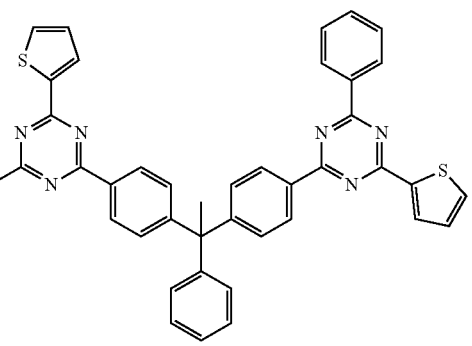
Compound 24
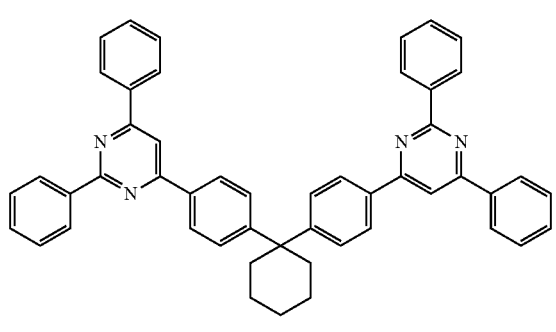
Compound 25
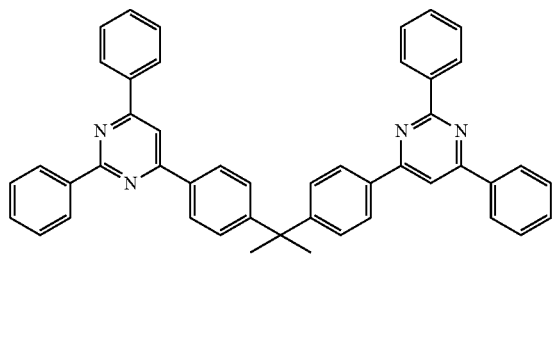
Compound 26
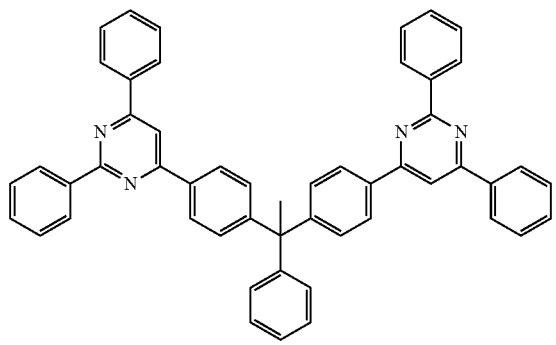

Compound 27
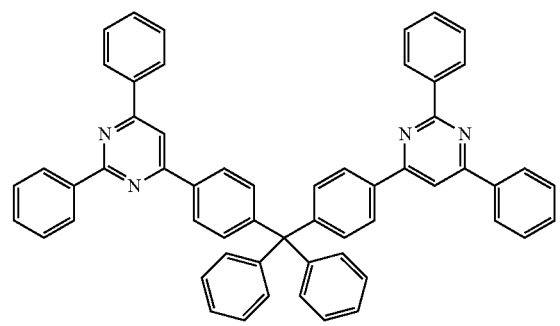
Compound 28
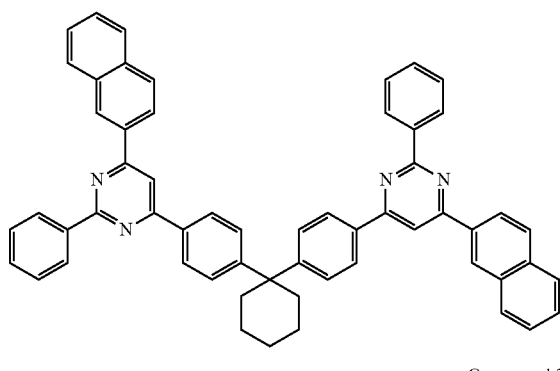
Compound 29
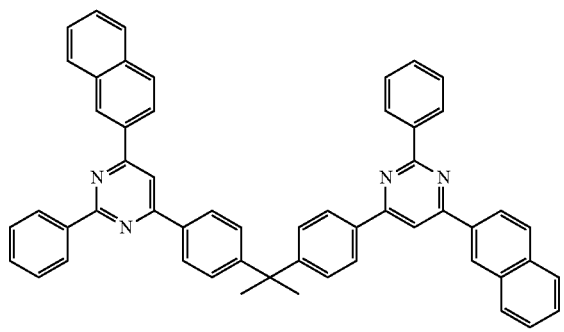
Compound 30
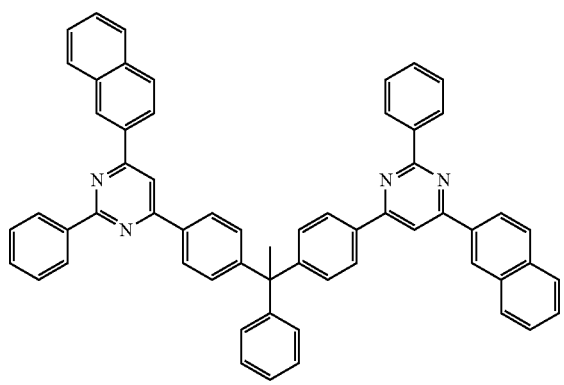
Compound 31
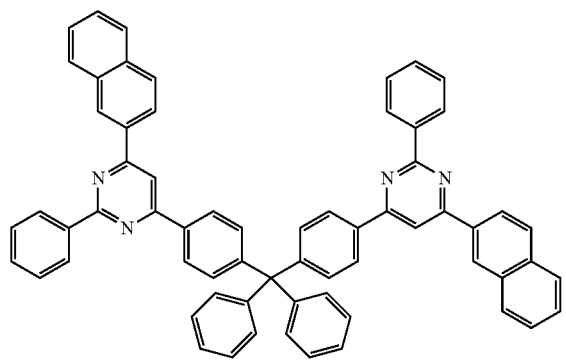
Compound 32
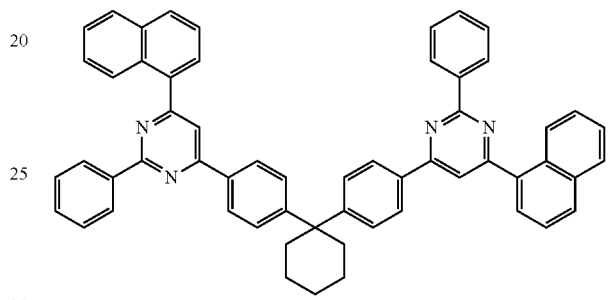
Compound 33
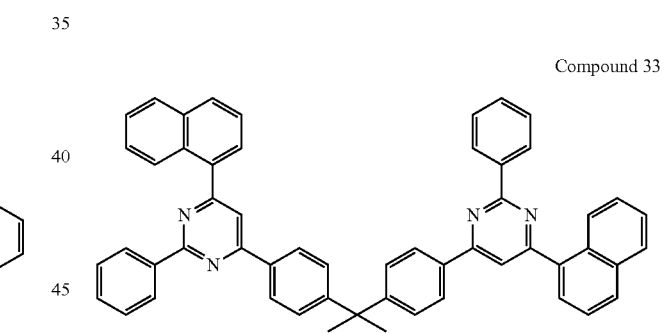
Compound 34
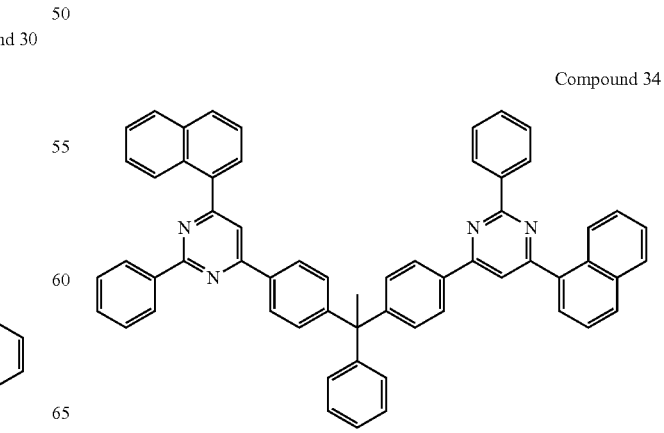

Compound 35
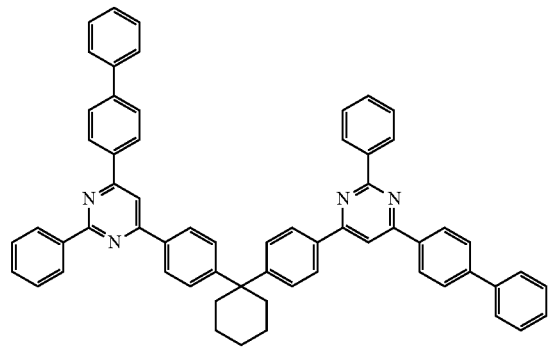
Compound 36
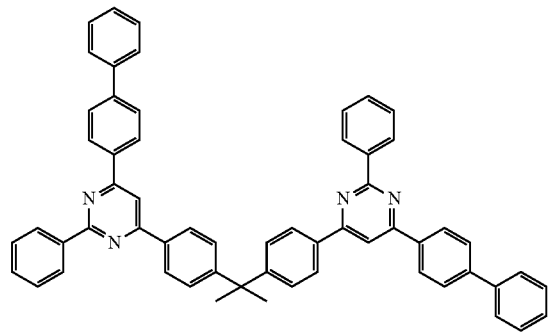
Compound 37
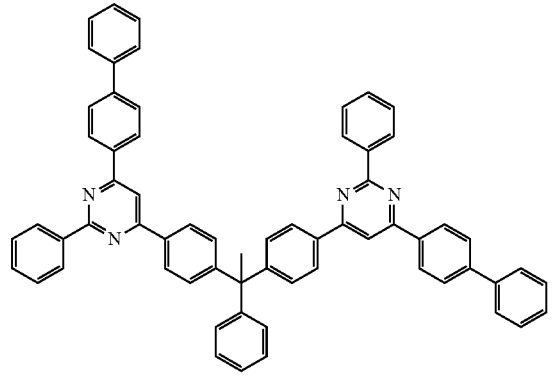
Compound 38
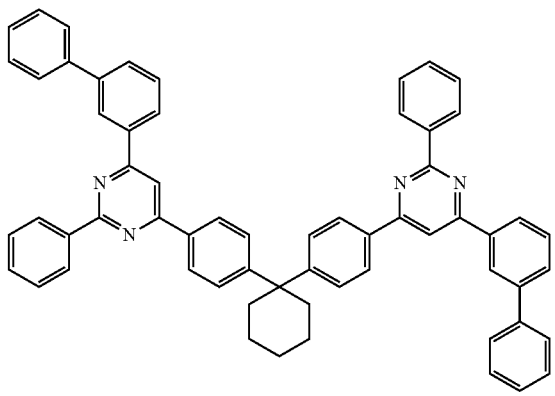
Compound 39
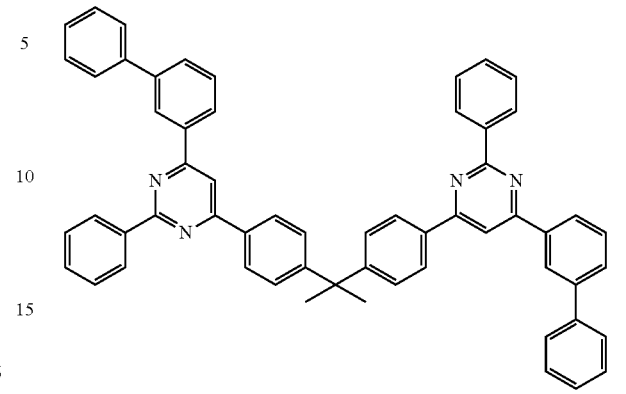
Compound 40
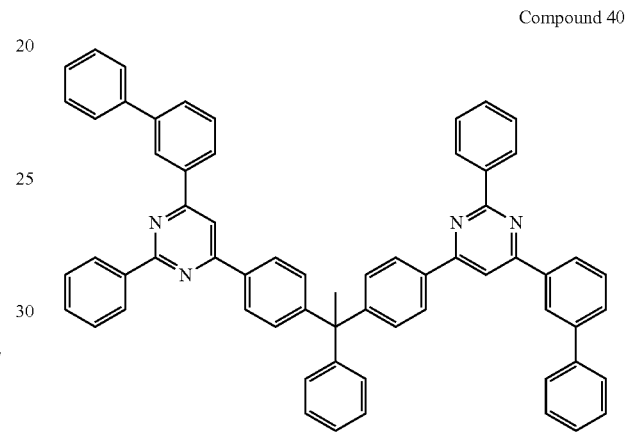
Compound 41
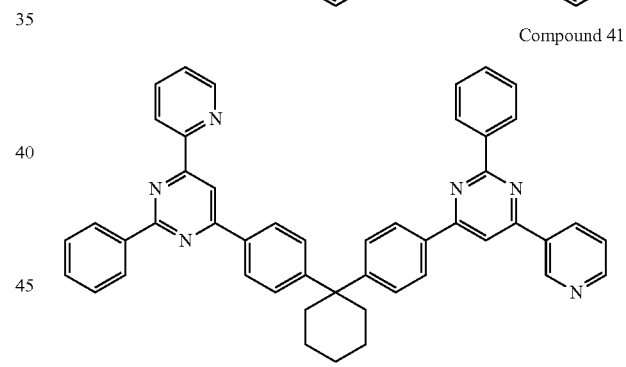
Compound 42
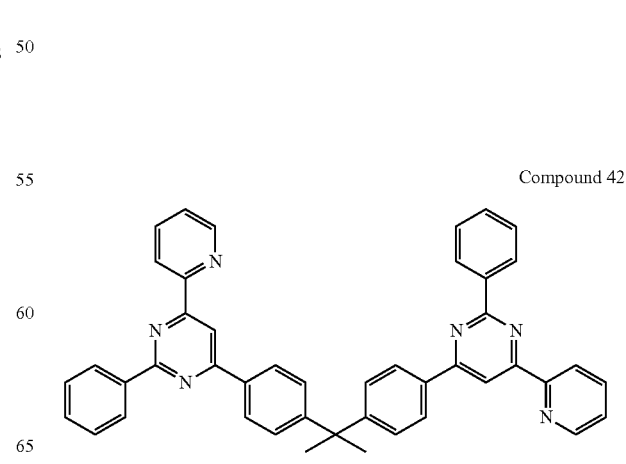

Compound 43
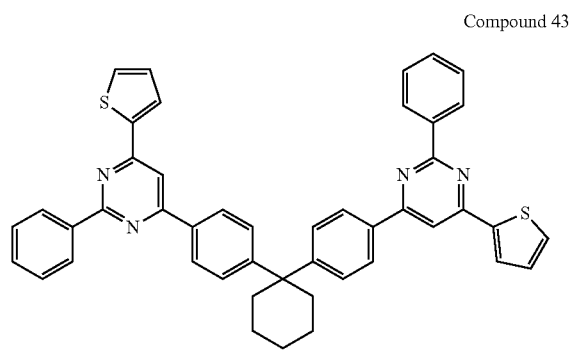
Compound 44
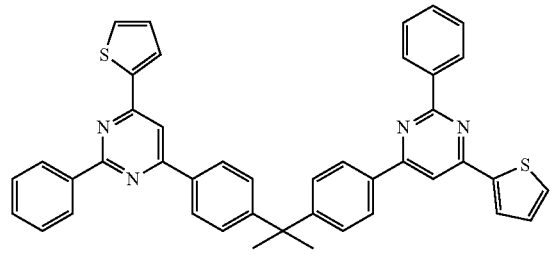
Compound 45
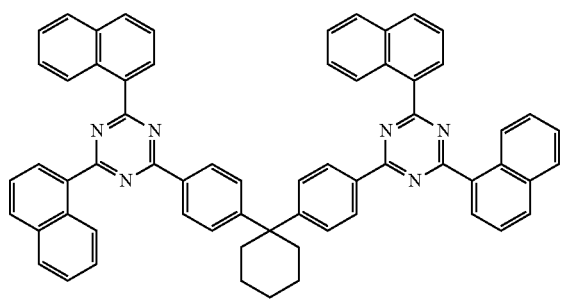
Compound 46
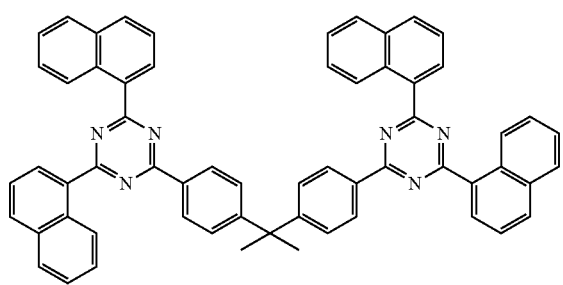
Compound 47
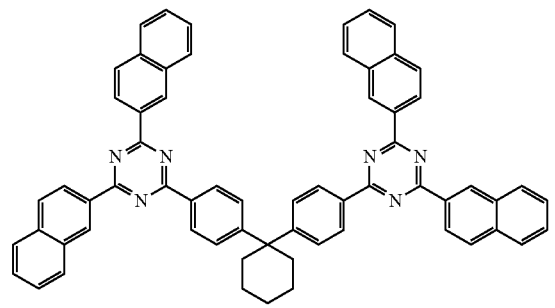
Compound 48
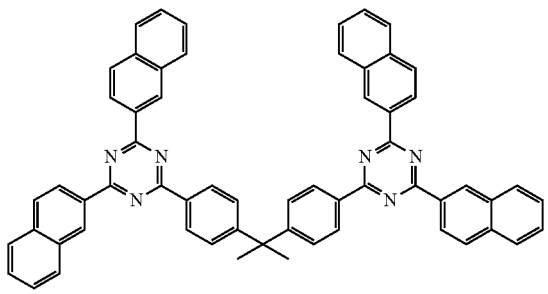
Compound 49
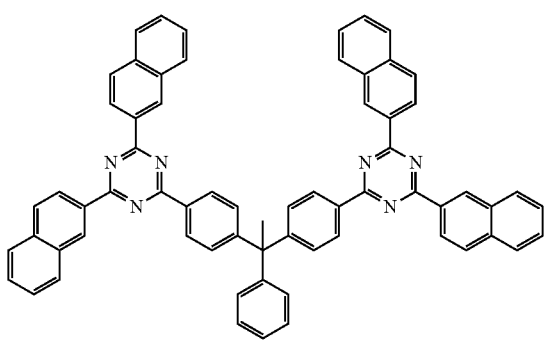
Compound 50
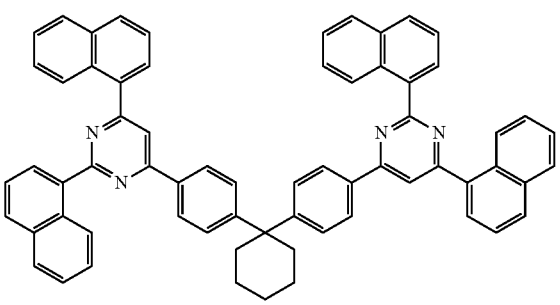
Compound 51
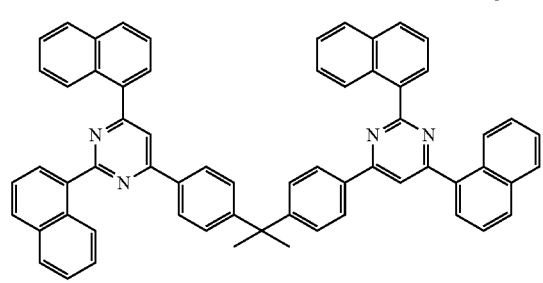
Compound 52
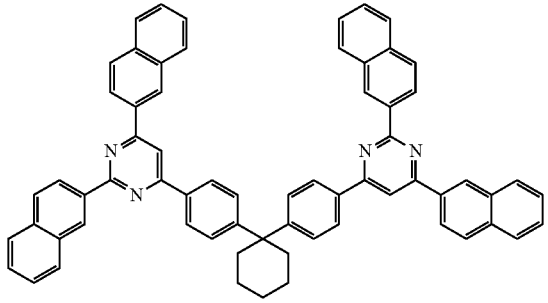

Compound 53
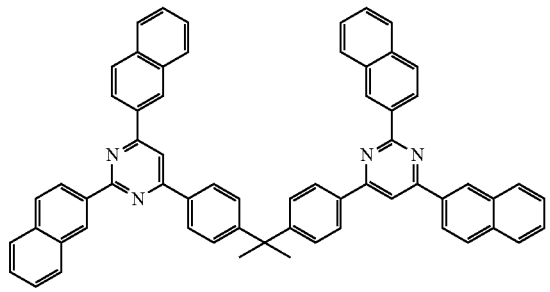
Compound 54
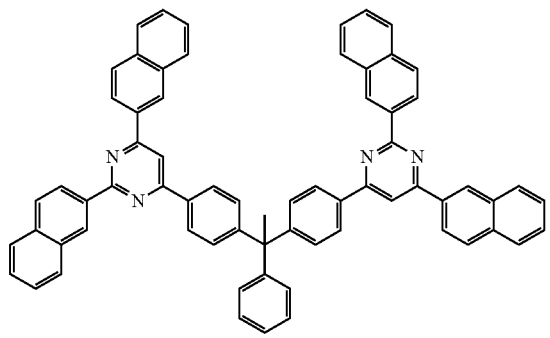
Compound 55
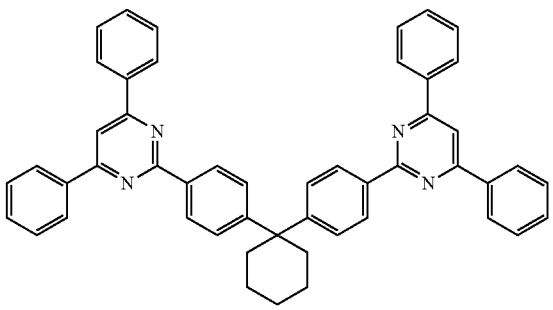
Compound 56
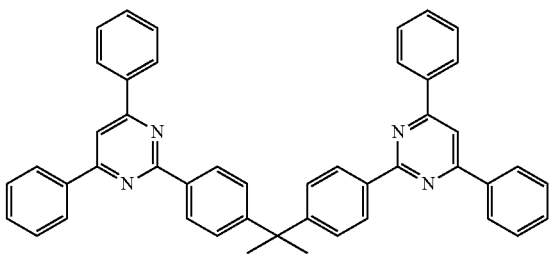
Compound 57
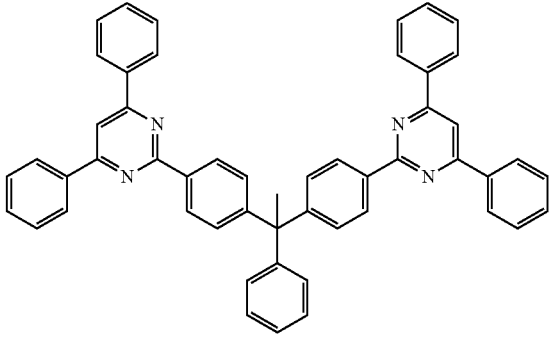
Compound 58
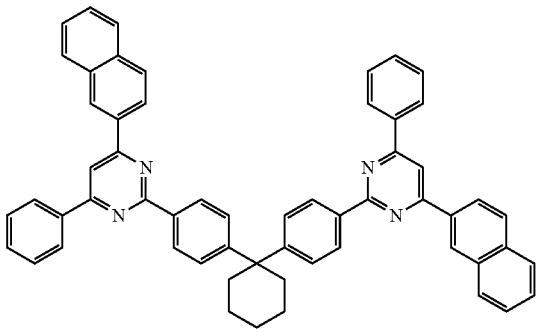
Compound 59
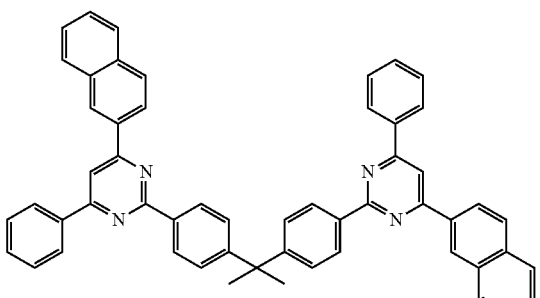
Compound 60
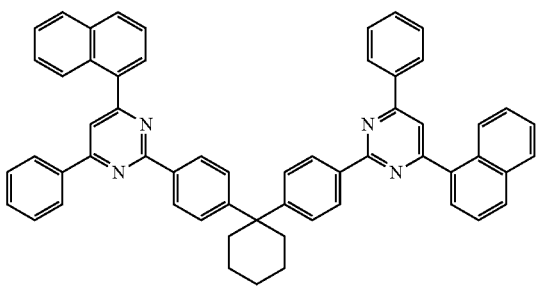
Compound 61
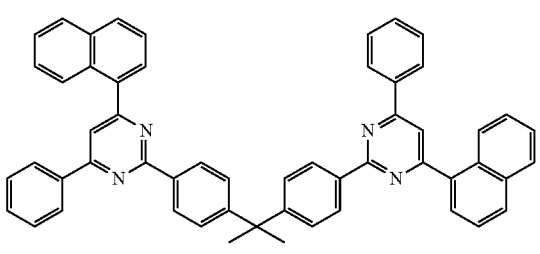
Compound 62
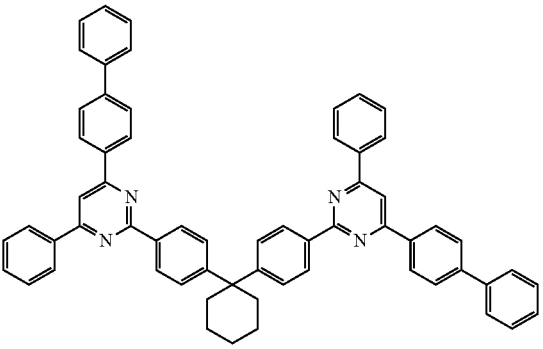

Compound 63
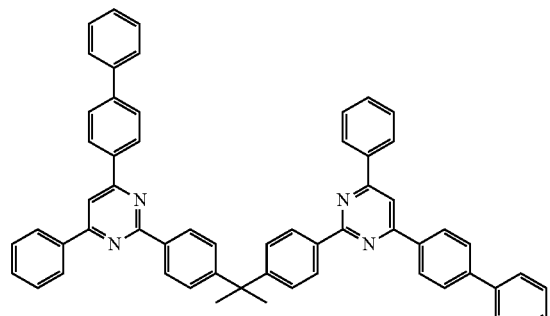
Compound 64
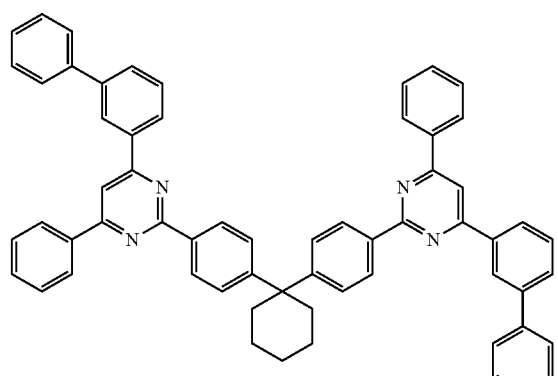
Compound 65
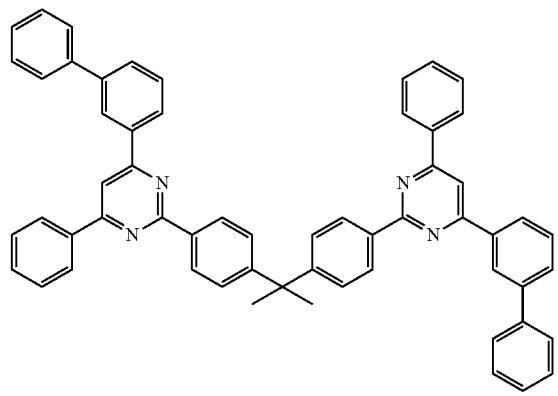
Compound 66
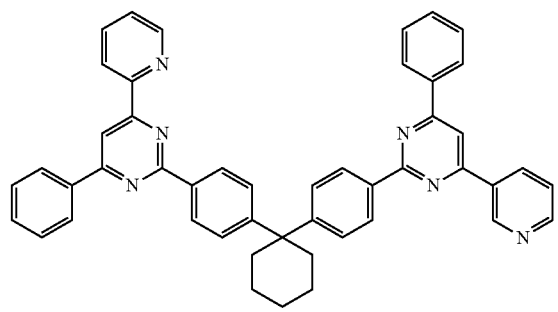
Compound 67
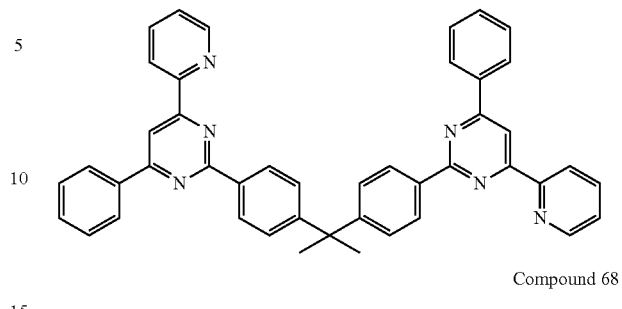
Compound 68
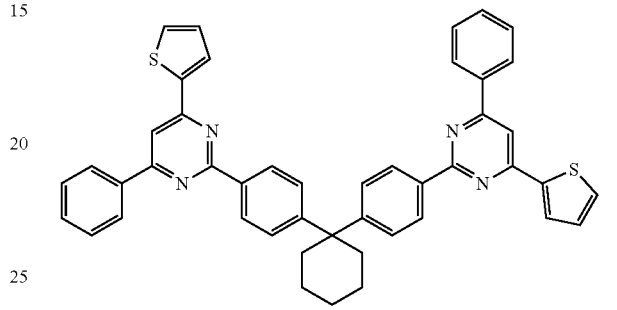
Compound 69
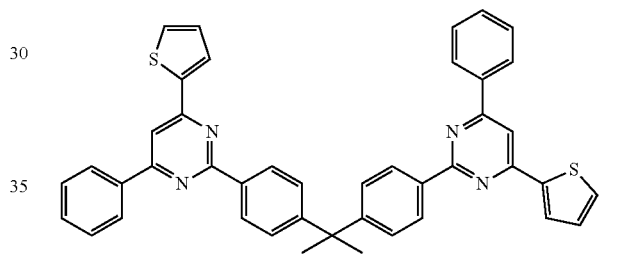
Compound 70
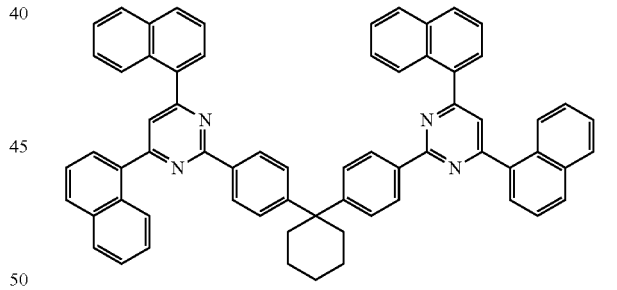
Compound 71
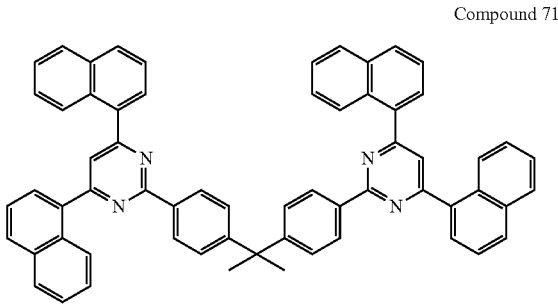

Compound 72
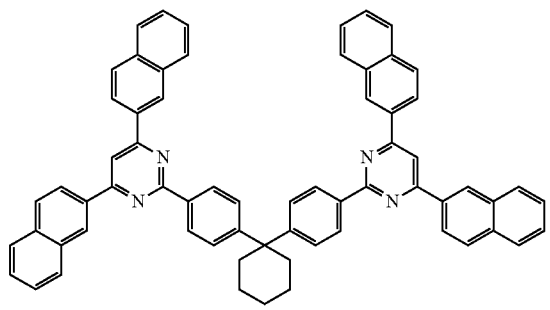
Compound 73
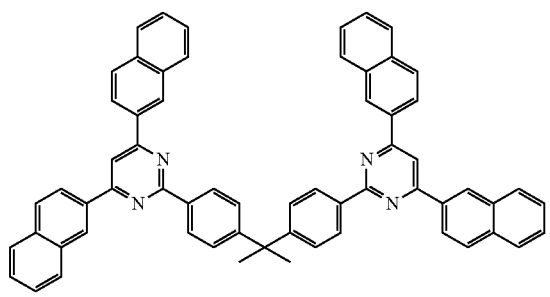
Compound 74
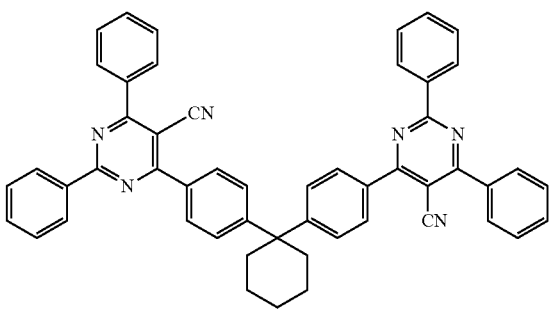
Compound 75
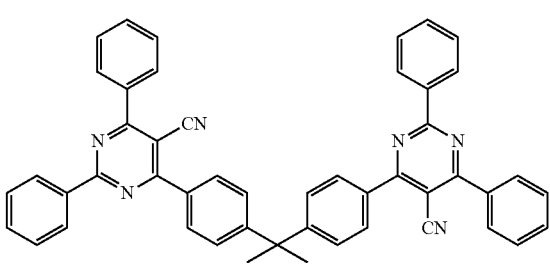
Compound 76
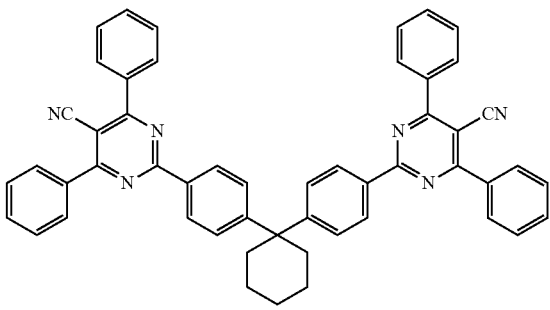
Compound 77
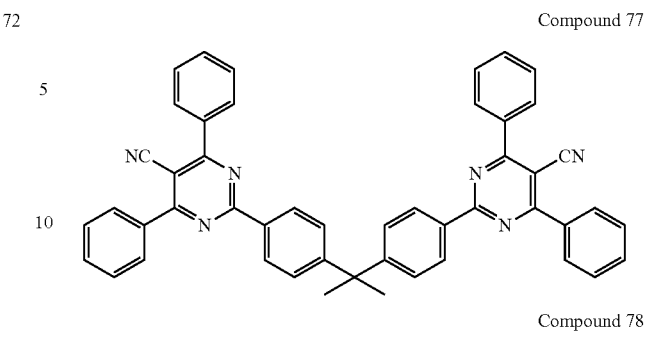
Compound 78
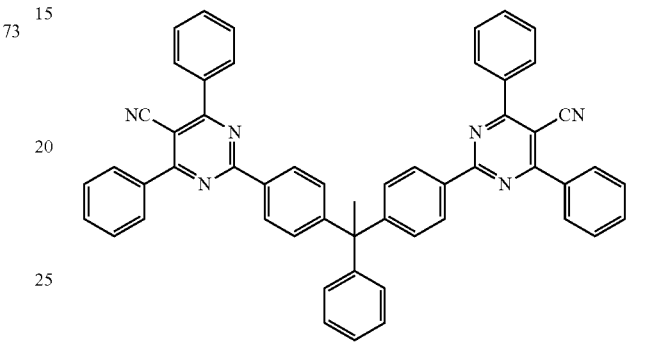
Compound 79
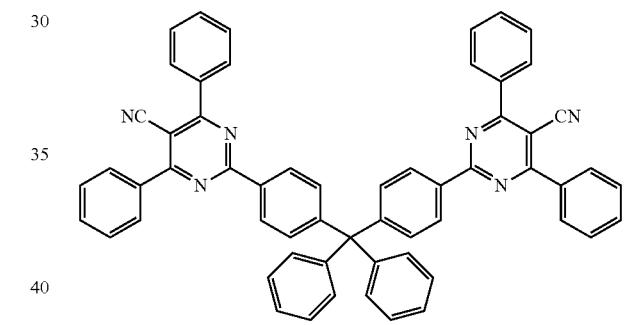
Compound 80
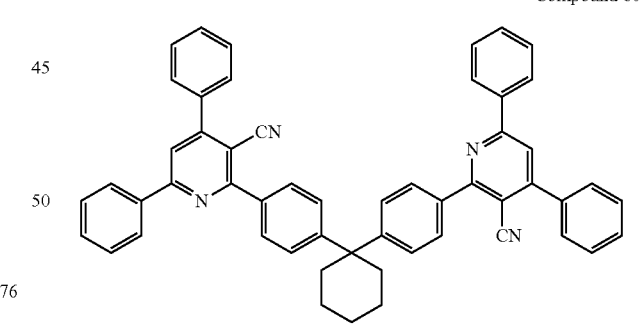
Compound 81
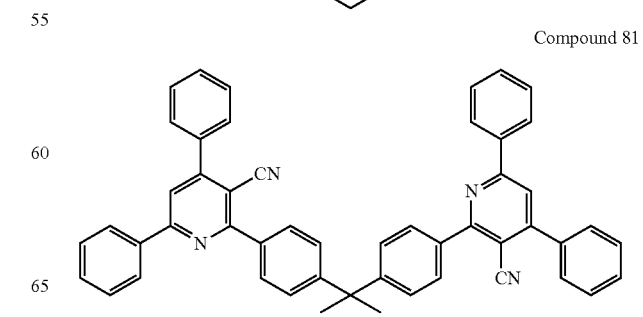

Compound 82
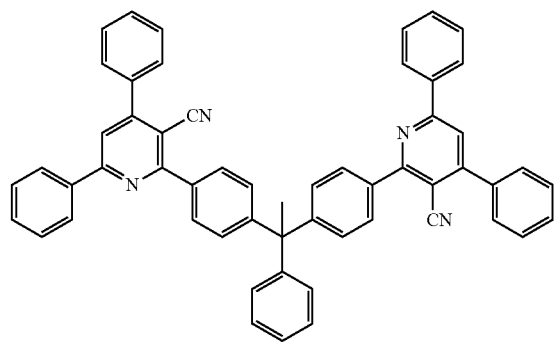
Compound 89
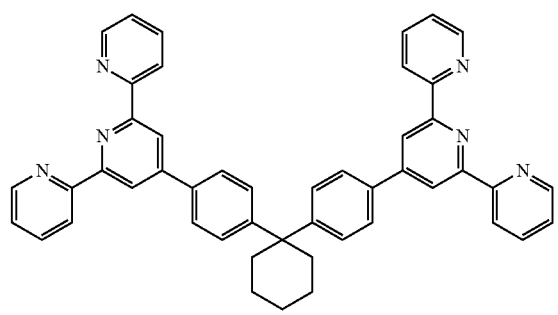
Compound 90
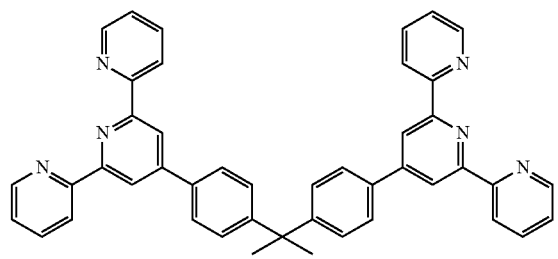
Compound 91
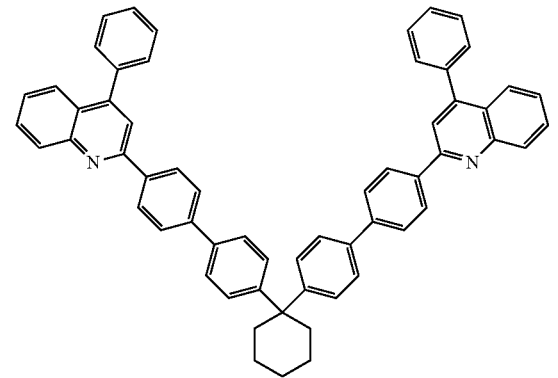
Compound 92
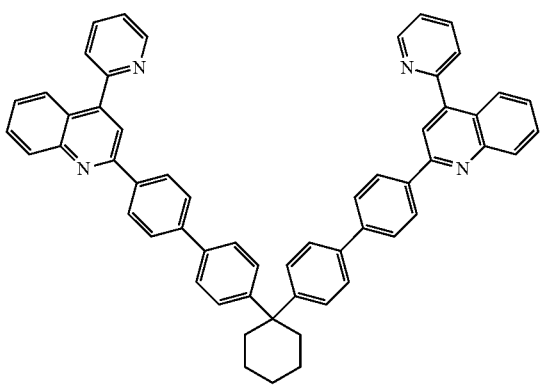
Compound 93
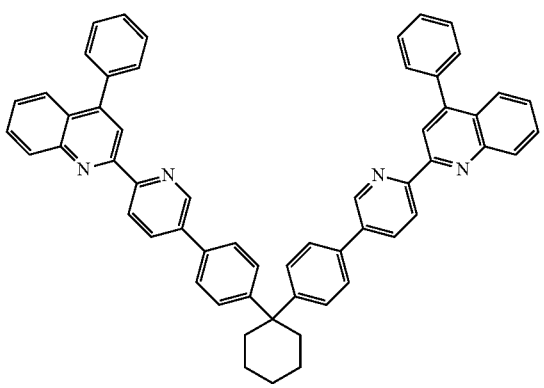
Compound 94
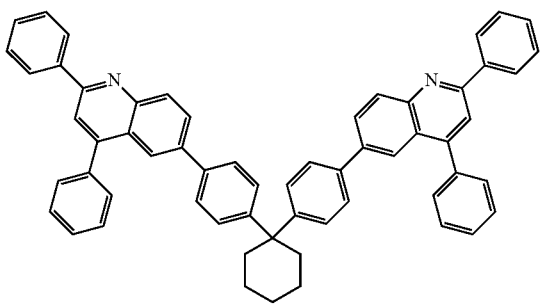
Compound 95
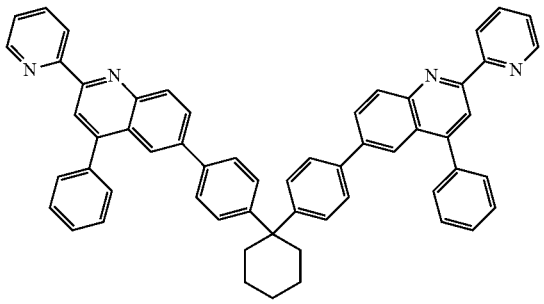

Compound 96
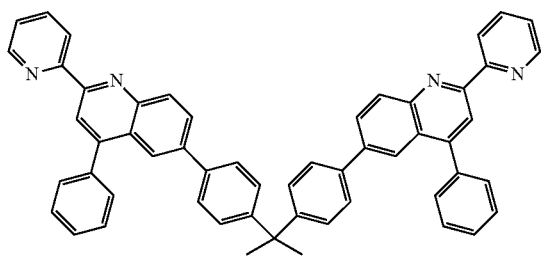
Compound 97
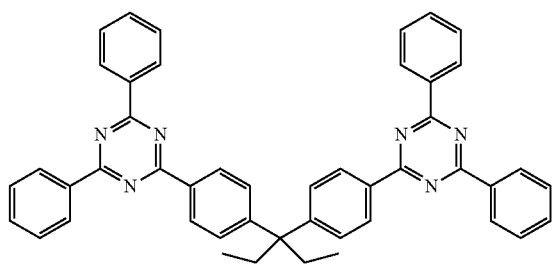
Compound 98
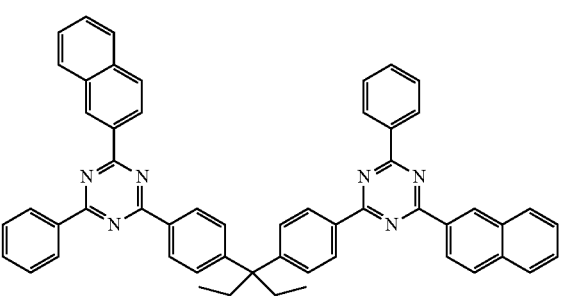
Compound 99
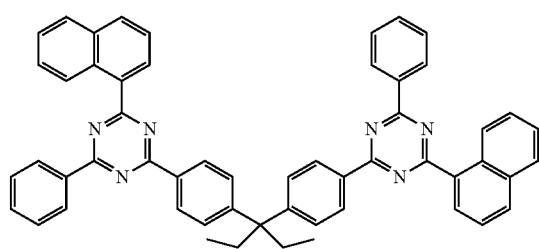
Compound 100
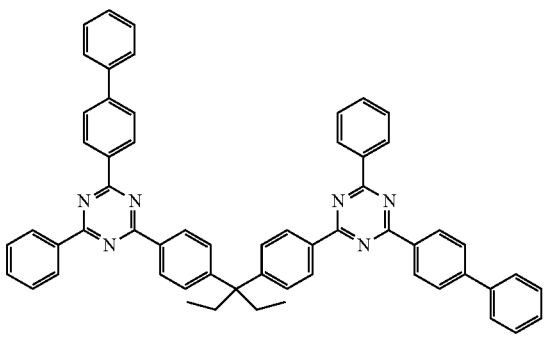
Compound 101
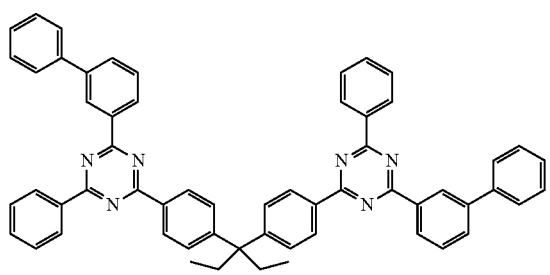
Compound 102
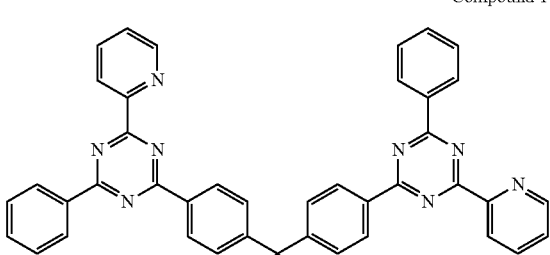
Compound 103
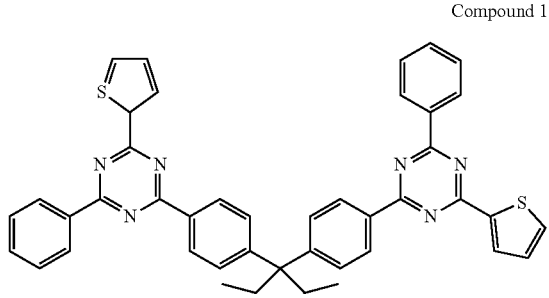
Compound 104
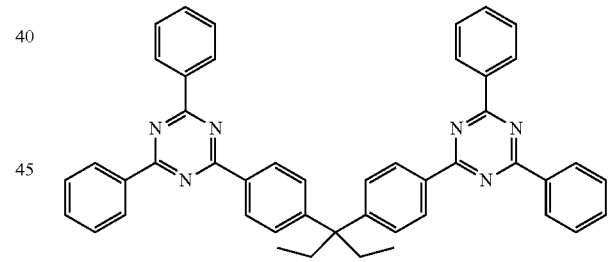
Compound 105
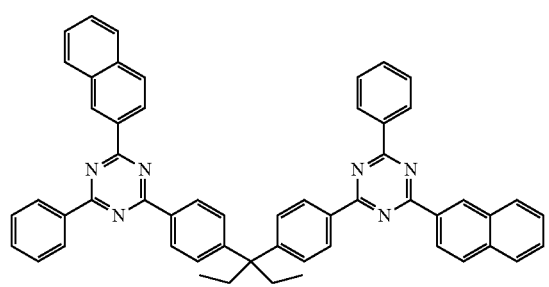

Compound 106
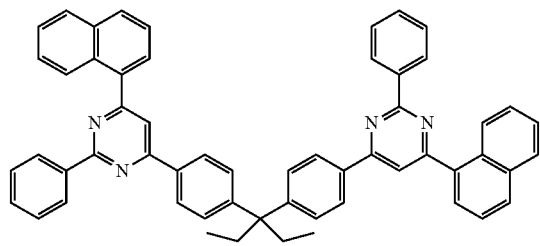
Compound 107
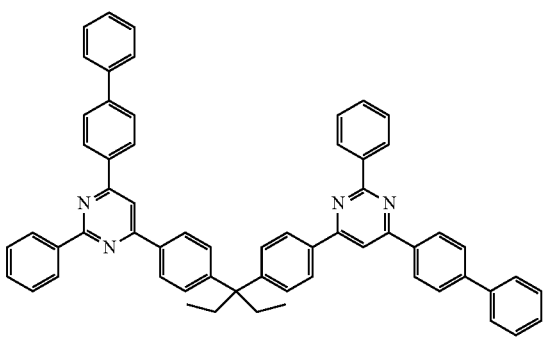
Compound 108
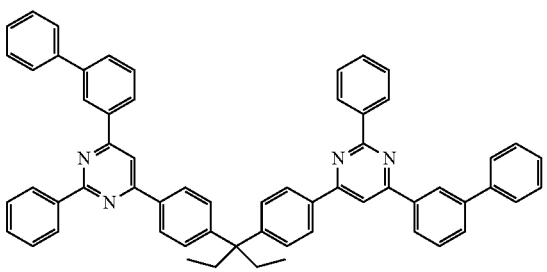
Compound 109
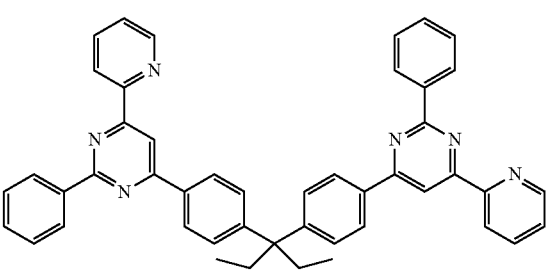
Compound 110
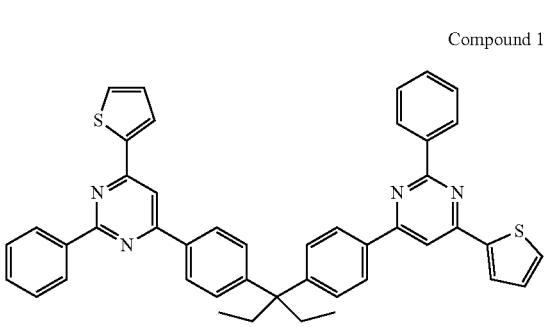
Compound 111
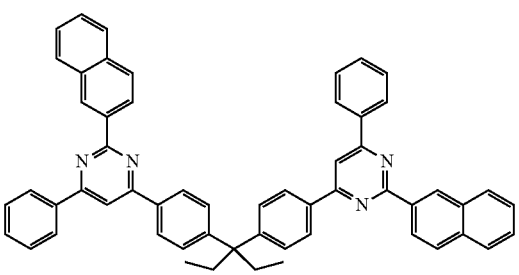
Compound 112
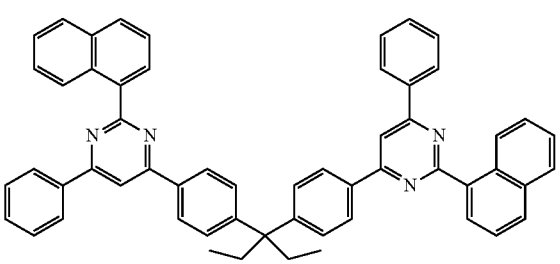
Compound 113
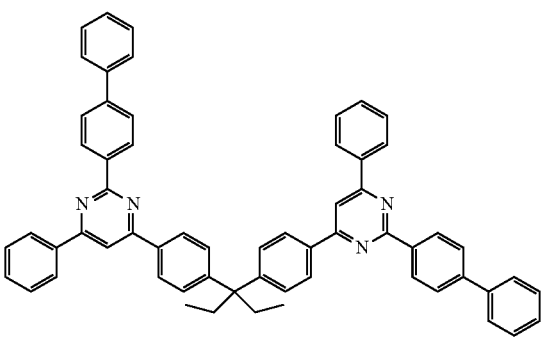
Compound 114
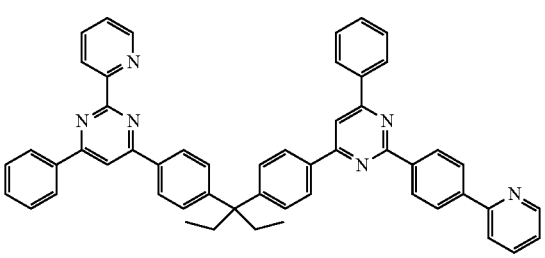
Compound 115
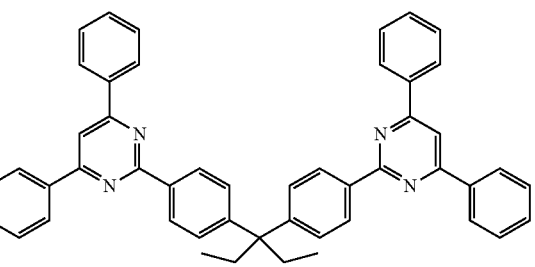

Compound 116
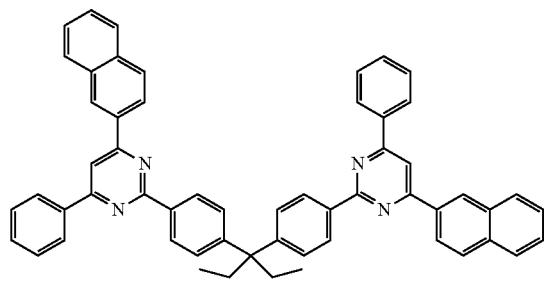
Compound 117
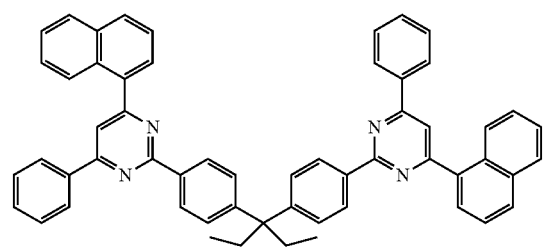
Compound 118
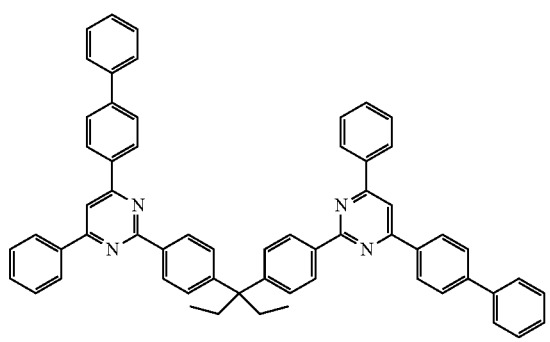
Compound 119
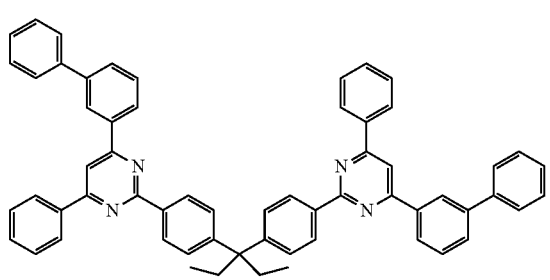
Compound 120
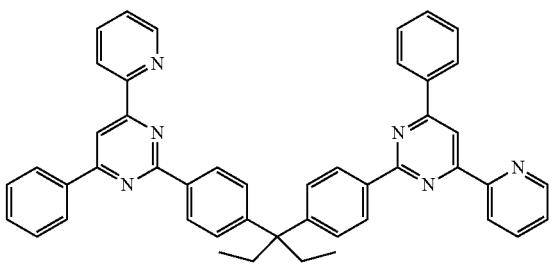
Compound 121
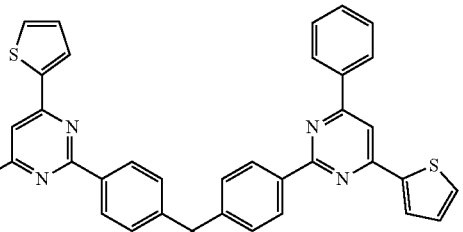
Compound 122
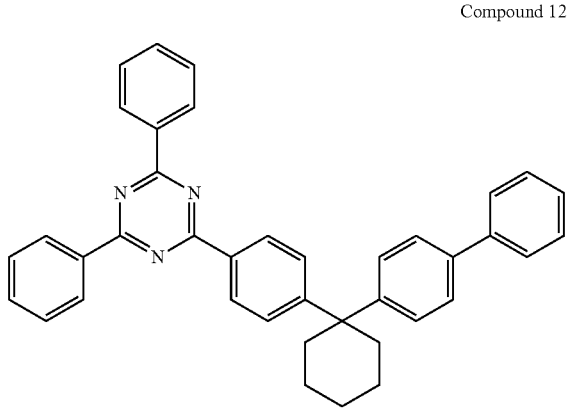
Compound 123
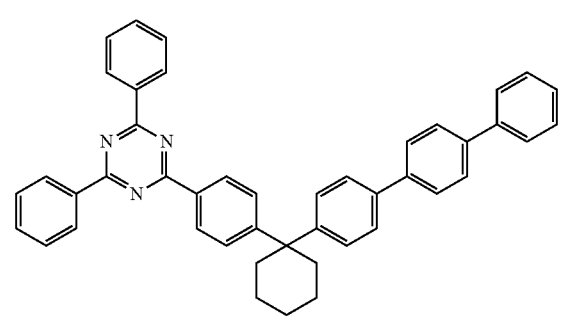
Compound 124
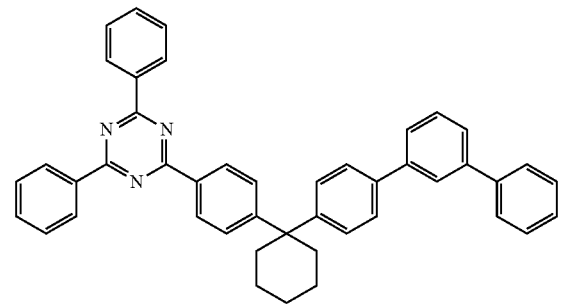

Compound 125
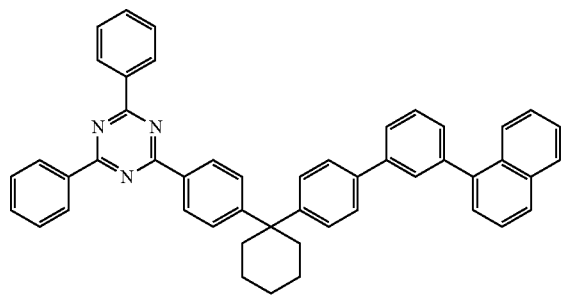
Compound 126
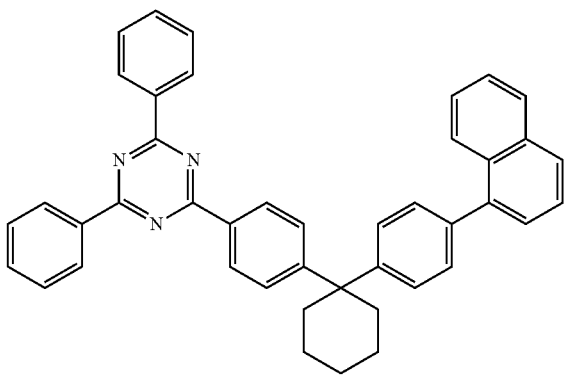
Compound 127
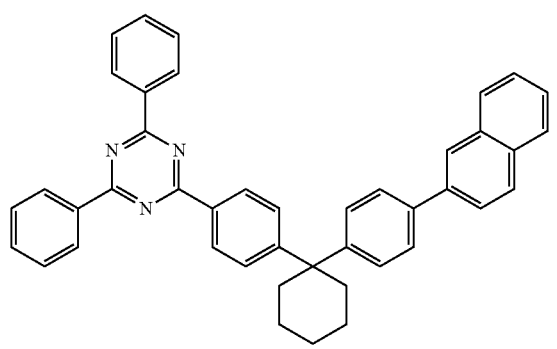
Compound 128
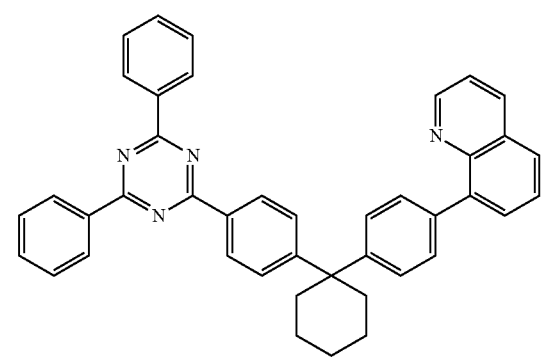
Compound 129
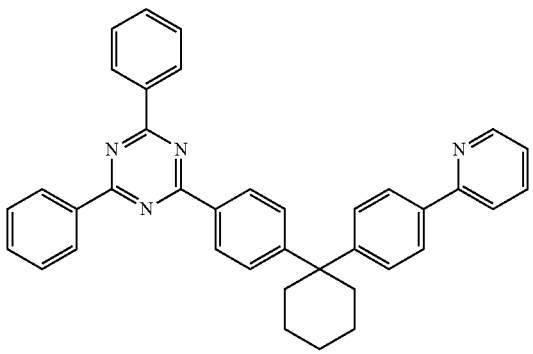
Compound 130
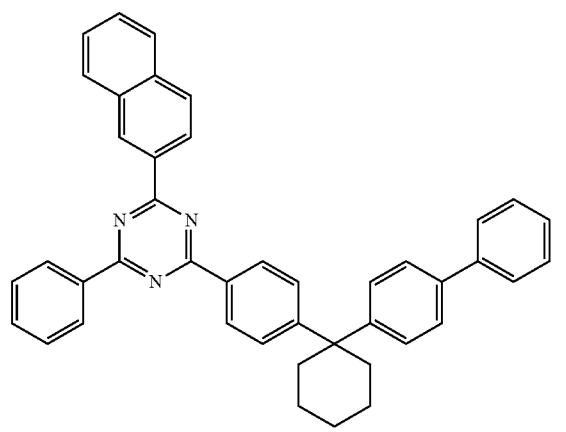
Compound 131
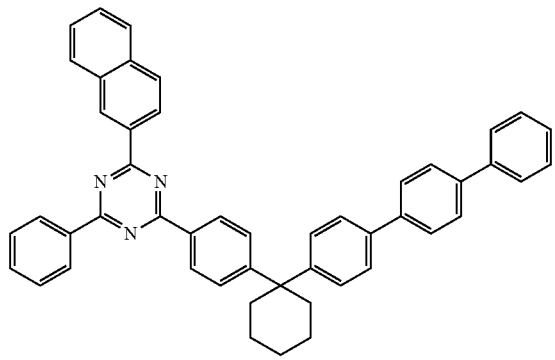
Compound 132
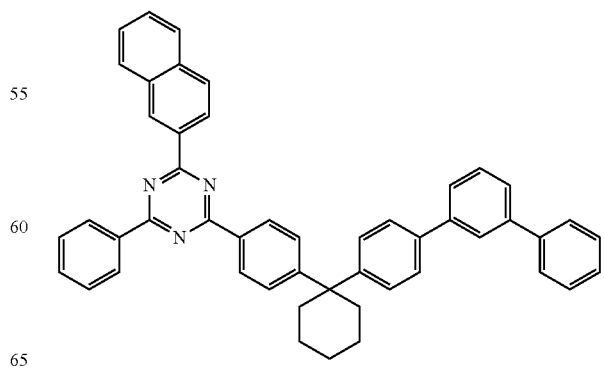

Compound 133
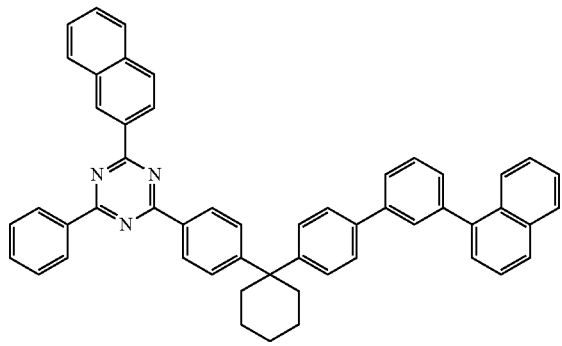
Compound 134
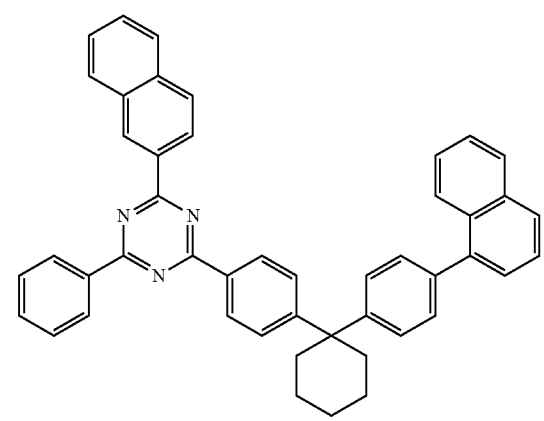
Compound 135
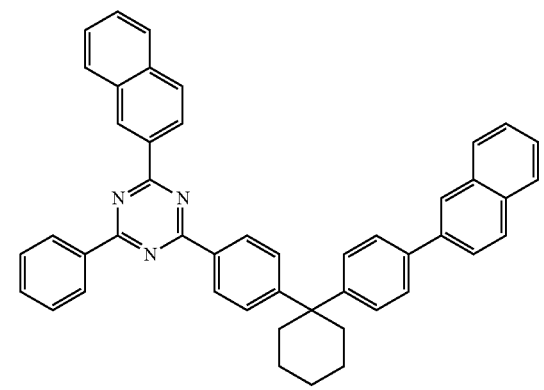
Compound 136
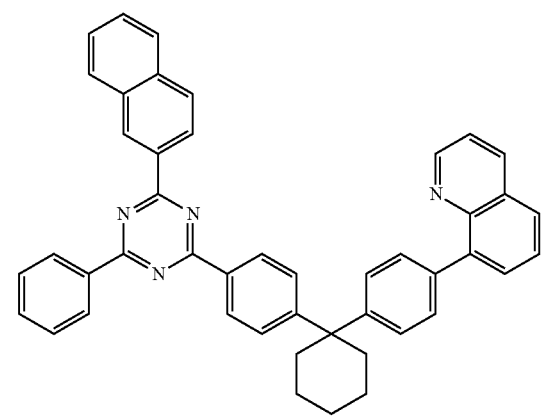
Compound 137
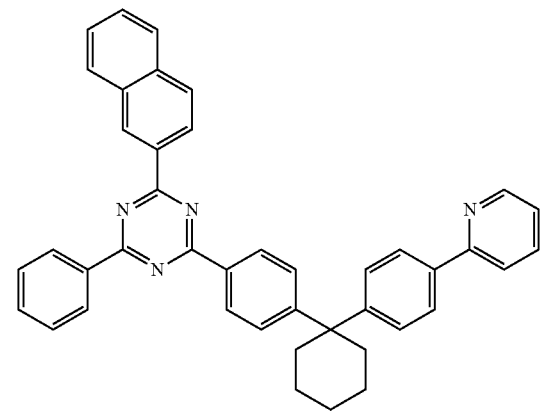
Compound 138
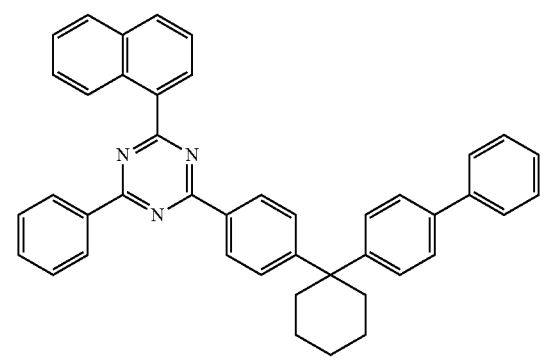
Compound 139
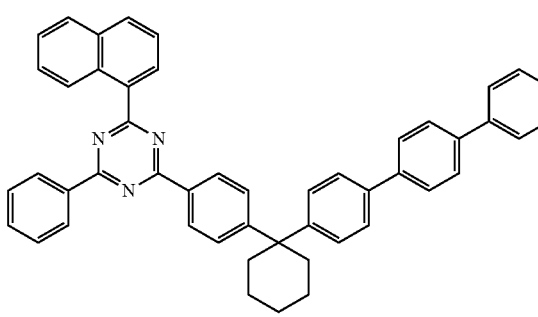
Compound 140
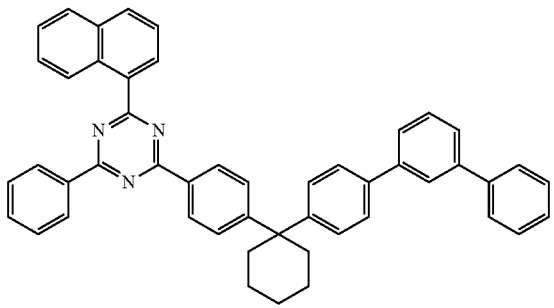

Compound 141
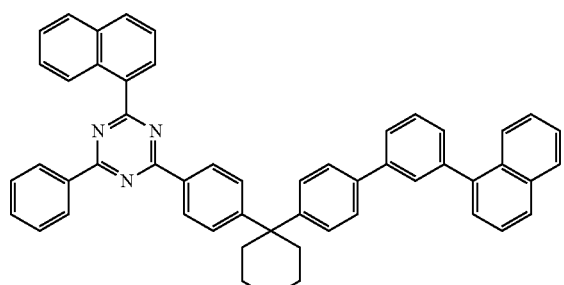
Compound 142
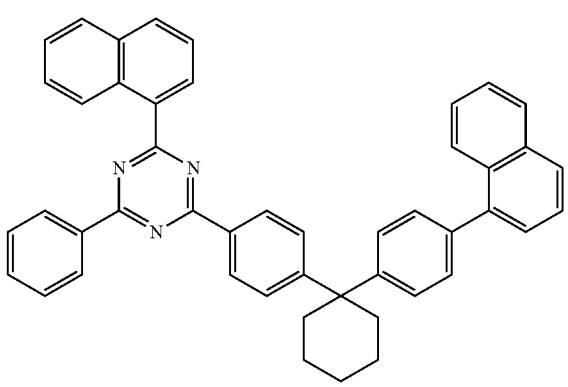
Compound 143
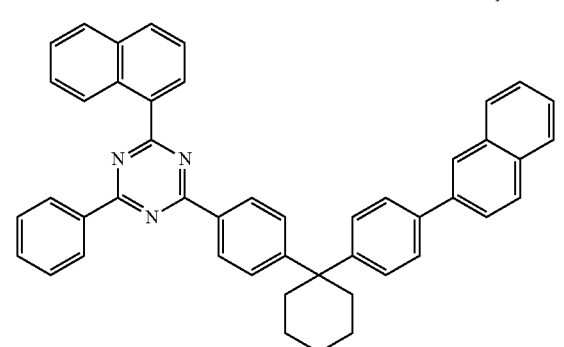
Compound 144
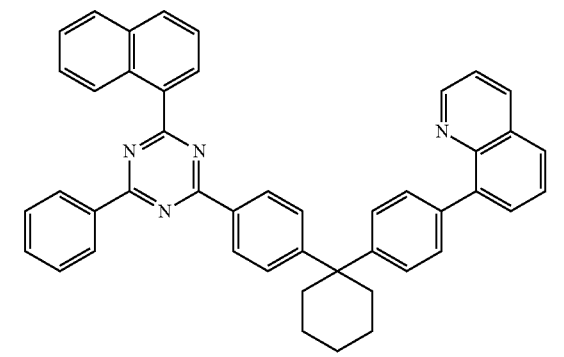
Connpound 145
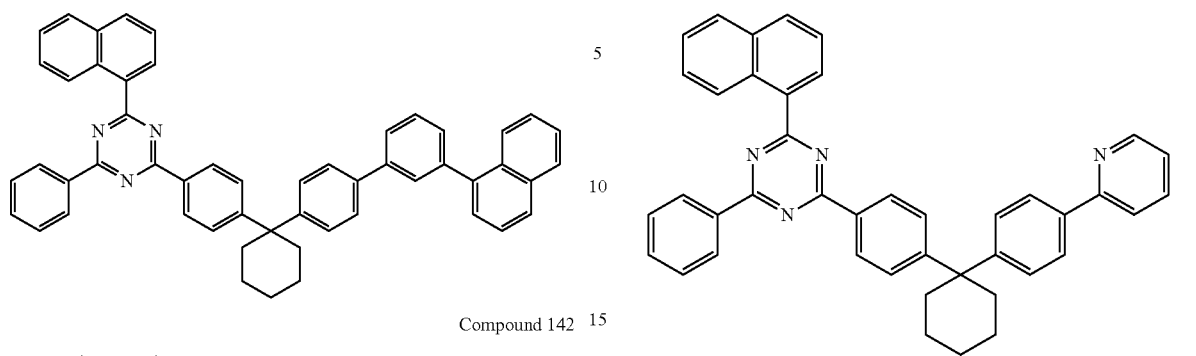
Compound 146
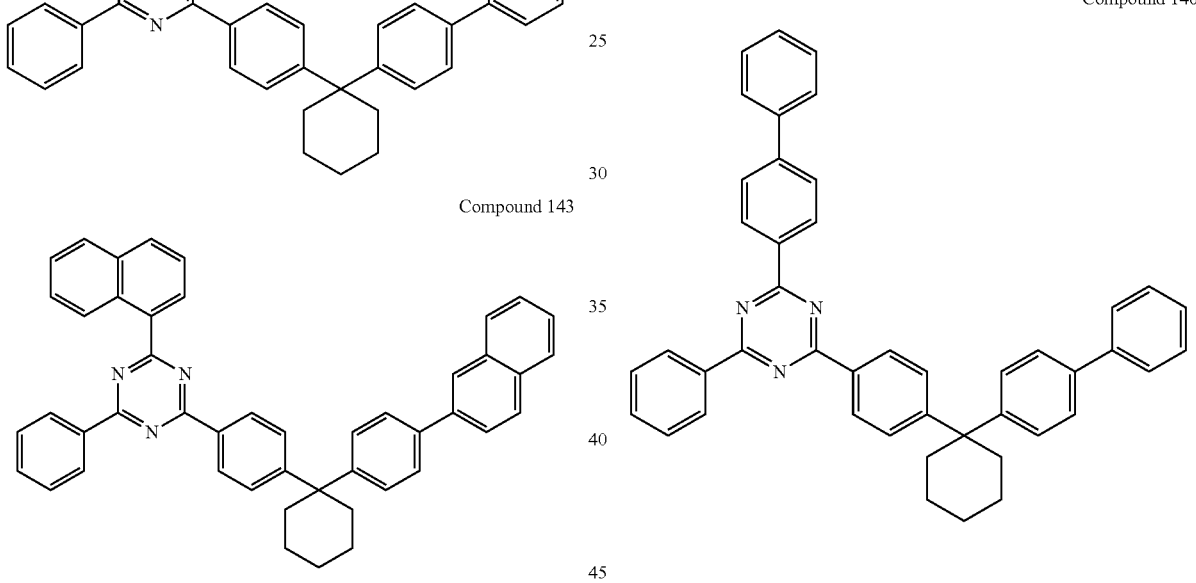
Compound 147
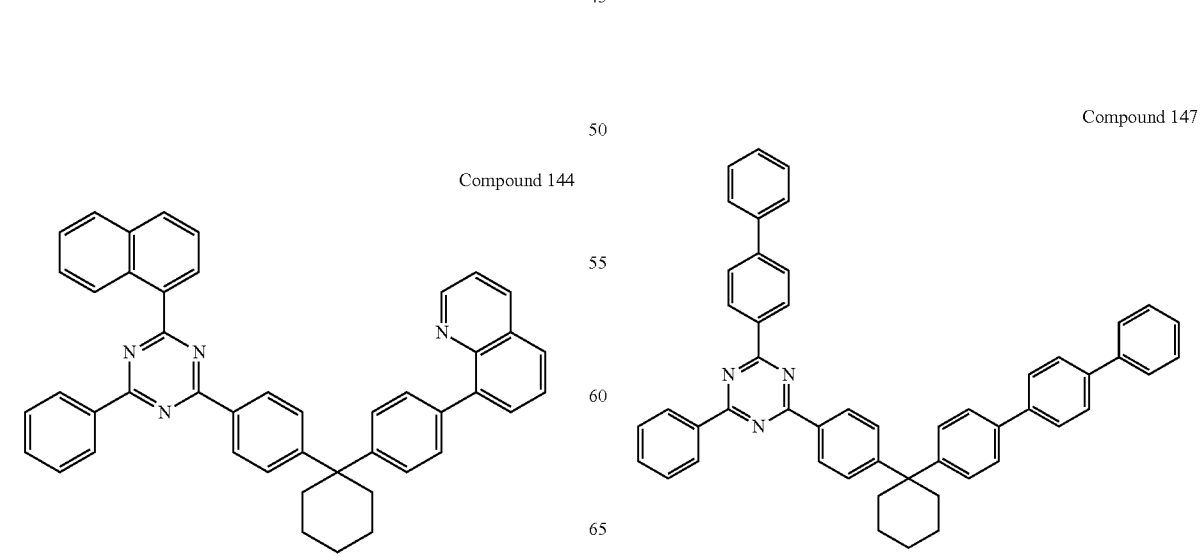

-continued
Compound 148
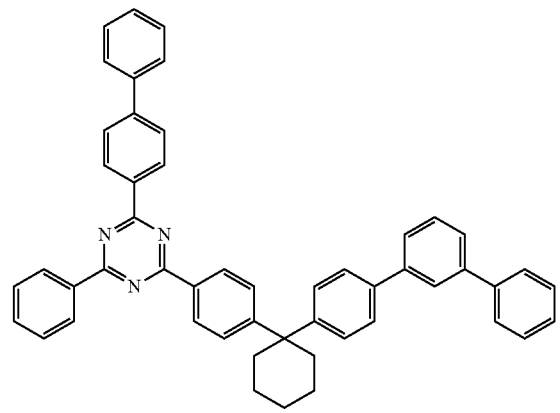
Compound 149
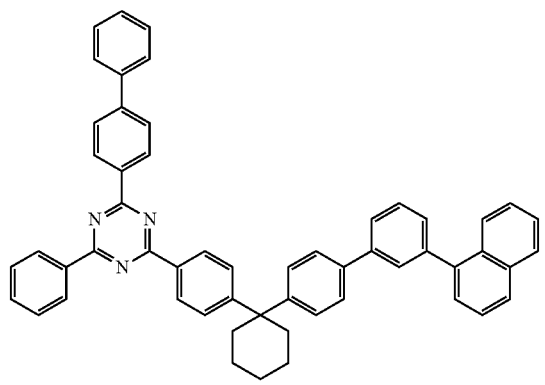
Compound 150
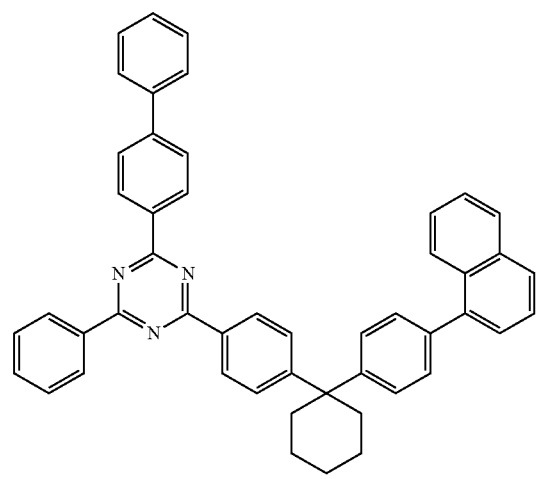
Compound 151
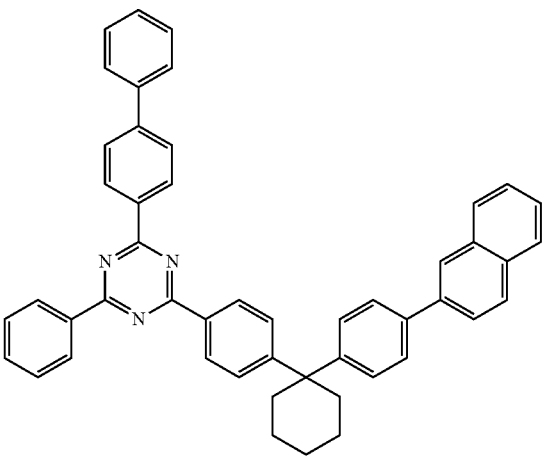
Compound 152
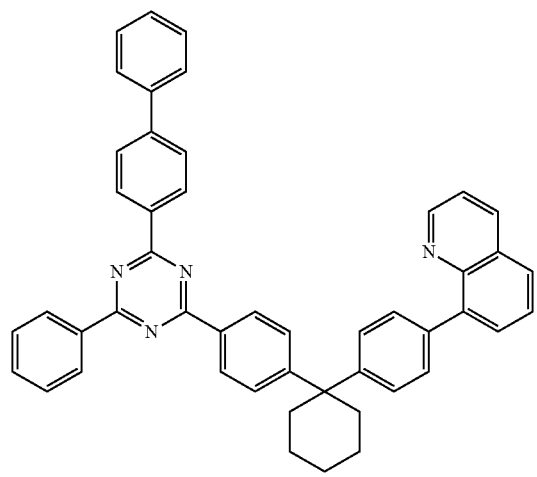
Compound 153
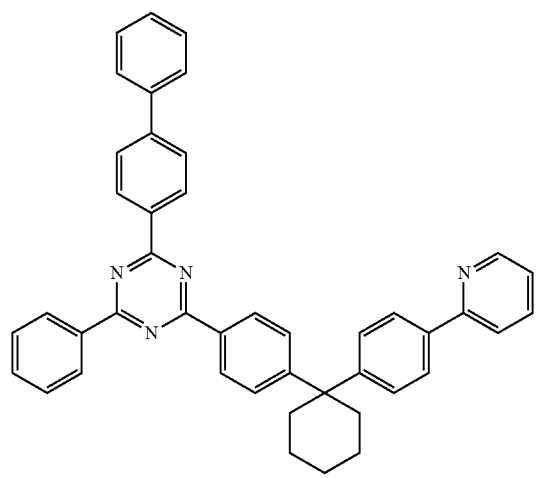

Compound 154
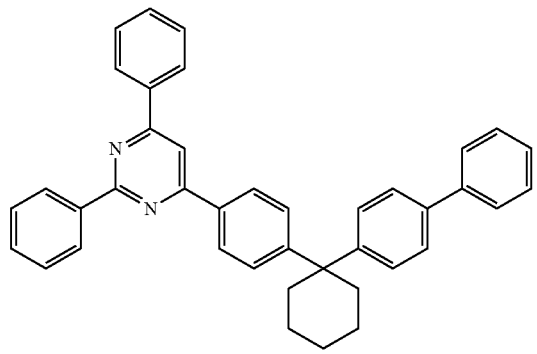
Compound 155
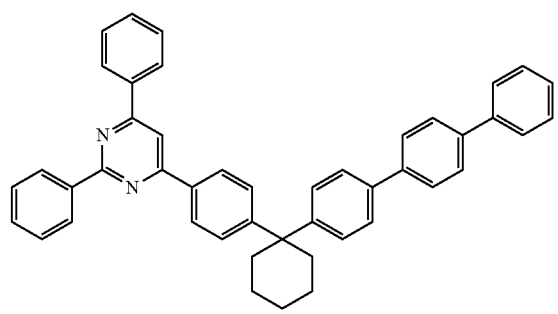
Compound 156
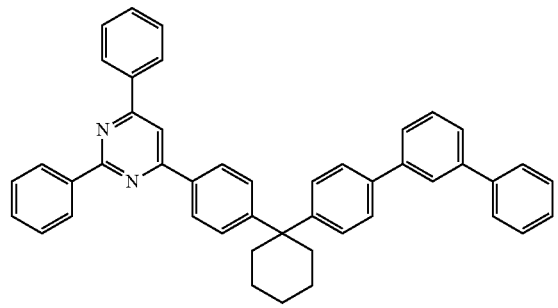
Compound 157
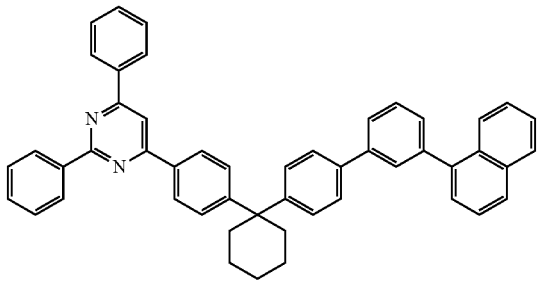
Compound 158
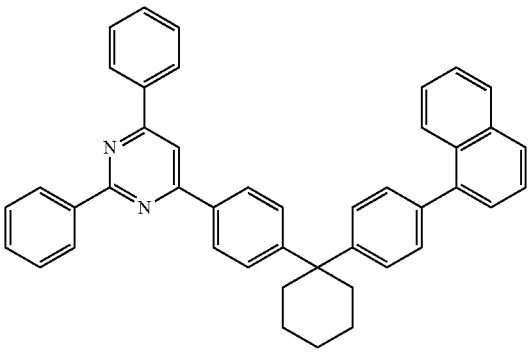
Compound 159
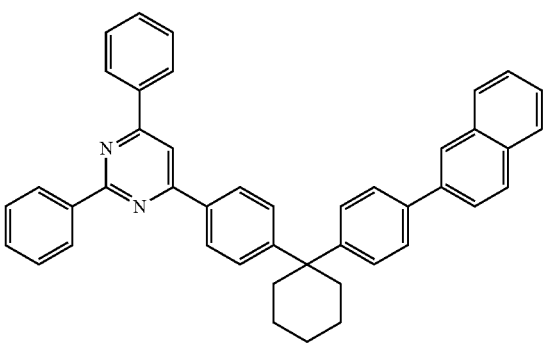
Compound 160
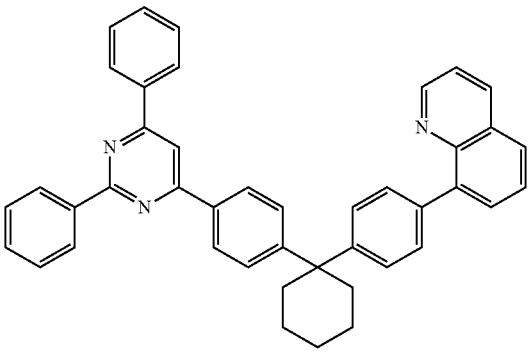
Compound 161
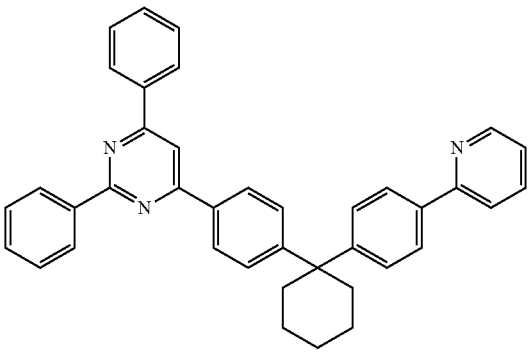

Compound 162
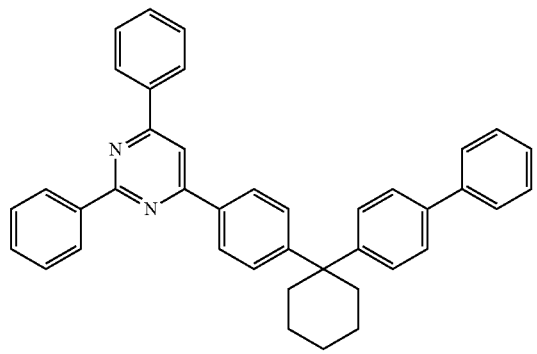
Compound 163
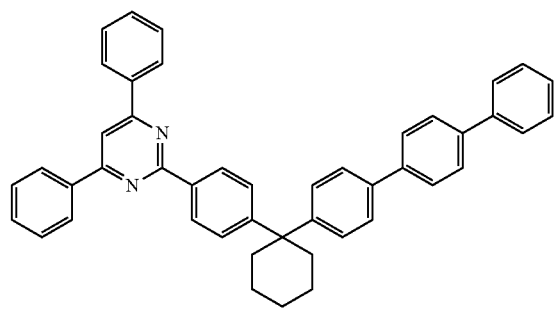
Compound 164
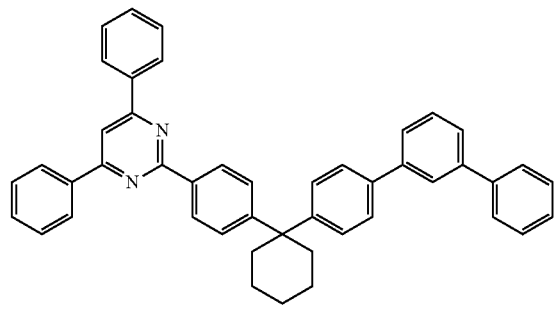
Compound 165
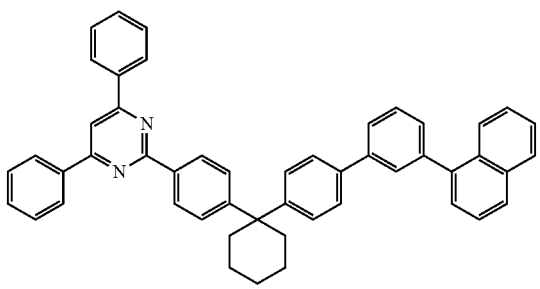
Compound 166
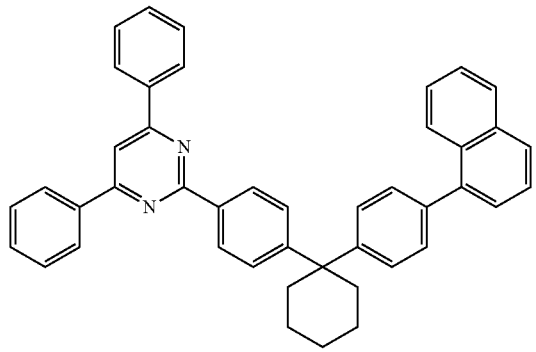
Compound 167
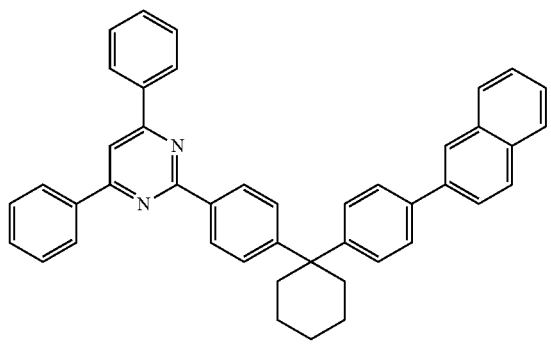
Compound 168
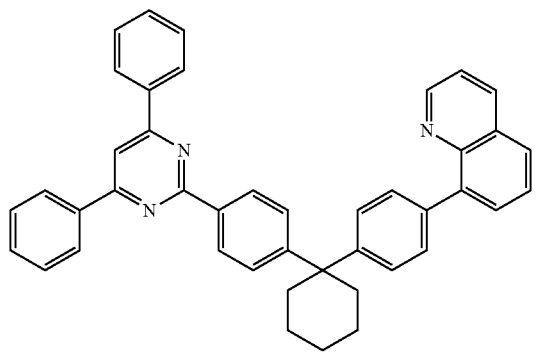
Compound 169
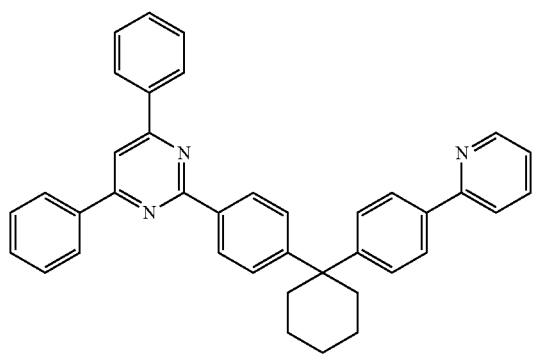

-continued
Compound 170
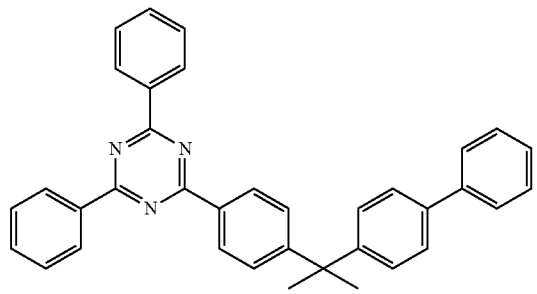
Compound 171
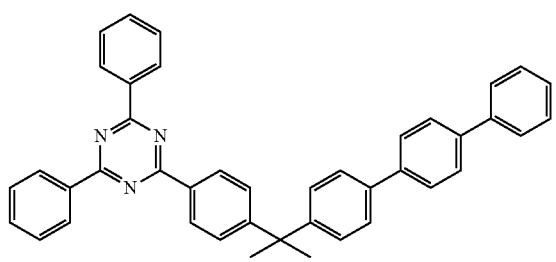
Compound 172
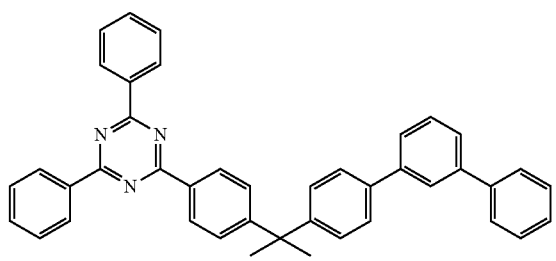
Compound 173
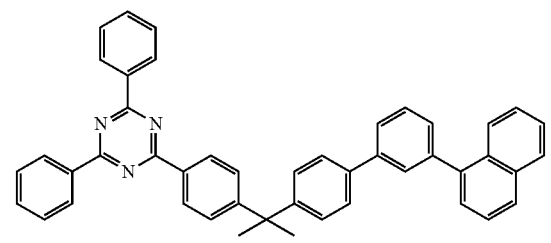
Compound 174
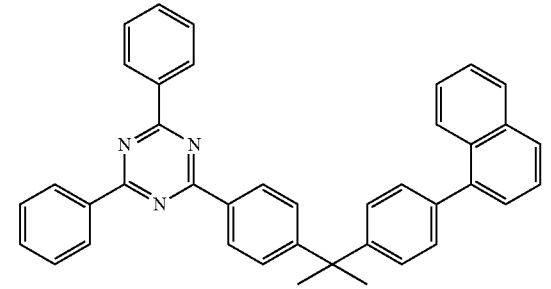
-continued
Compound 175
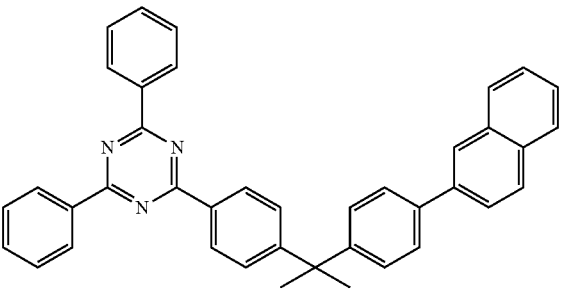
Compound 176
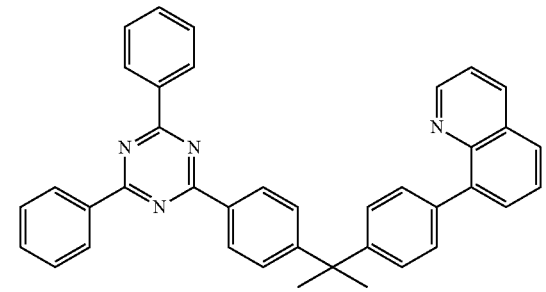
Compound 177
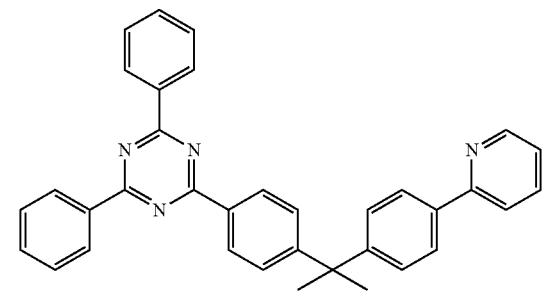
Compound 178
Compound 179
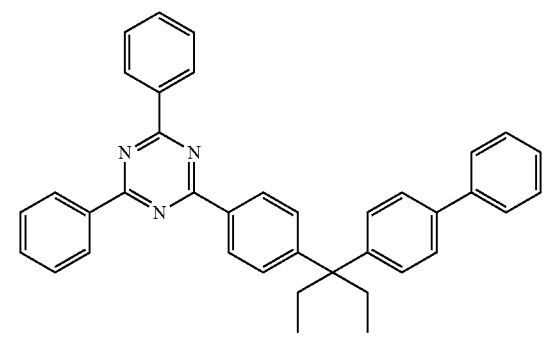

Compound 180
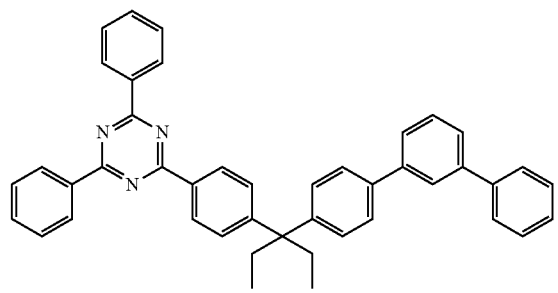
Compound 181
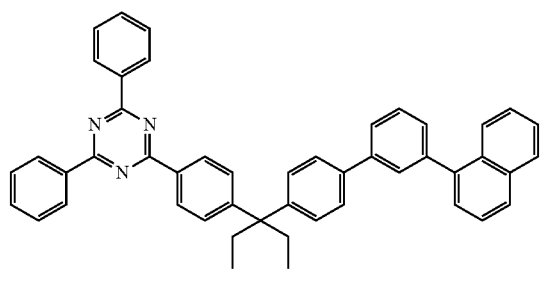
Compound 182
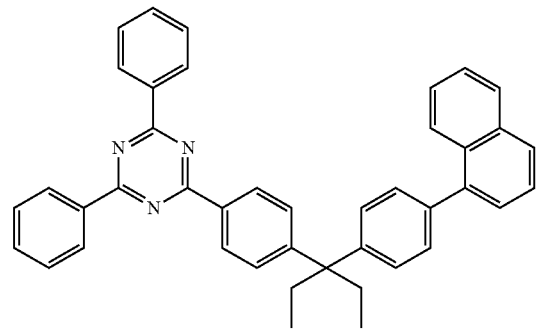
Compound 183
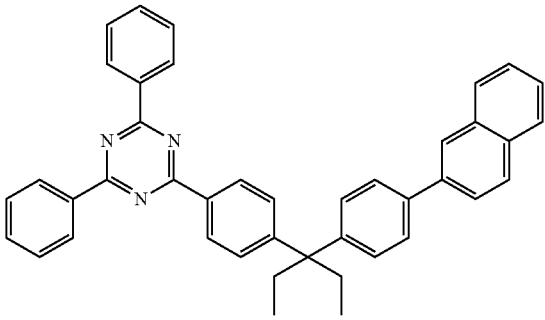
Compound 184
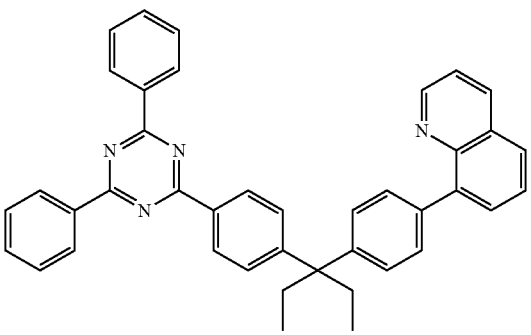
Compound 185
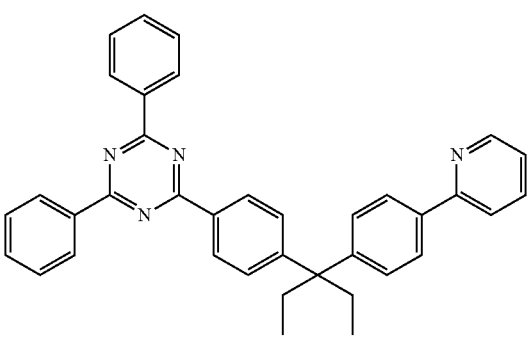
Compound 186
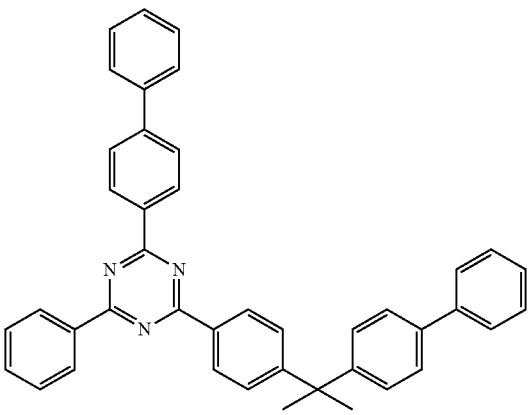
Compound 187
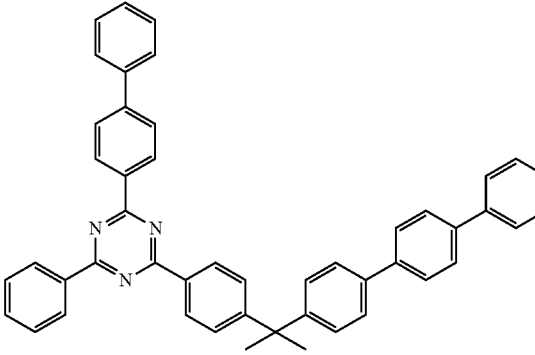

Compound 188
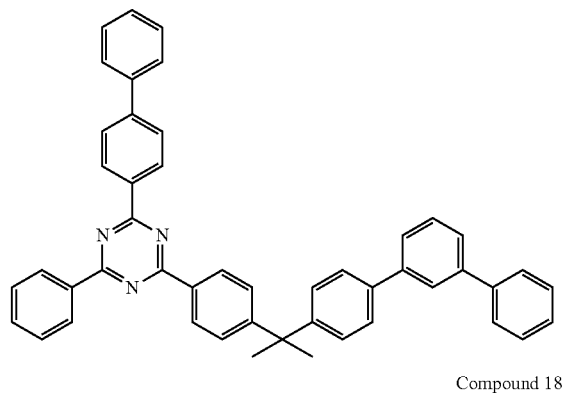
Compound 189
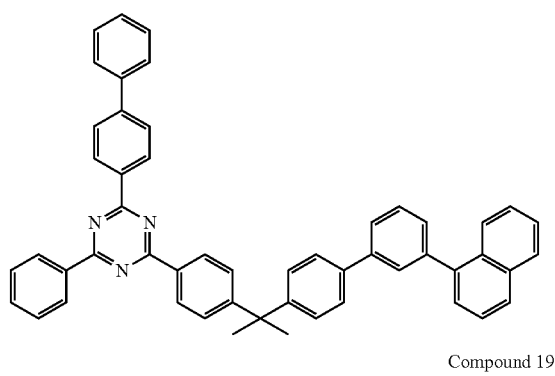
Compound 190
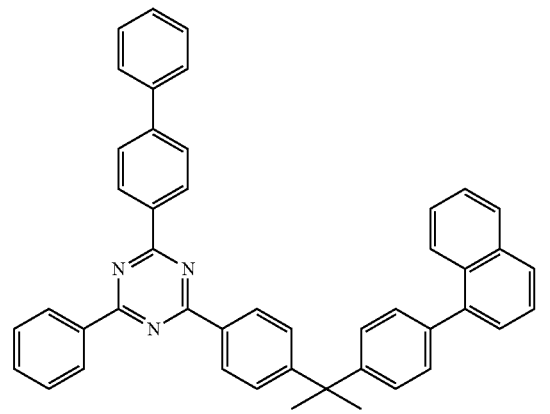
Compound 191
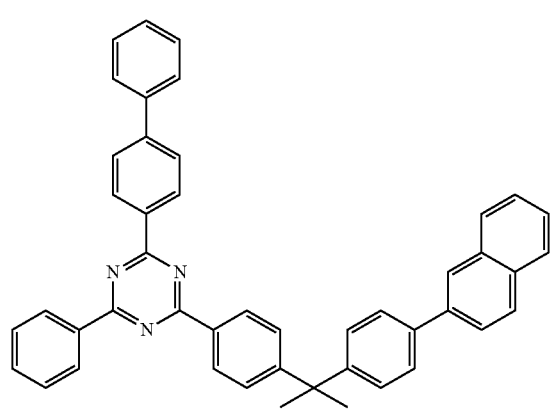
Compound 192
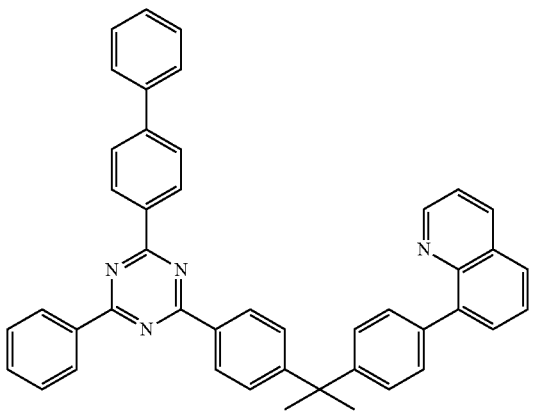
Compound 193
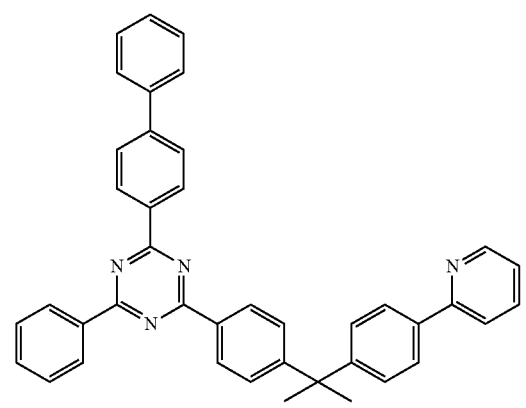
Compound 194
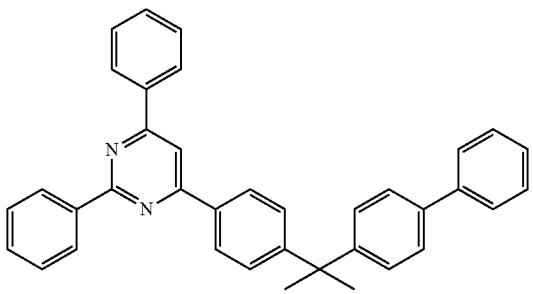
Compound 195
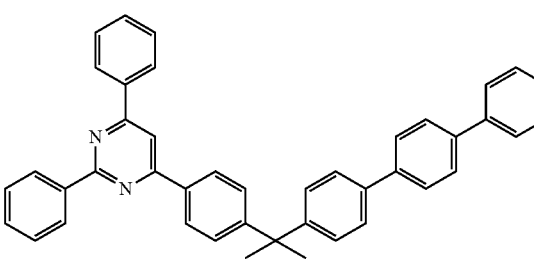

Compound 196
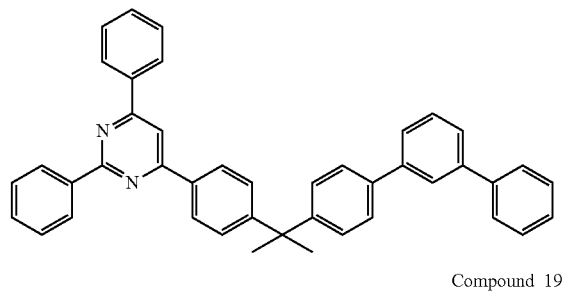
Compound 197
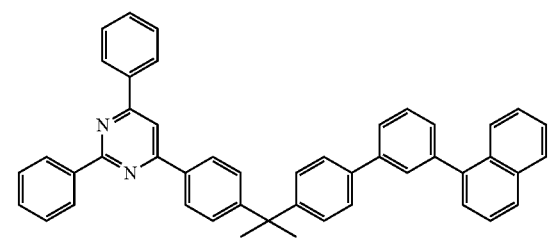
Compound 198
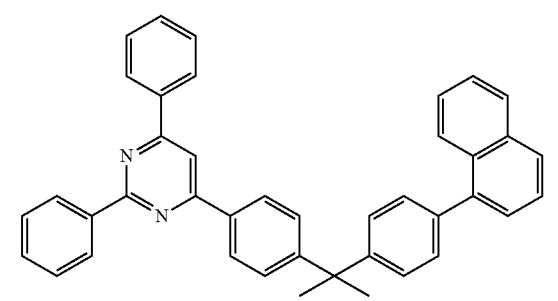
Compound 199
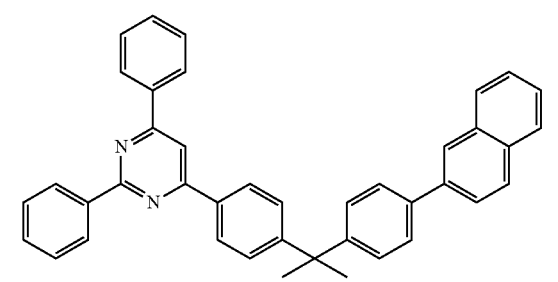
Compound 200
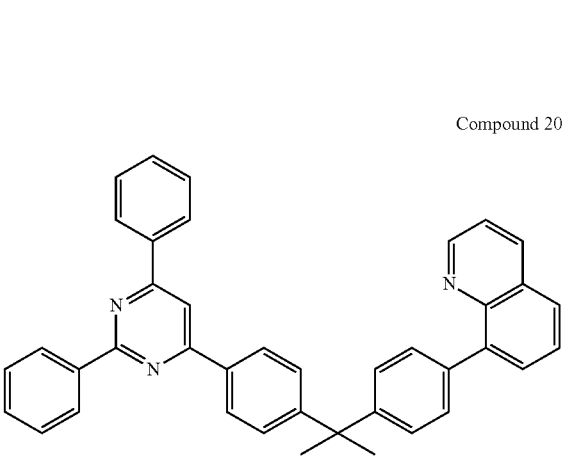
Compound 201
Compound 202
Compound 203
Compound 204
Compound 205

Compound 206

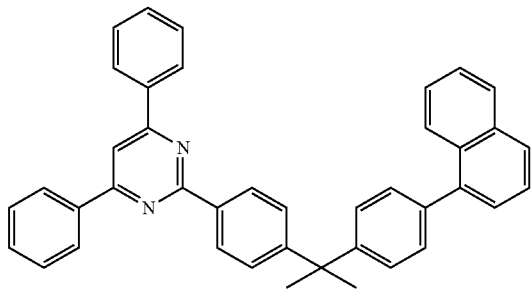

Compound 207

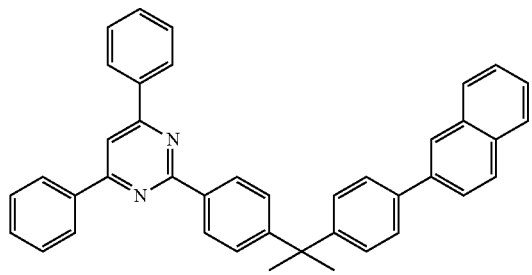

Compound 208

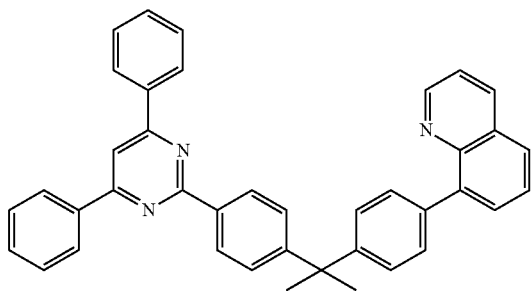

Compound 209

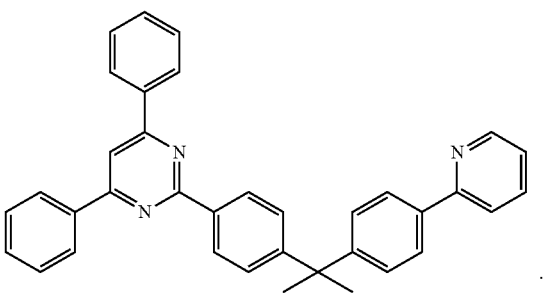

10. The organic light emitting device of claim 1, wherein Chemical Formula a is represented by any one of the following Chemical Formulae a-1 to a-3:

[Chemical Formula a-1]

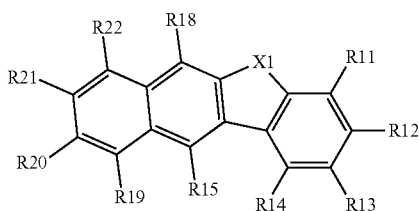

[Chemical Formula a-2]

[Chemical Formula a-3]

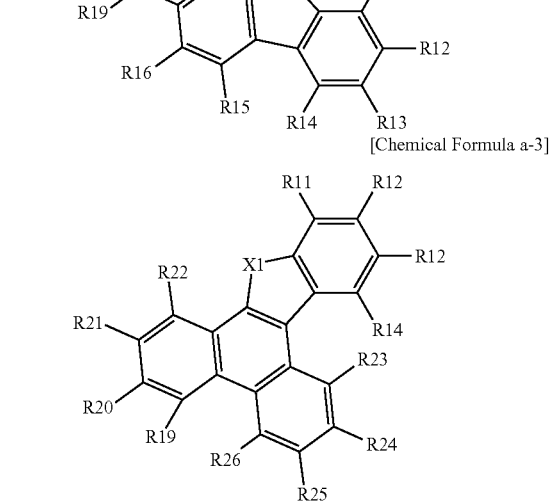

wherein, in Chemical Formulae a-1 to a-3,

X1 and R11 to R16 and R18 have the same definitions as in Chemical Formula a, and R19 to R26 are the same as or different from each other, and each independently hydrogen; halogen; a hydroxyl group; a nitrile group; a substituted or unsubstituted amine group; a substituted or unsubstituted linear or branched alkyl group having 1 to 20 carbon atoms; a substituted or unsubstituted linear or branched alkoxy group having 1 to 20 carbon atoms; a substituted or unsubstituted monocyclic or multicyclic aryloxy group having 6 to 30 carbon atoms; a substituted or unsubstituted monocyclic or multicyclic arylthioxy group having 6 to 30 carbon atoms; a substituted or unsubstituted monocyclic or multicyclic aryl group having 6 to 30 carbon atoms; or a substituted or unsubstituted monocyclic or multicyclic heteroaryl group having 5 to 30 carbon atoms, or adjacent groups bond to each other to form a substituted or unsubstituted ring.

11. The organic light emitting device of claim 1, wherein the anthracene derivative represented by Chemical Formula 2 is represented by any one of the following Chemical Formulae 2-1 to 2-5:

[Chemical Formula 2-1]

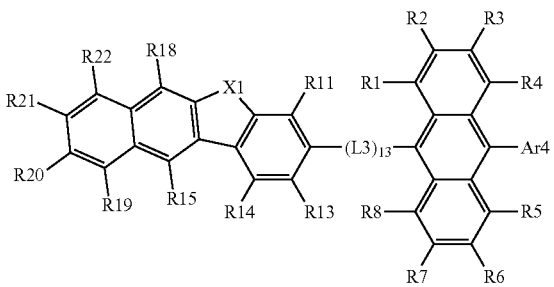

-continued

[Chemical Formula 2-2]

[Chemical Formula 2-3]

[Chemical Formula 2-4]

[Chemical Formula 2-5]

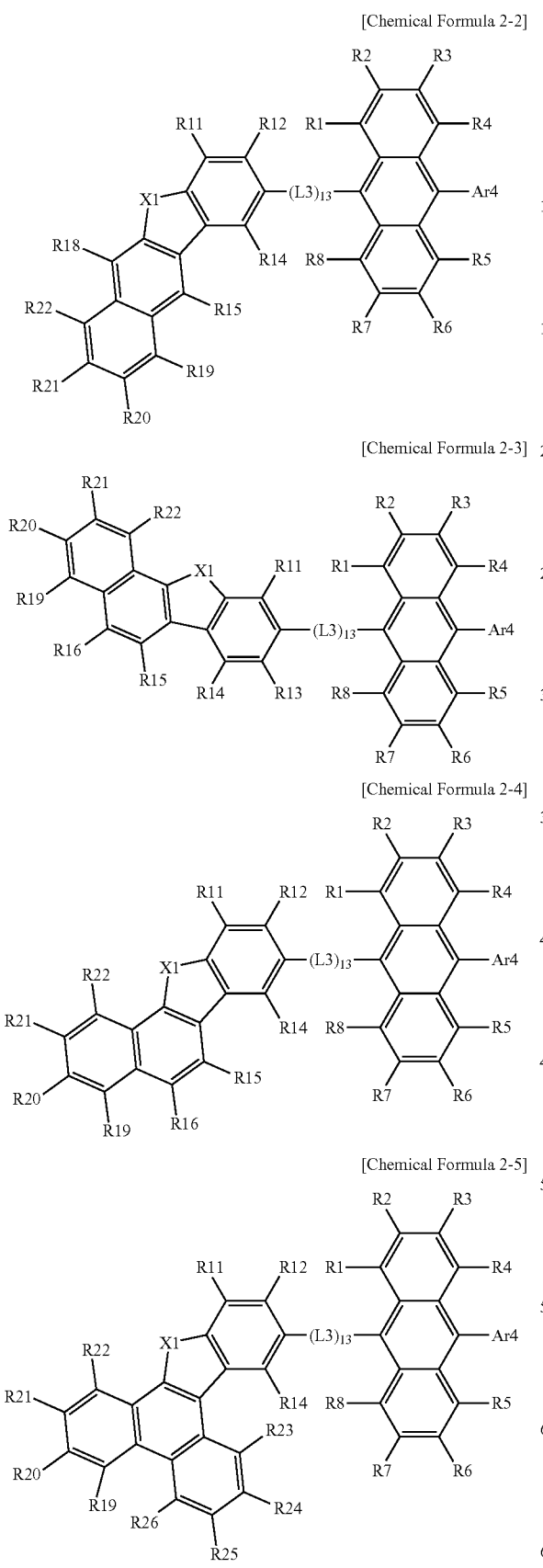

wherein, in Chemical Formulae 2-1 to 2-5,

R1 to R8, L3, 13 and Ar4 have the same definitions as in Chemical Formula 2;

X1 and R11 to R18 have the same definitions as in Chemical Formula a; and

R19 to R26 are the same as or different from each other, and each independently hydrogen; halogen; a hydroxyl group; a nitrile group; a substituted or unsubstituted amine group; a substituted or unsubstituted linear or branched alkyl group having 1 to 20 carbon atoms; a substituted or unsubstituted linear or branched alkoxy group having 1 to 20 carbon atoms; a substituted or unsubstituted monocyclic or multicyclic aryloxy group having 6 to 30 carbon atoms; a substituted or unsubstituted monocyclic or multicyclic arylthioxy group having 6 to 30 carbon atoms; a substituted or unsubstituted monocyclic or multicyclic aryl group having 6 to 30 carbon atoms; or a substituted or unsubstituted monocyclic or multicyclic heteroaryl group having 5 to 30 carbon atoms, or adjacent groups bond to each other to form a substituted or unsubstituted ring.

12. The organic light emitting device of claim 1, wherein the anthracene derivative represented by Chemical Formula 2 is represented by any one of the following compounds:

compound 2-1

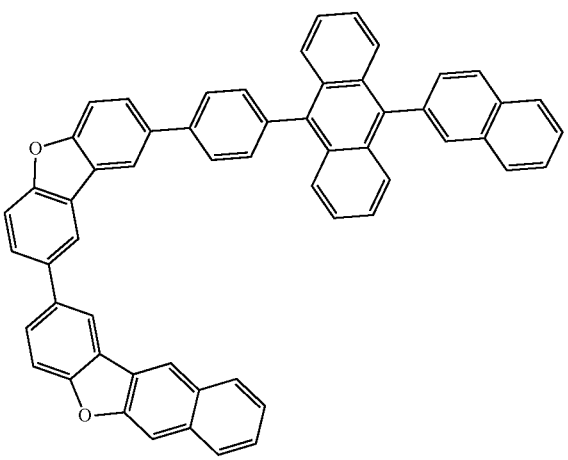

compound 2-2

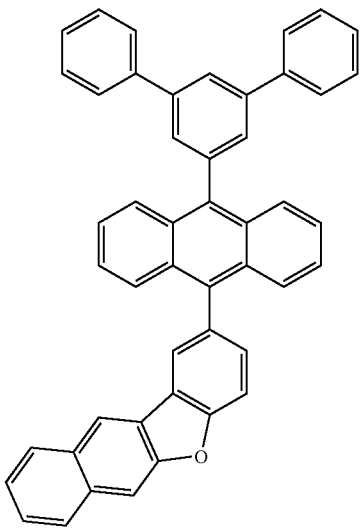

compound 2-3
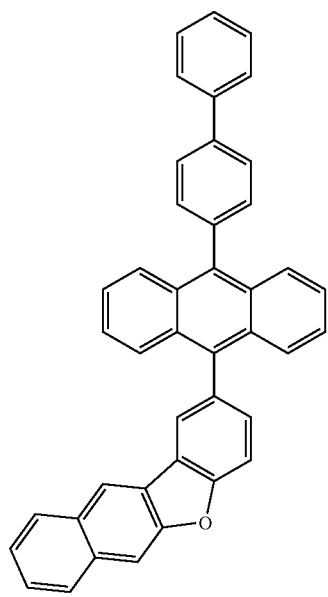
compound 2-4
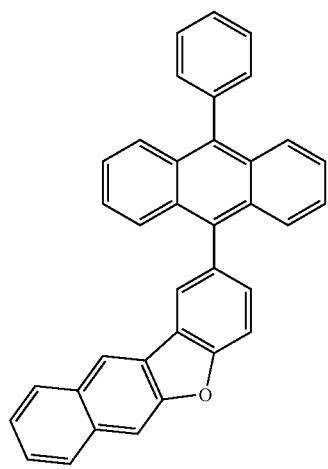
compound 2-5
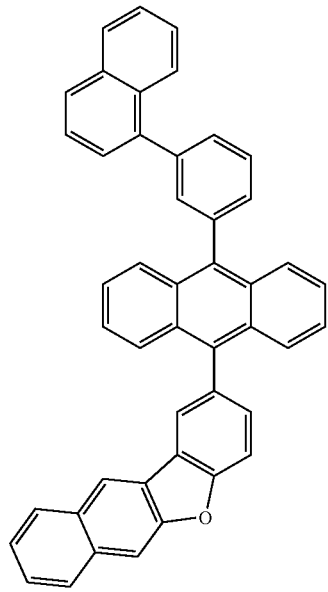
compound 2-6
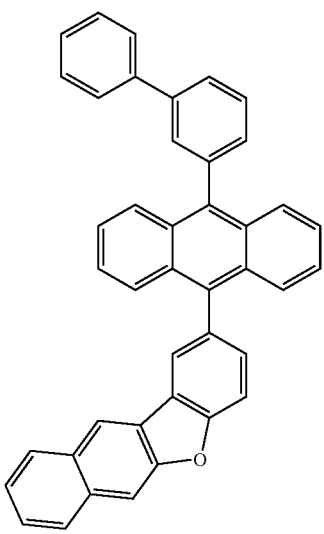
compound 2-7
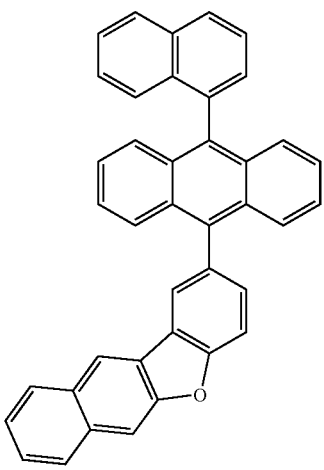
compound 2-8
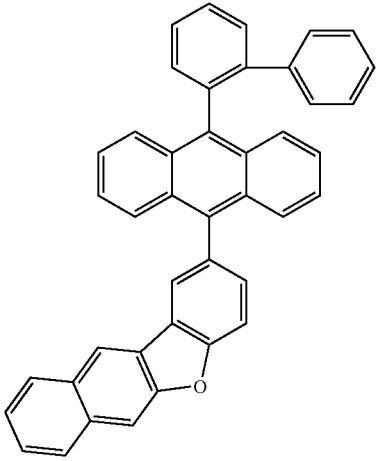

compound 2-9
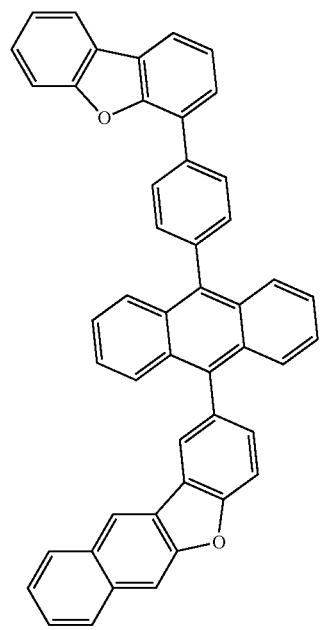
compound 2-11
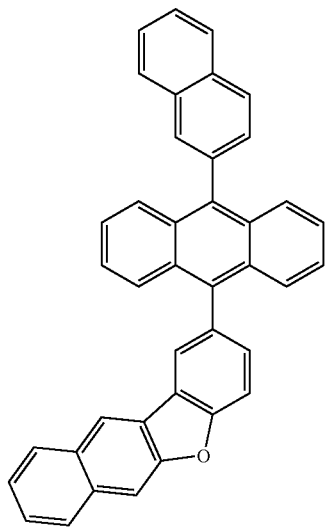
compound 2-12
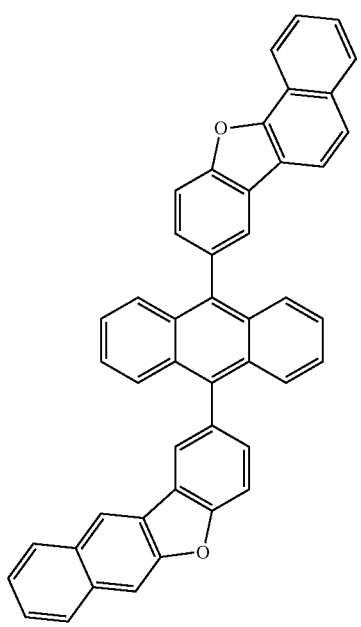
compound 2-10
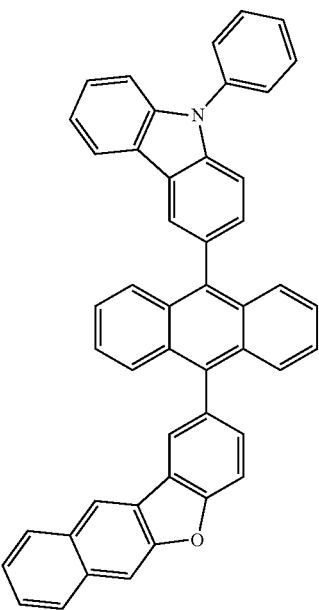
compound 2-13
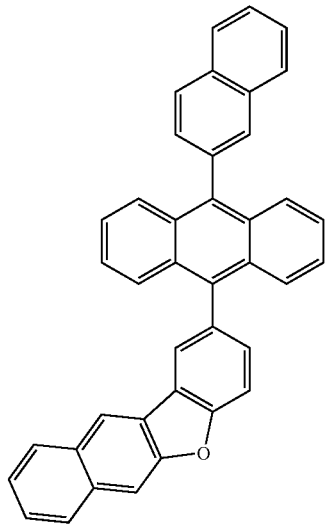

compound 2-14
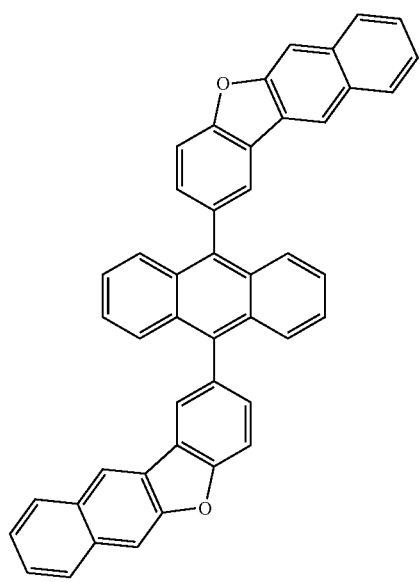
compound 2-15
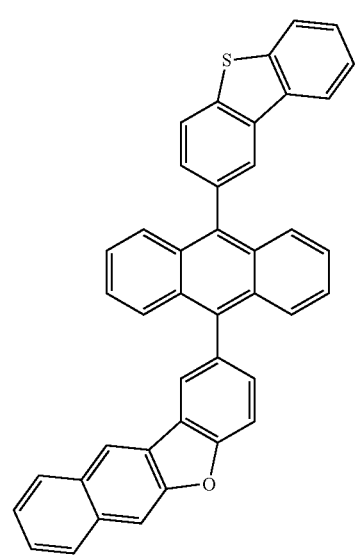
compound 2-16
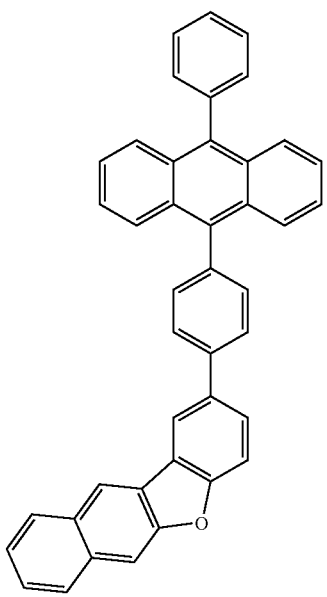
compound 2-17
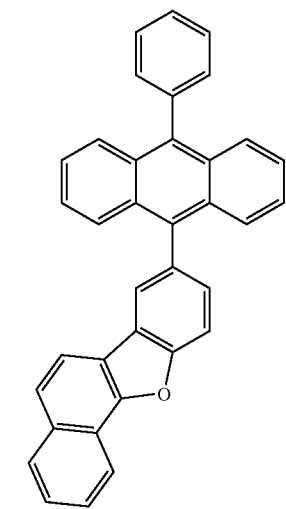

compound 2-18
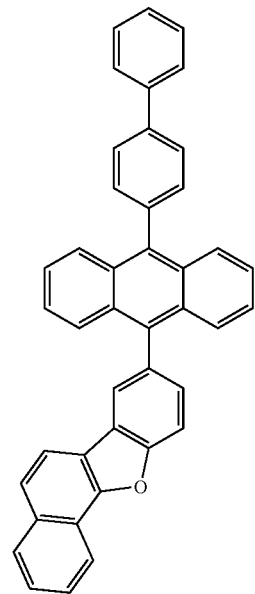
compound 2-19
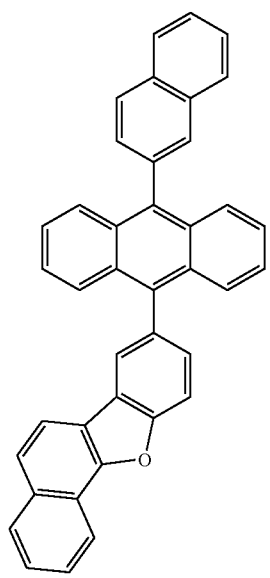
compound 2-20
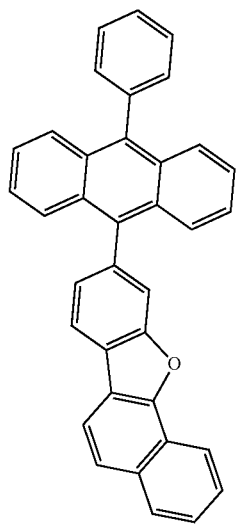
compound 2-21
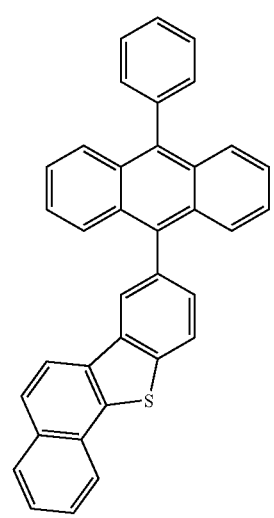
compound 2-22
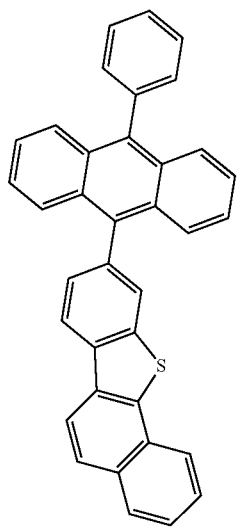

compound 2-23
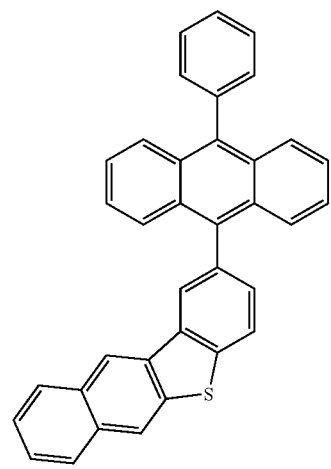
compound 2-24
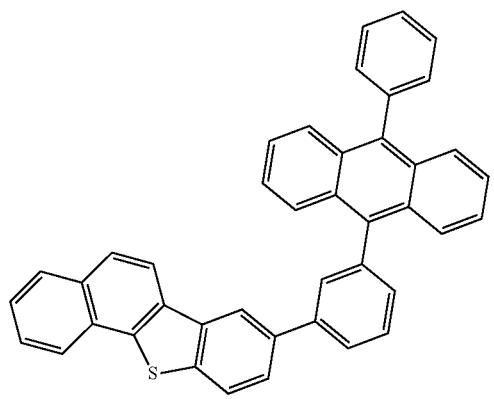
compound 2-25
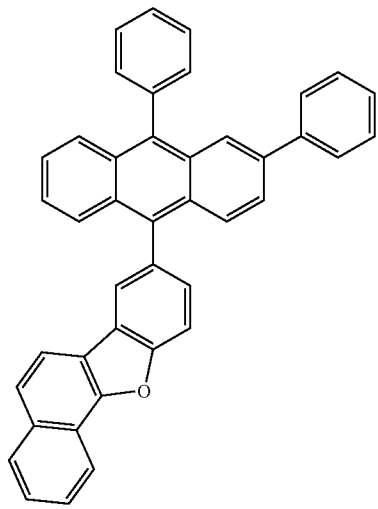
compound 2-26
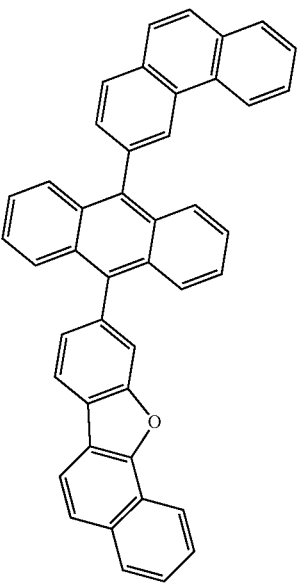
compound 2-27
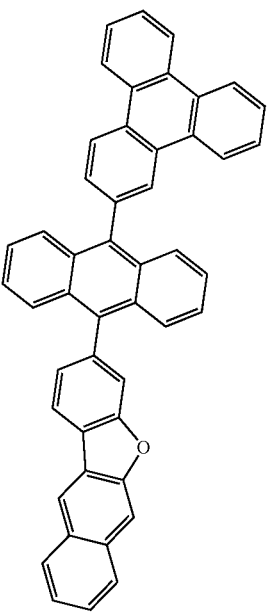

compound 2-28
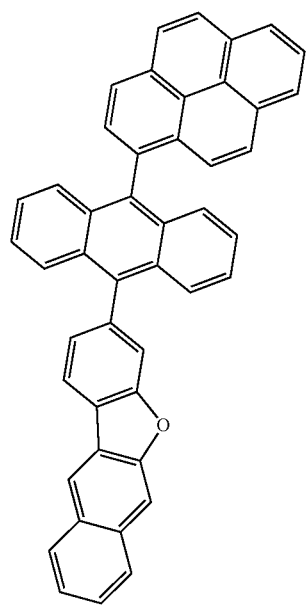
compound 2-29
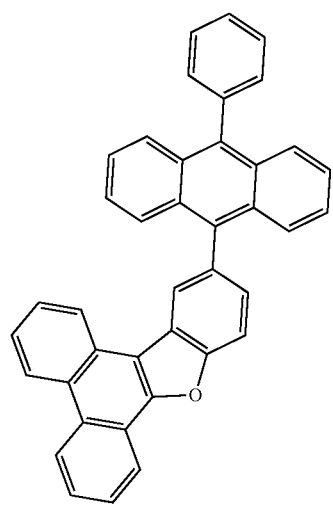
compound 2-30
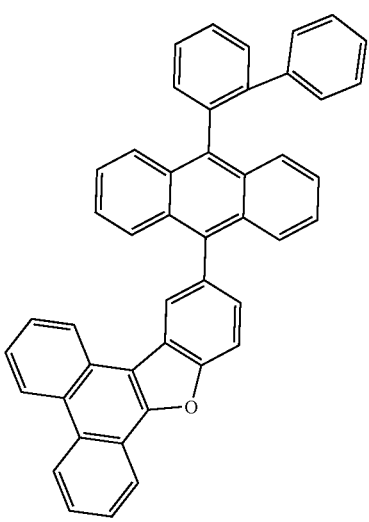
compound 2-31
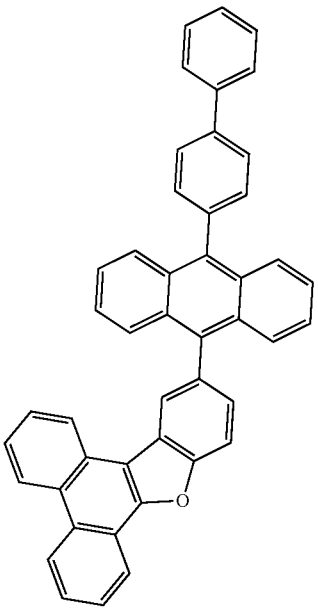
compound 2-32
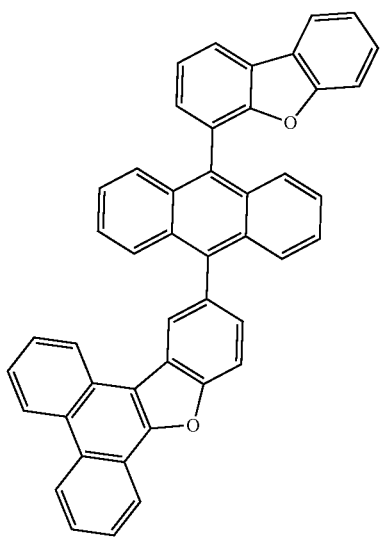
compound 2-33
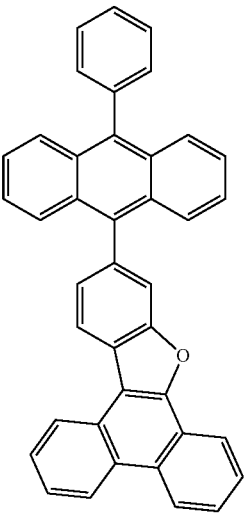

compund 2-34
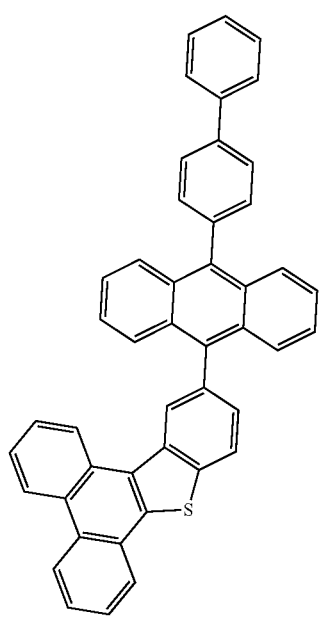
compund 2-36
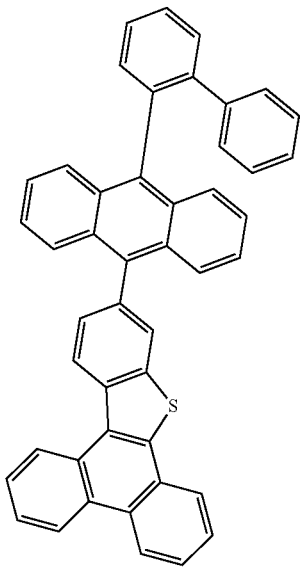
compound 2-37
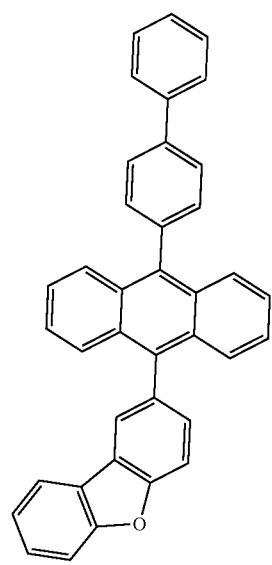
compound 2-35
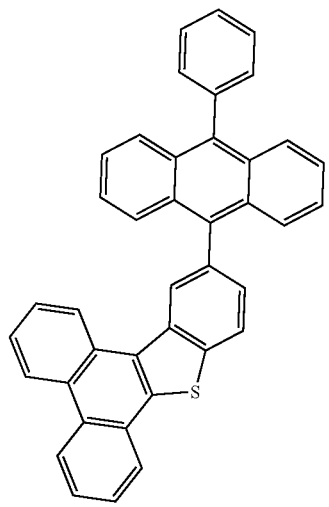
compound 2-38
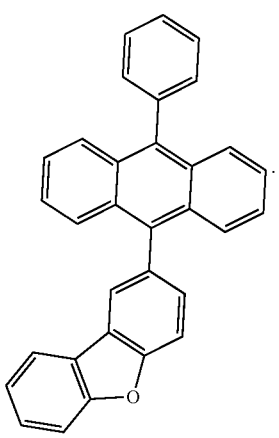

13. The organic light emitting device of claim 1, wherein the anthracene derivative represented by Chemical Formula 2 is included in the light emitting layer in an amount of 30 mol % to 100 mol % based on a total weight of the light emitting layer.

14. The organic light emitting device of claim 1, wherein the anthracene derivative represented by Chemical Formula 2 is a host material.

15. The organic light emitting device of claim 1, wherein the light emitting layer further contains a dopant material.

16. The organic light emitting device of claim 15, wherein the dopant material is an arylamine compound.

17. The organic light emitting device of claim 15, wherein the dopant material is a styrylamine compound.

18. The organic light emitting device of claim 15, wherein the dopant material is an amine derivative represented by the following Chemical Formula 3:

[Chemical Formula 3]

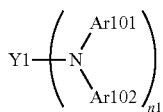

wherein, in Chemical Formula 3,

Y1 is a substituted or unsubstituted multicyclic mono to tetravalent aromatic hydrocarbon group having 10 to 50 carbon atoms;

Ar101 and Ar102 are the same as or different from each other, and each independently a substituted or unsubstituted monocyclic or multicyclic aryl group having 6 to 50 carbon atoms; or a monocyclic or multicyclic heteroaryl group having 2 to 50 carbon atoms;

n1 is an integer of 1 to 4; and when n1 is 2 or greater, structures in the two or more parentheses are the same as or different from each other.

19. The organic light emitting device of claim 18, wherein Chemical Formula 3 is an amine derivative represented by any one of the following Chemical Formulae 3-1 to 3-4:

[Chemical Formula 3-1]

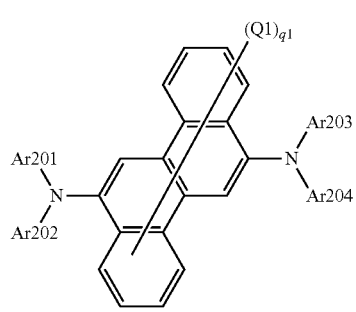

[Chemical Formula 3-2]

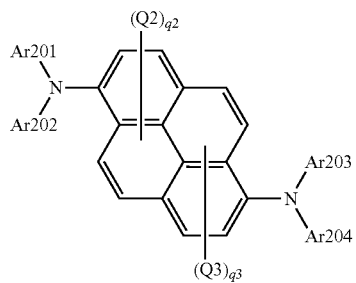

[Chemical Formula 3-3]

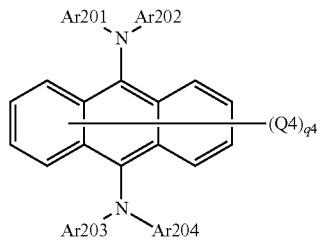

[Chemical Formula 3-4]

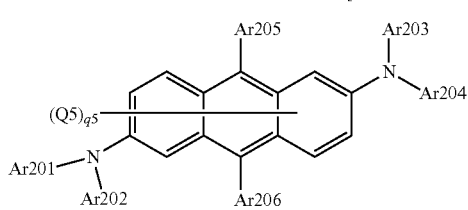

wherein, in Chemical Formulae 3-1 to 3-4,

Ar201 to Ar206 are the same as or different from each other, and each independently a substituted or unsubstituted monocyclic or multicyclic aryl group having 6 to 50 carbon atoms; or a monocyclic or multicyclic heteroaryl group having 2 to 50 carbon atoms;

Q1 to Q5 are the same as or different from each other, and each independently hydrogen; halogen; a hydroxyl group; a nitrile group; a substituted or unsubstituted amine group; a substituted or unsubstituted linear or branched alkyl group having 1 to 20 carbon atoms; a substituted or unsubstituted linear or branched alkoxy group having 1 to 20 carbon atoms; a substituted or unsubstituted monocyclic or multicyclic aryloxy group having 6 to 30 carbon atoms; a substituted or unsubstituted monocyclic or multicyclic arylthioxy group having 6 to 30 carbon atoms; a substituted or unsubstituted monocyclic or multicyclic aryl group having 6 to 30 carbon atoms; or a substituted or unsubstituted monocyclic or multicyclic heteroaryl group having 5 to 30 carbon atoms;

q1 is an integer of 1 to 10;

q2 and q3 are each an integer of 1 to 4;

q4 is an integer of 1 to 8;

q5 is an integer of 1 to 6; and when q1 to q5 are each 2 or greater, structures in the two or more parentheses are the same as or different from each other.

* * * * *